US012691101B2

(12) United States Patent
Choi et al.

(10) Patent No.: US 12,691,101 B2
(45) Date of Patent: Jul. 28, 2026

(54) COMPOUND AND METHOD FOR PREVENTING OR TREATING OF RESPIRATORY DISEASES COMPRISING THE SAME AS AN ACTIVE INGREDIENT

(71) Applicant: YONSEI UNIVERSITY, UNIVERSITY - INDUSTRY FOUNDATION (UIF), Seoul (KR)

(72) Inventors: Jae Young Choi, Seoul (KR); Gyoonhee Han, Seoul (KR); Wan Namkung, Incheon (KR); Sung Ha Park, Seoul (KR); Moo Suk Park, Seoul (KR)

(73) Assignee: YONSEI UNIVERSITY, UNIVERSITY—INDUSTRY FOUNDATION (UIF), Seoul (KR)

( * ) Notice: Subject to any disclaimer, the term of this patent is extended or adjusted under 35 U.S.C. 154(b) by 1050 days.

(21) Appl. No.: 17/601,114

(22) PCT Filed: Apr. 1, 2020

(86) PCT No.: PCT/KR2020/004464
§ 371 (c)(1),
(2) Date: Oct. 4, 2021

(87) PCT Pub. No.: WO2020/204602
PCT Pub. Date: Oct. 8, 2020

(65) Prior Publication Data

US 2022/0193041 A1 Jun. 23, 2022

(30) Foreign Application Priority Data

Apr. 2, 2019 (KR) ........................ 10-2019-0038246

(51) Int. Cl.

| | |
|---|---|
| ***A61K 31/422*** | (2006.01) |
| ***A61K 9/00*** | (2006.01) |
| ***A61K 31/341*** | (2006.01) |
| ***A61K 31/381*** | (2006.01) |
| ***A61K 31/40*** | (2006.01) |
| ***A61K 31/415*** | (2006.01) |
| ***A61K 31/421*** | (2006.01) |
| ***A61K 31/426*** | (2006.01) |
| ***A61K 31/427*** | (2006.01) |
| ***A61K 31/4439*** | (2006.01) |
| ***A61K 31/454*** | (2006.01) |
| ***A61K 31/4709*** | (2006.01) |
| ***A61K 31/519*** | (2006.01) |
| ***A61P 11/06*** | (2006.01) |
| ***C07D 207/337*** | (2006.01) |
| ***C07D 209/20*** | (2006.01) |
| ***C07D 231/12*** | (2006.01) |
| ***C07D 263/42*** | (2006.01) |
| ***C07D 277/30*** | (2006.01) |
| ***C07D 307/54*** | (2006.01) |
| ***C07D 333/24*** | (2006.01) |
| ***C07D 333/60*** | (2006.01) |
| ***C07D 413/04*** | (2006.01) |
| ***C07D 413/06*** | (2006.01) |
| ***C07D 413/10*** | (2006.01) |
| ***C07D 413/12*** | (2006.01) |

(Continued)

(52) U.S. Cl.

CPC .......... *A61K 31/422* (2013.01); *A61K 9/0056* (2013.01); *A61K 31/341* (2013.01); *A61K 31/381* (2013.01); *A61K 31/40* (2013.01); *A61K 31/415* (2013.01); *A61K 31/421* (2013.01); *A61K 31/426* (2013.01); *A61K 31/427* (2013.01); *A61K 31/4439* (2013.01); *A61K 31/454* (2013.01); *A61K 31/4709* (2013.01); *A61K 31/519* (2013.01); *A61P 11/06* (2018.01); *C07D 207/337* (2013.01); *C07D 209/20* (2013.01); *C07D 231/12* (2013.01); *C07D 263/42* (2013.01); *C07D 277/30* (2013.01); *C07D 307/54* (2013.01); *C07D 333/24* (2013.01); *C07D 333/60* (2013.01); *C07D 413/04* (2013.01); *C07D 413/06* (2013.01); *C07D 413/10* (2013.01); *C07D 413/12* (2013.01); *C07D 413/14* (2013.01); *C07D 417/06* (2013.01); *C07D 495/04* (2013.01)

(58) Field of Classification Search

None
See application file for complete search history.

(56) References Cited

U.S. PATENT DOCUMENTS 7,659,277 B2 * 2/2010 Alroy .................... A61K 31/00 514/270
2004/0180943 A1 9/2004 Augelli-Szafran et al.

FOREIGN PATENT DOCUMENTS

EP 0422900 4/1991
EP 1695968 8/2006

(Continued)

OTHER PUBLICATIONS

Lee et al., Inhibition of Pendrin by a small molecule reduces Lipopolysaccharides-induced acute Lung Injury. Theranostics, 2020, 10, p. 9913-9922.*

(Continued)

*Primary Examiner* — Po-Chih Chen
(74) *Attorney, Agent, or Firm* — LEX IP MEISTER, PLLC

(57) ABSTRACT

The present invention relates to a novel compound, and a composition for preventing or treating of respiratory disease comprising the novel compound, E- or Z-isomer thereof, optical isomer thereof, a mixture of two isomers thereof, precursor thereof, pharmaceutically acceptable salt thereof or solvate thereof as an active ingredient.

4 Claims, 19 Drawing Sheets

(51) Int. Cl.

| | |
|---|---|
| ***C07D 413/14*** | (2006.01) |
| ***C07D 417/06*** | (2006.01) |
| ***C07D 495/04*** | (2006.01) |

(56) References Cited

FOREIGN PATENT DOCUMENTS

| | | |
|---|---|---|
| JP | 2006-096708 | 4/2006 |
| JP | 2021525728 | 9/2021 |
| KR | 2015-0126687 | 11/2015 |
| WO | 2005-007141 | 1/2005 |
| WO | 2008056356 | 5/2008 |
| WO | 2010094009 | 8/2010 |
| WO | 2011-064661 | 6/2011 |
| WO | 2019-231993 | 12/2019 |
| WO | 2019231935 | 12/2019 |

OTHER PUBLICATIONS

Chemical Abstract Registry No. 931056-91-6, indexed in the Registry File on Stn Cas Online Apr. 19, 2007.*

Chemical Abstract Registry No. 1018143-16-2, indexed in the Registry File on Stn Cas Online Apr. 29, 2008.*

Schafer, S., Kolkhof, P. Failure is an option: learning from unsuccessful proof-of-concept trials. Drug Discovery Today. Nov. 2008, 13, 913-916.*

Horig, H., Pullman, W. From bench to clinic and back: Perspective on the 1st IQPC Translational Research conference. Journal of Translational Medicine. Dec. 2004, 2, 44.*

Chemical Abstract Registry No. 1390899-00-9, indexed in the Registry File on STN CAS ONLINE Aug. 14, 2012.*

Registry(STN)[online], Apr. 29, 2018, Search date: Apr. 24, 2024, CAS Registration No. 2221732-34-7.

Registry(STN)[online], Apr. 29, 2018, Search date: Apr. 24, 2024, CAS Registration No. 2221376-50-5.

Registry(STN)[online], Apr. 29, 2018, Search date: Apr. 24, 2024, CAS Registration No. 2221335-90-4.

Registry(STN)[online], Apr. 26, 2018, Search date: Apr. 24, 2024, CAS Registration No. 2219971-42-1.

Registry(STN)[online], Apr. 26, 2018, Search date: Apr. 24, 2024, CAS Registration No. 2219438-63-6.

Registry(STN)[online], Apr. 25, 2018, Search date: Apr. 24, 2024, CAS Registration No. 2219352-23-3.

Registry(STN)[online], Apr. 25, 2018, Search date: Apr. 24, 2024, CAS Registration No. 2218999-93-8.

Registry(STN)[online], Apr. 25, 2018, Search date: Apr. 24, 2024, CAS Registration No. 2218982-73-9.

Dayana Abboud et al., "A strategy to discover decoy chemokine ligands with an anti-inflammatory activity", Scientific Reports vol. 5,pp. 1-14, Oct. 7, 2015.

Sanjay D. Sawant et al., "Molecular docking and synthesis of 8-substituted 3,4-dihydro-6-methyl-4-(2,4-dinitrophenyl) imidazo[1,5-b][1,2,4]triazin-2(8H)-one derivatives as novel antiasthmatic agents", Journal of Applicable Chemistry, vol. 2,Nr:3, pp. 372-384, Apr. 2013.

Elena Serrano et al., "Stereoselective Synthesis of 1,3-Diaminotruxillic Acid Derivatives: An Advantageous Combination of C-H- ortho -Palladation and On-Flow [2+2]-Photocycloaddition in Microreactors", Chemistry—A European Journal, vol. 22,Nr:1,pp. 144-152, 2016.

Topuzyan V O et al, "Derivatives of [alpha], [beta]-dehydro amino acids: III. Reaction of 4-arylmethylidene-4,5-dihydro-1,3-oxazol-5-ones with hexamethyldisilazane", Russian Journal of Organic Chemistry, Maik Nauka - Interperiodica, RU, (Jan. 1, 2007), vol. 43, doi:10.1134/S1070428007060127, ISSN 1070-4280, pp. 868-871.

Alan R Katritzky et al, "Synthesis and photochemistry of pH-sensitive GFP chromophore analogs", Tetrahedron Letters, vol. 52, No. 17, doi: 10.1016/J.TETLET.2010.12.082, ISSN 0040-4039, (2011), pp. 2224-2227.

Cativiela, C.; Diaz De Villegas, M. D.; Mayoral, J. A.; Melen, "Synthesis and stereospecific ring opening of the (Z/E)-isomers of 2-methyl(phenyl)-4-(thienylmethylene)-5(4H)-oxazolone", SYNTHESIS, (1983), vol. 11, doi::10.1055/s-1983-30556, ISSN 0039-7881, pp. 899-902.

Eiden F. et al, "4-Pyranyliden-oxazolone-(5)", Archiv Der Pharmazie, Weinheim, (Jan. 1, 1967), vol. 300, No. 3, doi:10.1002/ardp.19673000305, ISSN 0365-6233, pp. 211-225.

Singhal, O. P.; Ittyerah, P. I., "2-Thiophenecarboxaldehyde: Condensation with some acyl glycines", CAPLUS, Chemical Abstracts Service, Columbus, Ohio, US, (1965), Database accession No. 1965:498270 (CAPLUS printout only).

Regberg Tor et al, "Novel Affinity Ligands for Chromatography Using Combinatorial Chemistry", Combinatorial Chemistry and High Throughput Screening, NL, (May 1, 2011), vol. 14, No. 4, doi:10.2174/138620711795222482, ISSN 1386-2073, pp. 267-278.

EPO, Search Report of EP 20782123.2 dated Dec. 2, 2022.

Registry (STN) [online], Mar. 27, 2021, Search date: Dec. 2, 2024, CAS Registry No. 329081-63-2, total 1 page.

Registry (STN) [online], Apr. 17, 2007, Search date: Dec. 2, 2024, CAS Registry No. 930416-15-2, total 1 page.

Registry (STN) [online], Apr. 17, 2007, Search date: Dec. 2, 2024, CAS Registry No. 930496-08-5, total 1 page.

Registry (STN) [online], Jan. 4, 2001, Search date: Dec. 2, 2024, CAS Registry No. 312724-89-3, total 1 page.

Registry (STN) [online], Apr. 28, 2011, Search date: Dec. 2, 2024, CAS Registry No. 1287284-76-7, total 1 page.

Registry (STN) [online], Jan. 4, 2001, Search date: Dec. 2, 2024, CAS Registry No. 312716-34-0, total 1 page.

Registry (STN) [online], Apr. 23, 2007, Search date: Dec. 2, 2024, CAS Registry No. 932008-70-3, total 1 page.

Registry (STN) [online], Apr. 23, 2007, Search date: Dec. 2, 2024, CAS Registry No. 932008-38-3, total 1 page.

Registry (STN) [online], Jun. 17, 2002, Search date: Dec. 2, 2024, CAS Registry No. 431067-49-1, total 1 page.

EPO, Office Action of EP 20782123.2 dated Aug. 27, 2025, total 10 pages.

Database CAPLUS [Online] Chemical Abstract Service, Columbus, Ohio, US; Jan. 1, 1981, Eweiss, N. F. et al: "Synthesis of heterocycles. III. A convenient route to substituted thieno[3,2-c]pyridines", XP093306436, Database Accession No. 1982:217733, total 2 pages.

Database CAPLUS [Online] Chemical Abstract Service, Columbus, Ohio, US; Jan. 1, 2015, Atia., Abdul Jabar Kh et al: "Synthesis of new heterocyclic compounds derived from 3-chlorobenzo[b]thiophene-2-carbonyl chloride", XP093306900, Database Accession No. 2015:1424707, total 2 pages.

Elena SerraNo et al., "Stereoselective Synthesis of 1,3-Diaminotruxillic Acid Derivatives: An Advantageous Combination of C-H-ortho-Palladation and On-Flow [2+2]-Photocycloaddition in Microreactors", Chemistry—A European Journal, vol. 22, No. 1, Nov. 24, 2015, XP055744974, total 20 pages.

Sanjay D. Sawant et al., "Molecular docking and synthesis of 8-substituted 3,4-dihydro-6-methyl-4-(2,4-dinitrophenyl) imidazo[1,5-b][1,2,4]triazin-2(8H)-one derivatives as novel antiasthmatic agents", Journal of Applicable Chemistry, vol. 2, No. 3, Apr. 28, 2013, pp. 372-384, XP055744973.

Dayana Abboud et al., "A strategy to discover decoy chemokine ligands with an anti-inflammatory activity", Scientific Reports, vol. 5, 14746, Oct. 7, 2015, p. 1-14, XP055744972.

Database CAPLUS [Online] Chemical Abstracts Service, Columbus, Ohio, US; 1965, Singhal, O.P.: Ittyerah, P. I.: "2-Thiophenecarboxaldehyde: Condensation with some acyl glycines", XP002807902, retrieved from STN accession No.DN:63: 98270, Database Accession No. 1965: 498270, total 2 pages.

* cited by examiner

【FIG. 1】
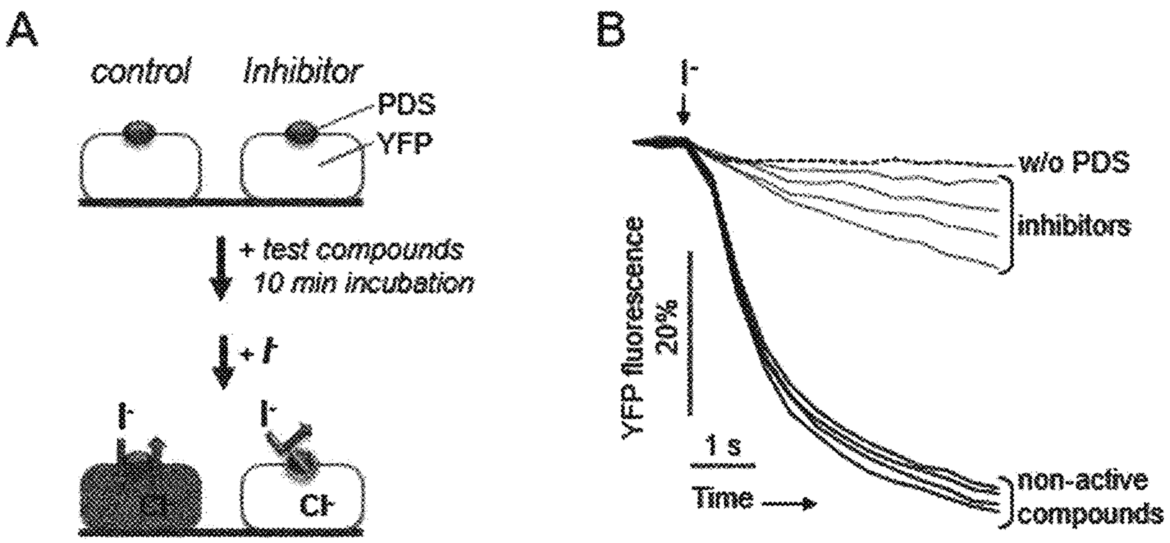
【FIG. 2】
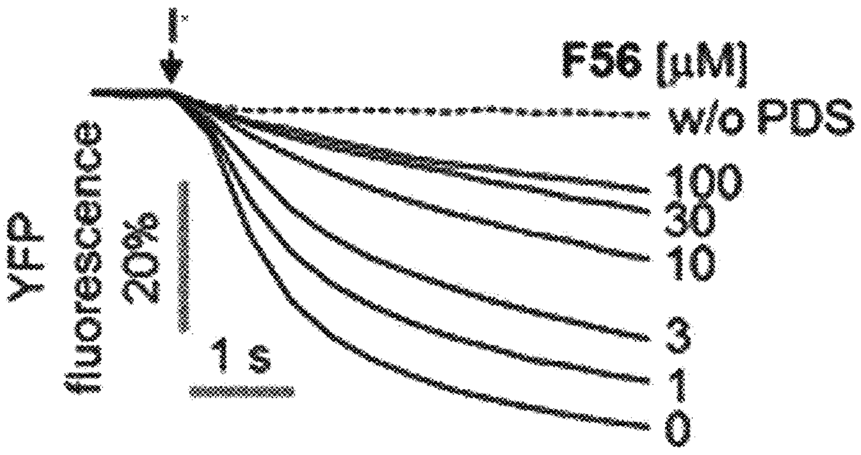

【FIG. 3】
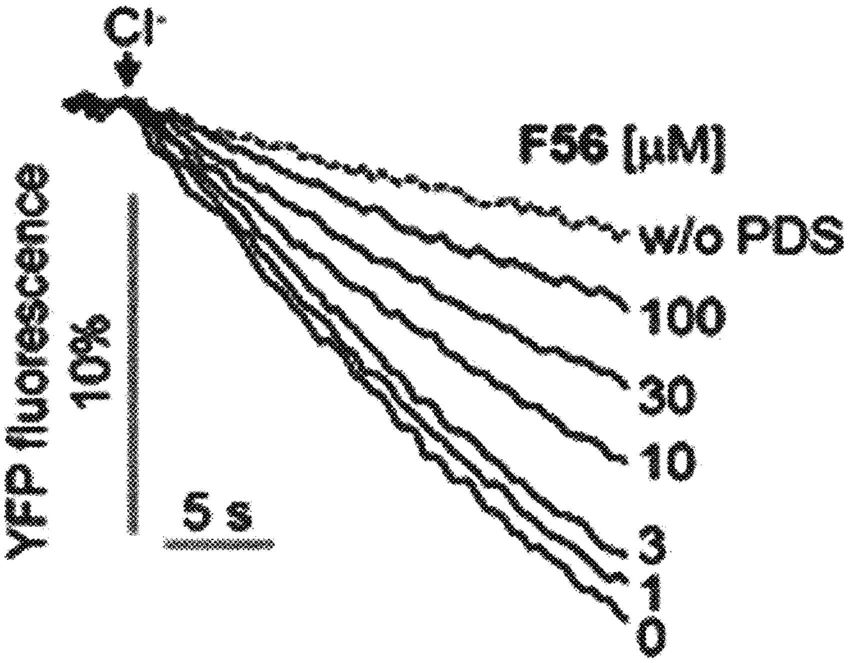
【FIG. 4a】
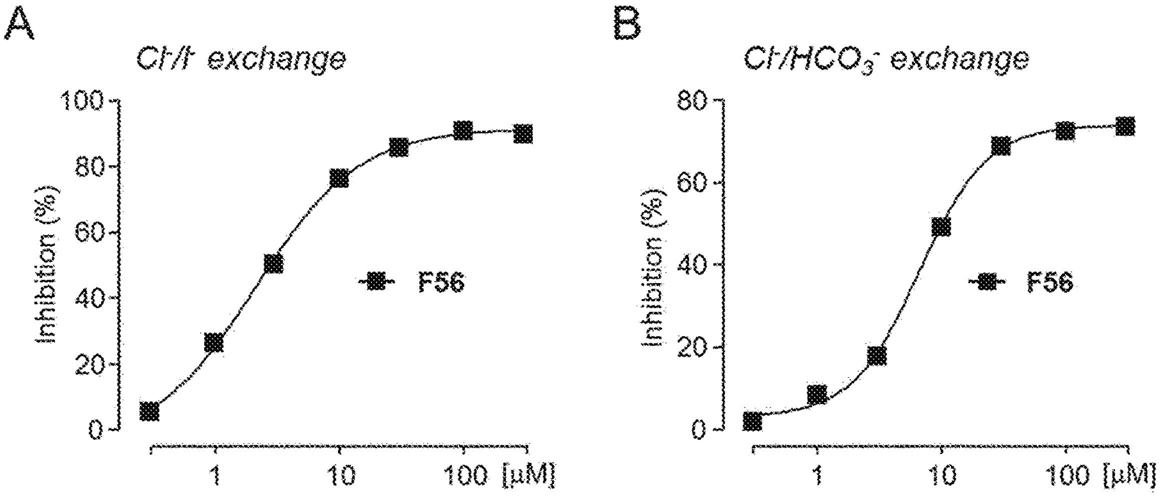

【FIG. 4b】
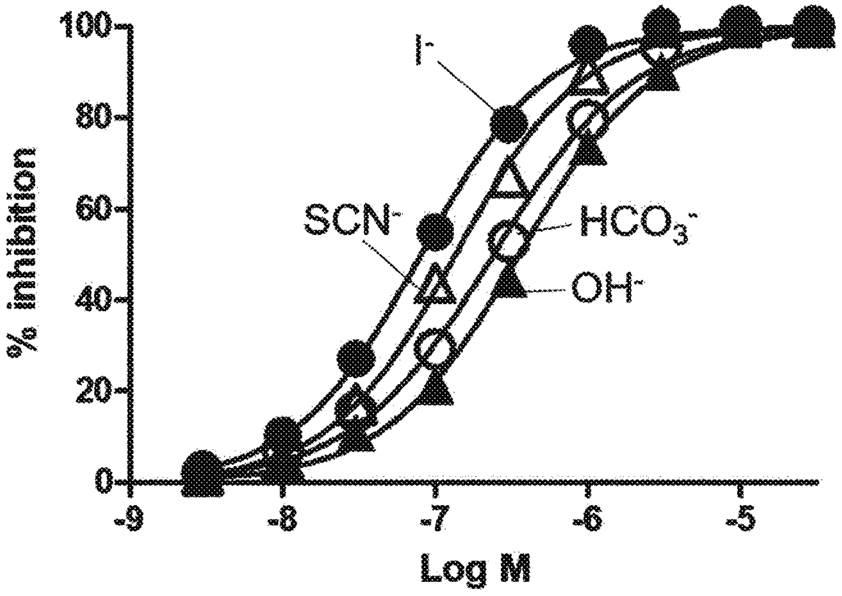

【FIG. 5a】
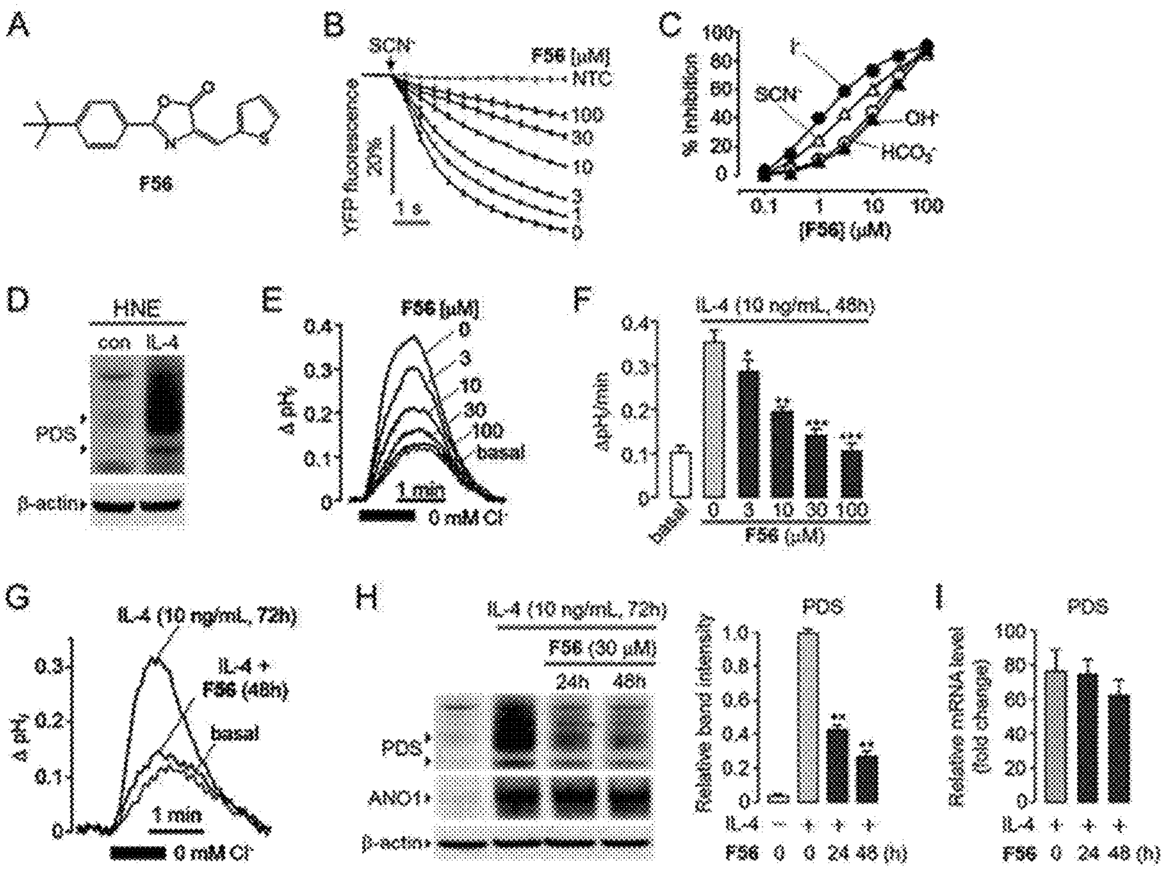

【FIG. 5b】
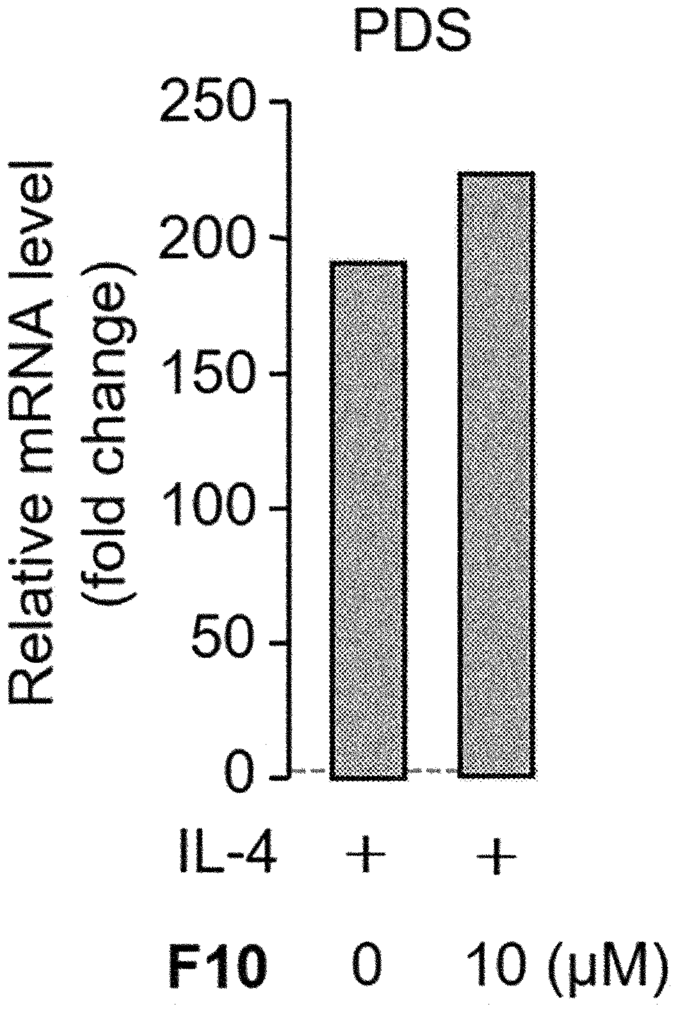

【FIG. 6a】
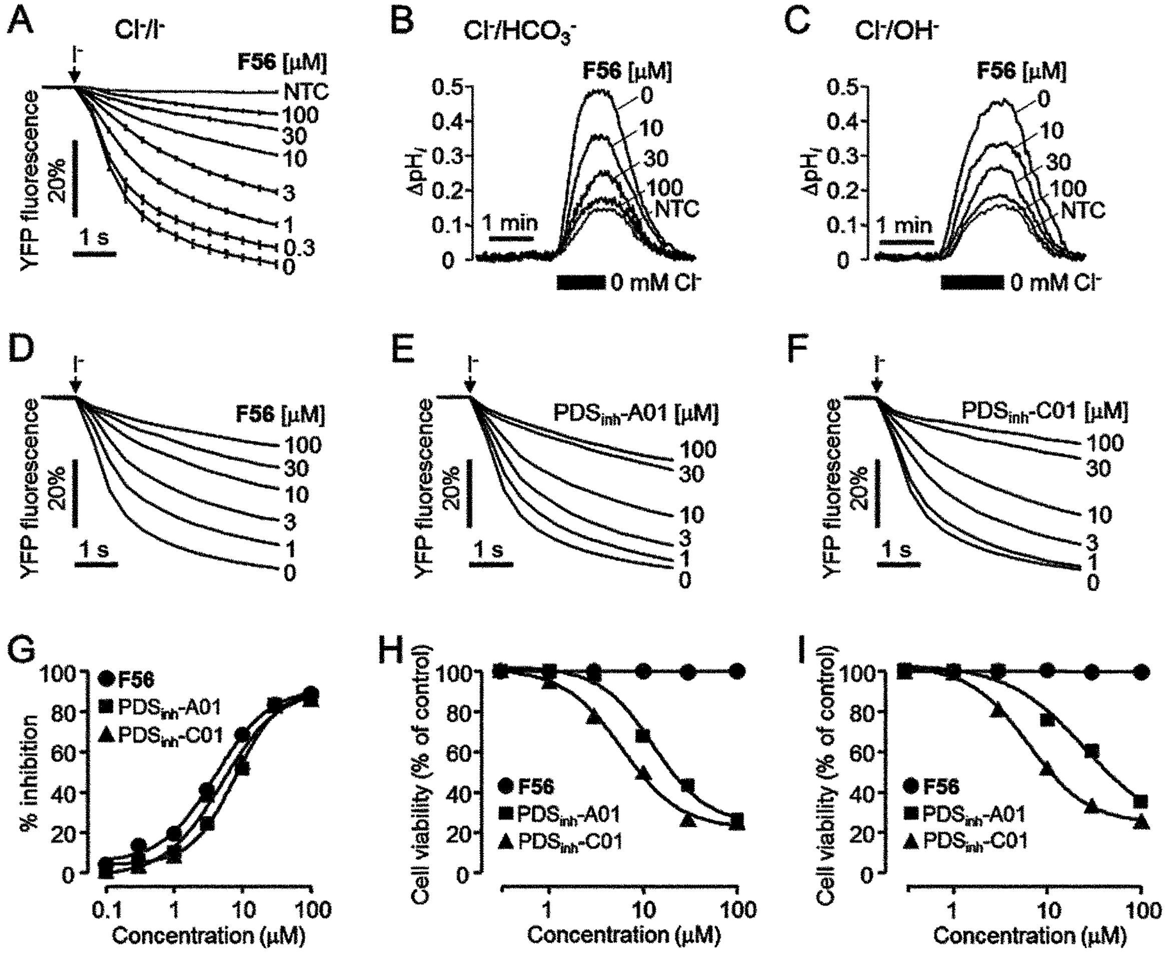
【FIG. 6b】
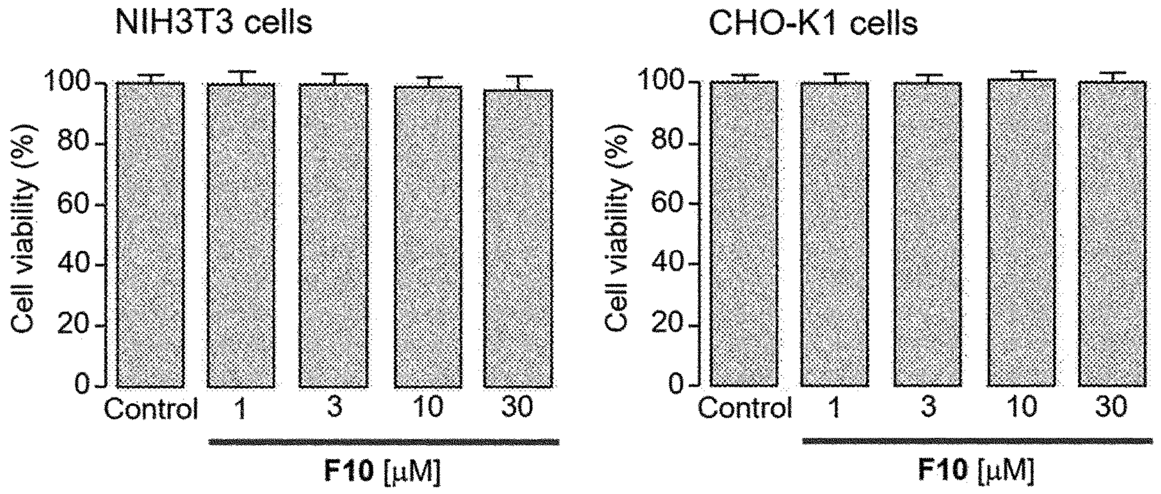

【FIG. 7a】
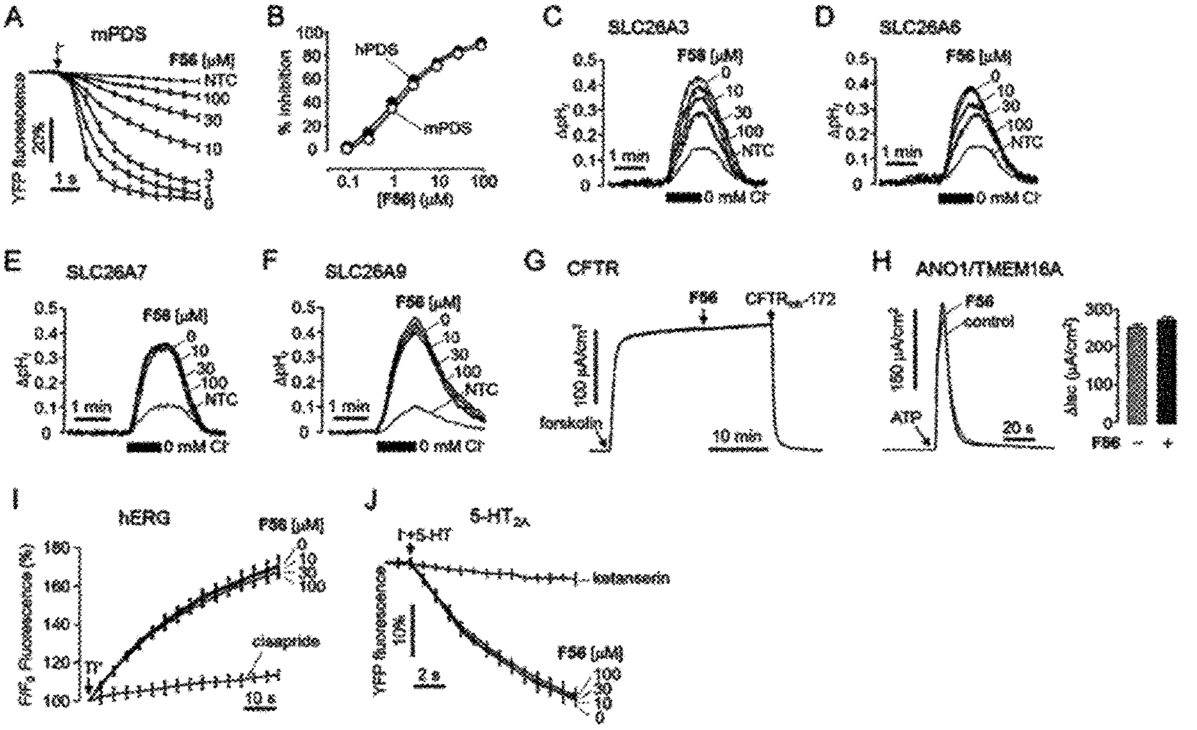
【FIG. 7b】
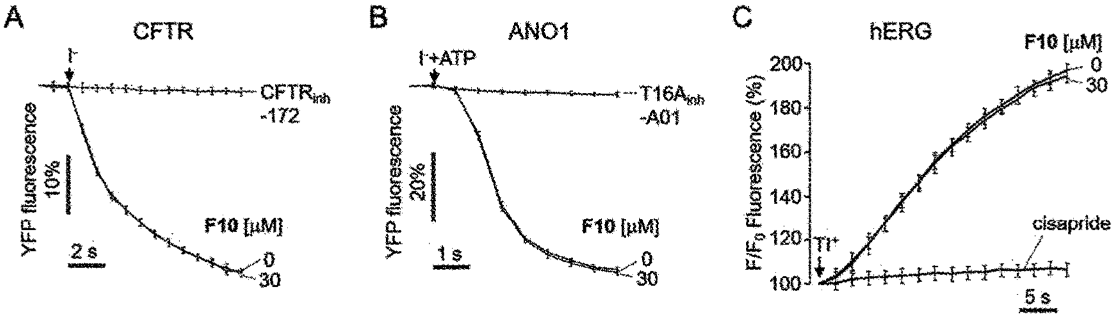

【FIG. 8a】
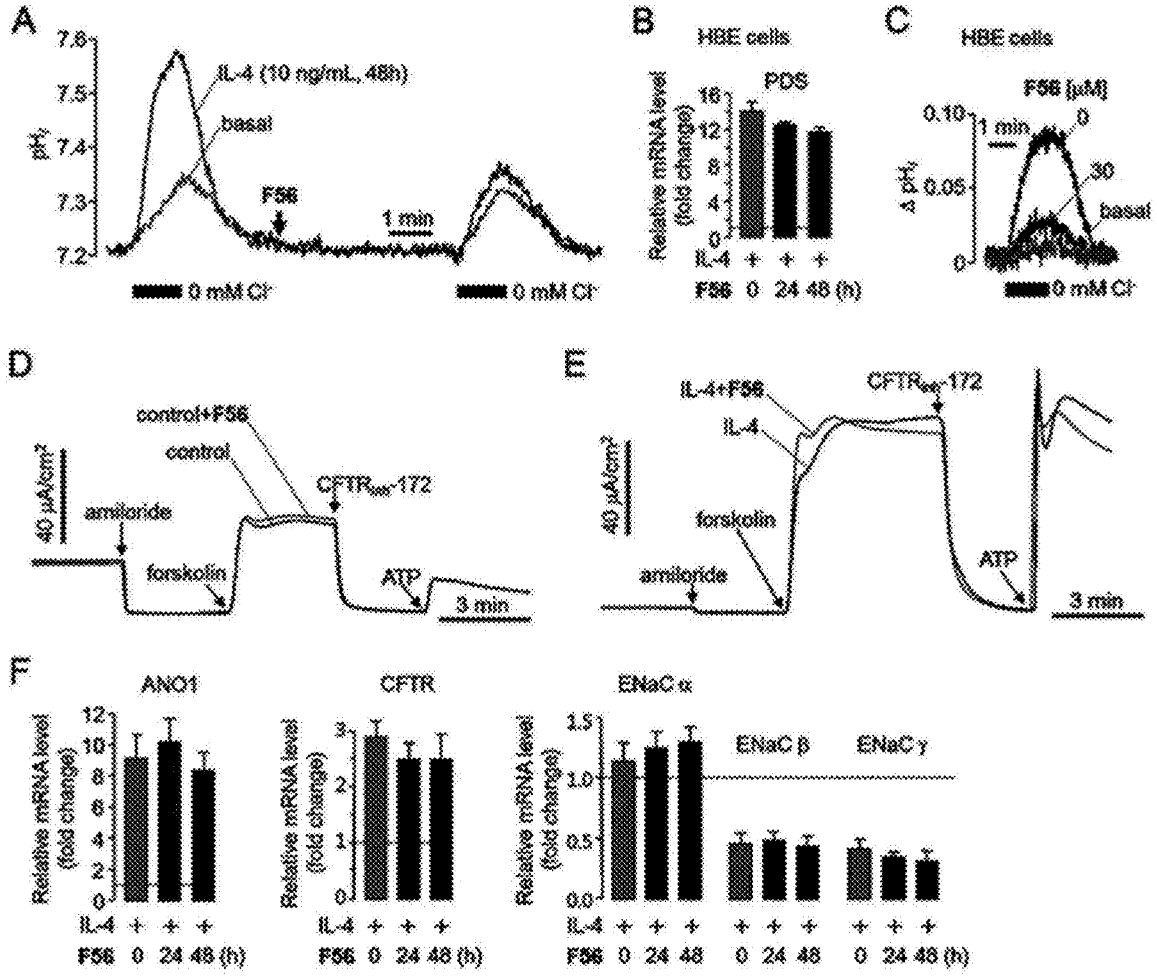
【FIG. 8b】
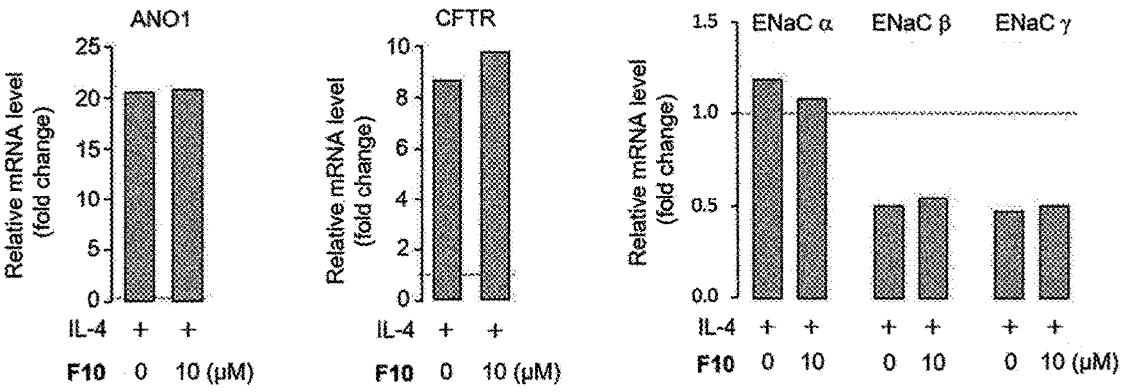

【FIG. 9a】
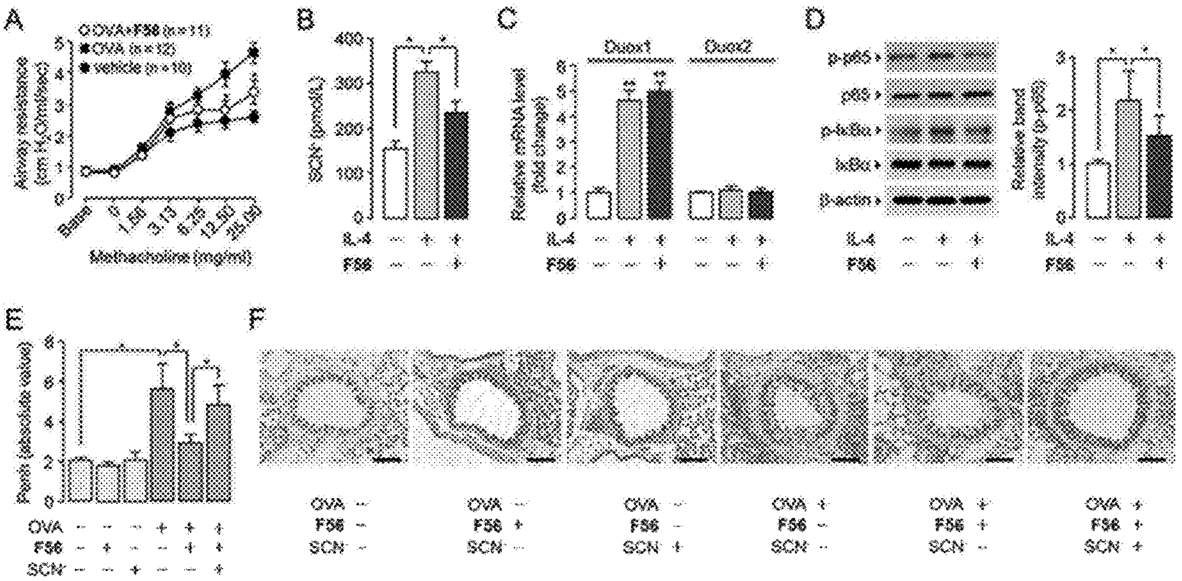
【FIG. 9b】
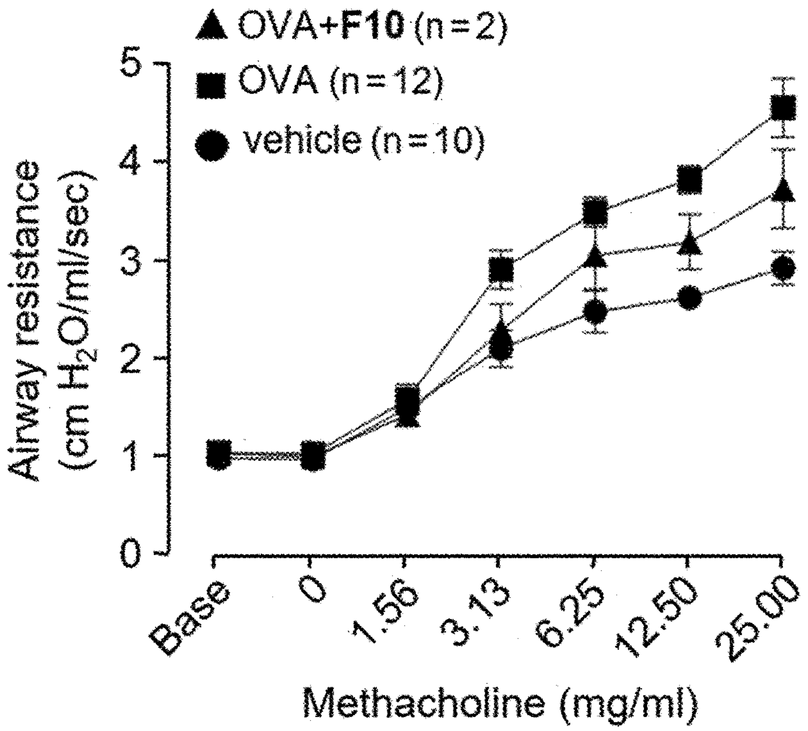

【FIG. 10】
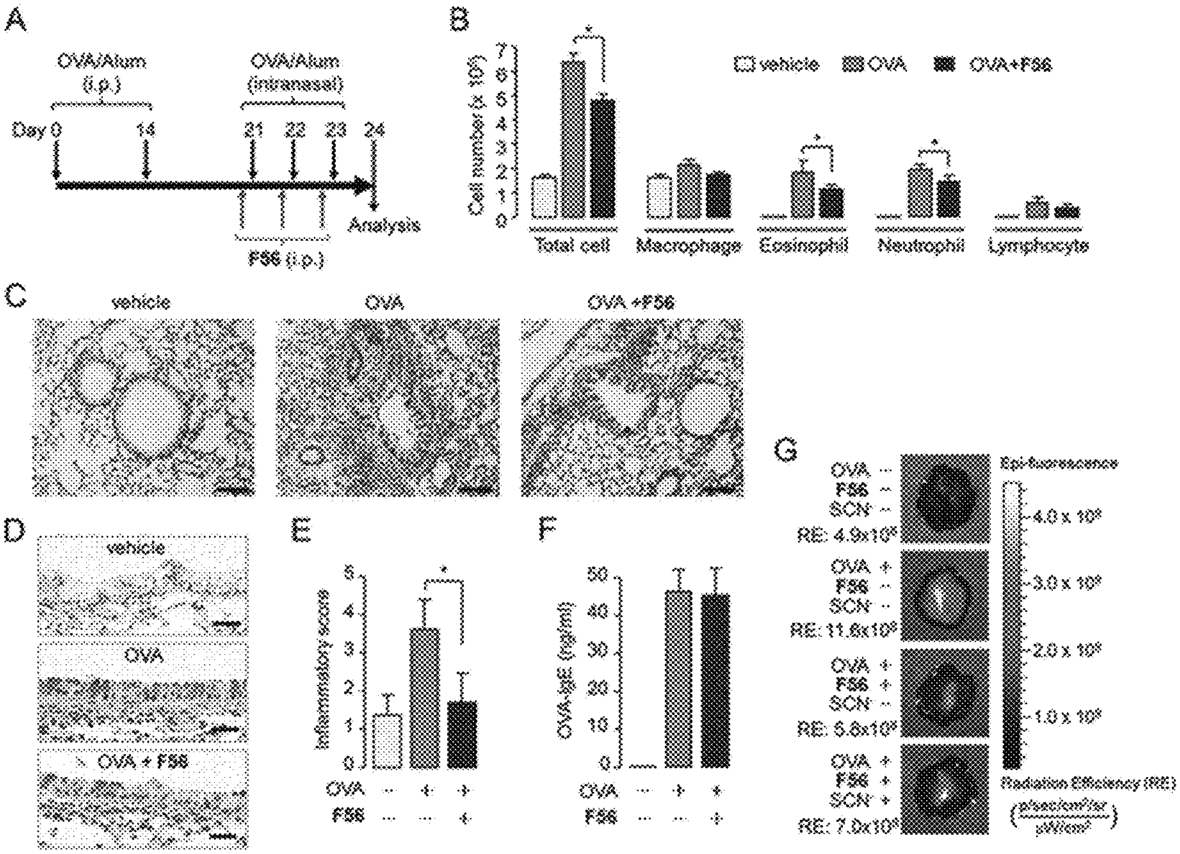

【FIG. 11】
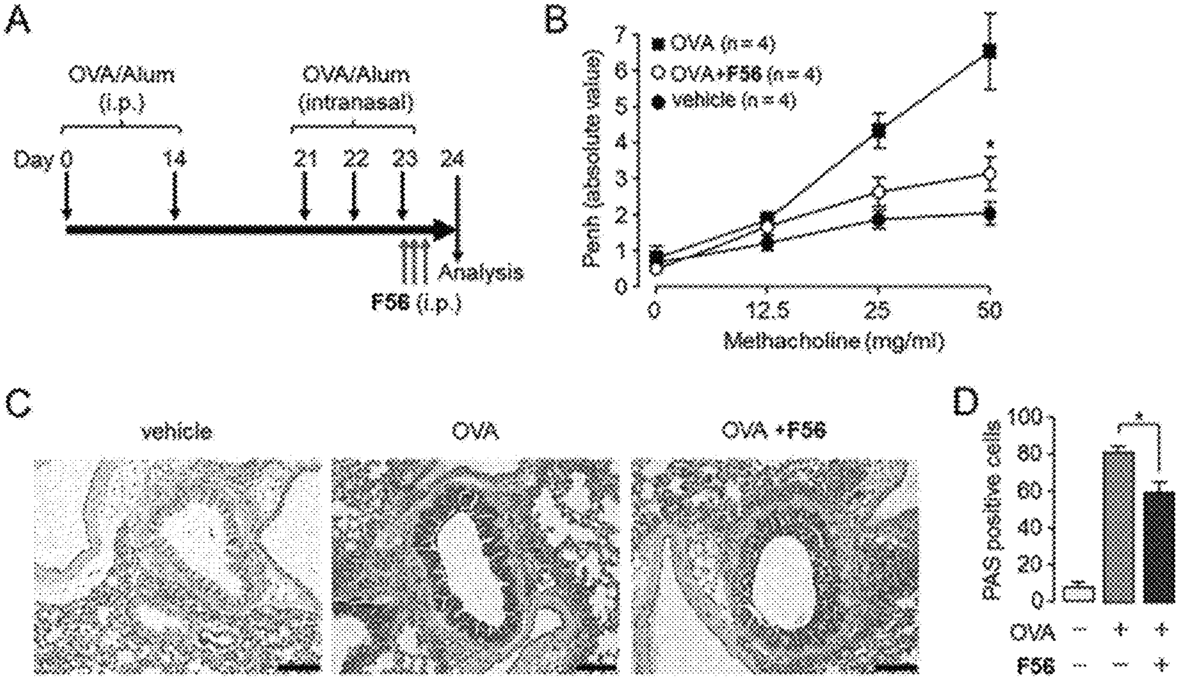
【FIG. 12a】
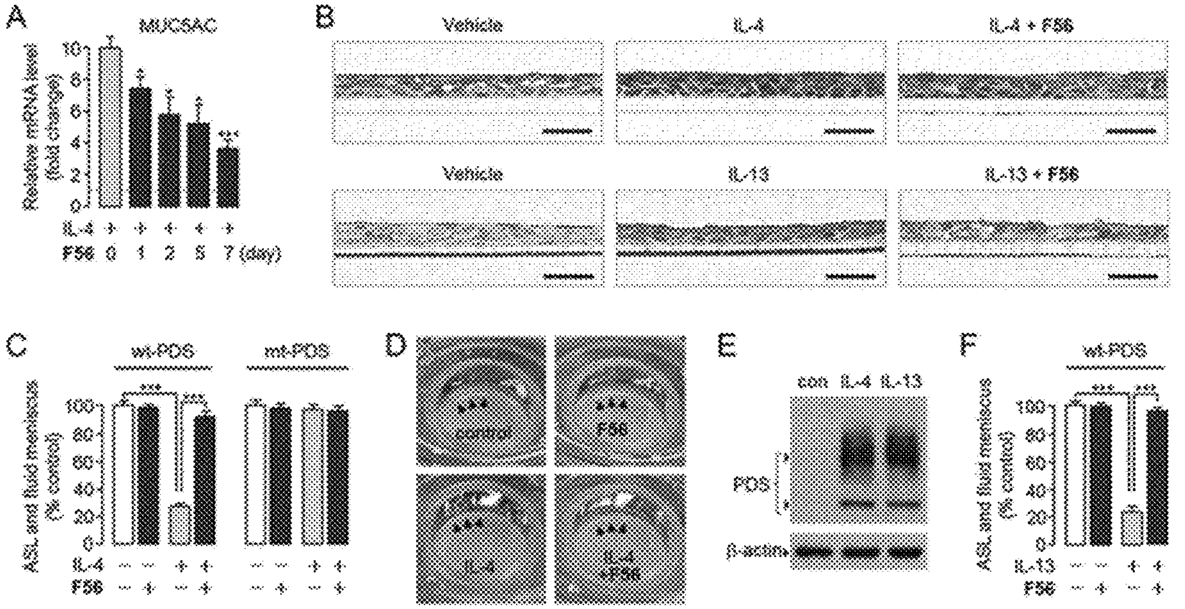

【FIG. 12b】
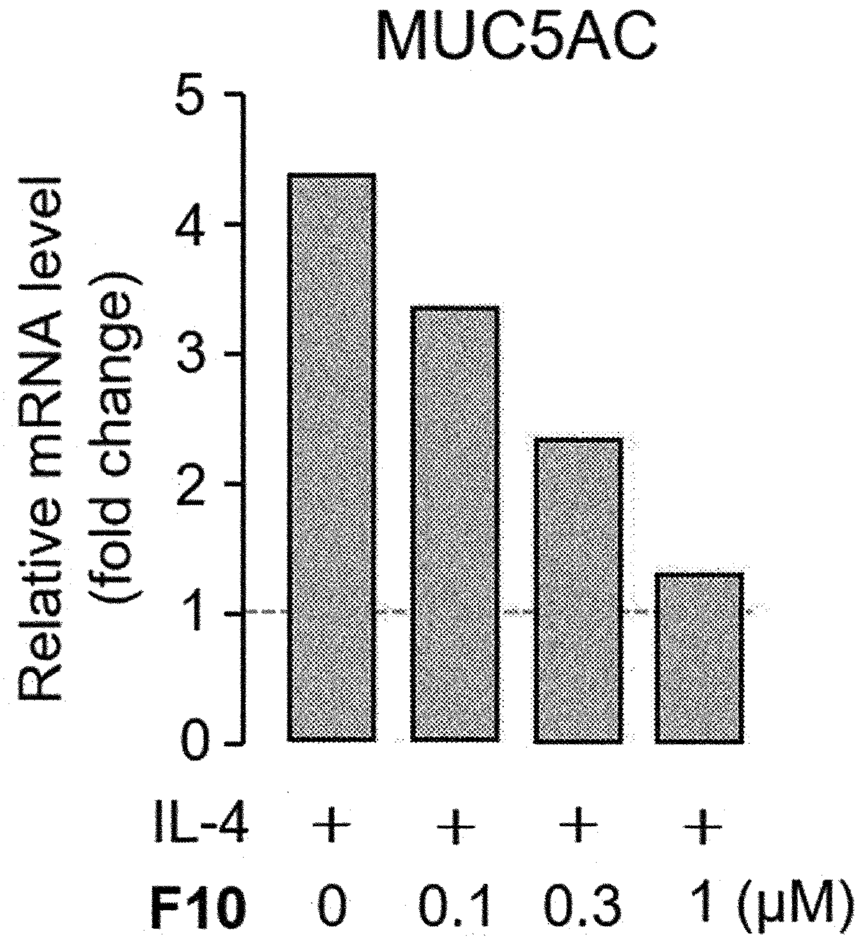

【FIG. 13】
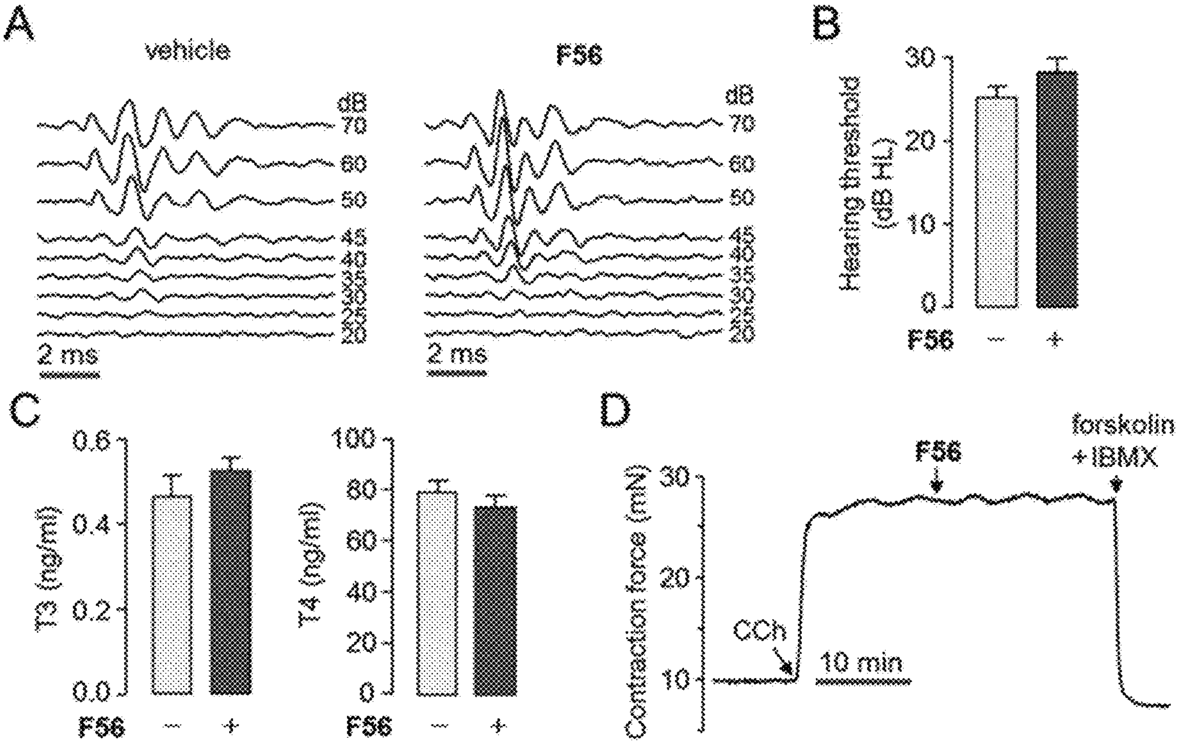

【FIG. 14】
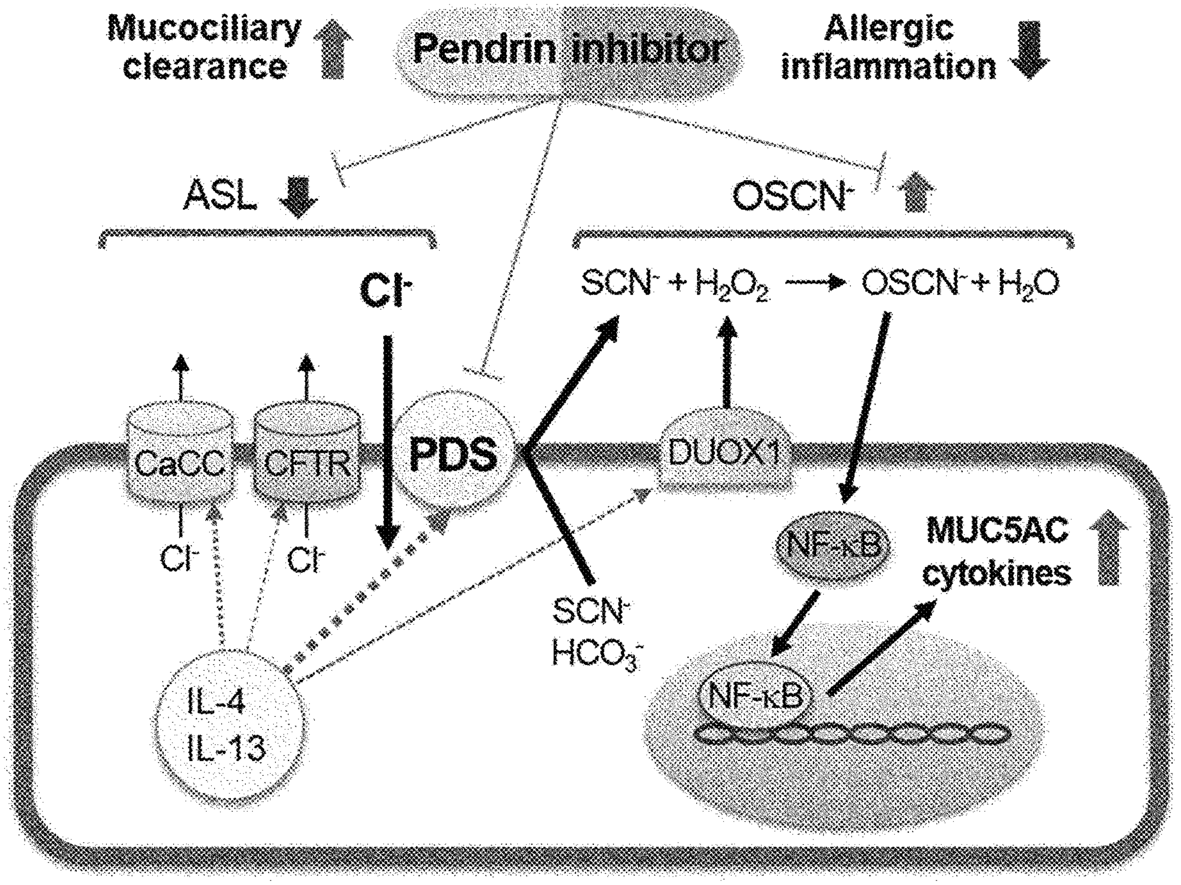

【FIG. 15】
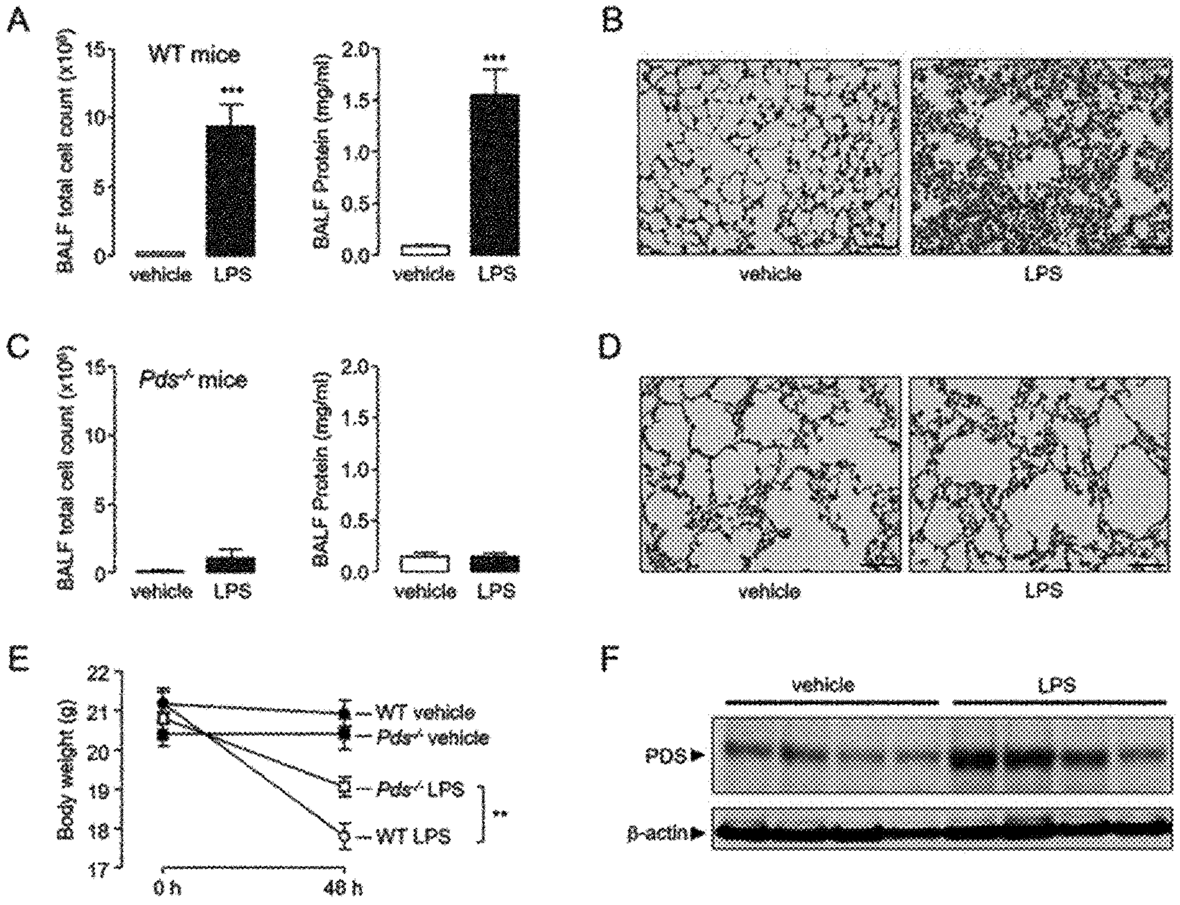

【FIG. 16】
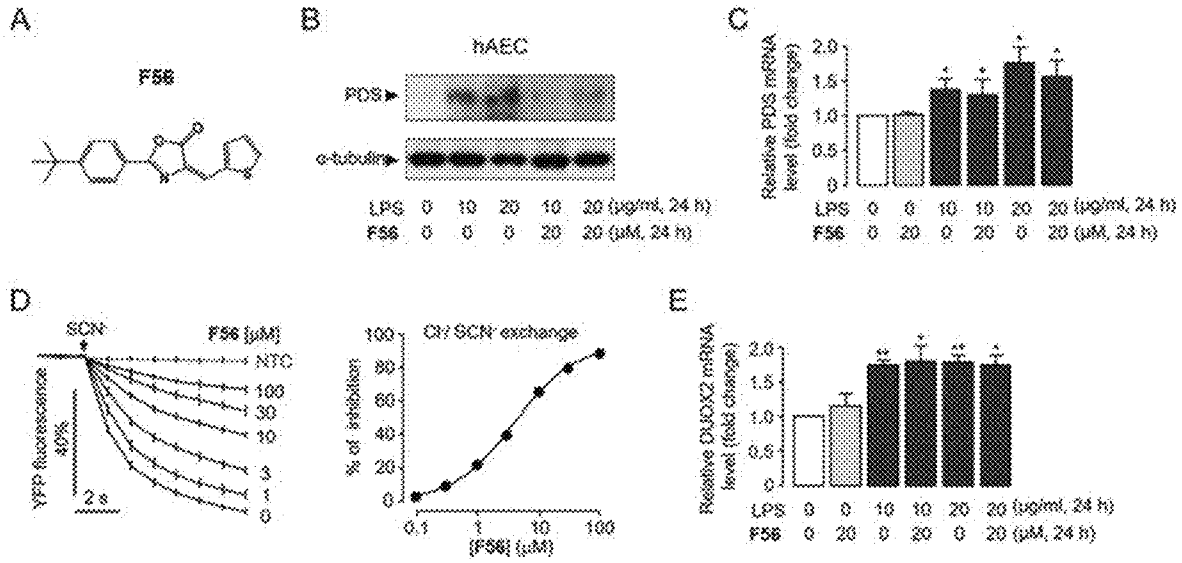
【FIG. 17】
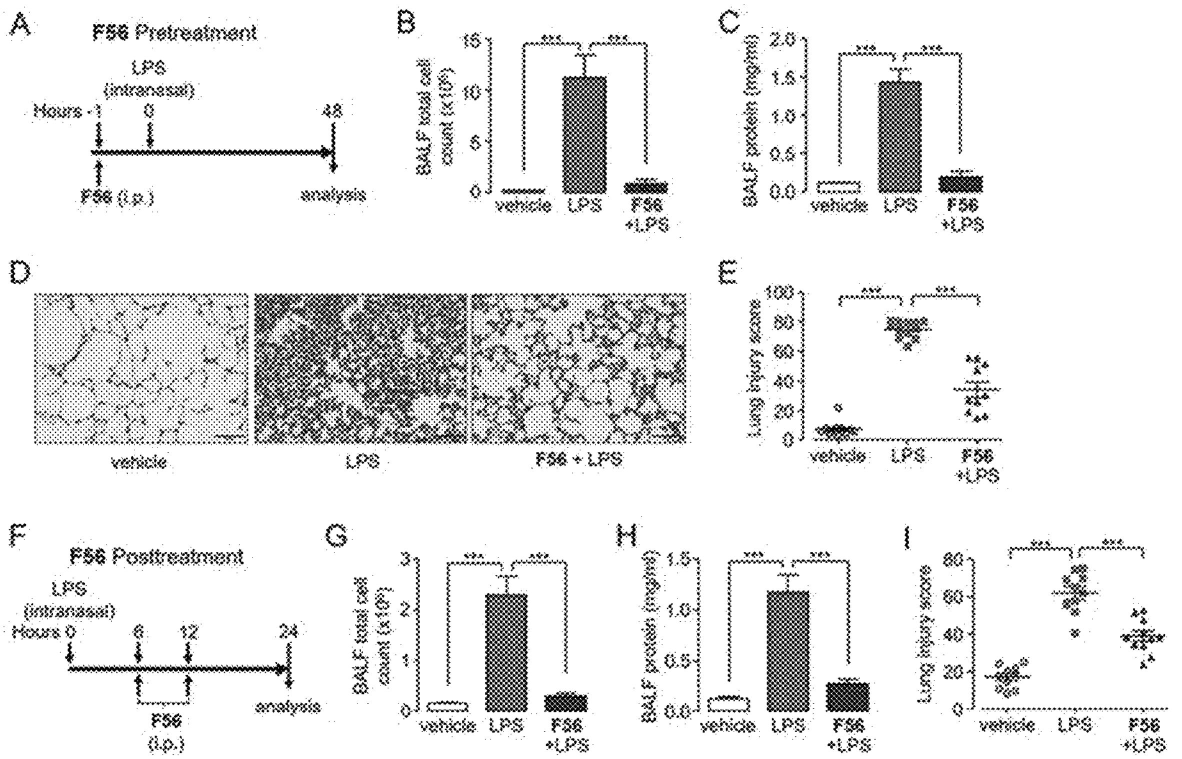

【FIG. 18】
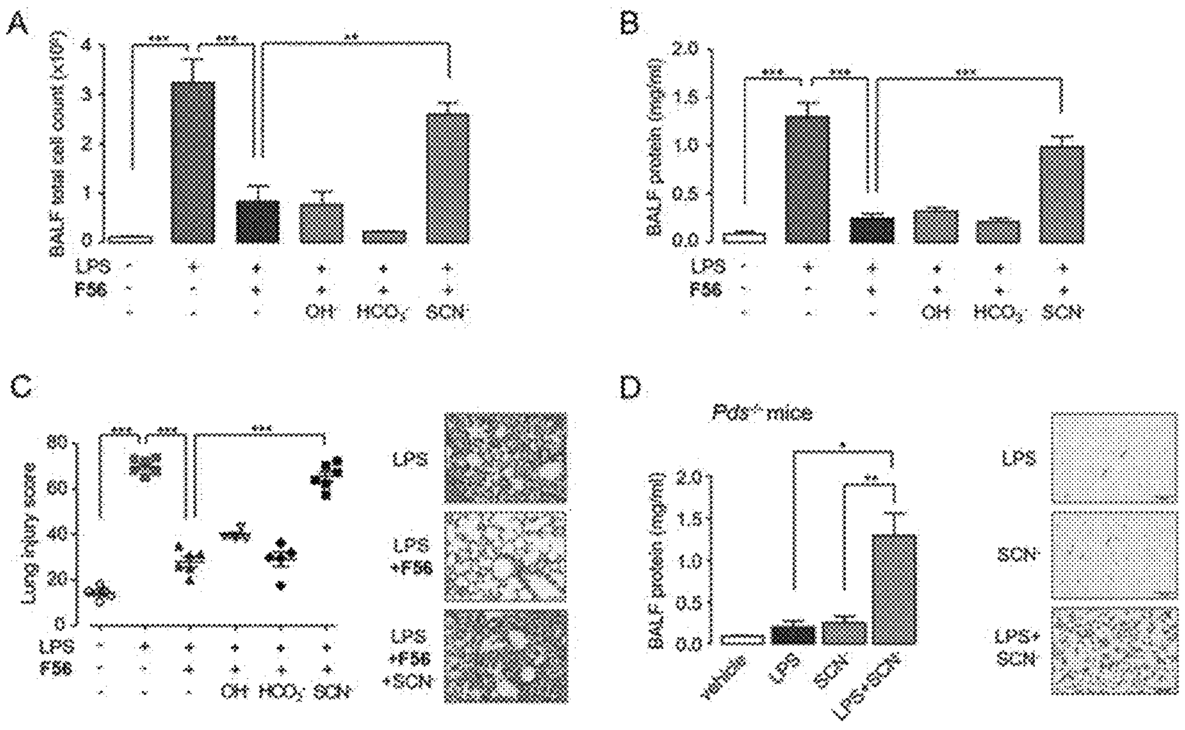

【FIG. 19】
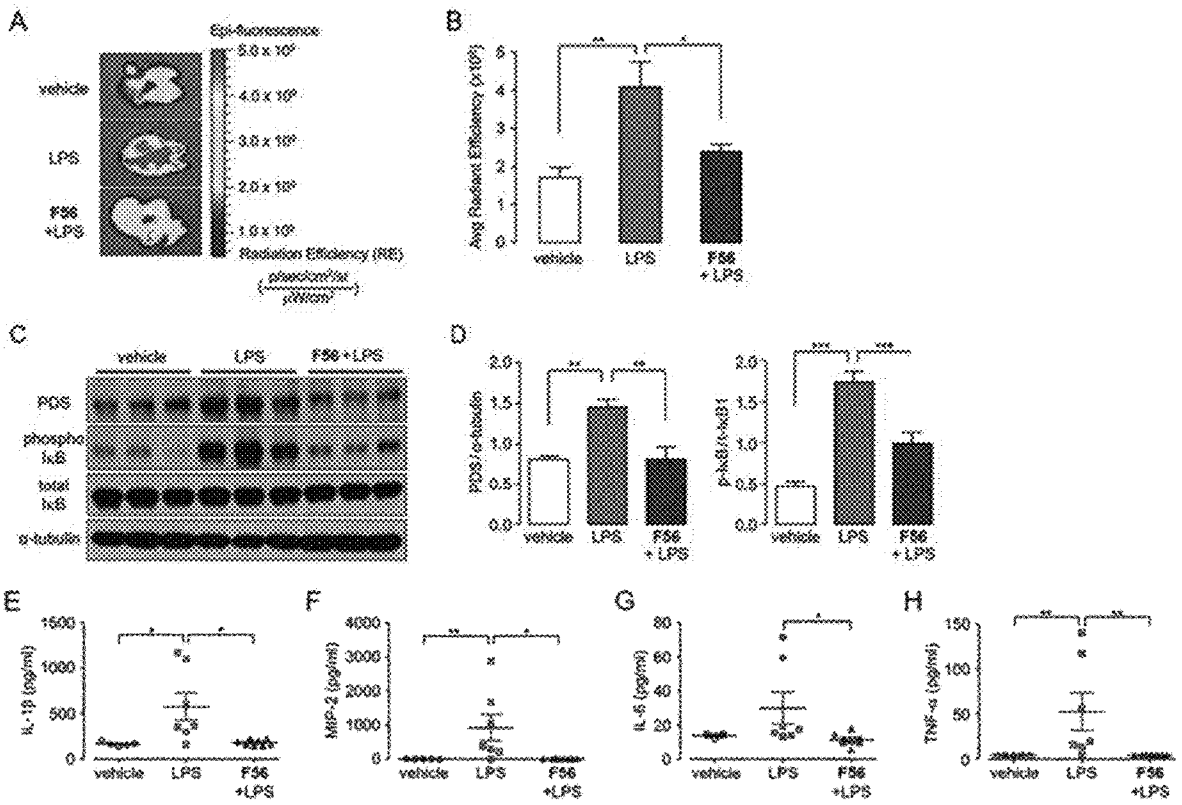
【FIG. 20】
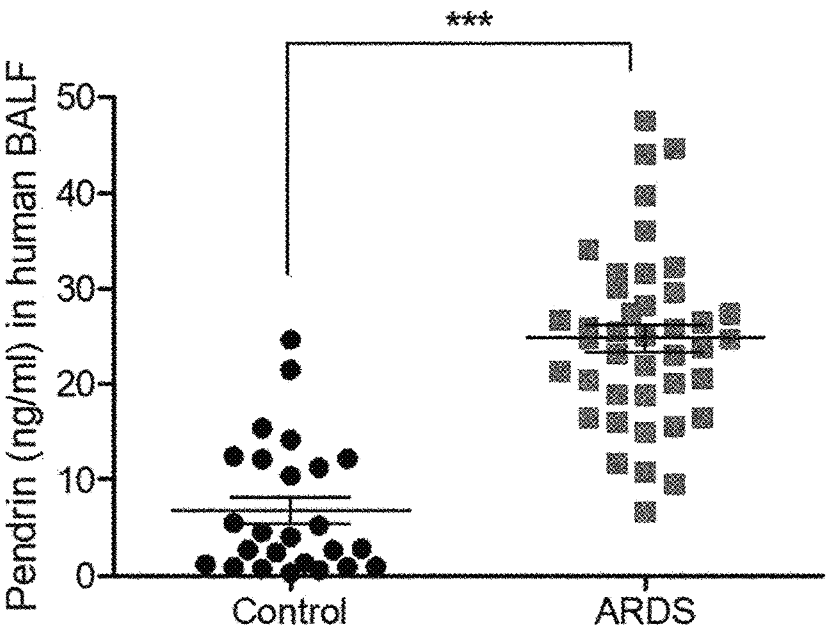

【FIG. 21】
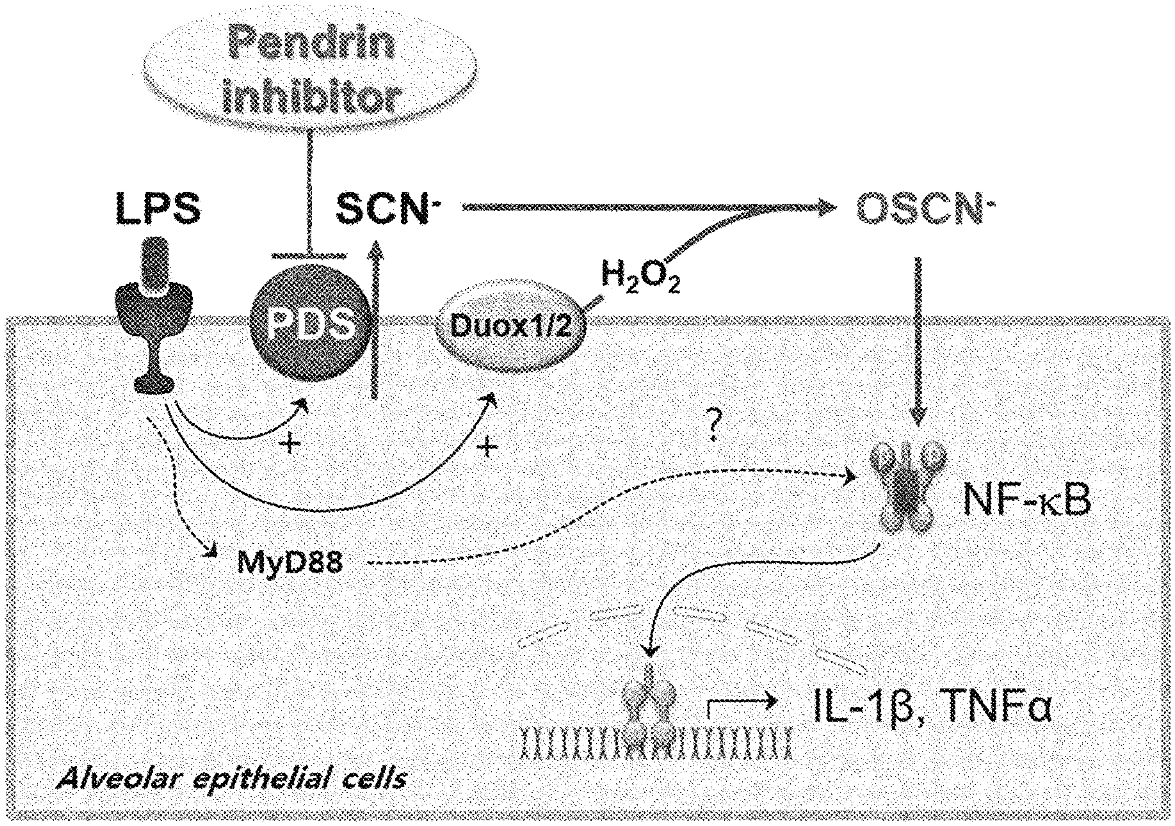

COMPOUND AND METHOD FOR PREVENTING OR TREATING OF RESPIRATORY DISEASES COMPRISING THE SAME AS AN ACTIVE INGREDIENT

TECHNICAL FIELD

The present invention relates to a novel compound and a composition for preventing or treating respiratory disease comprising the same as an active ingredient.

BACKGROUND ART

Pendrin is encoded by SLC26A4 gene, an anion exchanger and a member of SLC26 gene family, and exchanges $Cl^-$ to anions such as $HCO_3^-$, $I^-$, $OH^-$ and $SCN^-$. Pendrin is a cell membrane protein expressed in the luminal membrane of airway epithelial cells. However, pendrin expression is strongly upregulated in inflammatory airway disease such as chronic obstructive pulmonary disease (COPD), allergic rhinitis, asthma, *Bordetella pertussis* infection, acute lung injury (ALI), acute respiratory distress syndrome (ARDS) and common cold caused by rhinovirus, and upregulation of pendrin is observed when they are cultured with IL-4, IL-13 and IL-17A in primary airway epithelial cells. Interestingly, pendrin knockout (KO) improves airway inflammation in all mouse models for COPD, allergic rhinitis, asthma, *Bordetella pertussis* infection and rhinovirus infection. The pathophysiological role of pendrin in airway infection has not been clearly defined. However, a new evidence shows that pendrin is associated with preservation of airway surface liquid (ASL) volume and regulation of mucus production in the inflammatory airway disease.

ASL volume increase in primary mouse tracheal epithelial cell culture by IL-13 was significantly higher in pendrin KO mice compared to the WT mouse control group. IL-13 induced ASL volume increase in primary human nasal epithelial (HNE) cell culture of deaf patients carrying the pendrin mutant (DFNB4) was significantly higher than that of the normal control group. In addition, inhibition of pendrin by a pendrin inhibitor significantly increased IL-13 induced ASL volume in the primary culture of human bronchial epithelial cells. These findings suggest that down-regulation of pendrin may have a beneficial effect on the regulation of ASL volume homeostasis in inflammatory airway disease.

Excessive production of mucus is a common feature of inflammatory airway disease such as asthma and COPD. Pendrin overexpression significantly increased MUC5AC gene expression in human lung cancer line NCI-H292 cells and mouse lung tissue. While IL-3 treatment significantly increased MUC5AC gene expression in HNE cells from a normal subject, IL-13 induced upregulation of MUC5AC was completely abolished in HNE cells from deaf patients carrying a pendrin mutant. These research results suggest that downregulation of pendrin may be beneficial in the treatment of asthma and COPD.

DISCLOSURE

Technical Problem

The present invention is based on the discovery that a certain compound can act as a pendrin inhibitor with the potential to treat respiratory disease. The present invention is based on the discovery that some compounds found through cell-based HTS screening for identification of a small molecule pendrin inhibitor or a novel newly designed compound can provide a potential therapeutic treatment for respiratory disease (inflammatory airway disease) such as asthma, acute or chronic bronchitis, allergic rhinitis, acute respiratory infection, cystic fibrosis, acute respiratory distress syndrome (ARDS), acute lung injury (ALI) or chronic obstructive pulmonary disease (COPD), or the like. The present invention is based on the discovery that some small molecules can show that pendrin down-regulation reduced IL-13 induced up-regulation of MUC5AC gene expression in HNE cells differentiated from a normal subject. In addition, some molecules have been used as a pendrin inhibitor to improve airway inflammation in a mouse model of ovalbumin (OVA) induced allergic asthma.

Technical Solution

In one aspect, the present invention provides a compound represented by the following Chemical formula 1, E- or Z-isomer thereof, optical isomer thereof, a mixture of two isomers thereof, precursor thereof, pharmaceutically acceptable salt thereof or solvate thereof:

[Chemical formula 1]

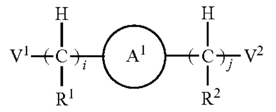

in the Chemical formula 1, $V^1$ and $V^2$ are aryl, heteroaryl, $C_3$~$C_7$ cycloalkyl, heterocycloalkyl, $C_1$~$C_6$ alkyl, $C_1$~$C_6$ heteroalkyl, $C_2$~$C_{10}$ alkenyl, $C_0$~$C^3$ methylenehydrazine, $C_2$~$C_{10}$ alkynyl, $S(O)_i(C_1$~$C_6$ alkyl), $OS(O)_i$(aryl), $S(O)_iNR^3R^4$, $C(O)R^3$, $OR^3$, $OCOR^3$, $NR^3C(O)OR^4$, $NR^3C(O)R^4$, $C(O)NR^3R^4$ or $NR^3R^4$, and one of the aryl, heteroaryl, $C_3$~$C_7$ cycloalkyl, heterocycloalkyl, $C_1$~$C_6$ alkyl, $C_1$~$C_6$ heteroalkyl, $C_2$~$C_{10}$ alkenyl, $C_0$~$C_3$ methylenehydrazine, $C_2$~$C_{10}$ alkynyl, $S(O)_i(C_1$~$C_6$ alkyl), $OS(O)_i$(aryl), $S(O)_iNR^3R^4$, $C(O)R^3$, $OR^3$, $OCOR^3$, $NR^3C(O)OR^4$, $NR^3C(O)R^4$, $C(O)NR^3R^4$ and $NR^3R^4$ is optionally substituted to one or more groups independently selected from hydrogen, oxo, halogen, cyano, azido, nitro, trifluoromethyl, trifluoromethoxy, sulfanyl, aryl, $C_1$~$C_{10}$ alkylaryl, $C_3$~$C_7$ cycloalkyl, heteroaryl, heterocycloalkyl, $C_1$~$C_{10}$ alkyl, $C_2$~$C_{10}$ alkenyl, $C_2$~$C_{10}$ alkynyl, $C_3$~$C_6$ cycloalkyl, $S(O)_i(C_1$~$C_6$ alkyl), $S(O)_iNR^3(C_1$~$C_6$ alkyl), $C(O)OR^3$, $C(O)R^3$, $OR^3$, $OCR^3F_2$, $OCOR^3$, $NR^3C(O)OR^4$, $NR^3C(O)R^4$, $C(O)NR^3R^4$, and $NR^3R^4$, and one of the aryl, $C_1$~$C_{10}$ alkylaryl, $C_3$~$C_7$ cycloalkyl, heteroaryl, heterocycloalkyl, $C_1$~$C_{10}$ alkyl, $C_2$~$C_{10}$ alkenyl, $C_2$~$C_{10}$ alkynyl, $C_3$~$C_6$ cycloalkyl, $S(O)_i(C_1$~$C_6$ alkyl), $S(O)_iNR^3(C_1$~$C_6$ alkyl), $C(O)OR^3$, $C(O)R^3$, $OR^3$, $OCR^3F_2$, $OCOR^3$, $NR^3C(O)OR^4$, $NR^3C(O)R^4$, $C(O)NR^3R^4$ and $NR^3R^4$ is optionally substituted to one or more groups independently selected from hydrogen, oxo, halogen, cyano, azido, nitro, trifluoromethyl, trifluoromethoxy, aryl, $C_1$~$C_{10}$ alkylaryl, arylalkyl, $C_3$~$C_7$ cycloalkyl, heteroaryl, heterocycloalkyl, $C_1$~$C_{10}$ alkyl, $C_2$~$C_{10}$ alkenyl, $C_2$~$C_{10}$ alkynyl, $C_3$~$C_6$ cycloalkyl, $S(O)_i(C_1$~$C_6$ alkyl), $S(O)_i$(aryl), $S(O)_i$(heteroaryl), $S(O)_iNR^3(C_1$~$C_6$ alkyl), $C(O)OR^3$, $C(O)R^3$, $OR^3$, $OCR^3F_2$, $OCOR^3$, $NR^3C(O)OR^4$, $NR^3C(O)R^4$, C(O) $NR^3R^4$ and $NR^3R^4$, and i and j are independently 0, 1 or 2, and $R^1$ and $R^2$ are independently selected from the group consisting of hydrogen, halogen, cyano, azido, nitro, trifluoromethyl, trifluoromethoxy, sulfanyl, aryl, $C_1$~$C_{10}$ alkylaryl, heteroaryl, heterocyclyl, $C_1$~$C_{10}$ alkyl, $C_2$~$C_{10}$ alkenyl, $C_2$~$C_{10}$ alkynyl, $C_3$~$C_6$ cycloalkyl, $S(O)_i(C_1$~$C_6$ alkyl), $C(O)OR^3$, $C(O)R^3$, $OR^3$, $NR^3C(O)OR^4$, $C(O)NR^3R^4$ and $NR^3R^4$, and one of the aryl, heteroaryl, $C_1$~$C_{10}$ alkyl, $C_2$~$C_{10}$ alkenyl, $C_2$~$C_{10}$ alkynyl, $C_3$~$C_6$ cycloalkyl, $S(O)_i(C_1$~$C_6$ alkyl), C(O) $OR^3$, $C(O)R^3$, $OR^3$, $NR^3C(O)OR^4$, $C(O)NR^3R^4$ and $NR^3R^4$ is optionally substituted to one or more groups independently selected from oxo, halogen, cyano, azido, nitro, trifluoromethyl, trifluoromethoxy, aryl, heteroaryl, heterocyclyl, $C_1$~$C_{10}$ alkyl, $C_2$~$C_{10}$ alkenyl, $C_2$~$C_{10}$ alkynyl, $C_3$~$C_6$ cycloalkyl, $S(O)_i(C_1$~$C_6$ alkyl), $C(O)OR^3$, $C(O)R^3$, $OR^3$, $NR^3C(O)OR^4$, $C(O)NR^3R^4$ and $NR^3R^4$, and $R^3$ and $R^4$ are independently selected from the group consisting of hydrogen, cyano, azido, nitro, trifluoromethyl, trifluoromethoxy, sulfanyl, aryl, aryl($C_1$~$C_{10}$ alkyl), $C_1$~$C_{10}$ alkylaryl, heteroaryl, heteroaryl($C_1$~$C_{10}$ alkyl), $C_1$~$C_{10}$ alkylheteroaryl, $C_1$~$C_{10}$ alkyl, $C_2$~$C_6$ alkenyl, $C_2$~$C_6$ alkynyl, $C_3$~$C_6$ cycloalkyl, heterocyclyl and trifluoromethyl, and one of the aryl, aryl ($C_1$~$C_{10}$ alkyl), $C_1$~$C_{10}$ alkylaryl, heteroaryl, heteroaryl($C_1$~$C_{10}$ alkyl), $C_1$~$C_{10}$ alkylheteroaryl, $C_1$~$C_{10}$ alkyl, $C_2$~$C_6$ alkenyl, $C_2$~$C_6$ alkynyl, $C_3$~$C_6$ cycloalkyl and heterocyclyl is optionally substituted to one or more groups independently selected from hydrogen, oxo, halogen, cyano, azido, nitro, trifluoromethyl, trifluoromethoxy, aryl, heteroaryl, heterocyclyl, $C_1$~$C_{10}$ alkyl, $C_2$~$C_{10}$ alkenyl, $C_2$~$C_{10}$ alkynyl, $C_3$~$C_6$ cycloalkyl, $S(O)_i(C_1$~$C_6$ alkyl), $C(O)OR^3$, $C(O)R^3$, $OR^3$, $NR^3C(O)OR^4$, $C(O)NR^3R^4$ and $NR^3R^4$, or $R^3$ and $R^4$ can be cyclized to a 4 to 10 membered carbocyclic, heterocyclic, aromatic or heteroaromatic ring, and one of the carbocyclic, heterocyclic, aromatic or heteroaromatic ring is optionally substituted to one or more groups independently selected from hydrogen, oxo, halogen, cyano, azido, nitro, trifluoromethyl, trifluoromethoxy, aryl, $C_1$~$C_{10}$ alkylaryl, heteroaryl, heterocyclyl, $C_1$~$C_{10}$ alkyl, $C_2$~$C_{10}$ alkenyl, $C_2$~$C_{10}$ alkynyl, $C_3$~$C_6$ cycloalkyl, $S(O)_i(C_1$~$C_6$ alkyl), $C(O)OR^3$, $C(O)R^3$, $OR^3$, $NR^3C(O)OR^4$, $C(O)NR^3R^4$ and $NR^3R^4$, and $A^1$ is represented by

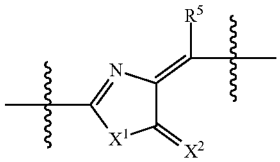

or

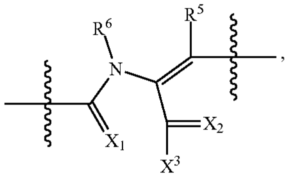

, and $X^1$ and $X^2$ are independently selected from the group consisting of O, S, $CHR^4$ and $NR^4$, and $X^3$ is selected from the group consisting of hydrogen, $OR^3$, aryl, heteroaryl, $C_3$~$C_7$ cycloalkyl, heterocycloalkyl, $C_1$~$C_6$ alkyl, $C_1$~$C_6$ heteroalkyl, $C_2$~$C_{10}$ alkenyl, $C_0$~$C_3$ methylenehydrazine, $C_2$~$C_{10}$ alkynyl, $S(O)_i$ ($C_1$~$C_6$ alkyl), $S(O)_iNR^3$, $C(O)R^3$, $OC(O)R^3$, $(O)COR^3$, $NR^3C(O)OR^3$, $NR^3C(O)R^3$, $C(O)NR^3$ and $NR^3R^4$ and one of the $OR^3$, aryl, heteroaryl, $C_3$~$C_7$ cycloalkyl, heterocycloalkyl, $C_1$~$C_6$ alkyl, $C_1$~$C_6$ heteroalkyl, $C_2$~$C_{10}$ alkenyl, $C_0$~$C_3$ methylenehydrazine, $C_2$~$C_{10}$ alkynyl, $S(O)_i(C_1$~$C_6$ alkyl), $S(O)_iNR^3$, C(O) $R^3$, $OC(O)R^3$, $(O)COR^3$, $NR^3C(O)OR^3$, $NR^3C(O)R^3$, $C(O)NR^3$ and $NR^3R^4$ is optionally selected from the group independently selected from hydrogen, oxo, halogen, cyano, azido, nitro, trifluoromethyl, trifluoromethoxy, sulfanyl, aryl, $C_1$~$C_{10}$ alkylaryl, $C_3$~$C_7$ cycloalkyl, heteroaryl, heterocycloalkyl, $C_1$~$C_{10}$ alkyl, $C_2$~$C_{10}$ alkenyl, $C_2$~$C_{10}$ alkynyl, $C_3$~$C_6$ cycloalkyl, $S(O)_i(C_1$~$C_6$ alkyl), $S(O)_iNR^3(C_1$~$C_6$ alkyl), C(O) $OR^3$, $C(O)R^3$, $OR^3$, $OCR^3F_2$, $OCOR^3$, $NR^3C(O)OR^4$, $NR^3C(O)R^4$, $C(O)NR^3R^4$ and $NR^3R^4$, and one of the aryl, $C_1$~$C_{10}$ alkylaryl, $C_3$~$C_7$ cycloalkyl, heteroaryl, heterocycloalkyl, $C_1$~$C_{10}$ alkyl, $C_2$~$C_{10}$ alkenyl, $C_2$~$C_{10}$ alkynyl, $C_3$~$C_6$ cycloalkyl, $S(O)_i(C_1$~$C_6$ alkyl), $S(O)_iNR^3(C_1$~$C_6$ alkyl), $C(O)OR^3$, $C(O)R^3$, $OR^3$, $OCR^3F_2$, $OCOR^3$, $NR^3C(O)OR^4$, $NR^3C(O)R^4$, C(O) $NR^3R^4$ and $NR^3R^4$ is optionally substituted to one or more groups independently selected from hydrogen, oxo, halogen, cyano, azido, nitro, trifluoromethyl, trifluoromethoxy, sulfanyl, aryl, $C_1$~$C_{10}$ alkylaryl, arylalkyl, $C_3$~$C_7$ cycloalkyl, heteroaryl, heterocycloalkyl, $C_1$~$C_{10}$ alkyl, $C_2$~$C_{10}$ alkenyl, $C_2$~$C_{10}$ alkynyl, $C_3$~$C_6$ cycloalkyl, $S(O)_i(C_1$~$C_6$ alkyl), $S(O)_i$(aryl), $S(O)_i$(heteroaryl), $S(O)_iNR^3(C_1$~$C_6$ alkyl), $C(O)OR^3$, $C(O)R^3$, $OR^3$, $OCR^3F_2$, $OCOR^3$, $NR^3C(O)OR^4$, $NR^3C(O)R^4$, $C(O)NR^3R^4$ and $NR^3R^4$, and $R^5$ and $R^6$ are independently selected from the group consisting of hydrogen, cyano, azido, nitro, trifluoromethyl, trifluoromethoxy, sulfanyl, aryl, $C_1$~$C_{10}$ alkylaryl, heteroaryl, heterocyclyl, $C_1$~$C_{10}$ alkyl, $C_2$~$C_6$ alkenyl, $C_2$~$C_6$ alkynyl, $C_3$~$C_6$ cycloalkyl, heterocyclyl, aryl, heteroaryl and trifluoromethyl, and one of the alkyl, alkenyl, alkynyl, cycloalkyl, heterocyclyl, aryl, $C_1$~$C_{10}$ alkylaryl and heteroaryl regions is optionally selected from one or more groups independently selected from hydrogen, oxo, halogen, cyano, azido, nitro, trifluoromethyl, trifluoromethoxy, aryl, arylalkyl, heteroaryl, heteroarylalkyl, heterocyclyl, $C_1$~$C_{10}$ alkyl, $C_2$~$C_{10}$ alkenyl, $C_2$~$C_{10}$ alkynyl, $C_3$~$C_6$ cycloalkyl, $S(O)_i(C_1$~$C_6$ alkyl), $S(O)_i$(aryl), $S(O)_i$(heteroaryl), $S(O)_iNR^3R^4$, $C(O)OR^3$, $C(O)R^3$, $OR^3$, $NR^3C(O)OR^4$, $C(O)NR^3R^4$ and $NR^3R^4$, and one of the aryl, arylalkyl, heteroaryl, heteroarylalkyl, heterocyclyl, $C_1$~$C_{10}$ alkyl, $C_2$~$C_{10}$ alkenyl, $C_2$~$C_{10}$ alkynyl, $C_3$~$C_6$ cycloalkyl, $S(O)_i(C_1$~$C_6$ alkyl), $S(O)_i$(aryl), $S(O)_i$(heteroaryl), $S(O)_iNR^3R^4$, $C(O)OR^3$, $C(O)R^3$, $OR^3$, $NR^3C(O)OR^4$, $C(O)NR^3R^4$ and $NR^3R^4$ is optionally selected from one or more groups independently selected from hydrogen, oxo, halogen, cyano, azido, nitro, trifluoromethyl, trifluoromethoxy, aryl, arylalkyl, heteroaryl, heteroarylalkyl, heterocyclyl, $C_1$~$C_{10}$ alkyl, $C_2$~$C_{10}$ alkenyl, $C_2$~$C_{10}$ alkynyl, $C_3$~$C_6$ cycloalkyl, $S(O)_i(C_1$~$C_6$ alkyl), $S(O)_i$(aryl), $S(O)_i$(heteroaryl), $S(O)_iNR^3R^4$, $C(O)OR^3$, $C(O)R^3$, $OR^3$, $NR^3C(O)OR^4$, $C(O)NR^3R^4$ and $NR^3R^4$, or $R^5$ and $A^1$ can be cyclized to a 4 to 10 membered carbocyclic, heterocyclic, aromatic or heteroaromatic ring, and one of the carbocyclic, heterocyclic, aromatic or heteroaromatic ring is optionally substituted to one or more groups independently selected from oxo, halogen, cyano, azido, nitro, trifluoromethyl, trifluoromethoxy, aryl, $C_1$~$C_{10}$ alkylaryl, heteroaryl, heterocyclyl, $C_1$~$C_{10}$ alkyl, $C_2$~$C_{10}$ alkenyl, $C_2$~$C_{10}$ alkynyl, $C_3$~$C_6$ cycloalkyl, $S(O)_t(C_1$~$C_6$ alkyl), $C(O)OR^3$, $C(O)R^3$, $OR^3$, $NR^3C(O)OR^4$, $C(O)NR^3R^4$ and $NR^3R^4$.

In another aspect, the present invention provides a pharmaceutical composition for preventing or treating of respiratory disease (inflammatory airway disease), comprising at least one of the compounds, at least one E- or Z-isomer thereof, at least one optical isomer thereof, at least one mixture of two isomers thereof, at least one the precursor thereof, at least one pharmaceutically acceptable salt thereof or at least one solvate thereof as an active ingredient. In some embodiments, the composition may inhibit, prevent, improve or treat respiratory disease (inflammatory airway disease).

In an additional aspect, the present invention provides a composition comprising the compound represented by Chemical formula 1 or mixture thereof, and a composition comprising the compound represented by Chemical formula 1 or mixture thereof with a pharmaceutically acceptable carrier.

In an additional aspect, the present invention provides a use of the compound represented by Chemical formula 1 and pharmaceutical composition thereof, as a pendrin inhibitor.

In an additional aspect, the present invention provides the compound represented by Chemical formula 1 and pharmaceutical composition thereof, which specifically controls a chloride channel.

In an additional aspect, the present invention provides the compound represented by Chemical formula 1 and pharmaceutical composition thereof, which preserves the volume of airway surface liquid (ASL) and reduces separation of mucin.

In an additional aspect, the present invention provides a use for one or more respiratory diseases (inflammatory airway disease) selected from the group consisting of asthma, acute or chronic bronchitis, allergic rhinitis, acute respiratory infection, acute upper respiratory infection, cystic fibrosis, acute respiratory distress syndrome (ARDS), acute lung injury (ALI) and chronic obstructive pulmonary disease (COPD).

In an additional aspect, the present invention provides a use of the compound represented by Chemical formula 1, mixture thereof and pharmaceutical composition thereof, for preventing or improving of respiratory disease (inflammatory airway disease) as an active ingredient in a health functional food.

In an additional aspect, the present invention provides a use of the compound and pharmaceutical composition thereof as a pendrin inhibitor, for preventing or improving of respiratory disease (inflammatory airway disease) as an active ingredient in a health functional food.

In an additional aspect, the present invention provides the compound and pharmaceutical composition thereof, which specifically controls a chloride channel for preventing or improving of respiratory disease (inflammatory airway disease) as an active ingredient in a health functional food.

In an additional aspect, the present invention provides the compound and pharmaceutical composition thereof, which preserves the volume of airway surface liquid (ASL) and reduces separation of mucin, for preventing or improving of respiratory disease (inflammatory airway disease) as an active ingredient in a health functional food.

In an additional aspect, the present invention provides a use for preventing or improving of respiratory disease (inflammatory airway disease) as an active ingredient in a health functional food, and the respiratory disease (inflammatory airway disease) is one or more selected from the group consisting of asthma, acute or chronic bronchitis, allergic rhinitis, acute respiratory infection, acute upper respiratory infection, cystic fibrosis, acute respiratory distress syndrome (ARDS), acute lung injury (ALI) and chronic obstructive pulmonary disease (COPD).

Other aspects and advantages of the present invention will become apparent to those skilled in the art in consideration of the detailed description and drawings.

Advantageous Effects

According to the present invention, the novel compound can act as a pendrin inhibitor, and thus, consequently, it can be usefully used as a composition for preventing, treating or improving of respiratory disease (inflammatory airway disease, particularly, asthma or acute lung injury).

BRIEF DESCRIPTION OF THE DRAWINGS

FIG. 1 shows the principle of cell-based high throughput screening and its result.

FIG. 2 shows YFP fluorescence tracing showing an example of the inhibitory effect of F56 on $Cl^-/I^-$ exchange activity of pendrin in CHO-K1-YFP cells stably expressing human pendrin.

FIG. 3 shows inhibition of the pendrin-mediated $Cl^-/HCO_3^-$ exchange activity by F56. The application of a high concentration of $Cl^-$ induced intracellular pH reduction through pendrin-mediated $Cl^-/HCO_3^-$ exchange, and resulted in reduction of YFP fluorescence. The indicated concentration of the pendrin inhibitor was pretreated for 10 minutes.

FIG. 4(*a*) shows the summary of F56 dose-response for inhibition of the pendrin-mediated $Cl^-/I^-$ and $Cl^-/HCO_3^-$ exchange activity (mean±S.E., n=4-5).

FIG. 4(*b*) shows the summary of F10 dose-response for inhibition of the pendrin-mediated $Cl^-/I^-$, $Cl^-/SCN^-$, $Cl^-/HCO_3^-$ and $Cl^-/OH^-$ exchange activity (mean±S.E., n=3).

FIG. 5(*a*) shows that a novel pendrin inhibitor, F56 blocks a pendrin-mediated cell response in IL-4-stimulated HNE cells. (A) Chemical structure of F56. (B) Inhibitory effect of F56 for pendrin-mediated $Cl^-/SCN^-$ exchange activity (mean±S.E., n=5). (C) F56 dose-response for inhibition of pendrin-mediated $Cl^-/I^-$, $Cl^-/SCN^-$, $Cl^-/HCO_3^-$, and $Cl^-/OH^-$ exchange activity (mean±SE, n=4-5). (D) Representative protein expression result of pendrin (PDS) in untreated and IL-4-treated HNE cells. (E) Pendrin-mediated $Cl^-/HCO_3^-$ exchange in IL-4-treated HNE cells. (F) Initial rate of change at $\Delta pH_i$/min (mean±S.E., n=3-4). (G) $Cl^-/HCO_3^-$ exchange activity after exposure to F56 in IL-4-treated HNE cells. (H) Representative protein expression result to pendrin and AN01 in IL-4-treated HNE cells (mean±S.E., n=5). (I) PDS mRNA expression level is determined by real-time PCR in IL-4-treated HNE cells (mean±S.E., n=5). * $P<0.05$,  $P<0.01$, * $P<0.001$. NTC, non-transfected cells.

FIG. 5(*b*) shows the effect of F10 on the mRNA expression level of PDS. The PDS mRNA expression level is determined in 120 hours after F10 treatment by real-time quantitative PCR in IL-4-treated HNE cells.

FIG. 6(*a*) shows the pendrin-mediated $Cl^-$/base exchange activity in CHO-K1 cells expressing human pendrin. (A) Pendrin-mediated $Cl^-/I^-$ exchange activity (mean±S.E., n=5). The indicated concentration of F56 was pretreated for 10 minutes. (B, C) Representative tracing of intracellular pH. The application of $Cl^-$ free solution induced intracellular alkalization through pendrin-mediated $Cl^-/HCO_3^-$ and $Cl^-/OH^-$ exchange activity. The indicated concentration of F56 was pretreated for 10 minutes. (D-F) The pendrin-mediated $Cl^-/I^-$ exchange activity was measured in CHO-K1 cells expressing human pendrin. The indicated concentration of F56, $PDS_{inh}$-A01 and $PDS_{inh}$-C01 was pretreated for 10 minutes. (G) Summary of dose-response of F56, $PDS_{inh}$-A01 and $PDS_{inh}$-C01 (mean±S.E., n=3). (H, I) Effect of F56, $PDS_{inh}$-A01 and $PDS_{inh}$-C01 on the cell viability in NIH3T3 (H) and CHO-K1 (I) cells. The cells were treated with F56, $PDS_{inh}$-A01 and $PDS_{inh}$-C01 for 24 hours. The cell viability was measured by MTS colorimetric analysis (mean±S.E., n=3). NTC, non-transfected cells.

FIG. 6(*b*) shows the effect of F10 on the cell viability in NIH3T3 and CHO-K1 cells. The cells were treated with F10 for 24 hours. The cell viability was determined by MTS colorimetric analysis (mean±S.E., n=3).

FIG. 7(*a*) shows the characteristic of F56. (A) The inhibition of mouse pendrin (mPDS)-mediated $Cl^-/I^-$ exchange activity by F56 was measured in CHO-K1 cells (mean±S.E., n=5). The indicated concentration of F56 was pretreated for 10 minutes. (B) Summary of dose-response for inhibition of the human pendrin (hPDS)-mediated (closed circle, FIG. (a), C) and mPDS-mediated (open circle) $Cl^-/I^-$ exchange activity. (C-F) Representative traces of intracellular pH in CHO-K1 cells expressing SLC26A3, SLC26A6, SLC26A7 and SLC26A9 were shown. The application of $Cl^-$ free solution induced intracellular alkalization by $Cl^-/HCO_3^-$ exchange. The indicated concentration of F56 was pretreated for 10 minutes. (G) the effect of F56 (100 μM) on the CFTR chloride channel activity was measured in FRT cells expressing human CFTR. The CFTR current was activated by 20 μM forskolin and was inhibited by 10 μM $CFTR_{inh}$-172. (H) The effect of F56 (100 μM) on the AN01 chloride channel activity was measured in FRT cells expressing human AN01. Before 10 minutes prior to AN01 activation by 100 μM ATP, F56 was added. (Right) Peak current summary (mean±S.E., n=3). (I) The effect of F56 on the hERG (Kv11.1) potassium channel activity was measured in HEK293T cells expressing human Kv11.1 (mean±S.E., n=4). The indicated concentration of F56 was pretreated for 10 minutes. The hERG channel was inhibited by 50 μM cisapride. (J) The effect of F56 on the 5-$HT_{2A}$ channel activity was measured in FRT cells expressing human 5-$HT_{2A}$ (mean±S.E., n=4). The indicated concentration of F56 was pretreated for 10 minutes. The 5-$HT_{2A}$ channel was activated by 10 μM 5-HT and was inhibited by 10 μM ketanserin. *** P<0.001. NTC, non-transfected cells.

FIG. 7(*b*) shows the effect of F10 on the channel activity of CFTR, AN01 and hERG. (A) The effect of F10 (30 μM) on the CFTR channel was measured in FRT cells expressing human CFTR and mutant YFP. CFTR was activated by 20 μM forskolin and was inhibited by 10 μM $CFTR_{inh}$-172. (B) The effect of F10 (30 μM) on the AN01 channel activity was measured in FRT cells expressing human and mutant YFP. AN01 was activated by 100 μM ATP and was inhibited by 10 μM $T16A_{inh}$-A01. (C) The effect of F10 (30 μM) on the hERG (Kv11.1) potassium channel activity was measured in HEK293T cells expressing human Kv11.1 (mean±S.E., n=4). The hERG channel was inhibited by 50 μM cisapride.

FIG. 8(*a*) shows the effect of F56 on the pendrin and other ion channels in HNE cells. (A) Representative tracing of intracellular pH of treated (grey line) and IL-4 (10 ng/ml) treated HNE cells. Pendrin was inhibited by F56 (50 mM). (B) The mRNA expression level of pendrin was determined at the indicated time after treatment of F56 (30 mM) by real-time quantitative PCR in IL-4-treated HBE cells (mean±S.E., n=3). (C) The $Cl^-/HCO_3^-$ exchange activity was measured in IL-4-treated HBE cells. F56 was pretreated for 5 minutes. (D, E) Short circuit current record of HNE cells. Representative tracing showing the effect of F56 on the ENaC, CFTR and CaCC channel activity. After exposing to F56 (30 mM) for 48 hours, in presence or absence of IL-4, the channel activity was measured. Amiloride (100 μM), forskolin (20 μM, $CFTR_{inh}$-172 (10 μM) and ATP (100 μM) were added to the apical bath. (F) The AN01, CFTR and ENaC mRNA expression level was determined at the indicated time after treatment of F56 (30 mM) by real-time quantitative PCR in IL-4-treated HNE cells (mean±S.E., n=5) * P<0.05,  P<0.01, * P<0.001.

FIG. 8(*b*) shows the effect of F10 on the mRNA expression level of AN01, CFTR and ENaC. The AN01, CFTR and ENaC mRNA expression level was determined in 120 hours after treatment of F10 by real-time quantitative PCR in IL-4-treated HNE cells.

FIG. 9(*a*) shows that F56 improves airway inflammation through inhibition of pendrine/SCN-/NF-kB pathway in a mouse model of OVA-induced allergic asthma. (A) Airway resistance of animals sensitized and challenged with OVA. (B) Effect of IL-4 and F56 on SCN—-transport in HNE cells (mean±S.E., n=5). (C) Duox1 and Duox2 levels measured by real-time PCR after F56 treatment in IL-4-treated HNE cells (mean±S.E., n=3). (D) Protein expression level results for HNE cells treated with IL-4 in the presence or absence of F56. (Right) Comparison of phospho-p65 relative protein amounts (mean±S.E., n=3). (E) Airway resistance to methacholine challenge in OVA-sensitized mice (mean±S.E., n=3-4). (F) Representative PAS staining of airway tissue. Size bar, 100 μm. *P<0.05, **P<0.01.

FIG. 9(*b*) shows the effect of F10 on the airway resistance in animals sensitized and challenged with OVA.

FIG. 10 shows the improvement of allergic airway inflammation by F56 in an asthma mouse model. (A) Protocol of induction of allergic airway inflammation solution after allergen challenge in a wild-type mouse and time course. (B) Inflammatory cells of broncho-alveolar lavage fluid (BALF) were isolated by centrifugation and were stained with Diff-Quik staining reagent. The number of cells was quantified with an optical microscope (mean±S.E., n=10). (C) Representative histology of the airway stained with hematoxylin and eosin. Size bar, 100 μm. (D) Periodic acid-Schiff (PAS) staining of the airway part from the vehicle-treated, OVA-sensitized/challenged and F56 (10 mg/kg)-treated OVA-sensitized/challenged mice. Size bar, 50 μm. (E) Summary of the inflammatory score (mean±S.E., n=4). (F) OVA-specific IgE level in serum (mean±S.E., n=4). (G) The NF-kB expression was compared using IVIS system in the lung of NF-kB reporter mice. The lung was isolated from mice and fluorescence images (Ex 570, Em 620) were performed using IVIS spectra. The average fluorescence density of the images was analyzed using Image 4.3.1 software. * P<0.05.

FIG. 11 shows the improvement of allergic asthma by F56 in an established model of allergic asthma. (A) Protocol of induction of allergic airway inflammation solution after allergen antigen challenge in a wild-type mouse and time course. F56 (10 mg/kg three times/day) was applied after tertiary OVA challenge. (B) Airway reactivity measured by whole body plethysmography in an OVA-induced asthma model. Penh was measured in response to an increased dose of methacholine (mean±S.E., n=4). (C) Representative PAS staining of airway tissue. Size bar, 100 μm. (D) Summary of PAS positive cells (mean±S.E., n=4). * P<0.05.

FIG. 12(*a*) shows the effect of F56 on the mucous membrane production and ASL volume control in IL-4-treated HNE cells. (A) The MUC5AC mRNA expression level was determined at the indicated time after treatment of F56 (30 mM) in IL-4 (10 ng/ml)-treated HNE cells (mean±S.E., n=4). (B) Periodic acid-Schiff (PAS) staining showing goblet cell hyperplasia of IL-4 and IL-13 (10 ng/ml)-treated HNE cells in presence or absence of F56 (30 M) at Day 7. (C) Measurement of the total volume of ASL and fluid meniscus in HNE cells expressing wild-type (wt) or mutant (mt) PDS. The HNE cells were treated with IL-4 (10 ng/ml, 48 hours) in presence or absence of 30 mM F56 (mean±S.E., n=3-4). (D) Representative image of a transwell insert having normal HNE cells. Arrows indicate the fluid meniscus of HNE cells treated with IL-4 (10 ng/ml, 48 hours) in presence or absence of 30 mM F56. (E) Representative protein expression result of pendrin in IL-4 and IL-13-treated HNE cells. (F) Measurement of the total volume of ASL and fluid meniscus. The HNE cells were treated with IL-13 (10 ng/ml, 48 hours) in presence or absence of 30 mM F56 (mean±S.E., n=3-4). * P<0.05, *** P<0.001. Size bar, 30 μm.

FIG. 12(*b*) shows the effect of F10 on the mRNA expression level of MUC5AC. The MUC5AC mRNA expression level was determined in 120 hours after F10 treatment by real-time quantitative PCR in IL-4-treated HNE cells.

FIG. 13 shows the effect of F56 on the hearing threshold and plasma thyroid hormone value. (A) Representative example of ABR waveform from the control group and F56 (10 mg/kg/yl for 7 days)-treated mice. (B) Summary of the hearing threshold (mean±S.E., n=8-10). (C) The serum level of T3 and T4 was measured in F56 (10 mg/kg/yl for 7 days)-treated and non-treated mice (mean±S.E., n=4). (D) Representative force tracing showing airway smooth muscle (ASM) contraction response in a rat tracheal ring. F56 (30 mM) was applied after induction of ASM contraction by carbachol (CCh) at a submaximal concentration (300 nM). ASM relaxation was induced by forskolin and IBMX.

FIG. 14 is a schematic diagram showing a possible role of a pendrin inhibitor in airway inflammation. The pendrin inhibitor may reduce NF-kB activation by blocking $SCN^-$ transport in the airway epithelium and enhance the mucous membrane removal by inhibiting upregulated pendrin-mediated ASL deficiency in the airway inflammation.

FIG. 15 shows that pendrin deficiency weakens LPS-induced lung injury in mice. LPS (10 mg/kg) or a vehicle (PBS) was intranasally administered to wild-type (WT) and pendrin-null ($Pds^{-/-}$) mice. (A) The total number of broncho-alveolar lavage (BAL) cells and BAL protein concentration were analyzed in 48 hours after LPS or PBS administration in WT mice. (B) Representative image of H&E staining of lung tissue in 48 hours after LPS or PBS administration (x400), size bar: 50 μm. (C) The total number of BAL cells and BAL protein concentration were analyzed in 48 hours after LPS or PBS administration. (D) Representative image of H&E staining of lung tissue in 48 hours after LPS or PBS administration (x400), size bar: 50 μm. (E) The mouse body weight changes. (F) Representative protein expression result of pendrin in lung lysates of LPS non-treated and treated WT mice. The provided data were analyzed by Student's unpaired two-tailed t test, mean±SEM (n=6-8 mice per group), * P<0.05,  P<0.01, * P<0.001.

FIG. 16 shows that a novel pendrin inhibitor (F56) blocked the pendrin activity in human alveolar epithelial cells. (A) Chemical structure of pendrin inhibitor F56. (B) Representative protein expression result of pendrin (PDS) in human alveolar epithelial cells (hAEC). (C) The PDS mRNA level was measured by real-time quantitative PCR in hAEC (mean±S.E., n=3). (D) Inhibitory effect of F56 on the human wild-type pendrin-mediated $Cl^-/SCN^-$ exchange activity in hAEC expressing human pendrin (mean±S.E., n=10). The indicated concentration of F56 was pretreated for 10 minutes. (Right) Summary of dose-response. (E) The DUOX2 mRNA level was measured by real-time quantitative PCR (mean±S.E., n=3~4). * P<0.05, ** P<0.01 vs control group. Student's unpaired two-tailed t test.

FIG. 17 shows that F56 inhibited an LPS-induced acute lung injury phenotype in mice. (A) F56 (10 mg/kg) was intraperitoneally injected before 1 hour prior to LPS treatment. (B) BALF total cell number. (C) BALF protein concentration. (D) Representative image of H&E ling tissue staining (×400), size bar: 50 μm. (E) Lung injury score. (F) F56 (10 mg/kg) was intraperitoneally injected at 6 hours and 12 hours after LPS inhalation. (G) BALF total cell number. (H) BALF protein concentration. (I) Lung injury score. The provided data were analyzed by one-way ANOVA with Bonferroni's post hoc test, mean±SEM (n=10-12 mice per group), ***P<0.001.

FIG. 18 shows the $SCN^-$-triggered LPS-induced lung injury in presence of F56 or pendrin null mice. (A) BALF total cell number. LPS (10 mg/kg, in), F56 (10 mg/kg, ip), NaOH (100 mM, in), $NaHCO_3$ (100 mM, in) and NaSCN (100 mM, in) were treated to WT mice. (B) BALF protein concentration. (C) Lung injury score. (Right) Representative lung tissue stained with H&E (×400), size bar: 50 μm. (D) BALF protein concentration in pendrin-null mice. NaSCN (100 mM, i.n.) was applied to LPS-treated pendrin-null mice. (Right) Representative mouse BALF cytospin stained with Diff-Quik staining. Inflammatory cells, particularly, neutrocytes (red arrow) were increased after LPS+NaSCN exposure compared to LPS or NaSCN alone. The black arrow indicates macrophages (×200), size bar: 100 μm. The provided data were analyzed by one-way ANOVA with Bonferroni's post hoc test, mean±SEM (n=5-6 mice per group), * P<0.05,  P<0.01, * P<0.001.

FIG. 19 shows that F56 blocked the NF-κ route in LPS-induced acute lung injury and reduced the level of pro-inflammatory cytokine. (A) Representative image of lung of NF-κ/SPC-Cre mice which is exposed to LPS (10 mg/kg) and is treated with F56 (10 mg/kg) or a vehicle. IVIS image fluorescence is represented by radiant efficiency. (B) The average fluorescence was quantified by analysis of interested regions using Living Image software. The provided data were mean±SEM (n=9-10 mice per group). (C) Representative protein expression result in lung lysates. (D) The relative protein level was measured by density measurement for pendrin and phospho-I κ. (mean±SEM, n=6 per group), (E-H) The IL-1β CXCL2/MIP-2, IL-6 and TNF-α level was measured by ELISA in lung tissue lysates. The provided data were analyzed by one-way ANOVA with Bonferroni's post hoc test, mean±SEM (n=7-8 mice per group), * P<0.05,  P<0.01,  P<0.001.

FIG. 20 shows the pendrin level of human BALF. ARDS patients due to pneumonia showed the increased pendrin value compared to the control patients (uninfected). The pendrin level was measured from human BALF supernatant by ELISA (control group n=25, ARDS n=41). Analyzed by Student's unpaired two-tailed t test, * $P<0.05$,  $P<0.01$, * $P<0.001$.

FIG. 21 shows a schematic diagram for a role of pendrin and its inhibitor in LPS-induced lung injury. $SCN^-$ is actively transported from the apical surface of the alveolar epithelium to the lung lumen by pendrin. $SCN^-$ is catalyzed to $OSCN^-$ by peroxidase with $H_2O_2$. The resulting $OSCN^-$ activates NF-κ and induces inflammatory cytokine release, neutrophil infiltration and subsequent lung injury. The pendrin inhibitor, F56 blocks transepithelial transport of $SCN^-$ which inhibits $OSCN^-$-induced NF-κ activation and subsequent onset of ALI.

BEST MODE

1. Definition

Unless defined otherwise, all technical and scientific terms used herein have the meaning commonly understood by those skilled in the art to which this disclosure belongs. The following references provide those skilled in the art with general definitions of many of the terms used herein: The Cambridge Dictionary of Science and Technology (Walker ed., 1988); The Glossary of Genetics, 5th Ed., R. Rieger et. al. (eds.), Springer Verlag (1991); and Hale & Marham, The Harper Collins Dictionary of Biology (1991). As used herein, the following terms have the meanings mentioned below, unless specified otherwise.

Unless specifically stated or clear from the context, the term used herein "or" is understood as inclusive.

Unless specifically stated or clear from the context, the term used herein "about" is understood within the general acceptance range of the art, for example, within two standard deviations of the mean. About may be understood to be within 10%, 9%, 8%, 7%, 6%, 5%, 4%, 3%, 2%, 1%, 0.5%, 0.1%, 0.05% or 0.01% of the stated value. Unless otherwise clear from the context, all numerical values provided herein are modified by the term about.

The terms "activator, "drug" and "pharmaceutical formulation" are interchangeably used herein to refer to a chemical material or compound which induces a desired pharmacological effect (for example, such as reduction of inflammation) when administered to a subject by any means described herein (for example, any animal including a human or non-human animal).

"Additive" used herein may refer to any additional ingredient which can be added to the composition and chemical formula described herein. For example, providing that the additional ingredient is pharmaceutically acceptable for a particular condition being treated, the additive may include an excipient (for example, one or more excipients), an anti-oxidant (for example, one or more anti-oxidants), a stabilizer (for example, one or more stabilizers), a preservative (for example, one or more preservatives), a pH adjusting agent and/or buffers (for example, one or more pH adjusting agents and/or buffers), an isotonic adjusting agent (for example, one or more isotonic adjusting agents), a thickener (for example, one or more thickeners), a suspending agent (for example, one or more suspending agents), a binding agent (for example, one or more binding agents), a viscosity increasing agent (for example, one or more viscosity increasing agents), and the like. In addition, the additive may comprise a treatment agent and a drug delivery modifier, and an enhancer such as calcium phosphate, magnesium stearate, talc, monosaccharides, disaccharides, starch, gelatin, cellulose, methyl cellulose, sodium carboxymethyl cellulose, dextrose, hydroxypropyl-beta-cyclodextrin, polyvinylpyrrolidone, low melting point wax and ion exchange resin, and a combination of any two or more thereof. Other appropriate pharmaceutically acceptable excipients are described in "Remington's Pharmaceutical Sciences" Mack Pub. Co., New Jersey (1991), and "Remington: The Science and Practice of Pharmacy", Lippincott Williams & Wilkins, Philadelphia, 20th edition (2003) and 21st edition (2005), incorporated herein as a reference. The additive described herein may be used as any appropriate drug.

The term used herein "administration" means oral administration, suppository, topical contact intravenous, parenteral, intraperitoneal, intramuscular, intralesional, intrathecal, intranasal, intravitreal or subcutaneous administration, or a sustained release device such as implantation of a small-osmotic pump to a subject. The administration is administered by any route including parenteral and transmucosal (for example, oral, intranasal, intrapulmonary, intrarectal, intrabuccal, intravaginal, intraocular and dermal) routes.

"Analogue" and "derivative" are interchangeably used herein, and refer to a compound that has the same core as the parent compound, but differ from the parent compound in the order of bonding, in the absence or presence of one or more atoms and/or groups of atoms, and combinations thereof. The derivative may differ from the parent compound in one or more substituents present on the core which may comprise for example, one or more atoms, functional groups or substructures. In addition, the derivative may differ from the parent compound in the order of boning between atoms in the core. In general, the derivative may be at least theoretically, predicted to be formed from the parent compound through a chemical and/or physical process.

"Anti-oxidant" used herein may refer to an artificial or natural substance capable of preventing or delaying a certain type of damage and/or oxidation. The anti-oxidants are found in many foods including fruits and vegetables. In addition, they can be used as a dietary supplement. Exemplary anti-oxidants may include β-carotene, lutein, lycopene, selenium, vitamin A, vitamin C and vitamin E. Furthermore, other anti-oxidants known to those skilled in the art may be used. The anti-oxidant described herein may be used in an any appropriate amount.

"Co-administration" means that a compound or composition described herein is administered simultaneously immediately prior to or immediately following administration of an additional treatment or activator or additive described herein. The compound or composition of the present disclosure may be administered alone or co-administered to a patient. Co-administration is construed to include administration of the compounds individually or in combination (one or more compounds or agents) simultaneously or sequentially. If desired, agents may also be combined with other active substances.

In the present disclosure, comprise, "comprising", "containing" and "having" and the like may have the meaning belonging to them and may mean "include", "including" and the like; and "consisting essentially of" or "consist essentially of" may likewise have the meaning pertaining to them, and the terms are open-ended and permits the existence of more than the recited, unless the basic or novel features of the recited are altered by the existence of more than the recited, but prior art examples are excluded.

"Simultaneous administration" used herein includes at least in part, overlap of duration. For example, when two agents (for example, any agent or class of agents described herein having bioactivity) are administered simultaneously, their administration occurs within a certain desired time period. Administration of formulations may start and end on the same day. In addition, administration of one formulation may precede administration of a second formulation as long as the two agents are taken at least once on the same day. Similarly, administration of one formulation may be extended beyond administration of a second formulation as long as two formulations are taken at least once on the same day. To include simultaneous administration of a bioactive agent/a formulation, it is not necessary to take them at the same time each day.

"Effective amount" or "therapeutically effective amount" used herein is an amount sufficient to affect a desired biological effect such as a beneficial result including a clinical result. Thus, "effective amount" depends on the circumstances in which it is applied. An effective amount may vary depending on factors known in the art, such as the disease state, age, gender and body weight of an individual being treated. Several divided doses may be administered daily or the dose may be proportionally reduced as indicated by urgency of the therapeutic situation. In addition, the composition/formulation of the present disclosure may be administered as often as necessary to achieve a therapeutic amount.

The term used herein "gel" may refer to a material that is not readily flowable liquid and is not a solid, i.e., semi-solid. The gel may be formed from a natural or synthetic substance. The gel is not aligned and is slightly aligned, exhibiting birefringent, liquid crystal properties. The gel may be administered topically.

The term used herein "respiratory disease" has a common medical meaning and includes asthma, acute or chronic bronchitis, allergic rhinitis, acute upper respiratory infection, cystic fibrosis, acute respiratory distress syndrome (ARDS), acute lung injury (ALI) or chronic obstructive pulmonary disease (COPD) and diseases and disorders closely related to the respiratory system, but not limited thereto.

The term used herein "inhibition" means prevention, reduction, slowdown or stop. In one embodiment, when an amount or rate of a process or response occurring in the presence of a compound or composition is reduced by at least about 10%, compared with an amount or rate in the absence of the compound or composition, it is considered that the composition or compound inhibits the viability of at least one protein (for example, pendrin). In another embodiment, when an amount or rate of a process or response occurring in the presence of a compound or composition is reduced by at least about 20%, compared with an amount or rate in the absence of the compound or composition, it is considered that the composition or compound inhibits the process or response. In other embodiment, when an amount or rate of a process or response occurring in the presence of a compound or composition is reduced by about 25% or more, about 30%, about 40%, about 50%, about 60%, about 70%, about 75% or about 80%, compared with an amount or rate in the absence of the compound or composition, it is considered that the composition or compound inhibits one or more proteins (for example, pendrin). In other embodiment, it is considered that the compound or composition inhibits the viability of one or more proteins, i.e., blocks their development.

"Intermittent administration" used herein includes a period during which a formulation is administered (this may be considered a "first administration period"), a subsequent period during which a formulation is not ingested or is ingested in a lower dose (this may be considered an "off-period"), and a subsequent period during which a formulation is administered again (this may be considered an "second administration period). In general, during the second administration period, the dose level of the formulation is consistent with that administered during the first administration period, but it may be increased or decreased as medically necessary.

"Jelly" according to the present disclosure is composed of a gel, which is a semi-solid system composed of a suspension consisting of either small inorganic particles or large organic molecules infiltrated by a portion of liquid with high structurally cohesive matrix, generally, liquid containing water.

"Liquid" used herein is an administration form consisting of a composition in a liquid state. Liquid may be spilled; and it flows and behaves in a container at a room temperature. Liquid exhibits Newton or pseudoplastic flow behavior.

In an embodiment, "semi-liquid" used herein may have the properties of both liquids and other formulation (i.e., suspension, emulsion, solution, cream, gel, jelly, etc.).

The term used herein "Ointment" may refer to a highly viscous liquid or semi-liquid formulation that may be used in the therapeutic treatment of a disease, syndrome or condition.

"Pharmaceutically acceptable carrier" used herein includes physiologically appropriate any and all solvents, dispersive media, coating, anti-microbial and anti-fungal agents, isotonic and absorption retardants, and the like. The type of the carrier may be selected on the basis of the intended administration route. The pharmaceutically acceptable carrier includes a sterile aqueous solution or dispersion and sterile powder for instant preparation of a sterile local solution or dispersion. The use of such media and agents for pharmaceutically active substances is well known in the art. As long as any conventional medium or agent is incompatible with the composition (for example, Chemical formula 1 described herein, a derivative or analogue of Chemical formula 1, or pharmaceutically acceptable salt, solvent, hydrate or polymorph thereof), its use is considered in the composition for the present disclosure.

"Pharmaceutical carrier" or "carrier" used herein may further include a pharmaceutically acceptable carrier, excipient or stabilizer which is non-toxic to cells or mammals in an adopted dose and concentration. The physiologically acceptable carrier is often an aqueous pH buffer solution. The example of the physiologically acceptable carrier includes a buffer such as phosphate, citrate and other organic acids; an anti-oxidant including ascorbic acid; a low molecular weight (less than about 10 residues of polypeptide); a protein such as serum albumin, gelatin or immunoglobulin; a hydrophilic polymer such as polyvinylpyrrolidone; an amino acid such as glycine, glutamine, asparagine, arginine or lysine; a monosaccharide, a disaccharide and other carbohydrate including glucose, mannose or dextrin; a chelating agent such as EDTA; a sugar-alcohol such as mannitol or sorbitol; a counter ion forming a salt such as sodium; and/or a nonionic surfactant such as Tween™, polyethylene glycol (PEG) and Pluronics™. Additionally, 'pharmaceutically acceptable' means that it is approved or may be approved by a federal or state government regulatory agency or a corresponding agency in a country other than the United States, or that it is listed in the United States Pharmacopoeia or other generally approved pharmacopoeia for use in animals, and more particularly, in humans.

The term "pharmaceutically acceptable salt or complex" refers to a salt or complex represented by the following specified Chemical formula 1. The example of this salt includes a base addition salt formed by a response of a compound represented by Chemical formula 1 which has an organic or inorganic base such as hydroxide, carbonate or bicarbonate of a metal cation as selected from the group consisting of alkali metals (for example, sodium, potassium or lithium) and alkali earth metals (for example, calcium or magnesium) or has primary, secondary or tertiary alkyl amine, but not limited thereto. An amine salt induced from methylamine, dimethylamine, trimethylamine, ethylamine, diethylamine, triethylamine, morpholine, N-methyl-D-glutamine, N,N'-bis(phenylmethyl)-1,2-ethanediamine, tromethamine, ethanolamine, diethanolamine, ethylene diamine, N-methylmorpholine, procaine, piperidine, piperazine, and the like is considered to be within the range of the present invention.

Furthermore, "salt" or "salt form" or "pharmaceutically acceptable salt" used herein may include a base addition salt (from with free carboxyl or other anionic groups) derived from an inorganic base such as for example, sodium, potassium, ammonium, calcium or ferric hydroxide, and an organic base such as for example, isopropylamine, trimethylamine, 2-ethylamino-ethanol, histidine, procaine, and the like. This salt is formed as an acid addition salt having any free cationic group, and for example, it is generally formed with an inorganic acid such as hydrochloric acid, sulfuric acid or phosphoric acid, or an organic acid such as acetic acid, citric acid, p-toluenesulfonic acid, methanesulfonic acid, oxalic acid, tartaric acid, mandelic acid, and the like. The salt of the present disclosure may include an amine salt formed by protonation of an amino group having an inorganic acid such as hydrochloric acid, hydrobromic acid, hydriodic acid, sulfuric acid, phosphoric acid, and the like. In addition, the salt of the present disclosure includes an amine salt formed by protonation of an amino group having an appropriate organic acid such as p-toluenesulfonic acid, acetic acid, and the like.

The term used herein "pH agent" or "buffer" may refer to a compound or buffer useful as a pH adjusting agent. This may include a glycerol buffer, citrate buffer, borate buffer, acetate buffer, gluconate buffer, phosphate buffer or citrate-phosphate buffer, but not limited thereto. The pH agent or buffer may be used in an any appropriate amount.

The term used herein "preservative" may refer to a substance or chemical substance which prevents an undesirable change of a compound or composition or chemical formula described herein. The appropriate preservative may include for example, benzalkonium chloride, thimerosal, chlorobutanol, methyl paraben, propyl paraben, phenylethyl alcohol, edetate disodium sorbate, onamer m polyquat, cetyl bromide, cetyl pyridinium chloride, benzyl bromide, EDTA, phenyl mercury nitrate, phenyl mercury acetate, thimerosal, Merthiolate, acetate and phenyl mercury borate, polymyxin B sulfate, methyl and propyl paraben, tertiary ammonium chloride, sodium benzoate, sodium propionate and sodium perborate, and other agents known to those skilled in the art or a combination thereof. The preservative may be used in any appropriate amount.

The term used herein, "prevent", "preventing" or "prevention" and other grammatical equivalents includes for reduction of incidence of a syndrome, as well as for preventing development, occurrence, interference or avoidance of the syndrome of a disease or condition. The prevention may be complete (i.e., no detectable symptoms) or partial, so that fewer symptoms may be observed than in the absence of treatment. The term further includes prophylactic benefits. To prevent a disease or condition, the composition may be administered to a patient at risk of developing a specific disease or a patient reporting one or more physiological syndromes of the disease, although not necessarily diagnosing the disease.

Ranges provided herein are understood to be shorthand for all values within the ranges. For example, a range of 1 to 10 is understood to include not only all intermediate decimal values between the aforementioned integers such as 1.1, 1.2, 1.3, 1.4, 1.5, 1.6, 1.7, 1.8 and 1.9 but also any number, combination of numbers of subranges from the group consisting of 1, 2, 3, 4, 5, 6, 7, 8, 9 or 10. With respect to subranges, "nested subranges" extending from one of the endpoints of the range are particularly considered. For example, overlapping subranges of the example range of 1 to 50 may include 1 to 10, 1 to 20, 1 to 30, and 1 to 40 in one direction, or may include 50 to 40, 50 to 30, 50 to 20, and 50 to 10 in the other direction. The range may be expressed herein as "about" one specific value and/or "about" other specific value. When such range is expressed, other aspect includes one specific value and/or other specific value. Similarly, when values are expressed as approximations using the antecedent "about", it is understood that the specific value forms the other aspect. It is further understood that the endpoints of each range are significant in relation to the other endpoints and independently of the other endpoints. In addition, throughout the application, it is understood that data are provided in a number of different formats and these data represent endpoints and starting points and ranges for any combination of data points. For example, when a specific data point "10" and a specific data point "15" are disclosed, it is considered that between 10 and 15, as well as more than, more than or equal to, less than, less than or equal to, and equal to are disclosed. Furthermore, it is understood that each unit between two specific units is disclosed. For example, when 10 and 15 are disclosed, 11, 12, 13 and 14 are disclosed.

Additional excipients considered for use in the practice of the present disclosure are those available to those skilled in the art, for example, those found in the United States Pharmacopoeia Vol. XXII and National Formulary Vol. XVII, U.S. Pharmacopoeia Convention, Inc., Rockville, Md. (1989), of which related contents are incorporated herein as a reference.

"Semi-solid gel" according to the present disclosure is a semi-solid. The apparent viscosity of a semi-solid formulation may increase with concentration.

"Sequential administration" used herein includes that administration of two formulations (for example, a compound or composition described herein) occurs separately on the same day or does not occur on the same day (for example, occurs on consecutive days).

"Solution" according to the present disclosure may be a clear, homogeneous liquid administration form containing one or more chemical substances dissolved in a solvent or mixture of solvents that are miscible with one another. As molecules of a drug substance in a solution are uniformly dispersed, the used of the solution as an administration form generally provides assurance of a uniform dosage upon administration and good accuracy when the solution is diluted or otherwise mixed.

The term "solvent" used herein refers to an aqueous or non-aqueous liquid solvent. The selection of the solvent depends particularly on the solubility and mode of administration of a composition. The aqueous solvent may consist of only water, or may consist of water and one or more of miscible solvents, and may contain dissolved solutes such as sugars, buffers, salts or other excipients. More commonly used non-aqueous solvents are short-chain organic alcohols such as methanol, ethanol and propanol, short-chain ketones such as acetone, and polyalcohols such as glycerol.

"Subject" or "patient" means a human or non-human animal such as a mammal. The "subject" may include any animal including horses, dogs, cats, pigs, goats, rabbits, hamsters, monkeys, guinea pigs, rats, mice, lizards, snakes, sheep, cattle, fish and birds. The human subject may refer to a patient.

"Suspension" used herein is a liquid administration form containing solid particles dispersed in a liquid vehicle.

"Viscosity" used herein refers to the flow resistance of a fluid. A viscosity agent may be used herein, and for example, it includes polyvinyl alcohol, polyvinyl pyrrolidone, methyl cellulose, hydroxy propyl methyl cellulose, hydroxyethyl cellulose, carboxymethyl cellulose, hydroxy propyl cellulose, other agents known to those skilled in the art or combinations thereof.

The term "weight percentage" or "% (w/w)" refers to a percentage of a component in a solution calculated on the basis of the weight of the component and solvent. For example, 1% (w/w) solution of the component may have the component of 1 g dissolved in a solvent of 100 g. The term "volume percentage" or "% (v/v)" refers to a percentage of a component in a solution calculated on the basis of the volume of the component and solvent. For example, 1% (v/v) solution of the component may have the component of 1 ml dissolved in a solvent of 100 ml. The term "weight/volume percentage" or "% (w/v)" refers to a percentage of a component in a solution calculated on the basis of the weight of the component and the volume of the solvent. For example, the 1.0% (w/v) solution of the component may have the component of 1 g dissolved in a solvent of 100 ml.

The term "syndrome" used herein refers to a condition characterized by a group of symptoms that occur continuously together or a series of related symptoms. The syndrome (for example, acute respiratory distress syndrome) may be a set of medical signs and symptoms that are interrelated and often associated with a specific disease. On the other hand, a disease may be a health condition with a clearly defined reason behind it. However, the syndrome (from a Greek word meaning 'to run together') may cause a number of symptoms without an identifiable cause. They may imply the likelihood of an underlying disease or the likelihood that a disease will develop.

The term "treat", "treating" or "treatment" and other grammatical equivalents used herein include alleviation, attenuation, improvement or prevention of disease, condition (for example, acute respiratory distress syndrome) or symptoms, prevention of an additional symptom, improvement or prevention of fundamental metabolic causes of symptoms, inhibition of disease or condition, for example, development arrest of disease or condition, alleviation of disease or condition, regression of disease or condition, alleviation of condition caused by disease or condition, or stop of symptoms of disease or condition, and are intend to include prevention. The term further includes achieving a therapeutic benefit and/or prophylactic benefit. The therapeutic benefit means eradication or improvement of fundamental disorder being treated. In addition, since a therapeutic benefit is achieved by eradication or improvement of one or more of physiological symptoms related to the fundamental disorder, even though a patient may still suffer from the fundamental disorder, the improvement is observed in the patient.

The term "health functional food" refers to a food or food supplement prepared or processed with a raw material, functional ingredient, active pharmaceutical component or additive, useful for improving and/or nourishing and/or preserving the physiological functions of the human body.

The term "acute respiratory distress syndrome (ARDS)" refers to a medical condition occurred in a serious patient having extensive inflammation. ARDS is a clinical phenotype which may result form various pathologies such as pneumonia and sepsis. The alveolar barrier, surfactant dysfunction, abnormal clotting and extensive damage to cells forming activation of innate immune response are characteristics of ARDS.

The term "acute lung injury (ALI)" refers to an inflammatory syndrome and increased permeability related to hypoxemia and classical radiological appearance. At the most severe end of this spectrum is ARDS.

The term "airway surface liquid (ASL)" refers to a thin layer of fluid coating the apical surface of the airway epithelium. ASL plays a pivotal role in maintaining airway homeostasis. ASL volume, pH and ionic balance are directly involved in the regulation of anti-microbial activity, ciliary function and mucosal clearance.

The term "inflammatory airway disease" refers to various inflammatory airway diseases including asthma, acute or chronic bronchitis, allergic rhinitis, acute respiratory infection, acute upper respiratory infection, cystic fibrosis, acute respiratory distress syndrome (ARDS), acute lung injury (ALI), chronic obstructive pulmonary disease (COPD), and the like.

The term "inhibitor" used in the context of the present invention is defined as a molecule, two or more molecules or a pharmaceutical composition that completely or partially inhibits the activity of a target or two or more targets that induce a desired biological effect. The non-limitative examples of the target include an enzyme, a receptor, an ion-channel or transport (for example, pendrin), and the like. The "inhibitor" may inhibit the target reversibly or irreversibly, and reversible inhibition includes competitive inhibition, uncompetitive inhibition, non-competitive inhibition and mixed inhibition. The term "alkyl" includes straight-chain or branched-chain C1-C20 alkyl referring to a monovalent alkyl group having 1 to 20 carbon atoms, when used alone or with other terms. This term is exemplified as the group such as methyl, ethyl, n-propyl, i-propyl, n-butyl, s-butyl, i-butyl, t-butyl, n-pentyl, 1-ethylpropyl, 2-methylbutyl, 3-methylbutyl, 2,2-dimethyl propyl, n-hexyl, 2-methylpentyl, 3-methylpentyl, 4-methylpentyl, n-heptyl, 2-methylhexyl, 3-methylhexyl, 4-methylhexyl, 5-methylhexyl, n-heptyl, n-octyl, n-nonyl, n-decyl, tetrahydrogeranyl, n-dodecyl, n-tridecyl, n-tetradecyl, n-pentadecyl, n-hexadecyl, n-octadecyl, n-nonadecyl and n-eicosanyl, and the like. Preferably, this includes $C_1$-$C_9$ alkyl, more preferably, $C_1$-$C_6$ alkyl, particularly preferably, $C_1$-$C_4$ alkyl, and this similarly, represents a monovalent alkyl group having 1 to 9 carbon atoms, a monovalent alkyl group having 1 to 6 carbon atoms, and a monovalent alkyl group having 1 to 4 carbon atoms, respectively.

The term "alkenyl" includes straight-chain or branched-chain $C_2$-$C_{20}$ alkenyl, when used alone or with other terms. It may have any available number of double bonds at any available position, and the configuration of the double bond may be (E) or (Z) configuration. this term is exemplified as the group such as vinyl, allyl, isoprophenyl, 1-prophenyl, 2-methyl-1-prophenyl, 1-butenyl, 2-butenyl, 3-butenyl, 2-ethyl-1-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl, 5-hexenyl, 1-heptenyl, 1-octenyl, geranyl, 1-decenyl, 1-tetradecenyl, 1-octadecenyl, 9-octadecenyl, 1-eicosenyl and 3,7,11,15-tetramethyl-1-hexadecenyl, and the like. Preferably, this includes $C_2$-$C_8$ alkenyl, more preferably, $C_2$-$C_6$ alkenyl. Among them, vinyl or ethenyl (—CH═$CH_2$), n-2-prophenyl (allyl, —$CH_2$CH═$CH_2$), isoprophenyl, 1-prophenyl, 2-methyl-1-prophenyl, 1-butenyl, 2-butenyl, 3-methyl-2-butenyl, and the like are particularly preferable.

The term "alkynyl" includes straight-chain or branched-chain C2-C20 alkynyl, when used alone or with other terms. It may have any available number of triple bonds at any available position. This term is exemplified as a group such as an alkynyl group which may have 2 to 20 carbon atoms and any double bond or triple bond, like ethynyl (—C≡1-propynyl, 2-propynyl (propargyl: —CH2C≡2-butynyl, 2-penten-4-ynyl) and the like. In particular, this includes C2-C8 alkynyl, more preferably, C2-C6 alkynyl and the like. Preferably, it includes C2-C6 alkynyl referring to a group having 2 to 6 carbon atoms and having alkynyl unsaturation at one or two positions at least.

The term "heteroalkyl" refers to C1-C12-alkyl, preferably, C1-C6-alkyl, and at least one carbon is substituted to a heteroatom selected from O, N or S, including 2-methoxyethyl, and the like.

The term "aryl" refers to an unsaturated aromatic carbocyclic group of 6 to 14 carbon atoms having a single ring (for example, phenyl) or multi-condensed ring (for example, indenyl, naphthyl, 2,3-dihydro-1H-indenyl, 1, 2, 3, 4-tetrahydronaphthyl). The aryl includes phenyl, naphthyl, anthryl, phenanthrenyl, and the like.

The term "$C_1$-$C_6$ alkyl aryl" refers to an aryl group having a $C_1$-$C_6$ alkyl substituent including methyl phenyl, ethyl phenyl, t-butyl phenyl, and the like.

The term "aryl $C_1$-$C_6$ alkyl" refers to a $C_1$-$C_6$ alkyl group having an aryl substituent including 3-phenylpropanyl, benzyl, and the like.

The term "heteroaryl" refers to a monocyclic heteroaromatic, or bicyclic or tricyclic fused-ring heteroaromatic group. A specific examples of the heteroaromatic group includes optionally substituted pyridyl, pyrrolyl, pyrimidinyl, furyl, thienyl, imidazolyl, oxazolyl, isoxazolyl, thiazolyl, isothiazolyl, pyrazolyl, 1H-pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,3,4-triazinyl, 1,2,3-triazinyl, benzofuryl, [2,3-dihydro]benzofuryl, isobenzofuryl, benzothienyl, benzotriazolyl, isobenzothienyl, indolyl, isoindolyl, 3H-indolyl, benzimidazolyl, imidazo[1,2-a]pyridyl, benzothiazolyl, benzooxa-zolyl, quinolizinyl, quinazolinyl, phthalazinyl, quinoxalinyl, cinnolinyl, naphthyridinyl, pyrido[3,4-b]pyridyl, pyrido[3,2-b]pyridyl, pyrido[4,3-b]pyridyl, quinolyl, isoquinolyl, tetrazolyl, 5,6,7,8-tetrahydroquinolyl, 5,6,7,8-tetrahydroisoquinolyl, purinyl, pteridinyl, carbazolyl, xantheinyl, benzoquinolyl, benzo[d][1,3]dioxol-5-yl, 3,4-dihydro-1H-pyrano[4,3-c]pyridyl, quinolin-2(1H)-one, 4H-chromene, 1H-indole, and the like.

The term "$C_1$-$C_6$ alkyl heteroaryl" refers to a heteroaryl group having a $C_1$-$C_6$ alkyl substituent including methyl furyl, t-butyl furyl, and the like.

The term "heteroaryl $C_1$-$C_6$ alkyl" refers to a $C_1$-$C_6$ alkyl group having a heteroaryl substituent including furyl methyl, and the like.

The term "$C_2$-$C_6$ alkenyl aryl" refers to an aryl group having a $C_2$-$C_6$ alkenyl substituent including vinyl phenyl, and the like.

The term "aryl $C_2$-$C_6$ alkenyl" refers to a $C_2$-$C_6$ alkenyl group having an aryl substituent including phenyl vinyl, and the like.

The term "$C_2$-$C_6$ alkenyl heteroaryl" refers to a heteroaryl group having a $C_2$-$C_6$ alkenyl substituent including vinyl pyridinyl, and the like.

The term "heteroaryl $C_2$-$C_6$ alkenyl" refers to a $C_1$-$C_6$ alkenyl group having a heteroaryl substituent including pyridinyl vinyl, and the like.

The term "$C_3$-$C_8$-cycloalkyl" refers to a saturated carbocyclic group of 3 to 8 carbon atoms having a single ring (for example, cyclohexyl) or multi-condensed ring (for example, norbornyl). The cyclo alkyl includes cyclopentyl, cyclohexyl, norbonyl, and the like.

The term "heterocycloalkyl" refers to a $C_3$-$C_8$-cycloalkyl or multi-condensed ring according to the definition, in which 3 carbon atoms at maximum are substituted to heteroatoms selected from the group consisting of O, S and NR (R is defined as hydrogen or methyl). The heterocycloalkyl includes lactam or lactone. The non-limitative examples are pyrrolidinyl, piperidinyl, piperazinyl, morpholinyl, tetrahydro furanyl, decahydroisoquinolinyl, octahydro-1H-pyrano[3,4-c]pyridinyl, 4-methylen-5(4H)-one, pyrrolidin-2-one, and the like.

The term "$C_1$-$C_6$ alkyl $C_3$-$C_8$ cycloalkyl" refers to a $C_3$-$C_8$ cycloalkyl group having a $C_1$-$C_6$ alkyl substituent including methyl cyclopentyl, and the like.

The term "$C_3$-$C_8$-cycloalkyl $C_1$-$C_6$ alkyl" refers to a $C_1$-$C_6$ alkyl group having a $C_3$-$C_8$-cycloalkyl substituent including 3-cyclopentyl propyl, and the like.

The term "$C_1$-$C_6$ alkyl heterocycloalkyl" refers to a heterocycloalkyl group having a $C_1$-$C_6$ alkyl substituent including 4-methylpiperidinyl, and the like.

The term "heterocycloalkyl $C_1$-$C_6$ alkyl" refers to a $C_1$-$C_6$ alkyl group having a hetero cycloalkyl substituent including (1-methylpiperidin-4-yl)methyl, and the like.

The term "carboxy" refers to a group —C(O)OH.

The term "carboxy $C_1$-$C_6$ alkyl" refers to a $C_1$-$C_6$ alkyl group having a carboxy substituent including 2-carboxyethyl, and the like.

The term "acyl" refers to a group —C(O)R including acetyl, and the like, and then, R includes H, "alkyl" preferably, "$C_1$-$C_6$ alkyl" "aryl" "heteroaryl" "$C_3$-$C_8$ cycloalkyl" "heterocycloalkyl" "aryl $C_1$-$C_6$ alkyl" "heteroaryl $C_1$-$C_6$ alkyl" "$C_3$-$C_8$ cycloalkyl $C_1$-$C_6$ alkyl" or "heterocycloalkyl $C_1$-$C_6$ alkyl".

The term "acyl $C_1$-$C_6$ alkyl" refers to a $C_1$-$C_6$ alkyl group having an acyl substituent including 2-acetylethyl, and the like.

The term "acyl aryl" refers to an aryl group having an acyl substituent including 2-acetylphenyl, and the like.

The term "acyloxy" refers to a group —OC(O)R including acetyloxy, and the like, and then, R includes H, "C1-C6 alkyl", "C2-C6 alkenyl" "C2-C6 alkynyl" "C3-C8-cycloalkyl" "heterocycloalkyl" "aryl" "heteroaryl" "aryl C1-C6 alkyl", "heteroaryl C1-C6 alkyl" "aryl C2-C6 alkenyl" "heteroaryl C2-C6 alkenyl" "aryl C2-C6 alkynyl" "heteroaryl C2-C6 alkynyl" "C3-C8-cycloalkyl C1-C6 alkyl" or "heterocycloalkyl C1-C6 alkyl".

The term "acyloxy C1-C6 alkyl" refers to a C1-C6 alkyl group having an acyloxy substituent including 2-(ethylcarbonyloxy)ethyl, and the like.

The term "alkoxy" refers to a group —OR, and then, R includes "$C_1$-$C_6$ alkyl", "aryl", "heteroaryl", "aryl $C_1$-$C_6$ alkyl" or "heteroaryl $C_1$-$C_6$ alkyl". The preferable alkoxy group includes for example, methoxy, ethoxy, phenoxy, and the like.

The term "alkoxy $C_1$-$C_6$ alkyl" refers to a $C_1$-$C_6$ alkyl group having an alkoxy substituent including methoxyethyl, and the like.

The term “alkoxycarbonyl” refers to a group —C(O)OR, and then, R includes “$C_1$-$C_6$ alkyl”, “aryl”, “heteroaryl”, “aryl $C_1$-$C_6$ alkyl”, “heteroaryl $C_1$-$C_6$ alkyl” or “heteroalkyl”.

The term “alkoxycarbonyl C1-C6 alkyl” refers to a C1-C6 alkyl group having an alkoxycarbonyl substituent including 2-(benzyloxycarbonyl)ethyl, and the like.

The term “aminocarbonyl” refers to a group —C(O)NRR' including N-phenyl carbonyl, and the like, and then, R and R' are independently H, C1-C6 alkyl, aryl, heteroaryl, “aryl C1-C6 alkyl” or “heteroaryl C1-C6 alkyl”.

The term “aminocarbonyl C1-C6 alkyl” refers to an alkyl group having an aminocarbonyl substituent including 2-(dimethylaminocarbonyl)ethyl, N-ethyl acetamidyl, N,N-diethyl-acetamidyl, and the like.

The term “acylamino” refers to a group —NRC(O)R' including acetylamino, and the like, and then, R and R' are independently H, “$C_1$-$C_6$ alkyl” “$C_2$-$C_6$ alkenyl” “$C_2$-$C_6$ alkynyl” “$C_3$-$C_8$-cycloalkyl” “heterocycloalkyl” “aryl” “heteroaryl” “aryl $C_1$-$C_6$ alkyl”, “heteroaryl $C_1$-$C_6$ alkyl” “aryl $C_2$-$C_6$ alkenyl” “heteroaryl $C_2$-$C_6$ alkenyl” “aryl $C_2$-$C_6$ alkynyl” “heteroaryl $C_2$-$C_6$ alkynyl” “cycloalkyl $C_1$-$C_6$ alkyl” or “heterocycloalkyl $C_1$-$C_6$ alkyl”.

The term “acylamino $C_1$-$C_6$ alkyl” refers to a $C_1$-$C_6$ alkyl group having an acylamino substituent including 2-(propionylamino)ethyl, and the like.

The term “ureido” refers to a group —NRC(O)NR'R", and then, R, R' and R" are independently H, “$C_1$-$C_6$ alkyl” “alkenyl” “alkynyl” “$C_3$-$C_8$ cycloalkyl” “heterocycloalkyl” “$C_1$-$C_6$ aryl” “heteroaryl” “aryl $C_1$-$C_6$ alkyl”, “heteroaryl $C_1$-$C_6$ alkyl” “aryl $C_2$-$C_6$ alkenyl” “heteroaryl $C_2$-$C_6$ alkenyl” “aryl $C_2$-$C_6$ alkynyl” “heteroaryl $C_2$-$C_6$ alkynyl” “cycloalkyl $C_1$-$C_6$ alkyl” or “heterocycloalkyl $C_1$-$C_6$ alkyl”, and then, R' and R" may optionally form a 3-8 membered heterocycloalkyl ring, together with a nitrogen atom attached to them.

The term “ureido $C_1$-$C_6$ alkyl” refers to a $C_1$-$C_6$ alkyl group having a ureido substituent including 2-(N'-methylureido)ethyl, and the like.

The term “carbamate” refers to a group —NRC(O)OW, and then, R and R' are independently “$C_1$-$C_6$ alkyl” “$C_2$-$C_6$ alkenyl” “$C_2$-$C_6$ alkynyl” “$C_3$-$C_8$-cycloalkyl” “heterocycloalkyl” “aryl” “heteroaryl” “$C_1$-$C_6$ alkyl aryl”, “heteroaryl $C_1$-$C_6$ alkyl” “aryl $C_2$-$C_6$ alkenyl” “heteroaryl $C_2$-$C_6$ alkenyl” “aryl $C_2$-$C_6$ alkynyl” “heteroaryl $C_2$-$C_6$ alkynyl” “cycloalkyl $C_1$-$C_6$ alkyl” or “heterocycloalkyl $C_1$-$C_6$ alkyl”, and also, R may be hydrogen.

The term “amino” refers to a group —NRR', and then, R and R' are independently H, “$C_1$-$C_6$ alkyl”, “aryl”, “heteroaryl”, “$C_1$-$C_6$ alkyl aryl”, “$C_1$-$C_6$ alkyl heteroaryl” “cycloalkyl” or “heterocycloalkyl”, and then, R and R' may optionally form a 3-8 membered heterocycloalkyl ring, together with a nitrogen atom attached to them.

The term “amino alkyl” refers to an alkyl group having an amino substituent including 2-(1-pyrrolidinyl)ethyl, and the like.

The term “ammonium” refers to a positively charged group —$N^+$RR'R", and then, R, R' and R" are independently “$C_1$-$C_6$ alkyl”, “$C_1$-$C_6$ alkyl aryl”, “$C_1$-$C_6$ alkyl heteroaryl” “cycloalkyl” or “heterocycloalkyl”, and then, R and R' may optionally form a 3-8 membered heterocycloalkyl ring, together with a nitrogen atom attached to them.

The term “ammonium alkyl” refers to an alkyl group having an ammonium substituent including 1-ethylpyrrolidinium, and the like.

The term “halogen” refers to fluoro, chloro, bromo and iodic atoms.

The term “sulfonyloxy” refers to a group —$OSO_2$R, and then, R is selected from “$C_1$-$C_6$ alkyl” “$C_1$-$C_6$ alkyl” substituted with halogen, for example, —$OSO_2CF_3$ group, “$C_2$-$C_6$ alkenyl” “alkynyl” “$C_3$-$C_8$ cycloalkyl” “heterocycloalkyl” “aryl” “heteroaryl” “aryl $C_1$-$C_6$ alkyl”, “heteroaryl $C_1$-$C_6$ alkyl” “aryl $C_2$-$C_6$ alkenyl” “heteroaryl $C_2$-$C_6$ alkenyl” “aryl $C_2$-$C_6$ alkynyl” “heteroaryl $C_2$-$C_6$ alkynyl” “cycloalkyl $C_1$-$C_6$ alkyl” or “heterocycloalkyl alkyl”.

The term “sulfonyloxy $C_1$-$C_6$ alkyl” refers to an alkyl group having a sulfonyloxy substituent including 2-(methylsulfonyloxy)ethyl, and the like.

The term “sulfonyl” refers to a group “—$SO_2$R”, and then, R is selected from “aryl” “heteroaryl” “$C_1$-$C_6$ alkyl” “$C_1$-$C_6$ alkyl” substituted with halogen, for example, —$SO_2CF_3$, “$C_2$-$C_6$ alkenyl” “$C_2$-$C_6$ alkynyl” “$C_3$-$C_8$ cycloalkyl” “heterocycloalkyl” “aryl” “heteroaryl” “aryl $C_1$-$C_6$ alkyl”, “heteroaryl $C_1$-$C_6$ alkyl” “aryl $C_2$-$C_6$ alkenyl” “heteroaryl $C_2$-$C_6$ alkenyl” “aryl $C_2$-$C_6$ alkynyl” “heteroaryl $C_2$-$C_6$ alkynyl” “cycloalkyl $C_1$-$C_6$ alkyl” or “heterocycloalkyl $C_1$-$C_6$ alkyl”.

The term “sulfonyl $C_1$-$C_6$ alkyl” refers to an alkyl group having a sulfonyl substituent including 2-(methylsulfonyl) ethyl, and the like.

The term “sulfinyl” refers to a group “—S(O)R”, and then, R is selected from “alkyl”, “alkyl” substituted with halogen, for example, —SOCF3 group, “C2-C6 alkenyl” “C2-C6 alkynyl” “C3-C8 cycloalkyl” “heterocycloalkyl” “aryl” “heteroaryl” “aryl C1-C6 alkyl”, “heteroaryl C1-C6 alkyl” “aryl C2-C6 alkenyl” “heteroaryl C2-C6 alkenyl” “aryl C2-C6 alkynyl” “heteroaryl C2-C6 alkynyl” “C3-C8-cycloalkyl C1-C6 alkyl” or “heterocycloalkyl C1-C6 alkyl”.

The term “sulfinyl alkyl” refers to an alkyl group having a sulfinyl substituent including 2-(methylsulfinyl)ethyl, and the like.

The term “sulfanyl” refers to a group —SR, and then R includes H, “$C_1$-$C_6$ alkyl”, “$C_1$-$C_6$ alkyl” substituted with halogen, e.g., —$SCF_3$ group, “$C_2$-$C_6$ alkenyl” “$C_2$-$C_6$ alkynyl” “$C_3$-$C_3$-cycloalkyl” “heterocycloalkyl” “aryl” “heteroaryl” “aryl $C_1$-$C_6$ alkyl”, “heteroaryl $C_1$-$C_6$ alkyl” “aryl $C_2$-$C_6$ alkenyl” “heteroaryl $C_2$-$C_6$ alkenyl” “aryl $C_2$-$C_6$ alkynyl” “alkynylheteroaryl” “cycloalkyl $C_1$-$C_6$ alkyl” or “heterocycloalkyl $C_1$-$C_6$ alkyl”. The preferable sulfanyl group includes methylsulfanyl, ethylsulfanyl, and the like.

The term “sulfanyl C1-C6 alkyl” refers to a C1-C5-alkyl group having a sulfanyl substituent including 2-(ethylsulfanyl)ethyl, and the like.

The term “sulfonylamino” refers to a group —$NRSO_2$R', and then R and R' are independently “$C_1$-$C_6$ alkyl” “$C_2$-$C_6$ alkenyl” “$C_2$-$C_6$ alkynyl” “$C_3$-$C_8$-cycloalkyl” “heterocycloalkyl” “aryl” “heteroaryl” “aryl $C_1$-$C_6$ alkyl”, “heteroaryl $C_1$-$C_6$ alkyl” “aryl $C_2$-$C_6$ alkenyl” “heteroaryl $C_2$-$C_6$ alkenyl” “aryl $C_2$-$C_6$ alkynyl” “heteroaryl $C_2$-$C_6$ alkynyl” “$C_3$-$C_8$ cycloalkyl $C_1$-$C_6$ alkyl” or “heterocycloalkyl $C_1$-$C_6$ alkyl”.

The term “sulfonylamino C1-C6 alkyl” refers to an alkyl group having a sulfonylamino substituent including 2-(ethylsulfonylamino)ethyl, and the like.

The term “aminosulfonyl” refers to a group —SO2NRR', and then, R and R' are independently H, “$C_1$-$C_6$ alkyl” “$C_2$-$C_6$ alkenyl” “$C_2$-$C_6$ alkynyl” “$C_3$-$C_8$-cycloalkyl” “heterocycloalkyl” “aryl” “heteroaryl” “aryl $C_1$-$C_6$ alkyl”, “heteroaryl C1-C6 alkyl” “aryl alkenyl” “heteroaryl $C_2$-$C_6$ alkenyl” “aryl $C_2$-$C_6$ alkynyl” “heteroaryl $C_2$-$C_6$ alkynyl” “$C_3$-$C_8$-cycloalkyl $C_1$-$C_6$ alkyl” or “heterocycloalkyl $C_1$-$C_6$ alkyl”, and then, R and R' may optionally form a 3-8 membered heterocycloalkyl ring, together with a nitrogen atom attached to them. The aminosulfonyl group includes cyclohexylaminosulfonyl, piperidinylsulfonyl, and the like.

The term "aminosulfonyl $C_1$-$C_6$ alkyl" refers to a $C_1$-$C_6$ alkyl group having an aminosulfonyl substituent, including 2-(cyclohexylaminosulfonyl)ethyl, and the like.

Unless otherwise limited by the definition of an individual substituent, all the substituents should be understood to be all optionally substituted.

Unless otherwise limited by the definition of an individual substituent, the term "substituted" refers to a group substituted with 1 to 5 substituents selected from the group consisting of "$C_1$-$C_6$ alkyl", "$C_2$-$C_6$ alkenyl", "$C_2$-$C_6$ alkynyl", "$C_3$-$C_8$ cycloalkyl", "heterocycloalkyl", "$C_1$-$C_6$ alkyl aryl", "$C_1$-$C_6$ alkyl heteroaryl", "$C_1$-$C_6$ alkyl cycloalkyl", "$C_1$-$C_6$ alkyl heterocycloalkyl", "amino", "aminosulfonyl", "ammonium", "acyl amino", "amino carbonyl", "aryl", "heteroaryl", "sulfinyl", "sulfonyl", "alkoxy", "alkoxy carbonyl", "carbamate", "sulfonyl", "halogen", trihalomethyl, cyano, hydroxy, mercapto, nitro, and the like.

2. Compound

One aspect of the present invention provides a compound represented by the following Chemical formula 1, E- or Z-isomer thereof, optical isomer thereof, a mixture of two isomers thereof, precursor thereof, pharmaceutically acceptable salt thereof or solvate thereof:

[Chemical formula 1]

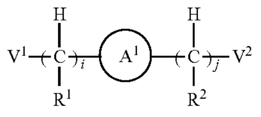

in the Chemical formula 1, $V^1$ and $V^2$ are aryl, heteroaryl, $C_3$~$C_7$ cycloalkyl, heterocycloalkyl, $C_1$~$C_6$ alkyl, $C_1$~$C_6$ heteroalkyl, $C_2$-$C_{10}$ alkenyl, $C_0$~$C_3$ methylenehydrazine, $C_2$~$C_{10}$ alkynyl, $S(O)_i(C_1$~$C_6$ alkyl), $OS(O)_i$(aryl), $S(O)_iNR^3R^4$, $C(O)R^3$, $OR^3$, $OCOR^3$, $NR^3C(O)OR^4$, $NR^3C(O)R^4$, $C(O)NR^3R^4$ or $NR^3R^4$, and one of the aryl, heteroaryl, $C_3$~$C_7$ cycloalkyl, heterocycloalkyl, $C_1$~$C_6$ alkyl, $C_1$~$C_6$ heteroalkyl, $C_2$~$C_{10}$ alkenyl, $C_0$~$C_3$ methylenehydrazine, $C_2$~$C_{10}$ alkynyl, $S(O)_i(C_1$~$C_6$ alkyl), $OS(O)_i$(aryl), $S(O)_iNR^3R^4$, $C(O)R^3$, $OR^3$, $OCOR^3$, $NR^3C(O)OR^4$, $NR^3C(O)R^4$, $C(O)NR^3R^4$ and $NR^3R^4$ is optionally substituted to one or more groups independently selected from hydrogen, oxo, halogen, cyano, azido, nitro, trifluoromethyl, trifluoromethoxy, sulfanyl, aryl, $C_1$~$C_{10}$ alkylaryl, $C_3$~$C_7$ cycloalkyl, heteroaryl, heterocycloalkyl, $C_1$~$C_{10}$ alkyl, $C_2$~$C_{10}$ alkenyl, $C_2$~$C_{10}$ alkynyl, $C_3$~$C_6$ cycloalkyl, $S(O)_i(C_1$~$C_6$ alkyl), $S(O)_iNR^3(C_1$~$C_6$ alkyl), $C(O)OR^3$, $C(O)R^3$, $OR^3$, $OCR^3F_2$, $OCOR^3$, $NR^3C(O)OR^4$, $NR^3C(O)R^4$, $C(O)NR^3R^4$, and $NR^3R^4$, and one of the aryl, $C_1$~$C_{10}$ alkylaryl, $C_3$~$C_7$ cycloalkyl, heteroaryl, heterocycloalkyl, $C_1$~$C_{10}$ alkyl, $C_2$~$C_{10}$ alkenyl, $C_2$~$C_{10}$ alkynyl, $C_3$~$C_6$ cycloalkyl, $S(O)_i(C_1$~$C_6$ alkyl), $S(O)_iNR^3(C_1$~$C_6$ alkyl), $C(O)OR^3$, $C(O)R^3$, $OR^3$, $OCR^3F_2$, $OCOR^3$, $NR^3C(O)OR^4$, $NR^3C(O)R^4$, $C(O)NR^3R^4$ and $NR^3R^4$ is optionally substituted to one or more groups independently selected from hydrogen, oxo, halogen, cyano, azido, nitro, trifluoromethyl, trifluoromethoxy, aryl, $C_1$~$C_{10}$ alkylaryl, arylalkyl, $C_3$~$C_7$ cycloalkyl, heteroaryl, heterocycloalkyl, $C_1$~$C_{10}$ alkyl, $C_2$~$C_{10}$ alkenyl, $C_2$~$C_{10}$ alkynyl, $C_3$~$C_6$ cycloalkyl, $S(O)_i(C_1$~$C_6$ alkyl), $S(O)_i$(aryl), $S(O)_i$(heteroaryl), $S(O)_iNR^3(C_1$~$C_6$ alkyl), $C(O)OR^3$, $C(O)R^3$, $OR^3$, $OCR^3F_2$, $OCOR^3$, $NR^3C(O)OR^4$, $NR^3C(O)R^4$, $C(O)NR^3R^4$ and $NR^3R^4$, and i and j are independently 0, 1 or 2, and $R^1$ and $R^2$ are independently selected from the group consisting of hydrogen, halogen, cyano, azido, nitro, trifluoromethyl, trifluoromethoxy, sulfanyl, aryl, $C_1$~$C_{10}$ alkylaryl, heteroaryl, heterocyclyl, $C_1$~$C_{10}$ alkyl, $C_2$~$C_{10}$ alkenyl, $C_2$~$C_{10}$ alkynyl, $C_3$~$C_6$ cycloalkyl, $S(O)_i(C_1$~$C_6$ alkyl), $C(O)OR^3$, $C(O)R^3$, $OR^3$, $NR^3C(O)OR^4$, $C(O)NR^3R^4$ and $NR^3R^4$, and one of the aryl, heteroaryl, $C_1$~$C_{10}$ alkyl, $C_2$~$C_{10}$ alkenyl, $C_2$~$C_{10}$ alkynyl, $C_3$~$C_6$ cycloalkyl, $S(O)_i(C_1$~$C_6$ alkyl), $C(O)OR^3$, $C(O)R^3$, $OR^3$, $NR^3C(O)OR^4$, $C(O)NR^3R^4$ and $NR^3R^4$ is optionally substituted to one or more groups independently selected from oxo, halogen, cyano, azido, nitro, trifluoromethyl, trifluoromethoxy, aryl, heteroaryl, heterocyclyl, $C_1$~$C_{10}$ alkyl, $C_2$~$C_{10}$ alkenyl, $C_2$~$C_{10}$ alkynyl, $C_3$~$C_6$ cycloalkyl, $S(O)_i(C_1$~$C_6$ alkyl), $C(O)OR^3$, $C(O)R^3$, $OR^3$, $NR^3C(O)OR^4$, $C(O)NR^3R^4$ and $NR^3R^4$, and $R^3$ and $R^4$ are independently selected from the group consisting of hydrogen, cyano, azido, nitro, trifluoromethyl, trifluoromethoxy, sulfanyl, aryl, aryl($C_1$~$C_{10}$ alkyl), $C_1$~$C_{10}$ alkylaryl, heteroaryl, heteroaryl($C_1$~$C_{10}$ alkyl), $C_1$~$C_{10}$ alkylheteroaryl, $C_1$~$C_{10}$ alkyl, $C_2$~$C_6$ alkenyl, $C_2$~$C_6$ alkynyl, $C_3$~$C_6$ cycloalkyl, heterocyclyl and trifluoromethyl, and one of the aryl, aryl ($C_1$~$C_{10}$ alkyl), $C_1$~$C_{10}$ alkylaryl, heteroaryl, heteroaryl($C_1$~$C_{10}$ alkyl), $C_1$~$C_{10}$ alkylheteroaryl, $C_1$~$C_{10}$ alkyl, $C_2$~$C_6$ alkenyl, $C_2$~$C_6$ alkynyl, $C_3$~$C_6$ cycloalkyl and heterocyclyl is optionally substituted to one or more groups independently selected from hydrogen, oxo, halogen, cyano, azido, nitro, trifluoromethyl, trifluoromethoxy, aryl, heteroaryl, heterocyclyl, $C_1$~$C_{10}$ alkyl, $C_2$~$C_{10}$ alkenyl, $C_2$~$C_{10}$ alkynyl, $C_3$~$C_6$ cycloalkyl, $S(O)_i(C_1$~$C_6$ alkyl), $C(O)OR^3$, $C(O)R^3$, $OR^3$, $NR^3C(O)OR^4$, $C(O)NR^3R^4$ and $NR^3R^4$, or $R^3$ and $R^4$ can be cyclized to a 4 to 10 membered carbocyclic, heterocyclic, aromatic or heteroaromatic ring, and one of the carbocyclic, heterocyclic, aromatic or heteroaromatic ring is optionally substituted to one or more groups independently selected from hydrogen, oxo, halogen, cyano, azido, nitro, trifluoromethyl, trifluoromethoxy, aryl, $C_1$~$C_{10}$ alkylaryl, heteroaryl, heterocyclyl, $C_1$~$C_{10}$ alkyl, $C_2$~$C_{10}$ alkenyl, C2~$C_{10}$ alkynyl, $C_3$~$C_6$ cycloalkyl, $S(O)_i(C_1$~$C_6$ alkyl), $C(O)OR^3$, $C(O)R^3$, $OR^3$, $NR^3C(O)OR^4$, $C(O)NR^3R^4$ and $NR^3R^4$, and $A^1$ is represented by

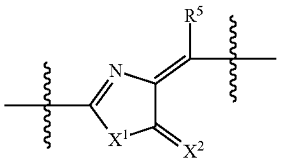

or

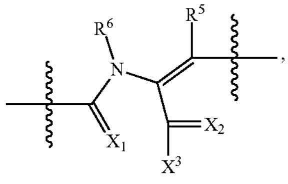

, and $X^1$ and $X^2$ are independently selected from the group consisting of O, S, $CHR^4$ and $NR^4$, and $X^3$ is selected from the group consisting of hydrogen, $OR^3$, aryl, heteroaryl, $C_3$~$C_7$ cycloalkyl, heterocycloalkyl, $C_1$~$C_6$ alkyl, $C_1$~$C_6$ heteroalkyl, $C_2$~$C_{10}$ alkenyl, $C_0$~$C_3$ methylenehydrazine, $C_2$~$C_{10}$ alkynyl, $S(O)_i$($C_1$~$C_6$ alkyl), $S(O)_iNR^3$, $C(O)R^3$, $OC(O)R^3$, $(O)COR^3$, $NR^3C(O)OR^3$, $NR^3C(O)R^3$, $C(O)NR^3$ and $NR^3R^4$ and one of the $OR^3$, aryl, heteroaryl, $C_3$~$C_7$ cycloalkyl, heterocycloalkyl, $C_1$~$C_6$ alkyl, $C_1$~$C_6$ heteroalkyl, $C_2$~$C_{10}$ alkenyl, $C_0$~$C_3$ methylenehydrazine, $C_2$~$C_{10}$ alkynyl, $S(O)_i$($C_1$~$C_6$ alkyl), $S(O)_iNR^3$, $C(O)R^3$, $OC(O)R^3$, $(O)COR^3$, $NR^3C(O)OR^3$, $NR^3C(O)R^3$, $C(O)NR^3$ and $NR^3R^4$ is optionally selected from the group independently selected from hydrogen, oxo, halogen, cyano, azido, nitro, trifluoromethyl, trifluoromethoxy, sulfanyl, aryl, $C_1$~$C_{10}$ alkylaryl, $C_3$~$C_7$ cycloalkyl, heteroaryl, heterocycloalkyl, $C_1$~$C_{10}$ alkyl, $C_2$~$C_{10}$ alkenyl, $C_2$~$C_{10}$ alkynyl, $C_3$~$C_6$ cycloalkyl, $S(O)_i$($C_1$~$C_6$ alkyl), $S(O)_iNR^3$($C_1$~$C_6$ alkyl), $C(O)OR^3$, $C(O)R^3$, $OR^3$, $OCR^3F_2$, $OCOR^3$, $NR^3C(O)OR^4$, $NR^3C(O)R^4$, $C(O)NR^3R^4$ and $NR^3R^4$, and one of the aryl, $C_1$~$C_{10}$ alkylaryl, $C_3$~$C_7$ cycloalkyl, heteroaryl, heterocycloalkyl, $C_1$~$C_{10}$ alkyl, $C_2$~$C_{10}$ alkenyl, $C_2$~$C_{10}$ alkynyl, $C_3$~$C_6$ cycloalkyl, $S(O)_i$($C_1$~$C_6$ alkyl), $S(O)_iNR^3$($C_1$~$C_6$ alkyl), $C(O)OR^3$, $C(O)R^3$, $OR^3$, $OCR^3F_2$, $OCOR^3$, $NR^3C(O)OR^4$, $NR^3C(O)R^4$, $C(O)NR^3R^4$ and $NR^3R^4$ is optionally substituted to one or more groups independently selected from hydrogen, oxo, halogen, cyano, azido, nitro, trifluoromethyl, trifluoromethoxy, sulfanyl, aryl, $C_1$~$C_{10}$ alkylaryl, arylalkyl, $C_3$~$C_7$ cycloalkyl, heteroaryl, heterocycloalkyl, $C_1$~$C_{10}$ alkyl, $C_2$~$C_{10}$ alkenyl, $C_2$~$C_{10}$ alkynyl, $C_3$~$C_6$ cycloalkyl, $S(O)_i$($C_1$~$C_6$ alkyl), $S(O)_i$(aryl), $S(O)_i$(heteroaryl), $S(O)_iNR^3$($C_1$~$C_6$ alkyl), $C(O)OR^3$, $C(O)R^3$, $OR^3$, $OCR^3F_2$, $OCOR^3$, $NR^3C(O)OR^4$, $NR^3C(O)R^4$, $C(O)NR^3R^4$ and $NR^3R^4$, and $R^5$ and $R^6$ are independently selected from the group consisting of hydrogen, cyano, azido, nitro, trifluoromethyl, trifluoromethoxy, sulfanyl, aryl, $C_1$~$C_{10}$ alkylaryl, heteroaryl, heterocyclyl, $C_1$~$C_{10}$ alkyl, $C_2$~$C_6$ alkenyl, $C_2$~$C_6$ alkynyl, $C_3$~$C_6$ cycloalkyl, heterocyclyl, aryl, heteroaryl and trifluoromethyl, and one of the alkyl, alkenyl, alkynyl, cycloalkyl, heterocyclyl, aryl, $C_1$~$C_{10}$ alkylaryl and heteroaryl regions is optionally selected from one or more groups independently selected from hydrogen, oxo, halogen, cyano, azido, nitro, trifluoromethyl, trifluoromethoxy, aryl, arylalkyl, heteroaryl, heteroarylalkyl, heterocyclyl, $C_1$~$C_{10}$ alkyl, $C_2$~$C_{10}$ alkenyl, $C_2$~$C_{10}$ alkynyl, $C_3$~$C_6$ cycloalkyl, $S(O)_i$($C_1$~$C_6$ alkyl), $S(O)_i$(aryl), $S(O)_i$(heteroaryl), $S(O)_iNR^3R^4$, $C(O)OR^3$, $C(O)R^3$, $OR^3$, $NR^3C(O)OR^4$, $C(O)NR^3R^4$ and $NR^3R^4$, and one of the aryl, arylalkyl, heteroaryl, heteroarylalkyl, heterocyclyl, $C_1$~$C_{10}$ alkyl, $C_2$~$C_{10}$ alkenyl, $C_2$~$C_{10}$ alkynyl, $C_3$~$C_6$ cycloalkyl, $S(O)_i$($C_1$~$C_6$ alkyl), $S(O)_i$(aryl), $S(O)_i$(heteroaryl), $S(O)_iNR^3R^4$, $C(O)OR^3$, $C(O)R^3$, $OR^3$, $NR^3C(O)OR^4$, $C(O)NR^3R^4$ and $NR^3R^4$ is optionally selected from one or more groups independently selected from hydrogen, oxo, halogen, cyano, azido, nitro, trifluoromethyl, trifluoromethoxy, aryl, arylalkyl, heteroaryl, heteroarylalkyl, heterocyclyl, $C_1$~$C_{10}$ alkyl, $C_2$~$C_{10}$ alkenyl, $C_2$~$C_{10}$ alkynyl, $C_3$~$C_6$ cycloalkyl, $S(O)_i$($C_1$~$C_6$ alkyl), $S(O)_i$(aryl), $S(O)_i$(heteroaryl), $S(O)_iNR^3R^4$, $C(O)OR^3$, $C(O)R^3$, $OR^3$, $NR^3C(O)OR^4$, $C(O)NR^3R^4$ and $NR^3R^4$, or $R^5$ and $A^1$ can be cyclized to a 4 to 10 membered carbocyclic, heterocyclic, aromatic or heteroaromatic ring, and one of the carbocyclic, heterocyclic, aromatic or heteroaromatic ring is optionally substituted to one or more groups independently selected from oxo, halogen, cyano, azido, nitro, trifluoromethyl, trifluoromethoxy, aryl, $C_1$~$C_{10}$ alkylaryl, heteroaryl, heterocyclyl, $C_1$~$C_{10}$ alkyl, $C_2$~$C_{10}$ alkenyl, $C_2$~$C_{10}$ alkynyl, $C_3$~$C_6$ cycloalkyl, $S(O)_i$($C_1$~$C_6$ alkyl), $C(O)OR^3$, $C(O)R^3$, $OR^3$, $NR^3C(O)OR^4$, $C(O)NR^3R^4$ and $NR^3R^4$.

The non-limitative examples of the compound include the following compounds described in Table 1 and Table 2.

TABLE 1

| Compound No. | Structural formula |
|---|---|
| F1 | 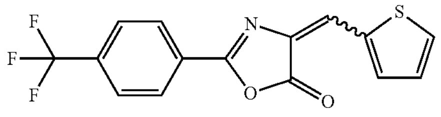 [SMILES: O=C1OC(c2ccc(C(F)(F)F)cc2)=NC1=Cc1cccs1] |
| F2 | 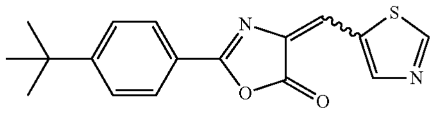 [SMILES: CC(C)(C)c1ccc(C2=NC(=Cc3cncs3)C(=O)O2)cc1] |
| F3 | 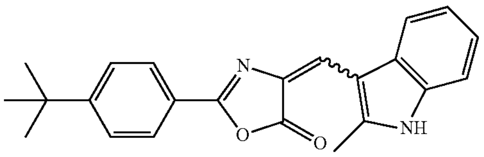 [SMILES: Cc1[nH]c2ccccc2c1C=C1N=C(c2ccc(C(C)(C)C)cc2)OC1=O] |

TABLE 1-continued
| Compound No. | Structural formula |
| --- | --- |
| F4 | 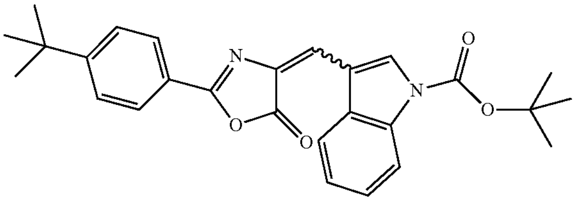 [SMILES: CC(C)(C)OC(=O)n1cc(C=C2N=C(c3ccc(C(C)(C)C)cc3)OC2=O)c2ccccc21] |
| F5 | 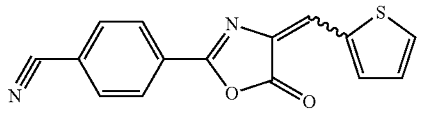 [SMILES: N#Cc1ccc(C2=NC(=Cc3cccs3)C(=O)O2)cc1] |
| F6 | 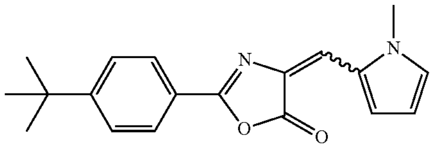 [SMILES: Cn1cccc1C=C1N=C(c2ccc(C(C)(C)C)cc2)OC1=O] |
| F7 | 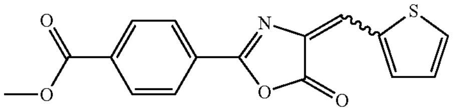 |
| F8 | 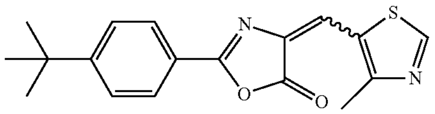 [SMILES: Cc1ncsc1C=C1N=C(c2ccc(C(C)(C)C)cc2)OC1=O] |
| F9 | 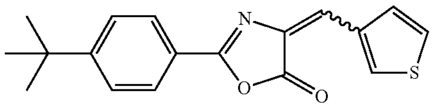 [SMILES: CC(C)(C)c1ccc(C2=NC(=Cc3ccsc3)C(=O)O2)cc1] |
| F10 | 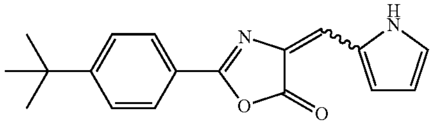 [SMILES: CC(C)(C)c1ccc(C2=NC(=Cc3ccc[nH]3)C(=O)O2)cc1] |
| F11 | 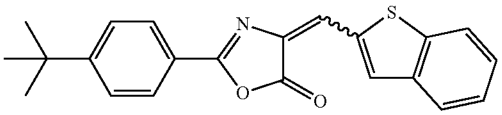 [SMILES: CC(C)(C)c1ccc(C2=NC(=Cc3cc4ccccc4s3)C(=O)O2)cc1] |
| F12 | 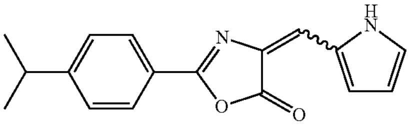 [SMILES: CC(C)c1ccc(C2=NC(=Cc3ccc[nH]3)C(=O)O2)cc1] |
| F13 | 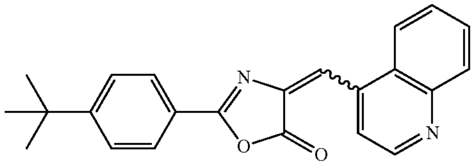 [SMILES: CC(C)(C)c1ccc(C2=NC(=Cc3ccnc4ccccc34)C(=O)O2)cc1] |
| F14 | 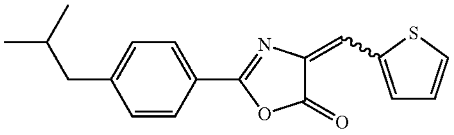 [SMILES: CC(C)Cc1ccc(C2=NC(=Cc3cccs3)C(=O)O2)cc1] |

TABLE 1-continued
| Compound No. | Structural formula |
|---|---|
| F15 | 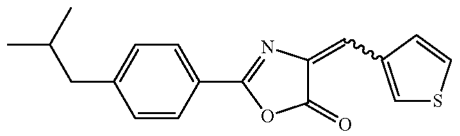 [SMILES: CC(C)Cc1ccc(C2=NC(=Cc3ccsc3)C(=O)O2)cc1] |
| F16 | 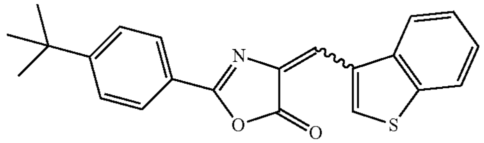 [SMILES: CC(C)(C)c1ccc(C2=NC(=Cc3csc4ccccc34)C(=O)O2)cc1] |
| F17 | 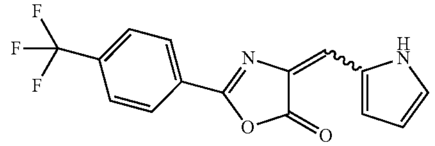 [SMILES: O=C1OC(c2ccc(C(F)(F)F)cc2)=NC1=Cc1ccc[nH]1] |
| F18 | 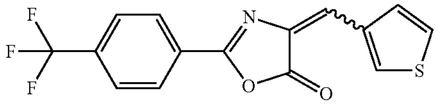 [SMILES: O=C1OC(c2ccc(C(F)(F)F)cc2)=NC1=Cc1ccsc1] |
| F19 | 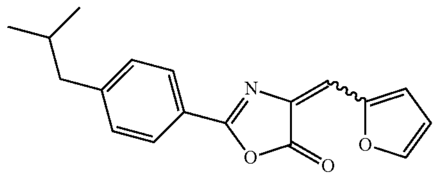 [SMILES: CC(C)Cc1ccc(C2=NC(=Cc3ccco3)C(=O)O2)cc1] |
| F20 | 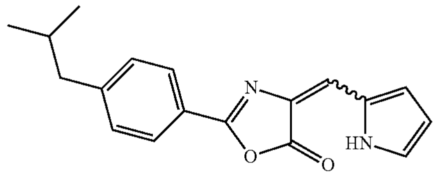 [SMILES: CC(C)Cc1ccc(C2=NC(=Cc3ccc[nH]3)C(=O)O2)cc1] |
| F21 | 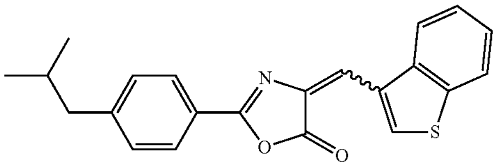 [SMILES: CC(C)Cc1ccc(C2=NC(=Cc3csc4ccccc34)C(=O)O2)cc1] |
| F22 | 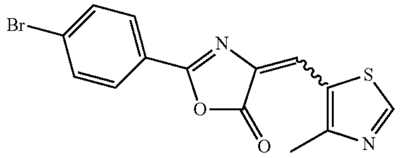 [SMILES: Cc1ncsc1C=C1N=C(c2ccc(Br)cc2)OC1=O] |
| F23 | 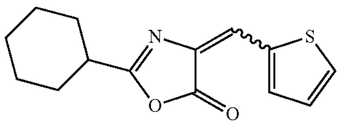 [SMILES: O=C1OC(C2CCCCC2)=NC1=Cc1cccs1] |
| F24 | 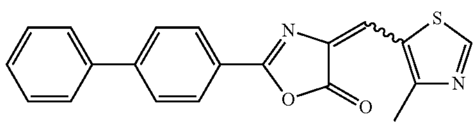 [SMILES: Cc1ncsc1C=C1N=C(c2ccc(-c3ccccc3)cc2)OC1=O] |

TABLE 1-continued
| Compound No. | Structural formula |
|---|---|
| F25 | 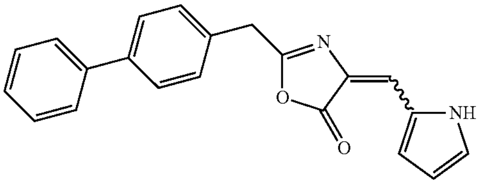 [SMILES: O=C1OC(Cc2ccc(-c3ccccc3)cc2)=NC1=Cc1ccc[nH]1] |
| F26 | 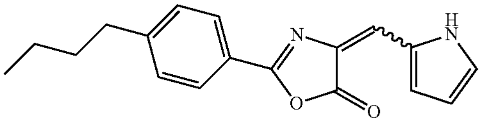 [SMILES: CCCCc1ccc(C2=NC(=Cc3ccc[nH]3)C(=O)O2)cc1] |
| F27 | 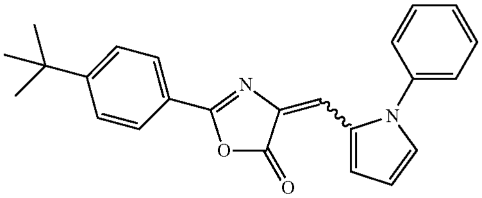 [SMILES: CC(C)(C)c1ccc(C2=NC(=Cc3cccn3-c3ccccc3)C(=O)O2)cc1] |
| F28 | 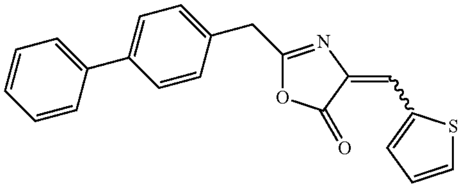 [SMILES: O=C1OC(Cc2ccc(-c3ccccc3)cc2)=NC1=Cc1cccs1] |
| F29 | 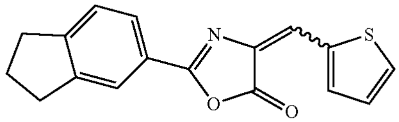 [SMILES: O=C1OC(c2ccc3c(c2)CCC3)=NC1=Cc1cccs1] |
| F30 | 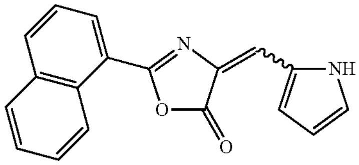 [SMILES: O=C1OC(c2cccc3ccccc23)=NC1=Cc1ccc[nH]1] |
| F31 | 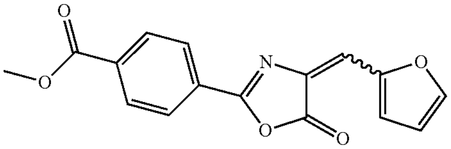 [SMILES: COC(=O)c1ccc(C2=NC(=Cc3ccco3)C(=O)O2)cc1] |
| F32 | 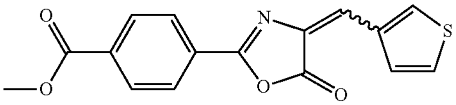 [SMILES: COC(=O)c1ccc(C2=NC(=Cc3ccsc3)C(=O)O2)cc1] |
| F33 | 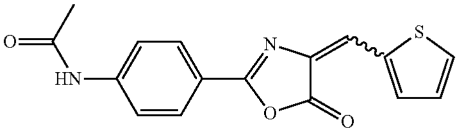 [SMILES: CC(=O)Nc1ccc(C2=NC(=Cc3cccs3)C(=O)O2)cc1] |

TABLE 1-continued
| Compound No. | Structural formula |
|---|---|
| F34 | 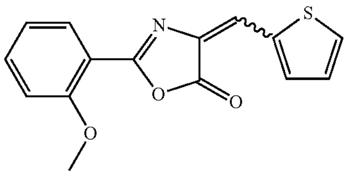 [SMILES: COc1ccccc1C1=NC(=Cc2cccs2)C(=O)O1] |
| F35 | 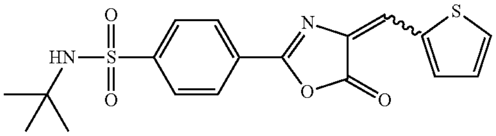 [SMILES: CC(C)(C)NS(=O)(=O)c1ccc(C2=NC(=Cc3cccs3)C(=O)O2)cc1] |
| F36 | 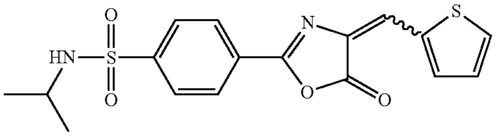 [SMILES: CC(C)NS(=O)(=O)c1ccc(C2=NC(=Cc3cccs3)C(=O)O2)cc1] |
| F37 | 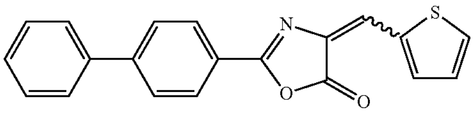 [SMILES: O=C1OC(c2ccc(-c3ccccc3)cc2)=NC1=Cc1cccs1] |
| F38 | 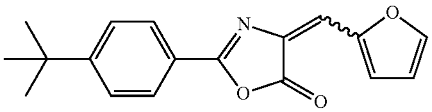 |
| F39 | 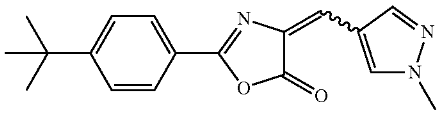 [SMILES: Cn1cc(C=C2N=C(c3ccc(C(C)(C)C)cc3)OC2=O)cn1] |
| F40 | 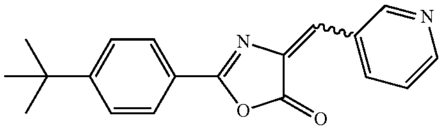 [SMILES: CC(C)(C)c1ccc(C2=NC(=Cc3cccnc3)C(=O)O2)cc1] |
| F41 | 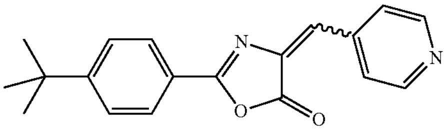 [SMILES: CC(C)(C)c1ccc(C2=NC(=Cc3ccncc3)C(=O)O2)cc1] |
| F42 | 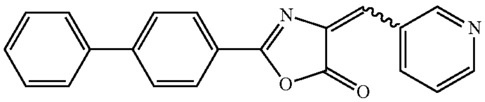 [SMILES: O=C1OC(c2ccc(-c3ccccc3)cc2)=NC1=Cc1cccnc1] |
| F43 | 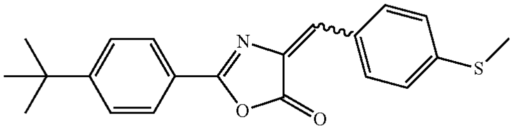 [SMILES: CSc1ccc(C=C2N=C(c3ccc(C(C)(C)C)cc3)OC2=O)cc1] |
| F44 | 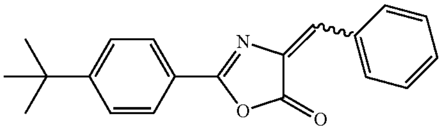 [SMILES: CC(C)(C)c1ccc(C2=NC(=Cc3ccccc3)C(=O)O2)cc1] |

TABLE 1-continued
| Compound No. | Structural formula |
| --- | --- |
| F45 | 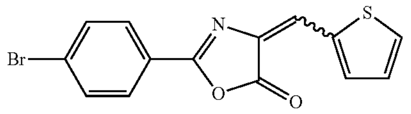 [SMILES: O=C1OC(c2ccc(Br)cc2)=NC1=Cc1cccs1] |
| F46 | 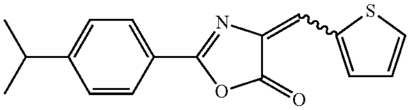 [SMILES: CC(C)c1ccc(C2=NC(=Cc3cccs3)C(=O)O2)cc1] |
| F47 | 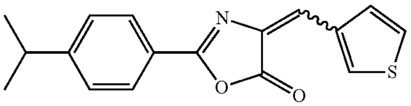 [SMILES: CC(C)c1ccc(C2=NC(=Cc3ccsc3)C(=O)O2)cc1] |
| F48 | 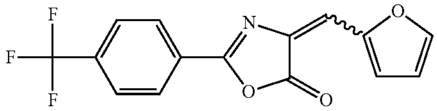 [SMILES: O=C1OC(c2ccc(C(F)(F)F)cc2)=NC1=Cc1ccco1] |
| F49 | 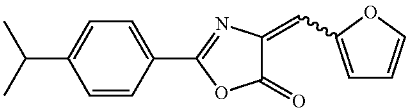 [SMILES: CC(C)c1ccc(C2=NC(=Cc3ccco3)C(=O)O2)cc1] |
| F50 | 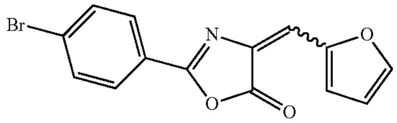 [SMILES: O=C1OC(c2ccc(Br)cc2)=NC1=Cc1ccco1] |
| F51 | 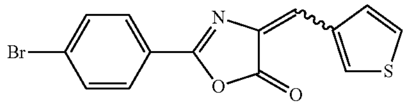 [SMILES: O=C1OC(c2ccc(Br)cc2)=NC1=Cc1ccsc1] |
| F52 | 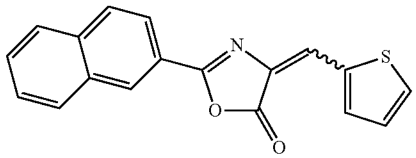 [SMILES: O=C1OC(c2ccc3ccccc3c2)=NC1=Cc1cccs1] |
| F53 | 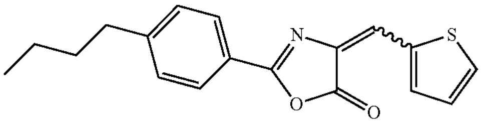 [SMILES: CCCCc1ccc(C2=NC(=Cc3cccs3)C(=O)O2)cc1] |
| F54 | 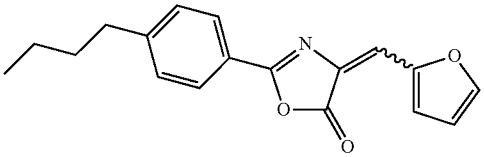 [SMILES: CCCCc1ccc(C2=NC(=Cc3ccco3)C(=O)O2)cc1] |
| F55 | 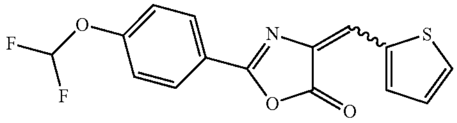 [SMILES: O=C1OC(c2ccc(OC(F)F)cc2)=NC1=Cc1cccs1] |

TABLE 1-continued
| Compound No. | Structural formula |
|---|---|
| F56 | 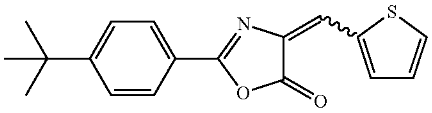 [SMILES: CC(C)(C)c1ccc(C2=NC(=Cc3cccs3)C(=O)O2)cc1] |
| F57 | 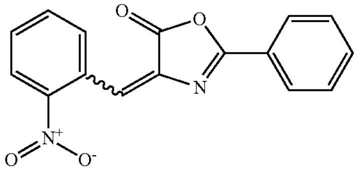 [SMILES: O=C1OC(c2ccccc2)=NC1=Cc1ccccc1[N+](=O)[O-]] |
| F58 | 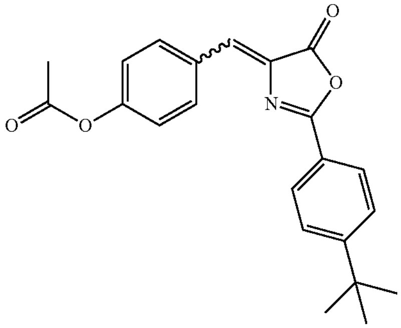 [SMILES: CC(=O)Oc1ccc(C=C2N=C(c3ccc(C(C)(C)C)cc3)OC2=O)cc1] |
| F59 | 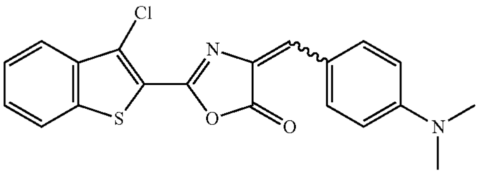 [SMILES: CN(C)c1ccc(C=C2N=C(c3sc4ccccc4c3Cl)OC2=O)cc1] |
| F60 | 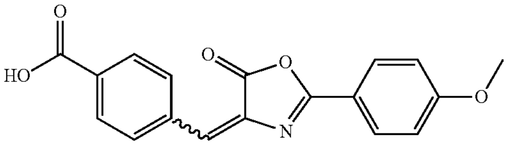 [SMILES: COc1ccc(C2=NC(=Cc3ccc(C(=O)O)cc3)C(=O)O2)cc1] |
| F61 | 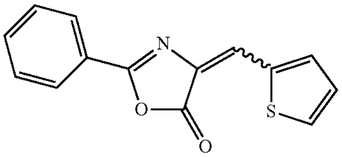 [SMILES: O=C1OC(c2ccccc2)=NC1=Cc1cccs1] |
| F62 | 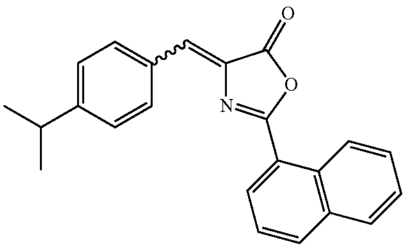 [SMILES: CC(C)c1ccc(C=C2N=C(c3cccc4ccccc34)OC2=O)cc1] |

TABLE 1-continued
| Compound No. | Structural formula |
| --- | --- |
| F63 | 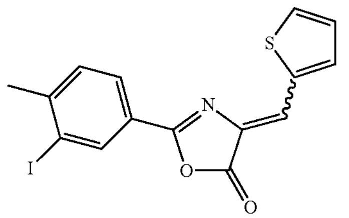 [SMILES: Cc1ccc(C2=NC(=Cc3cccs3)C(=O)O2)cc1I] |
| F64 | 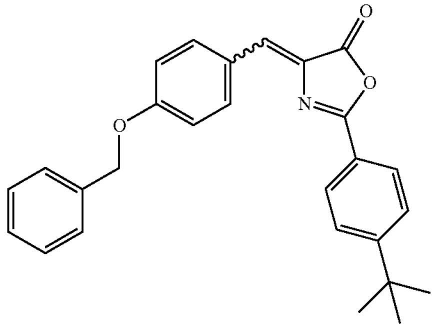 [SMILES: CC(C)(C)c1ccc(C2=NC(=Cc3ccc(OCc4ccccc4)cc3)C(=O)O2)cc1] |
| F65 | 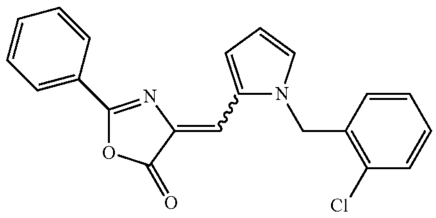 [SMILES: O=C1OC(c2ccccc2)=NC1=Cc1cccn1Cc1ccccc1Cl] |
| F66 | 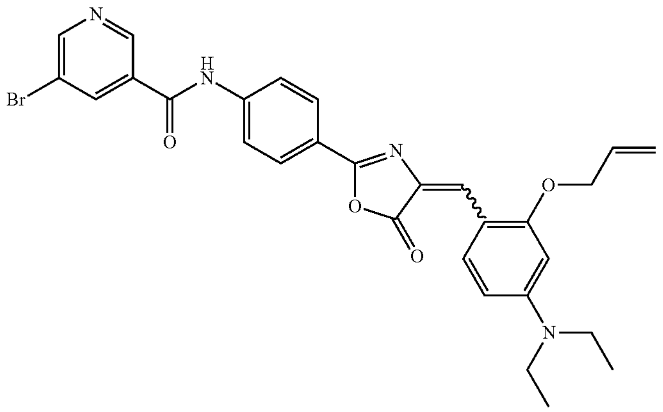 [SMILES: C=CCOc1cc(N(CC)CC)ccc1C=C1N=C(c2ccc(NC(=O)c3cncc(Br)c3)cc2)OC1=O] |
| F67 | 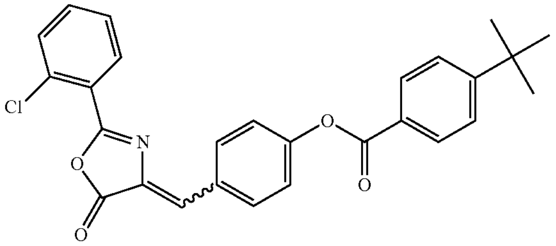 [SMILES: CC(C)(C)c1ccc(C(=O)Oc2ccc(C=C3N=C(c4ccccc4Cl)OC3=O)cc2)cc1] |

TABLE 1-continued
| Compound No. | Structural formula |
| --- | --- |
| F68 | 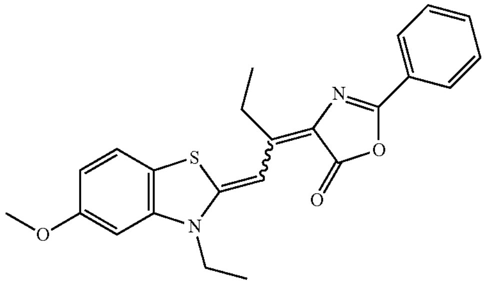 [SMILES: CCC(C=C1Sc2ccc(OC)cc2N1CC)=C1N=C(c2ccccc2)OC1=O] |
| F69 | 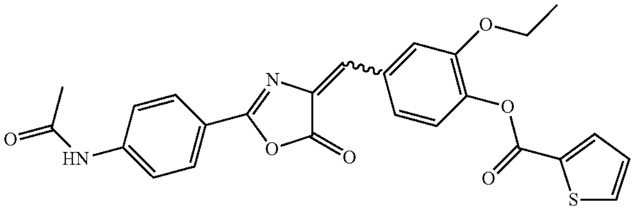 [SMILES: CCOc1cc(C=C2N=C(c3ccc(NC(C)=O)cc3)OC2=O)ccc1OC(=O)c1cccs1] |
| F70 | 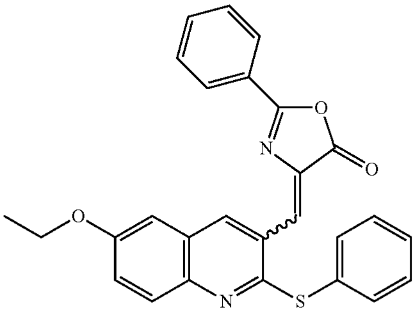 [SMILES: CCOc1ccc2nc(Sc3ccccc3)c(C=C3N=C(c4ccccc4)OC3=O)cc2c1] |
| F71 | 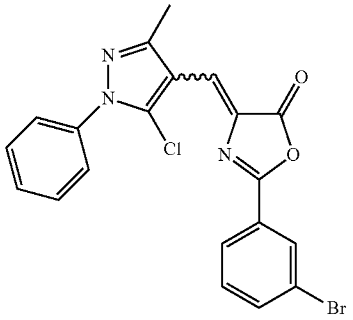 [SMILES: Cc1nn(-c2ccccc2)c(Cl)c1C=C1N=C(c2cccc(Br)c2)OC1=O] |
| F72 | 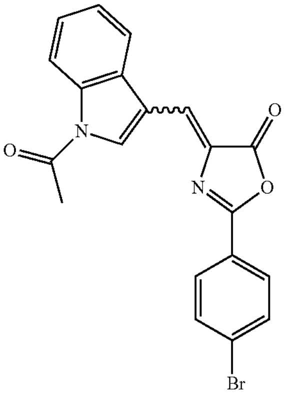 [SMILES: CC(=O)n1cc(C=C2N=C(c3ccc(Br)cc3)OC2=O)c2ccccc21] |

TABLE 1-continued
| Compound No. | Structural formula |
|---|---|
| F73 | 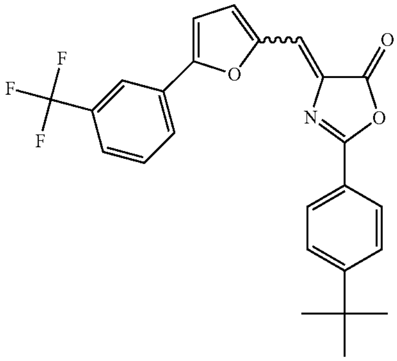 [SMILES: CC(C)(C)c1ccc(C2=NC(=Cc3ccc(-c4cccc(C(F)(F)F)c4)o3)C(=O)O2)cc1] |
| F74 | 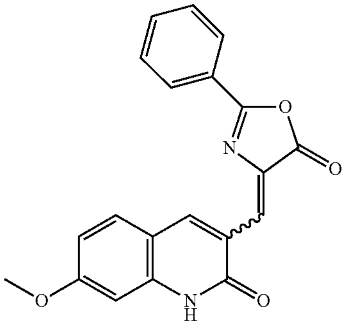 [SMILES: COc1ccc2cc(C=C3N=C(c4ccccc4)OC3=O)c(=O)[nH]c2c1] |
| F75 | 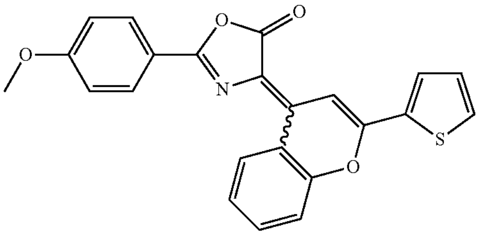 [SMILES: COc1ccc(C2=NC(=C3C=C(c4cccs4)Oc4ccccc43)C(=O)O2)cc1] |
| F76 | 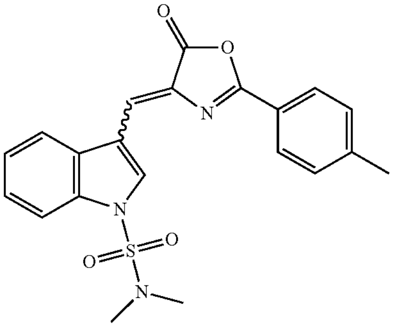 [SMILES: Cc1ccc(C2=NC(=Cc3cn(S(=O)(=O)N(C)C)c4ccccc34)C(=O)O2)cc1] |

TABLE 1-continued
| Compound No. | Structural formula |
| --- | --- |
| F77 | 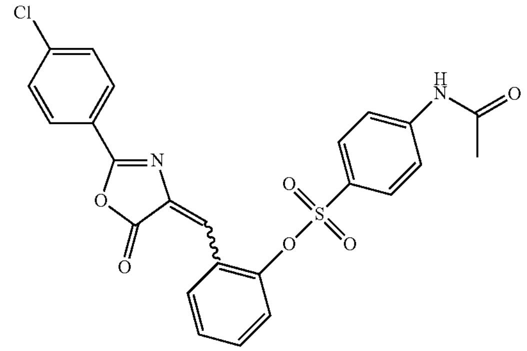 [SMILES: CC(=O)Nc1ccc(S(=O)(=O)Oc2ccccc2C=C2N=C(c3ccc(Cl)cc3)OC2=O)cc1] |
| F78 | 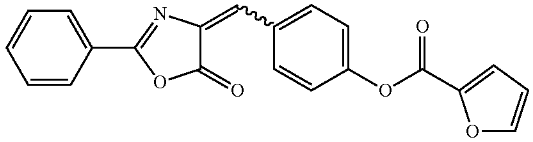 [SMILES: O=C1OC(c2ccccc2)=NC1=Cc1ccc(OC(=O)c2ccco2)cc1] |
| F79 | 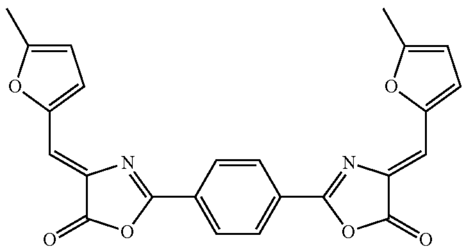 [SMILES: Cc1ccc(/C=C2\N=C(c3ccc(C4=N/C(=C\c5ccc(C)o5)C(=O)O4)cc3)OC2=O)o1] |
| F80 | 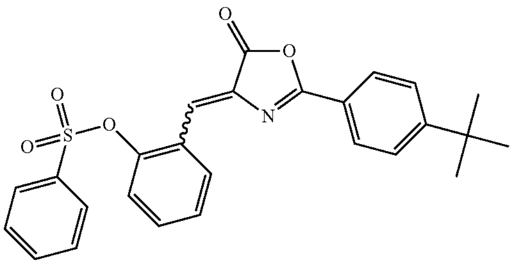 [SMILES: CC(C)(C)c1ccc(C2=NC(=Cc3ccccc3OS(=O)(=O)c3ccccc3)C(=O)O2)cc1] |
| F81 | 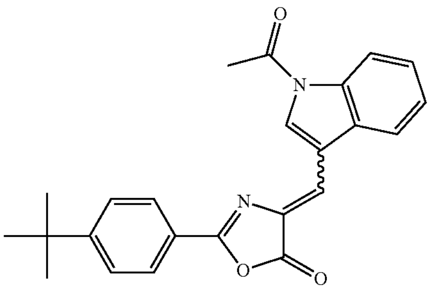 [SMILES: CC(=O)n1cc(C=C2N=C(c3ccc(C(C)(C)C)cc3)OC2=O)c2ccccc21] |

TABLE 1-continued
| Compound No. | Structural formula |
|---|---|
| F82 | 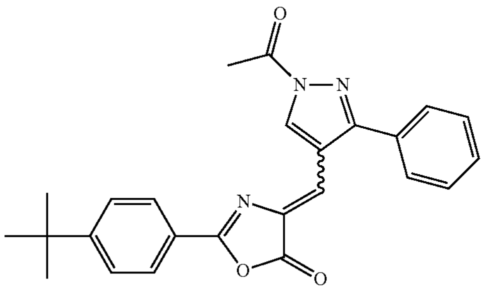 [SMILES: CC(=O)n1cc(C=C2N=C(c3ccc(C(C)(C)C)cc3)OC2=O)c(-c2ccccc2)n1] |
| F83 | 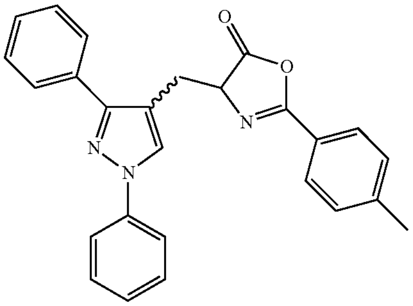 [SMILES: Cc1ccc(C2=NC(Cc3cn(-c4ccccc4)nc3-c3ccccc3)C(=O)O2)cc1] |
| F84 | 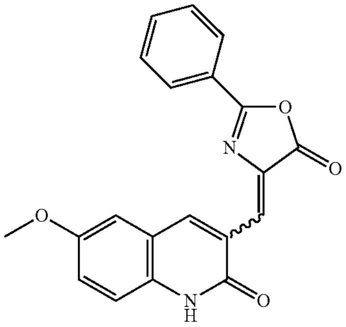 [SMILES: COc1ccc2[nH]c(=O)c(C=C3N=C(c4ccccc4)OC3=O)cc2c1] |
| F85 | 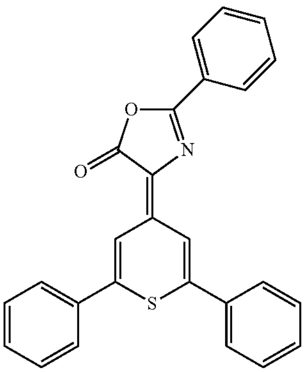 [SMILES: O=C1OC(c2ccccc2)=NC1=C1C=C(c2ccccc2)SC(c2ccccc2)=C1] |
| F86 | 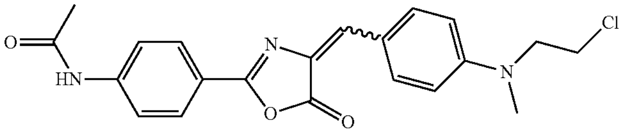 [SMILES: CC(=O)Nc1ccc(C2=NC(=Cc3ccc(N(C)CCCl)cc3)C(=O)O2)cc1] |

TABLE 1-continued
| Compound No. | Structural formula |
|---|---|
| F87 | 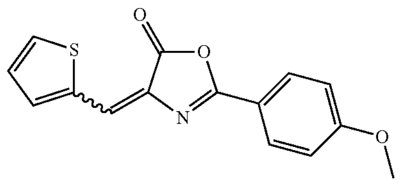 [SMILES: COc1ccc(C2=NC(=Cc3cccs3)C(=O)O2)cc1] |
| F88 | 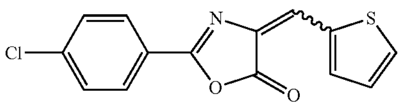 [SMILES: O=C1OC(c2ccc(Cl)cc2)=NC1=Cc1cccs1] |
| F89 | 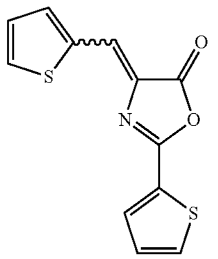 [SMILES: O=C1OC(c2cccs2)=NC1=Cc1cccs1] |
| F90 | 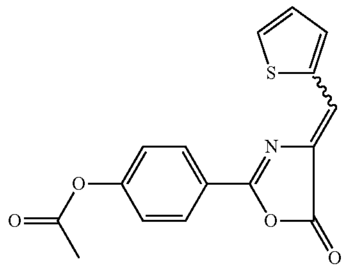 [SMILES: CC(=O)Oc1ccc(C2=NC(=Cc3cccs3)C(=O)O2)cc1] |
| F91 | 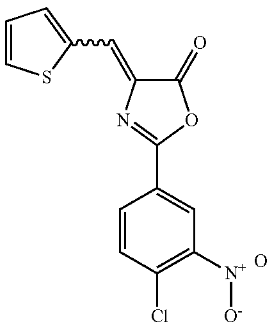 |
| F92 | 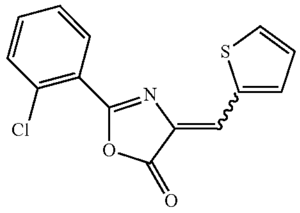 [SMILES: O=C1OC(c2ccccc2Cl)=NC1=Cc1cccs1] |

TABLE 1-continued
| Compound No. | Structural formula |
| --- | --- |
| F93 | 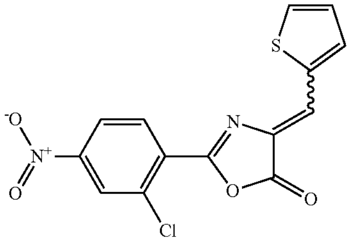 |
| F94 | 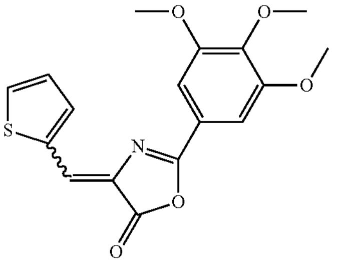 [SMILES: COc1cc(C2=NC(=Cc3cccs3)C(=O)O2)cc(OC)c1OC] |
| F95 | 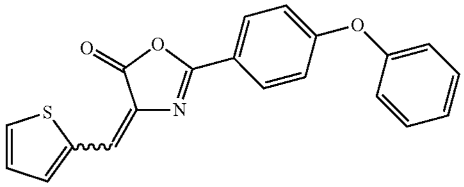 [SMILES: O=C1OC(c2ccc(Oc3ccccc3)cc2)=NC1=Cc1cccs1] |
| F96 | 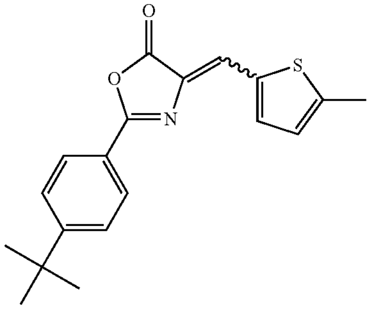 [SMILES: Cc1ccc(C=C2N=C(c3ccc(C(C)(C)C)cc3)OC2=O)s1] |
| F97 | 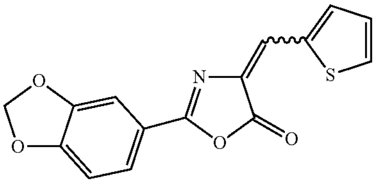 [SMILES: O=C1OC(c2ccc3c(c2)OCO3)=NC1=Cc1cccs1] |
| F98 | 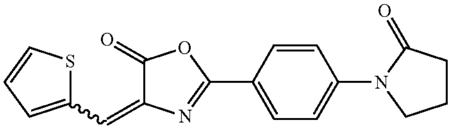 [SMILES: O=C1OC(c2ccc(N3CCCC3=O)cc2)=NC1=Cc1cccs1] |
| F99 | 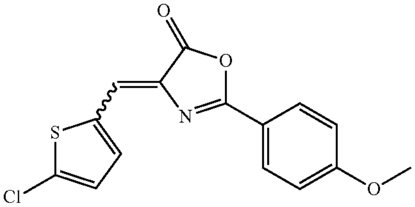 [SMILES: COc1ccc(C2=NC(=Cc3ccc(Cl)s3)C(=O)O2)cc1] |

TABLE 1-continued
| Compound No. | Structural formula |
| --- | --- |
| F100 | 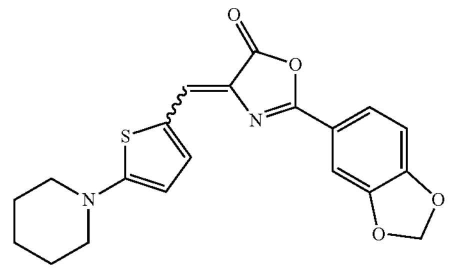 [SMILES: O=C1OC(c2ccc3c(c2)OCO3)=NC1=Cc1ccc(N2CCCCC2)s1] |
| F101 | 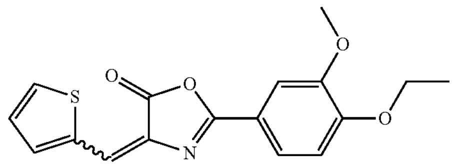 [SMILES: CCOc1ccc(C2=NC(=Cc3cccs3)C(=O)O2)cc1OC] |
| F102 | 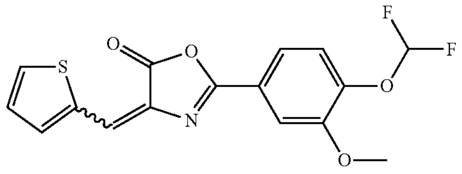 [SMILES: COc1cc(C2=NC(=Cc3cccs3)C(=O)O2)ccc1OC(F)F] |
| F103 | 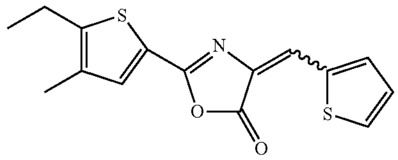 [SMILES: CCc1sc(C2=NC(=Cc3cccs3)C(=O)O2)cc1C] |
| F104 | 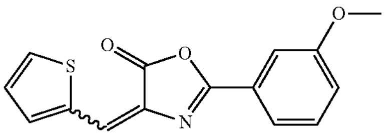 [SMILES: COc1cccc(C2=NC(=Cc3cccs3)C(=O)O2)c1] |
| F105 | 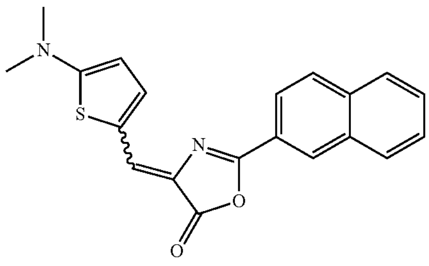 [SMILES: CN(C)c1ccc(C=C2N=C(c3ccc4ccccc4c3)OC2=O)s1] |
| F106 | 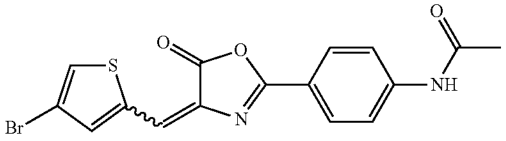 [SMILES: CC(=O)Nc1ccc(C2=NC(=Cc3cc(Br)cs3)C(=O)O2)cc1] |

TABLE 1-continued
| Compound No. | Structural formula |
|---|---|
| F107 | 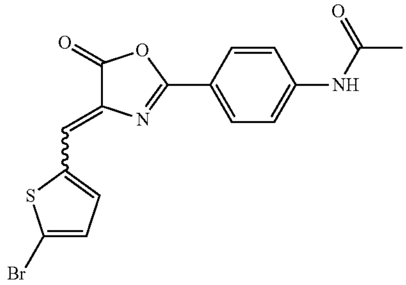 [SMILES: CC(=O)Nc1ccc(C2=NC(=Cc3ccc(Br)s3)C(=O)O2)cc1] |
| F108 | 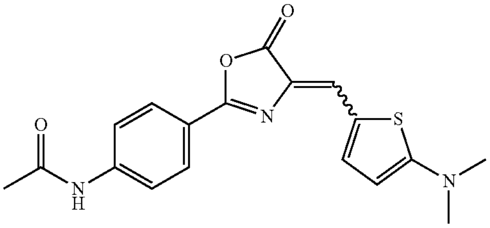 [SMILES: CC(=O)Nc1ccc(C2=NC(=Cc3ccc(N(C)C)s3)C(=O)O2)cc1] |
| F109 | 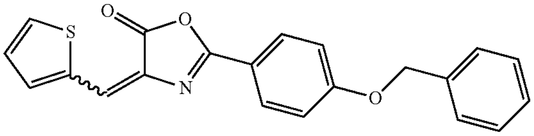 [SMILES: O=C1OC(c2ccc(OCc3ccccc3)cc2)=NC1=Cc1cccs1] |
| F110 | 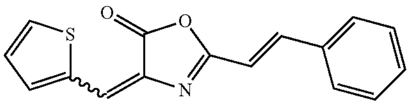 [SMILES: O=C1OC(/C=C/c2ccccc2)=NC1=Cc1cccs1] |
| F111 | 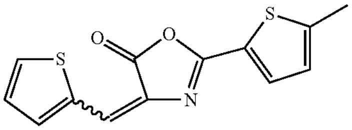 [SMILES: Cc1ccc(C2=NC(=Cc3cccs3)C(=O)O2)s1] |
| F112 | 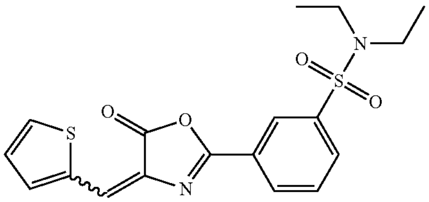 [SMILES: CCN(CC)S(=O)(=O)c1cccc(C2=NC(=Cc3cccs3)C(=O)O2)c1] |
| F113 | 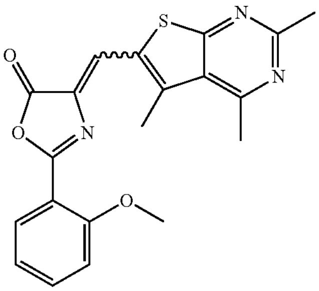 [SMILES: COc1ccccc1C1=NC(=Cc2sc3nc(C)nc(C)c3c2C)C(=O)O1] |

TABLE 1-continued
| Compound No. | Structural formula |
|---|---|
| F114 | 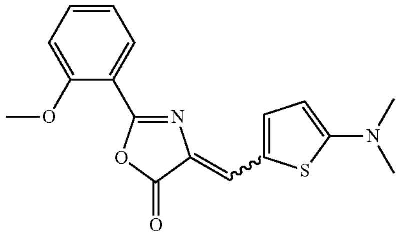 |
| F115 | 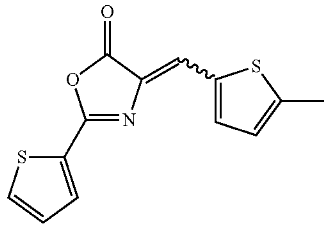 [SMILES: Cc1ccc(C=C2N=C(c3cccs3)OC2=O)s1] |
| F116 | 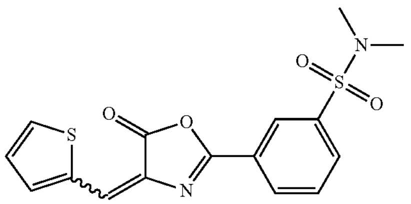 [SMILES: CN(C)S(=O)(=O)c1cccc(C2=NC(=Cc3cccs3)C(=O)O2)c1] |
| F117 | 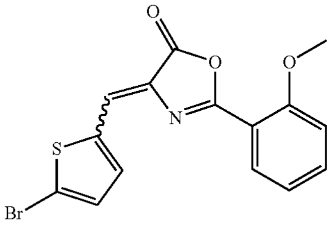 [SMILES: COc1ccccc1C1=NC(=Cc2ccc(Br)s2)C(=O)O1] |
| F118 | 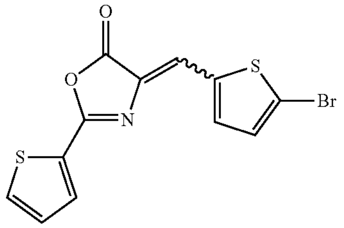 [SMILES: O=C1OC(c2cccs2)=NC1=Cc1ccc(Br)s1] |
| F119 | 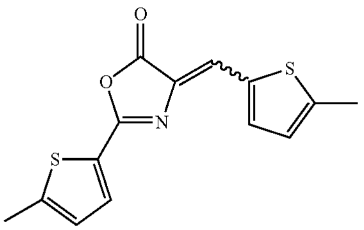 |

TABLE 1-continued
| Compound No. | Structural formula |
| --- | --- |
| F120 | 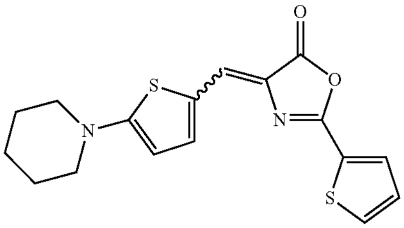 [SMILES: O=C1OC(c2cccs2)=NC1=Cc1ccc(N2CCCCC2)s1] |
| F121 | 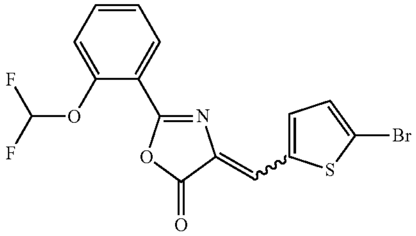 [SMILES: O=C1OC(c2ccccc2OC(F)F)=NC1=Cc1ccc(Br)s1] |
| F122 | 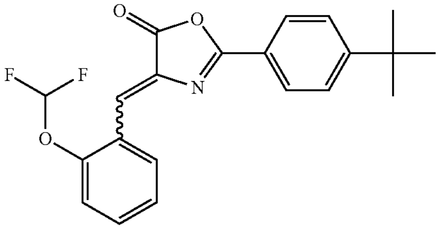 [SMILES: CC(C)(C)c1ccc(C2=NC(=Cc3ccccc3OC(F)F)C(=O)O2)cc1] |
| F123 | 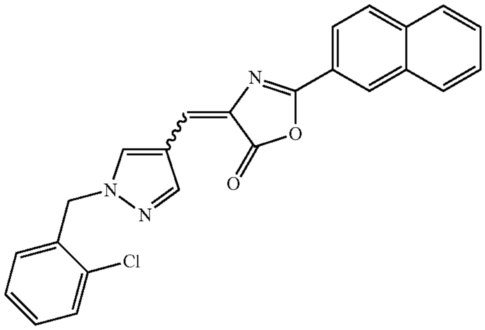 [SMILES: O=C1OC(c2ccc3ccccc3c2)=NC1=Cc1cnn(Cc2ccccc2Cl)c1] |
| F124 | 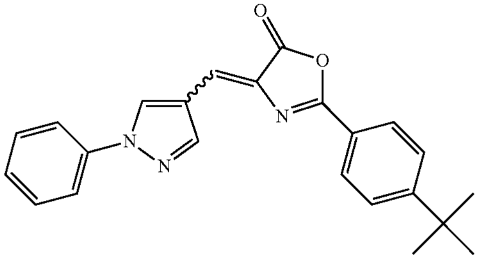 [SMILES: CC(C)(C)c1ccc(C2=NC(=Cc3cnn(-c4ccccc4)c3)C(=O)O2)cc1] |
| F125 | 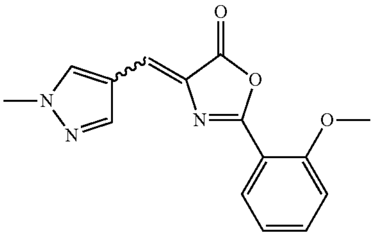 |

TABLE 1-continued
| Compound No. | Structural formula |
|---|---|
| F126 | 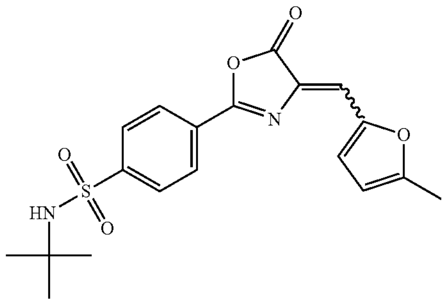 [SMILES: Cc1ccc(C=C2N=C(c3ccc(S(=O)(=O)NC(C)(C)C)cc3)OC2=O)o1] |
| F127 | 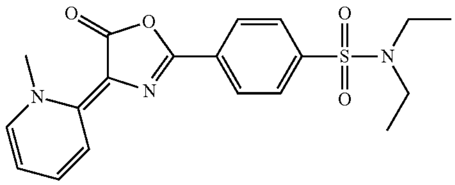 [SMILES: CCN(CC)S(=O)(=O)c1ccc(C2=N/C(=C3\C=CC=CN3C)C(=O)O2)cc1] |
| F128 | 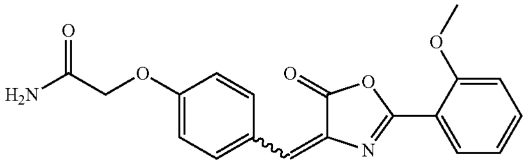 [SMILES: COc1ccccc1C1=NC(=Cc2ccc(OCC(N)=O)cc2)C(=O)O1] |
| F129 | 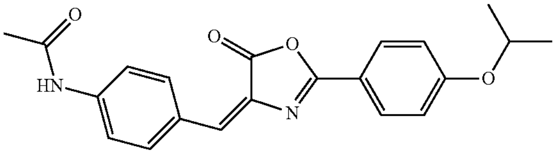 [SMILES: CC(=O)Nc1ccc(/C=C2/N=C(c3ccc(OC(C)C)cc3)OC2=O)cc1] |
| F130 | 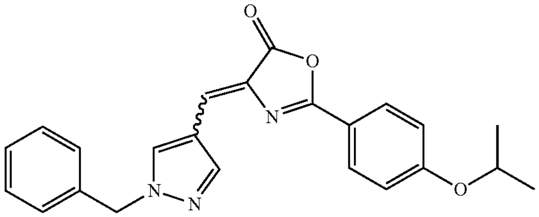 [SMILES: CC(C)Oc1ccc(C2=NC(=Cc3cnn(Cc4ccccc4)c3)C(=O)O2)cc1] |
| F131 | 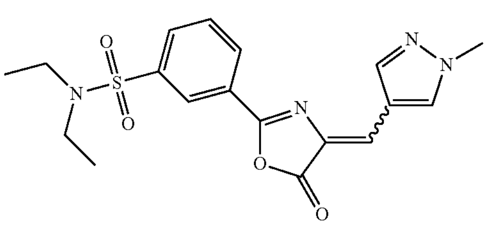 [SMILES: CCN(CC)S(=O)(=O)c1cccc(C2=NC(=Cc3cnn(C)c3)C(=O)O2)c1] |
| F132 | 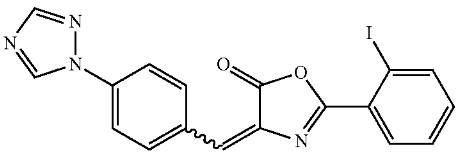 [SMILES: O=C1OC(c2ccccc2I)=NC1=Cc1ccc(-n2cncn2)cc1] |

TABLE 1-continued
| Compound No. | Structural formula |
|---|---|
| F133 | 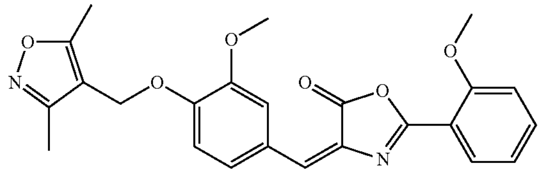 [SMILES: COc1cc(/C=C2/N=C(c3ccccc3OC)OC2=O)ccc1OCc1c(C)noc1C] |
| F134 | 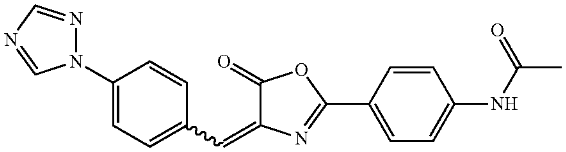 [SMILES: CC(=O)Nc1ccc(C2=NC(=Cc3ccc(-n4cncn4)cc3)C(=O)O2)cc1] |
| F135 | 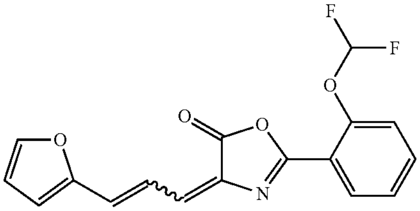 [SMILES: O=C1OC(c2ccccc2OC(F)F)=NC1=CC=Cc1ccco1] |
| F136 | 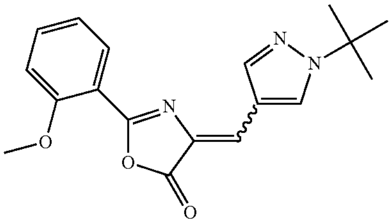 [SMILES: COc1ccccc1C1=NC(=Cc2cnn(C(C)(C)C)c2)C(=O)O1] |
| F137 | 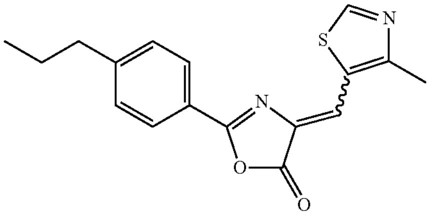 [SMILES: CCCc1ccc(C2=NC(=Cc3scnc3C)C(=O)O2)cc1] |
| F138 | 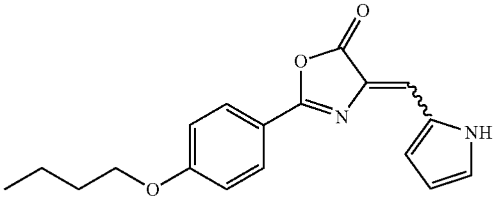 [SMILES: CCCCOc1ccc(C2=NC(=Cc3ccc[nH]3)C(=O)O2)cc1] |
| F139 | 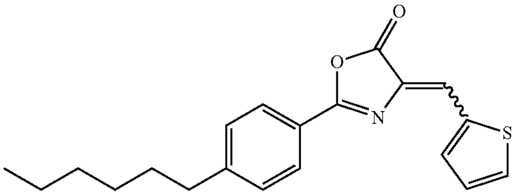 [SMILES: CCCCCCc1ccc(C2=NC(=Cc3cccs3)C(=O)O2)cc1] |

TABLE 1-continued
| Compound No. | Structural formula |
|---|---|
| F140 | 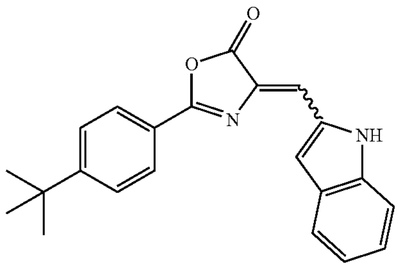 [SMILES: CC(C)(C)c1ccc(C2=NC(=Cc3cc4ccccc4[nH]3)C(=O)O2)cc1] |
| F141 | 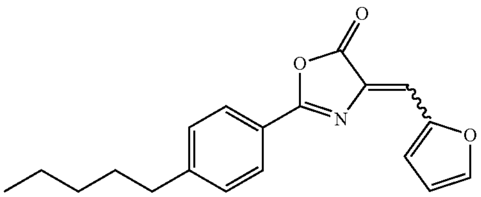 [SMILES: CCCCCc1ccc(C2=NC(=Cc3ccco3)C(=O)O2)cc1] |
| F142 | 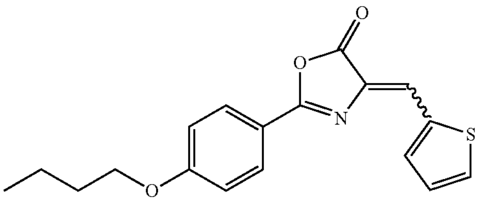 [SMILES: CCCCOc1ccc(C2=NC(=Cc3cccs3)C(=O)O2)cc1] |
| F143 | 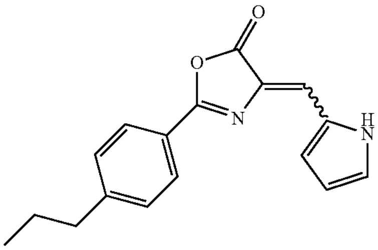 [SMILES: CCCc1ccc(C2=NC(=Cc3ccc[nH]3)C(=O)O2)cc1] |
| F144 | 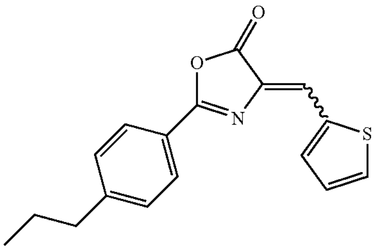 [SMILES: CCCc1ccc(C2=NC(=Cc3cccs3)C(=O)O2)cc1] |
| F145 | 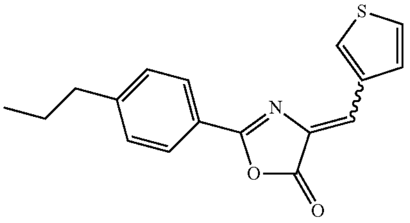 [SMILES: CCCc1ccc(C2=NC(=Cc3ccsc3)C(=O)O2)cc1] |

TABLE 1-continued
| Compound No. | Structural formula |
|---|---|
| F146 | 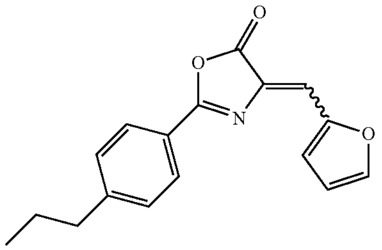 [SMILES: CCCc1ccc(C2=NC(=Cc3ccco3)C(=O)O2)cc1] |
| F147 | 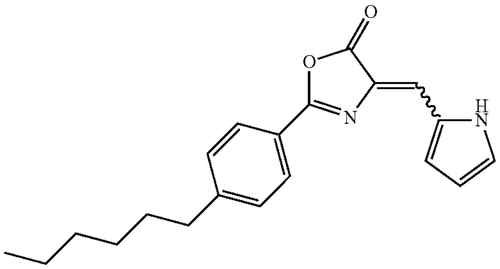 [SMILES: CCCCCCc1ccc(C2=NC(=Cc3ccc[nH]3)C(=O)O2)cc1] |
| F148 | 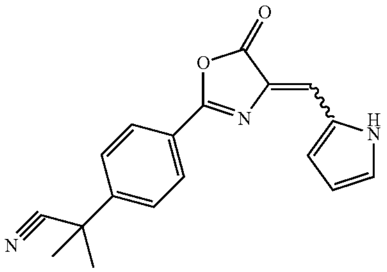 [SMILES: CC(C)(C#N)c1ccc(C2=NC(=Cc3ccc[nH]3)C(=O)O2)cc1] |
| F149 | 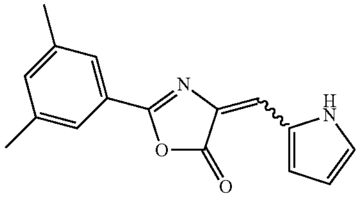 [SMILES: Cc1cc(C)cc(C2=NC(=Cc3ccc[nH]3)C(=O)O2)c1] |
| F150 | 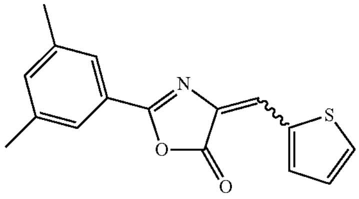 [SMILES: Cc1cc(C)cc(C2=NC(=Cc3cccs3)C(=O)O2)c1] |

TABLE 2
| Compound No. | Structural formula |
|---|---|
| G1 | 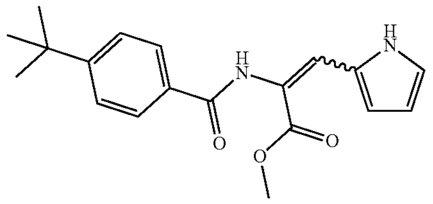 [SMILES: COC(=O)C(=Cc1ccc[nH]1)NC(=O)c1ccc(C(C)(C)C)cc1] |
| G2 | 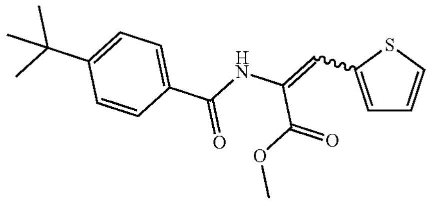 [SMILES: COC(=O)C(=Cc1cccs1)NC(=O)c1ccc(C(C)(C)C)cc1] |
| G3 | 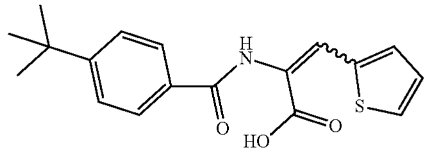 [SMILES: CC(C)(C)c1ccc(C(=O)NC(=Cc2cccs2)C(=O)O)cc1] |
| G4 | 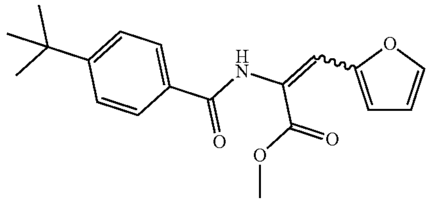 [SMILES: COC(=O)C(=Cc1ccco1)NC(=O)c1ccc(C(C)(C)C)cc1] |
| G5 | 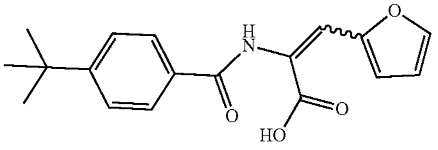 [SMILES: CC(C)(C)c1ccc(C(=O)NC(=Cc2ccco2)C(=O)O)cc1] |
| G6 | 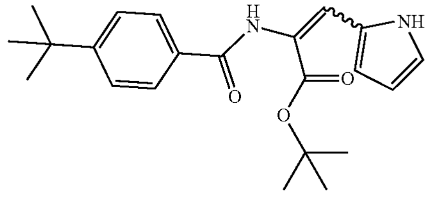 [SMILES: CC(C)(C)OC(=O)C(=Cc1ccc[nH]1)NC(=O)c1ccc(C(C)(C)C)cc1] |
| G7 | 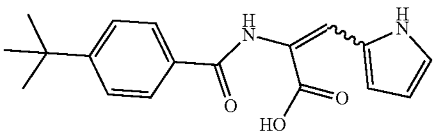 [SMILES: CC(C)(C)c1ccc(C(=O)NC(=Cc2ccc[nH]2)C(=O)O)cc1] |
| G8 | 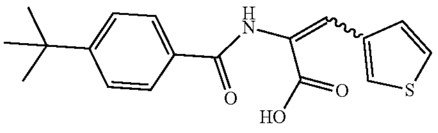 [SMILES: CC(C)(C)c1ccc(C(=O)NC(=Cc2ccsc2)C(=O)O)cc1] |
TABLE 2-continued
| Compound No. | Structural formula |
|---|---|
| G9 | 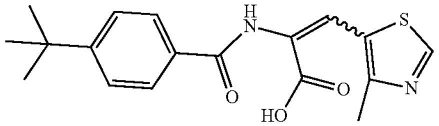 [SMILES: Cc1ncsc1C=C(NC(=O)c1ccc(C(C)(C)C)cc1)C(=O)O] |
| G10 | 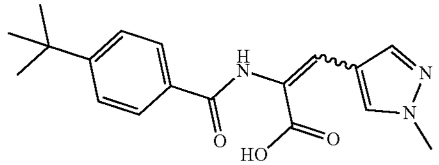 [SMILES: Cn1cc(C=C(NC(=O)c2ccc(C(C)(C)C)cc2)C(=O)O)cn1] |
| G11 | 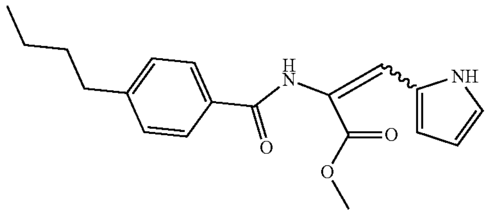 [SMILES: CCCCc1ccc(C(=O)NC(=Cc2ccc[nH]2)C(=O)OC)cc1] |
| G12 | 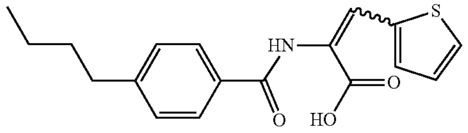 [SMILES: CCCCc1ccc(C(=O)NC(=Cc2cccs2)C(=O)O)cc1] |
| G13 | 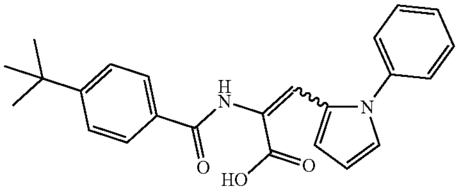 [SMILES: CC(C)(C)c1ccc(C(=O)NC(=Cc2cccn2-c2ccccc2)C(=O)O)cc1] |
| G14 | 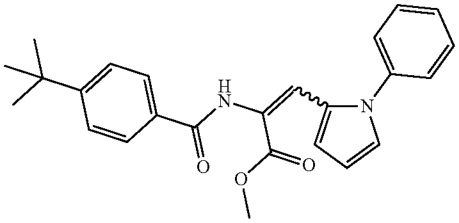 [SMILES: COC(=O)C(=Cc1cccn1-c1ccccc1)NC(=O)c1ccc(C(C)(C)C)cc1] |
| G15 | 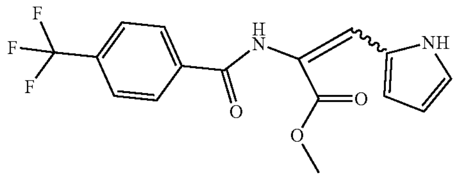 [SMILES: COC(=O)C(=Cc1ccc[nH]1)NC(=O)c1ccc(C(F)(F)F)cc1] |
| G16 | 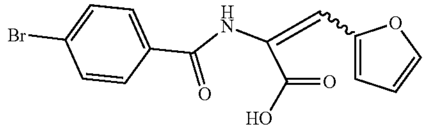 [SMILES: O=C(O)C(=Cc1ccco1)NC(=O)c1ccc(Br)cc1] |

TABLE 2-continued
| Compound No. | Structural formula |
| --- | --- |
| G17 | 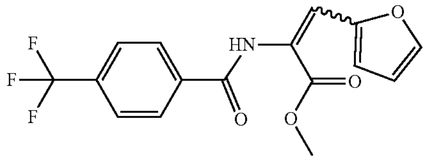 [SMILES: COC(=O)C(=Cc1ccco1)NC(=O)c1ccc(C(F)(F)F)cc1] |
| G18 | 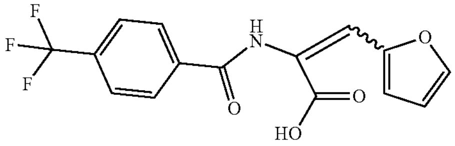 [SMILES: O=C(O)C(=Cc1ccco1)NC(=O)c1ccc(C(F)(F)F)cc1] |
| G19 | 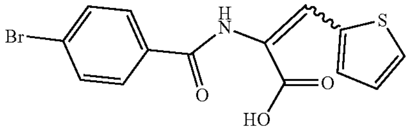 [SMILES: O=C(O)C(=Cc1cccs1)NC(=O)c1ccc(Br)cc1] |
| G20 | 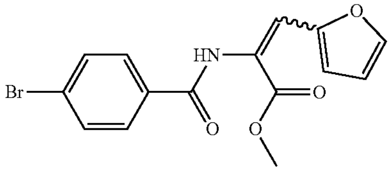 [SMILES: COC(=O)C(=Cc1ccco1)NC(=O)c1ccc(Br)cc1] |
| G21 | 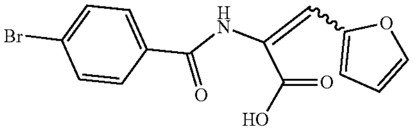 [SMILES: O=C(O)C(=Cc1ccco1)NC(=O)c1ccc(Br)cc1] |
| G22 | 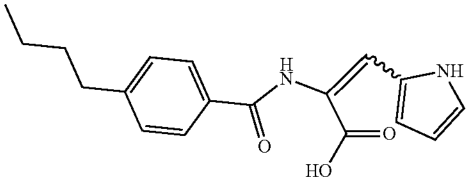 [SMILES: CCCCc1ccc(C(=O)NC(=Cc2ccc[nH]2)C(=O)O)cc1] |
| G23 | 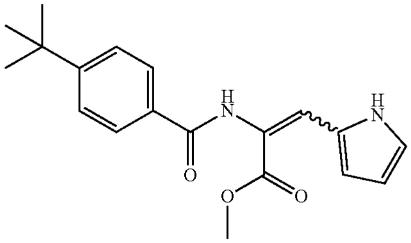 [SMILES: COC(=O)C(=Cc1ccc[nH]1)NC(=O)c1ccc(C(C)(C)C)cc1] |
| G24 | 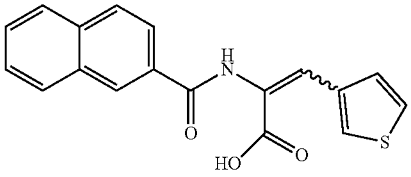 [SMILES: O=C(O)C(=Cc1ccsc1)NC(=O)c1ccc2ccccc2c1] |
TABLE 2-continued
| Compound No. | Structural formula |
| --- | --- |
| G25 | 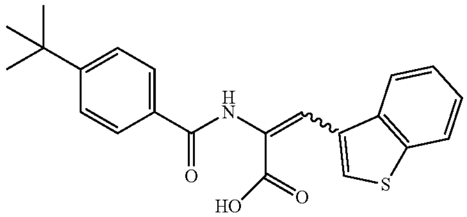 [SMILES: CC(C)(C)c1ccc(C(=O)NC(=Cc2csc3ccccc23)C(=O)O)cc1] |
| G26 | 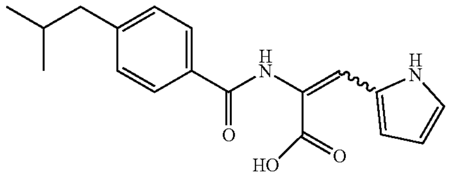 [SMILES: CC(C)Cc1ccc(C(=O)NC(=Cc2ccc[nH]2)C(=O)O)cc1] |
| G27 | 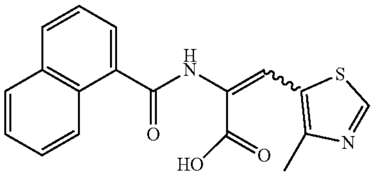 [SMILES: Cc1ncsc1C=C(NC(=O)c1cccc2ccccc12)C(=O)O] |
| G28 | 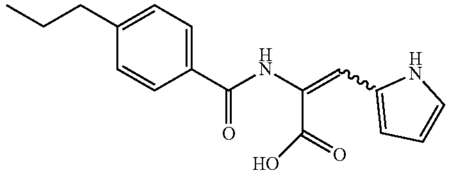 [SMILES: CCCc1ccc(C(=O)NC(=Cc2ccc[nH]2)C(=O)O)cc1] |
| G29 | 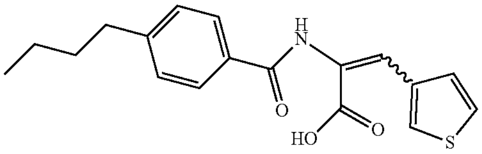 [SMILES: CCCCc1ccc(C(=O)NC(=Cc2ccsc2)C(=O)O)cc1] |
| G30 | 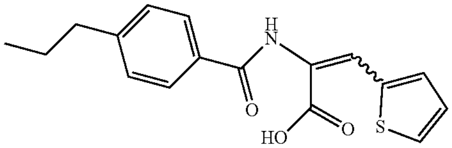 [SMILES: CCCc1ccc(C(=O)NC(=Cc2cccs2)C(=O)O)cc1] |
| G31 | 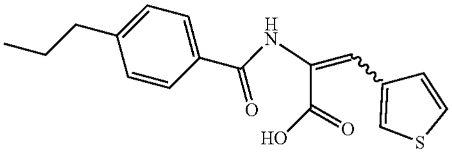 [SMILES: CCCc1ccc(C(=O)NC(=Cc2ccsc2)C(=O)O)cc1] |
| G32 | 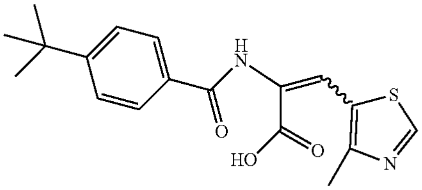 [SMILES: Cc1ncsc1C=C(NC(=O)c1ccc(C(C)(C)C)cc1)C(=O)O] |

TABLE 2-continued

| Compound No. | Structural formula |
|---|---|
| G33 | 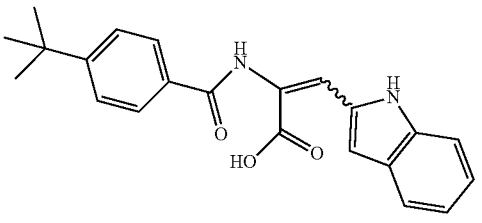 [SMILES: CC(C)(C)c1ccc(C(=O)NC(=Cc2cc3ccccc3[nH]2)C(=O)O)cc1] |
| G34 | 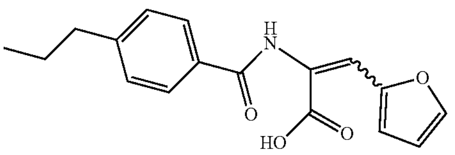 [SMILES: CCCc1ccc(C(=O)NC(=Cc2ccco2)C(=O)O)cc1] |
| G35 | 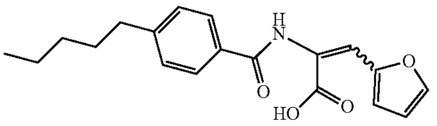 [SMILES: CCCCCc1ccc(C(=O)NC(=Cc2ccco2)C(=O)O)cc1] |
| G36 | 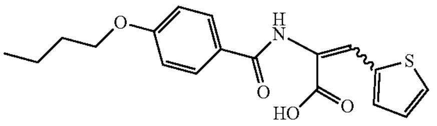 [SMILES: CCCCOc1ccc(C(=O)NC(=Cc2cccs2)C(=O)O)cc1] |
| G37 | 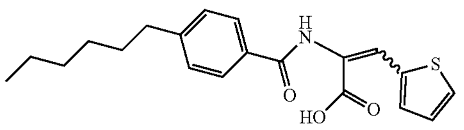 [SMILES: CCCCCCc1ccc(C(=O)NC(=Cc2cccs2)C(=O)O)cc1] |
| G38 | 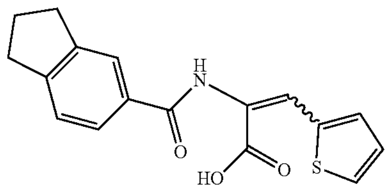 [SMILES: O=C(O)C(=Cc1cccs1)NC(=O)c1ccc2c(c1)CCC2] |
| G39 | 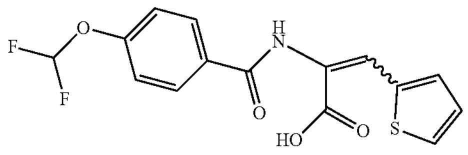 [SMILES: O=C(O)C(=Cc1cccs1)NC(=O)c1ccc(OC(F)F)cc1] |
| G40 | 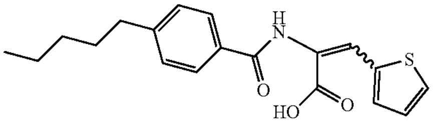 [SMILES: CCCCCc1ccc(C(=O)NC(=Cc2cccs2)C(=O)O)cc1] |
| G41 | 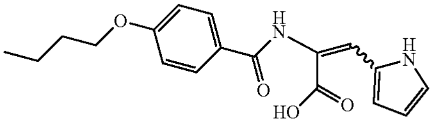 [SMILES: CCCCOc1ccc(C(=O)NC(=Cc2ccc[nH]2)C(=O)O)cc1] |
| G42 | 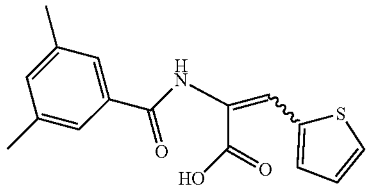 [SMILES: Cc1cc(C)cc(C(=O)NC(=Cc2cccs2)C(=O)O)c1] |

Herein, the term, 'compound of the present invention' and equivalent expressions include the aforementioned compound represented by Chemical formula 1, and this expression includes E- or Z-isomer thereof, optical isomer thereof, a mixture of two isomers thereof, precursor thereof, pharmaceutically acceptable salt thereof or solvate thereof, and is newly synthesized.

The present invention is further described by the following examples, unless they limit the scope of the present invention.

3. Preparation Method

Other aspect of the present invention provides a method for preparing the compound represented by Chemical formula 1. The synthesis method is well described in the detailed examples described herein.

In some embodiments, during organic synthesis, the use of a base may be an organic or inorganic base. Non-limitative examples of the organic base include pyridine, trimethylamine, N,N-diisopropylethylamine (DIPEA) and 1,8-diazabicyclo[5,4,0]undec-7-ene (DBU). Non-limitative examples of the inorganic base include sodium hydroxide, sodium carbonate, potassium carbonate, cesium carbonate and sodium hydride. They may be used either alone or in combination stoichiometrically or excessively. Non-limitative examples of the solvent that can be used include ether (for example, tetrahydrofuran (THF), diethyl ether and 1,2-dimethoxyethane), alcohol (for example, methanol, ethanol, propanol and butanol), dimethylformamide (DMF), dimethylsulfoxide (DMSO), dichloromethane (DCM), dichloroethane, water and acetone. The solvents may be used alone or in combination.

4. Composition/Formulation

The present invention includes the compound described herein and a pharmaceutical composition comprising a formulation suitable for administration of the compound described herein. Formulations of the pharmaceutical composition suitable for administration by any medically acceptable means are included. The pharmaceutical formulation may comprise a pharmaceutically acceptable additive or carrier suitable for means of administration and a pharmaceutically acceptable compound (composition).

The compound described herein may be a formulation (including a pharmaceutical composition) having an additive such as an excipient (for example, one or more excipients), an anti-oxidant (for example, one or more anti-oxidants), a stabilizer (for example, one or more stabilizers), a preservative (for example, one or more preservatives), a pH adjusting agent and/or buffers (for example, one or more pH adjusting agents and/or buffers), an isotonic adjusting agent (for example, one or more isotonic adjusting agents), a thickener (for example, one or more thickeners), a suspending agent (for example, one or more suspending agents), a binding agent (for example, one or more binding agents), a viscosity increasing agent (for example, one or more viscosity increasing agents), and the like, and is provided as a pharmaceutically acceptable additional ingredient for a particular condition to be treated. In some embodiments, the formulation may comprise a combination of the additional ingredient described herein (for example, 2, 3, 4, 5, 6, 7, 8 or more additional ingredients). In some embodiments, the additive may comprise for example, a treatment agent and a drug delivery modifier, and an enhancer such as calcium phosphate, magnesium stearate, talc, monosaccharides, disaccharides, starch, gelatin, cellulose, methyl cellulose, sodium carboxymethyl cellulose, dextrose, hydroxypropyl-beta-cyclodextrin, polyvinylpyrrolidone, low melting point wax and ion exchange resin, and a combination of any two or more thereof.

Other suitable pharmaceutically acceptable excipients are described in "Remington's Pharmaceutical Sciences" Mack Pub. Co., New Jersey (1991), and "Remington: The Science and Practice of Pharmacy", Lippincott Williams & Wilkins, Philadelphia, 20th edition (2003) and 21st edition (2005) incorporated herein as a reference.

The formulation of the composition described herein may be appropriate for oral administration which may be composed of inhalation, nose spray, intravenous, intramuscular injection, intravitreal injection, ointment or solution, suspension, semiliquid, semisolid, gel, semisolid gel, jelly, emulsion, ointment, tablet, liquid and cream. The tablet form may compose one or more of lactose, sucrose, mannitol, sorbitol, calcium phosphate, corn starch, potato starch, microcrystal cellulose, gelatin, colloidal silicon dioxide, talc, magnesium stearate, stearic acid and other excipient, a coloring agent, a filler, a binding agent, a diluent, a buffer, a moisturizer, a preservative, a flavoring agent, a dye, a disintegrating agent and a pharmaceutically suitable carrier. A capsule may contain an appropriate excipient with the compound or the compound may be used in a shell alone. All of these formulated compounds may be administered alone or co-administered, or intermittently administered, or sequentially or simultaneously administered.

5. Administration

The composition of the present invention includes one which may be administered by oral, parenteral, sublingual, dermal, rectal, transmucosal, local, through inhalation, buccal or intranasal administration, or be administered by any method of a combination thereof, but not limited thereto. The parenteral administration includes intravenous, intra-arterial, intraperitoneal, subcutaneous, intramuscular, intrathecal and intra-arterial administration, but not limited thereto. In addition, the composition of the present invention may be administered as an implant, and this allows slow release of the composition as well as slowly controlled intravenous administration.

The dose administered to an individual in a single or multiple dose will vary depending on various factors including pharmacokinetic characteristics, patient condition and characteristics (gender, age, weight, health, size), severity of symptoms, concurrent treatment, treatment frequency and desired effect.

According to one embodiment of the present invention, the compound and pharmaceutical formulation thereof according to the present invention may be administered alone or with a useful adjuvant for treatment of respiratory disorder or disease. According to another embodiment of the present invention, the compound and pharmaceutical formulation thereof according to the present invention may be administered with radiotherapy.

The present invention comprises administration of the compound or pharmaceutical formulation thereof according to the present invention, and the compound and pharmaceutical formulation thereof according to the present invention is administered simultaneously or sequentially to a subject before other therapy or adjuvant (for example, polypharmacy) useful for treatment of cancer, in a therapeutically effective amount. The compound or pharmaceutical formulation according to the present invention administered with the adjuvant may be administered by the same or different administration route(s) in the same or different composition(s).

In one embodiment, the patient according to the present invention may be a patient suffering respiratory disorder or disease such as bronchial asthma, bronchitis, allergic rhinitis, adult respiratory syndrome, cystic fibrosis, lung virus infection (influenza), lung high blood pressure, idiopathic lung fibrosis and chronic obstructive pulmonary disease (COPD).

6. Use According to the Present Invention

In other embodiment, the present invention provides a compound represented by Chemical formula 1 for preventing, improving or treating of respiratory disease (inflammatory airway disease), a mixture of the compound, or a use of a pharmaceutical composition thereof.

In other embodiment, the present invention provides a compound represented by Chemical formula 1 and a use of a pharmaceutical composition thereof as a pendrin inhibitor.

In other embodiment, a use of a compound represented by Chemical formula 1 and a pharmaceutical composition thereof is provided, and this preserves the volume of airway surface liquid (ASL) and reduces secretion of mucin.

In other embodiment, the present invention provides a use for respiratory disease (inflammatory airway disease) in one or more selected from the group consisting of asthma, acute or chronic bronchitis, allergic rhinitis, acute respiratory infection, cystic fibrosis, acute respiratory distress syndrome (ARDS), acute lung injury (ALI) or chronic obstructive pulmonary disease (COPD), or the like.

In other embodiment, the present invention provides a compound represented by Chemical formula 1 for preventing or improving of respiratory disease (inflammatory airway disease), a mixture of the compound or a use of a pharmaceutical composition thereof, as an active ingredient in a health functional food.

In other embodiment, the present invention provides a use of a compound represented by Chemical formula 1 and a pharmaceutical composition thereof as a pendrin inhibitor for preventing or improving of respiratory disease (inflammatory airway disease) as an active ingredient in a health functional food.

In other embodiment, the present invention provides a use of a compound represented by Chemical formula 1 and a pharmaceutical composition thereof, and this specifically controls a chloride channel for preventing or improving of respiratory disease (inflammatory airway disease) as an active ingredient in a health functional food.

In other embodiment, the present invention provides a use of a compound represented by Chemical formula 1 and a pharmaceutical composition thereof, and this preserves the volume of airway surface liquid (ASL) and reduces secretion of mucin for preventing or improving of respiratory disease (inflammatory airway disease) as an active ingredient in a health functional food.

In other embodiment, the present invention provides a use of a compound represented by Chemical formula 1 and a pharmaceutical composition thereof, and the respiratory disease (inflammatory airway disease) is one or more selected from the group consisting of asthma, acute or chronic bronchitis, allergic rhinitis, acute respiratory infection, cystic fibrosis, acute respiratory distress syndrome (ARDS), acute lung injury (ALI) or chronic obstructive pulmonary disease (COPD).

EXAMPLE

Non-limitative examples of detailed experiments which do not limit the entire experiments are described herein. The description of the present invention described herein serves as an example, and a person with general knowledge of the technology related to the present invention should understand that it can easily change it to other specific areas or forms without changing the technical spirit or essential features of the present invention. The present invention described illustratively suggests the following examples, but not limited thereto.

Names of compounds were generated by ChemDraw Professional V.15.1. The compound according to the present invention includes a compound represented by Chemical formula 1, tautomer thereof, geometrical isomer thereof (for example, e, z isomers), an optically active form as an optical isomer thereof, diastereomeric isomer thereof and racemate thereof, as well as pharmaceutically acceptable salt thereof. Derivatives exemplified herein may be prepared from a readily available starting material using the following general methods and procedures. Given typical or preferable experimental conditions (i.e., reaction temperature, time, moles of reagent, solvent, etc.), it will be understood that other experimental conditions may be used unless otherwise stated. Optimum reaction conditions may vary depending on particular reactants or solvents, but such conditions may be determined by those skilled in the art using routine optimization procedures.

The references cited herein are incorporated herein by reference in their entirety. The present invention is not limited in the scope to the specific embodiments described herein, which are intended as single examples of individual aspects of the present invention, and functionally equivalent methods and components are within the scope of the present invention. In practice, in addition to those illustrated and described herein, various modifications of the present invention will become apparent to those skilled in the art from the aforementioned description and attached drawings. Such modifications are intended to fall within the scope of the appended claims.

Example 1-2: Preparation of Novel Compounds

Some synthesized compounds may exist as an isomer or mixture of isomers due to the nature of synthetic chemistry or their intrinsic physical/chemical properties. In some cases, they may be interconverted to other isomers. For example, compound 'F1' means (E)-4-(thiophen-2-ylmethylene)-2-(4-(trifluoromethyl)phenyl)oxazol-5 (4H)-one, (Z)-4-(thiophen-2-ylmethylene)-2-(4-(trifluoromethyl)phenyl)oxazol-5(4H)-one or a mixture of two isomers. This phenomenon is well documented by the study of Graziano et al (Tetrahedron 62 (2006) 1165-1170).

Example 1.1: 4-(thiophen-2-ylmethylene)-2-(4-(trifluoromethyl)phenyl)oxazol-5 (4H)-one (F1)

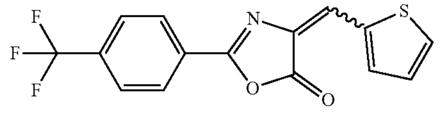 [SMILES: O=C1OC(c2ccc(C(F)(F)F)cc2)=NC1=Cc1cccs1]

Glycine (180 mg, 2.40 mmol) and 4-(trifluoromethyl) benzoyl chloride (0.411 ml, 2.758 mmol) were sequentially added to 10% NaOH solution (24 ml) at a room temperature under stirring, and they were stirred at this temperature for 2 hours. After acidifying to pH 2 by HCl aq. solution, the resulting solid was filtered through a filter funnel and the solid was washed with chloride to obtain 2-(4-(trifluoromethyl)benzamido)acetate. This 2-(4-(trifluoromethyl)benzamido)acetate (529 mg, 2.14 mmol) and 1-ethyl-3-(3-dimethylamino)propyl carbodiimide hydrochloride (410 mg, 2.14 mmol) were sequentially added to methylene chloride (21 ml) at a room temperature under stirring. Then, 1H-pyrrol-2-carbaldehyde (200 mg, 1.783 mmol) and triethylamine (0.497 ml, 3.567 mmol) were added at a room temperature under stirring and they were stirred at this temperature for 12 hours. The solvent was evaporated under decompression. The resulting solid was filtered through a filter funnel and they were washed with methanol to provide a desired product (4-(thiophen-2-ylmethylene)-2-(4-(trifluoromethyl)phenyl)oxazol-5 (4H)-one, F1).

$^1$H NMR (400 MHz, DMSO-$d_6$) δ8.22 (d, 2H, J=8.4 Hz), 8.08 (d, 1H, J=5.2 Hz), 7.96 (d, 2H, J=8.4 Hz), 7.86 (d, 1H, J=3.6 Hz), 7.79 (s, 1H), 7.24 (t, 1H, J=4.2 Hz).

ESI (m/z) 324 ($MH^+$).

Example 1.2: 2-(4-(tert-butyl)phenyl)-4-(thiazol-5-yl methylene)oxazol-5(4H)-one (F2)

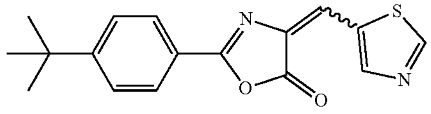 [SMILES: CC(C)(C)c1ccc(C2=NC(=Cc3cncs3)C(=O)O2)cc1]

Thionyl chloride (2.038 ml, 28.05 mmol) and dimethyl formamide (10 drops) were sequentially added to 4-tert-butylbenzoate (500 mg, 2.81 mmol) in methylene chloride under stirring and the mixture was heated for 12 hours. The solvent was evaporated to obtain an intermediate (0.542 ml, 2.758 mmol). Glycine (180 mg, 2.398 mmol) and this intermediate were sequentially added to 10% NaOH aq. solution (24 ml) at a room temperature under stirring, and they were stirred at this temperature for 2 hours. After acidifying to pH 2 with aq. HCl solution, the resulting solid was filtered with a filter funnel and washed with methylene chloride to obtain 2-(4-(tert-butyl)benzamido)acetate. 2-(4-(tert-butyl)benzamido)acetate (500 mg, 2.125 mmol) and 1-ethyl-3-(3-dimethylamino)propyl carbodiimide hydrochloride (448 mg, 2.338 mmol) were sequentially added to methylene chloride (21 ml) at a room temperature. Thiazol-5-carbaldehyde (216 mg, 1.913 mmol) and triethylamide (0.519 ml, 3.70 mmol) were sequentially added to this mixture at a room temperature under stirring and the whole mixture was stirred for 12 hours. The solvent was removed under decompression. The resulting solid was obtained through a filter funnel and the solid was washed with methanol to provide a desired product (2-(4-(tert-butyl) phenyl)-4-(thiazol-5-yl methylene)oxazol-5(4H)-one, F2).

$^1$H NMR (400 MHz, DMSO-$d_6$) δ 8.15 (d, 1H, J=2.8 Hz), 8.10 (d, 1H, J=2.8 Hz), 8.03 (d, 2H, J=8.4 Hz), 7.65 (d, 2H, J=8.4 Hz), 7.40 (s, 1H), 1.30 (s, 9H).

ESI (m/z) 313 (MH$^+$).

Example 1.3: 2-(4-(tert-butyl)phenyl)-4-((2-methyl-1H-indol-3-yl1)methylene)oxazol-5(4H)-one (F3)

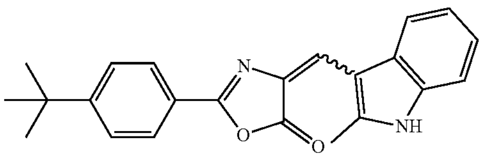 [SMILES: Cc1[nH]c2ccccc2c1C=C1N=C(c2ccc(C(C)(C)C)cc2)OC1=O]

Thionyl chloride (2.04 ml, 28.05 mmol) and dimethyl formamide (10 drops) were sequentially added to 4-tert-butylbenzoate (500 mg, 2.81 mmol) in methylene chloride under stirring and the mixture was heated for 12 hours. The solvent was evaporated to provide an intermediate (0.542 ml, 2.758 mmol). Glycine (180 mg, 2.398 mmol) and this intermediate were sequentially added to 10% NaOH aq. solution (24 ml) at a room temperature under stirring. The whole mixture was stirred at a room temperature for 2 hours. After acidifying to pH 2 with HCl, the resulting solid was obtained with a filter funnel and washed with methylene chloride to provide 2-(4-(tert-butyl)benzamido)acetate. 2-(4-(tert-butyl)benzamido)acetate (400 mg, 2.073 mmol) and 1-ethyl-3-(3-dimethylamino)propyl carbodiimide hydrochloride (433.54 mg, 2.262 mmol) were sequentially added to methylene chloride (20 ml) at a room temperature under stirring. 2-Methyl-1H-indol-3-carboaldehyde (300 mg, 1.885 mmol) and triethylamide (0.315 ml, 2.262 mmol) were sequentially added to this mixture at a room temperature under stirring and the whole mixture was stirred for 12 hours. The solvent was removed under decompression, and the resulting solid was obtained by filtering through a filter funnel. The solid was washed with methanol to provide a desired product (2-(4-(tert-butyl)phenyl)-4-((2-methyl-1H-indol-3-yl)methylene)oxazol-5(4H)-one, F3).

$^1$H NMR (400 MHz, DMSO-$d_6$) δ 12.25 (s, 1H), 9.16 (d, 1H, J=7.9 Hz), 7.96 (d, 2H, J=8.4 Hz), 7.61 (d, 2H, J=8.0 Hz), 7.37 (s, 2H), 7.25-7.18 (m, 2H), 2.62 (s, 3H), 1.30 (s, 9H).

ESI (m/z) 359 (MH$^+$), 357 (MH$^-$).

Example 1.4: tert-butyl 3-((2-(4-(tert-butyl)phenyl)-5-oxooxazol-4(5H)-ylidene)methyl)-1H-indol-1-carboxylate (F4)

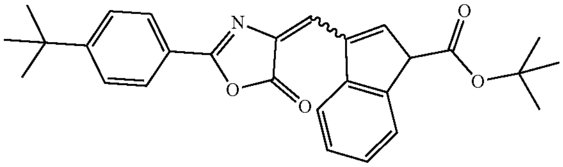 [SMILES: CC(C)(C)OC(=O)C1C=C(C=C2N=C(c3ccc(C(C)(C)C)cc3)OC2=O)c2ccccc21]

After adding di-tert-butyl dicarbonate (361 mg, 1.65 mmol) to the stirred solution of indole-5-carbaldehyde (200 mg, 1.38 mmol) in acetonitrile of 4 mL, 4-dimethylamino-pyridine (DMAP; 17 mg, 0.14 mmol) was added. The mixture was stirred at a room temperature for 2 hours. Water was added (20 mL) and the products was extracted with dichloromethane (3×20 mL). The organic layer was combined and it was dried on anhydrous sodium sulfate, and it was filtered and concentrated under decompression. The residues were purified by flash column chromatography (ethyl acetate:hexane=1:5) to obtain tert-butyl 3-formyl-1H-indole-1-carboxylate (Stage 1).

Thionyl chloride (2.0 ml, 28.05 mmol) and dimethyl formamide (10 drops) were sequentially added to 4-tert-butylbenzoate (500 mg, 2.81 mmol) in 0.1M methylene chloride under stirring. The mixture was heated for 12 hours and the solvent was evaporated under decompression to obtain an intermediate chloride (Stage 2). Glycine (180 mg, 2.398 mmol) and the intermediate chloride (0.542 ml, 2.758 mmol) were sequentially added to 10% NaOH aq. solution (23.98 ml) at a room temperature under decompression, and the mixture was stirred for 2 hours. The mixture was acidified with HCl until reaching pH 2, and the solid produced by passing through a filter funnel was obtained. The solid was washed with methylene chloride to provide 2-(4-(tert-butyl)benzamido)acetate (Stage 3). 2-(4-(tert-butyl)benzamido)acetate (200 mg, 0.85 mmol) and 1-ethyl-3-(3-dimethylamino)propyl carbodiimide hydrochloride (179.25 mg, 0.935 mmol) were sequentially added to methylene chloride (8.5 ml) at a room temperature under stirring. tert-butyl 3-formyl-1H-indole-1-carboxylate (208 mg, 0.085 mmol) and triethylamide (0.208 ml, 2.550 mmol) were sequentially added to this mixture at a room temperature under stirring and the whole mixture was stirred for 12 hours. At a room temperature, the solvent was removed under decompression and the resulting solid was obtained by passing through a filter funnel. The obtained solid was washed with methanol to provide a desired product (tert-butyl 3-((2-(4-(tert-butyl)phenyl)-5-oxooxazol-4(5H)-ylidene)methyl)-1H-indole-1-carboxylate, F4).

$^1$H NMR (400 MHz, DMSO-$d_6$) δ8.84 (s, 1H), 8.31 (d, J=7.6 Hz, 1H), 8.09 (d, J=7.9 Hz, 1H), 7.99 (d, J=8.4 Hz, 2H), 7.67-7.60 (m, 3H), 7.45-7.33 (m, 2H), 1.67 (s, 9H), 1.31 (s, 9H).

Example 1.5: 4-(5-Oxo-4-(thiophen-2-ylmethylene)-4,5-dihydrooxazol-2-yl)benzonitrile (F5)

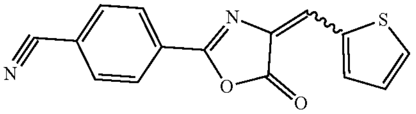 [SMILES: N#Cc1ccc(C2=NC(=Cc3cccs3)C(=O)O2)cc1]

Glycine (180 mg, 2.40 mmol) and 4-cyanobenzoyl chloride (460 mg, 2.76 mmol) were sequentially added to 10% NaOH solution (24 ml) at a room temperature under stirring and the mixture was stirred at this temperature for 2 hours. After acidifying the mixture with HCl until reaching pH 2, the resulting solid (2-(4-cyanobenzamido)acetate) was filtered through a filter funnel and then washed with methylene chloride. 2-(4-cyanobenzamido)acetate (400 mg, 1.96 mmol) and 1-ethyl-3-(3-dimethylamino)propyl carbodiimide hydrochloride (410 mg, 2.14 mmol) were sequentially added to methylene chloride (20 ml) at a room temperature under stirring and the mixture was stirred for 12 hours. Thiophen-2-carboaldehyde (200 mg, 1.783 mmol) and triethylamine (0.5 ml, 3.57 mmol) were sequentially added to this solution at a room temperature under stirring, and the whole mixture was stirred for 12 hours. The solvent was removed under decompression and the resulting solid was obtained by filtering a filter funnel. The solid was washed with methanol to provide a desired product (4-(5-oxo-4-(thiophen-2-ylmethylene)-4,5-dihydrooxazol-2-yl)benzonitrile, F5).

$^1$H NMR (400 MHz, DMSO-$d_6$) δ 8.18 (d, 2H, J=8.4 Hz), 8.07 (t, 3H, J=7.6 Hz), 7.87 (d, 1H, J=3.6 Hz), 7.81 (s, 1H), 7.25 (t, 1H, J=4.4 Hz).

Example 1.6: 2-(4-(tert-butyl)phenyl)-4-((1-methyl-1H-pyrrol-2-yl)methylene)oxazol-5 (4H)-one (F6)

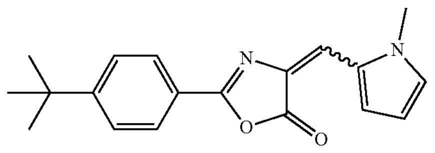 [SMILES: Cn1cccc1C=C1N=C(c2ccc(C(C)(C)C)cc2)OC1=O]

$^1$H NMR (400 MHz, DMSO-$d_6$) δ 7.95 (d, 2H, J=8.4 Hz), 7.58 (d, 3H, J=8.0 Hz), 7.24 (s, 1H), 7.17 (s, 1H), 6.33 (t, 1H, J=3.0 Hz), 3.78 (s, 3H), 1.29 (s, 9H).

ESI (m/z) 309 (MH$^+$)

Example 1.7: Methyl 4-(5-oxo-4-(thiophen-2-ylmethylene)-4,5-dihydrooxazol-2-yl)benzoate (F7)

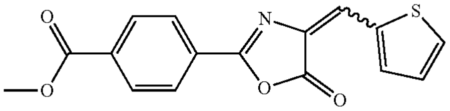 [SMILES: COC(=O)c1ccc(C2=NC(=Cc3cccs3)C(=O)O2)cc1]

$^1$H NMR (400 MHz, DMSO-$d_6$) δ 8.16 (q, 4H, J=8.8 Hz), 8.08 (d, 1H, J=5.2 Hz), 8.02 (s, 1H), 7.86 (d, 1H, J=3.6 Hz), 7.79 (s, 1H), 3.88 (s, 3H).

ESI (m/z) 314 (MH$^+$)

Example 1.8: 2-(4-(tert-butyl)phenyl)-4-((4-methylthiazol-5-yl)methylene)oxazol-5 (4H)-one (F8)

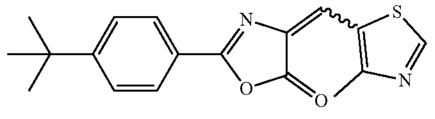 [SMILES: Cc1ncsc1C=C1N=C(c2ccc(C(C)(C)C)cc2)OC1=O]

$^1$H NMR (400 MHz, DMSO-$d_6$) δ 9.28 (s, 1H), 7.95 (d, 2H, J=8.4 Hz), 7.62 (d, 2H, J=8.4 Hz), 7.53 (s, 1H), 2.59 (s, 3H), 1.29 (s, 9H).

ESI (m/z) 327 (MH$^+$).

Example 1.9: 2-(4-(tert-butyl)phenyl)-4-(thiophen-3-ylmethylene)oxazol-5 (4H)-one (F9)

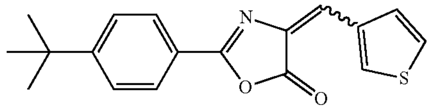 [SMILES: CC(C)(C)c1ccc(C2=NC(=Cc3ccsc3)C(=O)O2)cc1]

$^1$H NMR (400 MHz, DMSO-$d_6$) δ 8.44 (d, 1H, J=2.4 Hz), 8.01-7.99 (m, 3H), 7.71-7.69 (m, 1H), 7.59 (d, 2H, J=8.8 Hz), 7.37 (s, 1H), 1.29 (s, 9H).

ESI (m/z) 312 (MH$^+$).

Example 1.10: 4-((1H-pyrrol-2-yl) methylene)-2-(4-(tert-butyl)phenyl)oxazol-5 (4H)-one (F10)

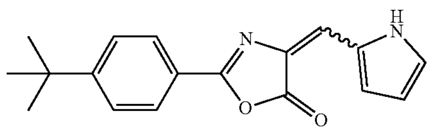 [SMILES: CC(C)(C)c1ccc(C2=NC(=Cc3ccc[nH]3)C(=O)O2)cc1]

$^1$H NMR (400 MHz, DMSO-$d_6$) δ 11.53 (s, 1H), 8.08 (d, 2H, J=8.2 Hz), 7.58 (d, 2H, J=8.3 Hz), 7.32 (s, 1H), 7.19 (s, 1H), 7.06 (s, 1H), 6.34 (s, 1H), 1.29 (s, 9H).

ESI (m/z) 295 (MH$^+$).

Example 1.11: 4-(Benzo[b]thiophen-2-ylmethylene)-2-(4-(tert-butyl)phenyl)oxazol-5 (4H)-one (F11)

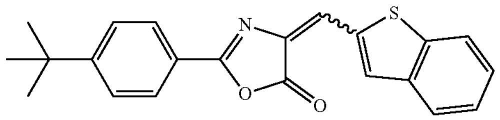 [SMILES: CC(C)(C)c1ccc(C2=NC(=Cc3cc4ccccc4s3)C(=O)O2)cc1]

$^1$H NMR (400 MHz, DMSO-$d_6$) δ 9.23 (s, 1H), 8.31 (d, 1H, J=8.0 Hz), 8.09 (d, 3H, J=8.4 Hz), 7.64-7.62 (m, 3H), 7.53-7.44 (m, 2H), 1.31 (s, 9H).

ESI (m/z) 362 (MH$^+$).

Example 1.12: 4-((1H-pyrrol-2-yl)methylene)-2-(4-isopropylphenyl)oxazol-5(4H)-one (F12)

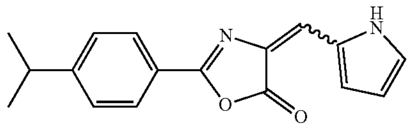 [SMILES: CC(C)c1ccc(C2=NC(=Cc3ccc[nH]3)C(=O)O2)cc1]

$^1$H NMR (400 MHz, DMSO-$d_6$) δ 11.52 (s, 1H), 8.08 (d, 2H, J=8.0 Hz), 7.43 (d, 2H, J=8.0 Hz), 7.32 (s, 1H), 7.19 (s, 1H), 7.05 (s, 1H), 6.34 (s, 1H), 3.01-2.91 (m, 1H), 1.21 (d, 6H, J=6.8 Hz).

ESI (m/z) 281 (MH$^+$).

Example 1.13: 2-(4-(tert-butyl)phenyl)-4-(quinolin-4-ylmethylene)oxazol-5 (4H)-one (F13)

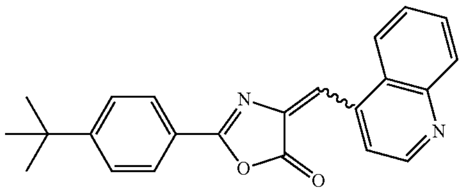 [SMILES: CC(C)(C)c1ccc(C2=NC(=Cc3ccnc4ccccc34)C(=O)O2)cc1]

$^{1}$H NMR (400 MHz, DMSO-$d_6$) δ 9.08 (d, 1H, J=4.4 Hz), 8.64 (d, 1H, J=4.8 Hz), 8.44 (d, 1H, J=8.4 Hz), 8.10-8.07 (m, 3H), 7.95 (s, 1H), 7.83 (t, 1H, J=7.6 Hz), 7.71 (d, 1H, J=8.0 Hz), 7.66 (d, 2H, J=8.0 Hz), 1.31 (s, 9H).

ESI (m/z) 357 ($MH^+$).

Example 1.14: 2-(4-Isobutylphenyl)-4-(thiophen-2-ylmethylene)oxazol-5 (4H)-one (F14)

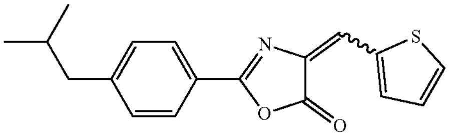 [SMILES: CC(C)Cc1ccc(C2=NC(=Cc3cccs3)C(=O)O2)cc1]

$^{1}$H NMR (400 MHz, DMSO-$d_6$) δ 8.01 (d, 1H, J=5.2 Hz), 7.96 (d, 2H, J=7.2 Hz), 7.81 (d, 1H, J=3.2 Hz), 7.67 (s, 1H), 7.39 (d, 2H, J=7.2 Hz), 7.22 (t, 1H, J=4.4 Hz), 2.53 (d, 2H, J=6.8 Hz), 1.91-1.81 (m, 1H), 0.84 (d, 6H, J=6.4 Hz).

ESI (m/z) 312 ($MH^+$).

Example 1.15: 2-(4-Isobutylphenyl)-4-(thiophen-3-ylmethylene)oxazol-5 (4H)-one (F15)

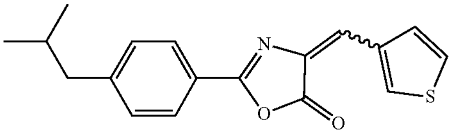 [SMILES: CC(C)Cc1ccc(C2=NC(=Cc3ccsc3)C(=O)O2)cc1]

$^{1}$H NMR (400 MHz, DMSO-$d_6$) δ 8.45 (d, 1H, J=2.4 Hz), 8.01-7.99 (m, 3H), 7.69 (q, 1H, J=2.8 Hz), 7.39 (s, 1H), 7.37 (s, 2H), 2.53 (d, 2H, J=7.2 Hz), 1.92-1.81 (m, 1H), 0.85 (d, 6H, J=6.8 Hz).

ESI (m/z) 312 ($MH^+$).

Example 1.16: 4-(Benzo[b]thiophen-3-ylmethylene)-2-(4-isopropylphenyl)oxazol-5(4H)-one (F16)

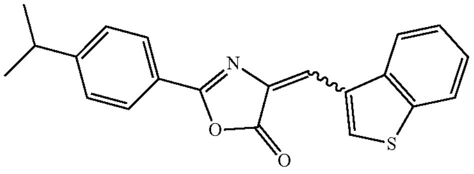 [SMILES: CC(C)c1ccc(C2=NC(=Cc3csc4ccccc34)C(=O)O2)cc1]

$^{1}$H NMR (400 MHz, DMSO-$d_6$) δ 9.24 (s, 1H), 8.30 (d, 1H, J=7.6 Hz), 8.09 (m, 3H), 7.61 (s, 1H), 7.52-7.44 (m, 4H), 3.03-2.96 (m, 1H), 1.22 (d, 6H, J=6.8 Hz).

Example 1.17: 4-((1H-pyrrol-2-yl)methylene)-2-(4-(trifluoromethyl)phenyl)oxazol-5(4H)-one (F17)

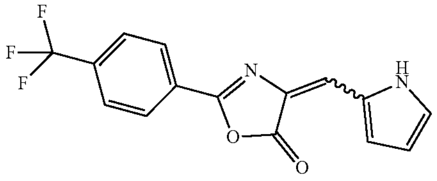 [SMILES: O=C1OC(c2ccc(C(F)(F)F)cc2)=NC1=Cc1ccc[nH]1]

$^{1}$H NMR (400 MHz, DMSO-$d_6$) δ 11.67 (s, 1H), 8.39 (d, 2H, J=7.6 Hz), 7.95 (d, 2H, J=8.0 Hz), 7.42 (s, 1H), 7.33 (s, 1H), 7.15 (s, 1H), 6.41 (s, 1H).

ESI (m/z) 305 ($MH^-$), 307 ($MH^+$)

Example 1.18: 4-(Thiophen-3-ylmethylene)-2-(4-(trifluoromethyl)phenyl)oxazol-5(4H)-one (F18)

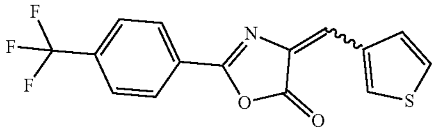 [SMILES: O=C1OC(c2ccc(C(F)(F)F)cc2)=NC1=Cc1ccsc1]

$^{1}$H NMR (400 MHz, DMSO-$d_6$) δ 8.55 (d, 1H, J=1.9 Hz), 8.32 (d, 2H, J=8.1 Hz), 8.07 (d, 1H, J=5.0 Hz), 7.98 (d, 2H, J=8.2 Hz), 7.78-7.74 (m, 1H), 7.53 (s, 1H).

Example 1.19: 4-(Furan-2-ylmethylene)-2-(4-isobutylphenyl)oxazol-5 (4H)-one (F19)

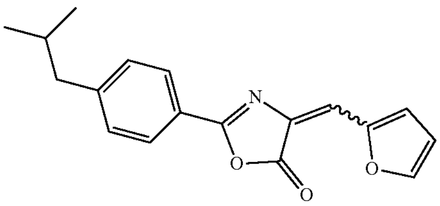 [SMILES: CC(C)Cc1ccc(C2=NC(=Cc3ccco3)C(=O)O2)cc1]

$^{1}$H NMR (400 MHz, DMSO-$d_6$) δ 8.04 (s, 1H), 7.97 (d, 2H, J=8.0 Hz), 7.55 (d, 1H, J=3.6 Hz), 7.36 (d, 2H, J=8.0 Hz), 7.14 (s, 1H), 6.79 (d, 1H, J=2.0 Hz), 2.52 (d, 2H, J=6.4 Hz), 1.90-1.80 (m, 1H), 0.84 (d, 6H, J=6.4 Hz)

Example 1.20: 4-((1H-pyrrol-2-yl)methylene)-2-(4-isobutylphenyl)oxazol-5 (4H)-one (F20)

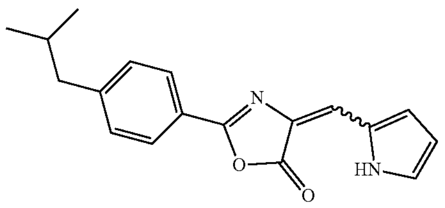 [SMILES: CC(C)Cc1ccc(C2=NC(=Cc3ccc[nH]3)C(=O)O2)cc1]

$^1$H NMR (400 MHz, DMSO-$d_6$) δ 11.51 (s, 1H), 8.06 (d, 2H, J=8.0 Hz), 7.34 (d, 2H, J=8.4 Hz), 7.31 (s, 1H), 7.18 (s, 1H), 7.04 (s, 1H), 6.33 (s, 1H), 2.51 (d, 2H, J=6.8 Hz), 1.90-1.80 (m, 1H), 0.84 (d, 6H, J=6.4 Hz).

Example 1.21: 4-(Benzo[b]thiophen-3-ylmethylene)-2-(4-isobutylphenyl)oxazol-5(4H)-one (F21)

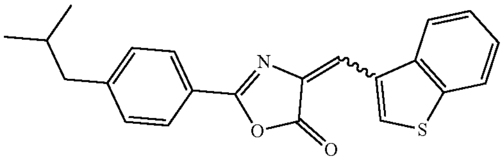 [SMILES: CC(C)Cc1ccc(C2=NC(=Cc3csc4ccccc34)C(=O)O2)cc1]

$^1$H NMR (400 MHz, DMSO-$d_6$) δ 9.24 (s, 1H), 8.29 (d, 1H, J=8.0 Hz), 8.08 (d, 3H, J=8.0 Hz), 7.60 (s, 1H), 7.52-7.43 (m, 2H), 7.39 (d, 2H, J=7.6 Hz), 2.54 (d, 2H, J=6.8 Hz), 1.89-1.84 (m, 1H), 0.85 (d, 6H, J=6.4 Hz).

Example 1.22: 2-(4-Bromophenyl)-4-((4-methylthiazol-5-yl)methylene)oxazol-5(4H)-one (F22)

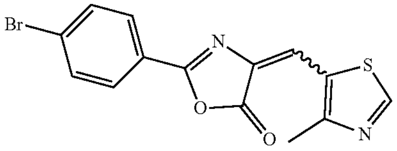 [SMILES: Cc1ncsc1C=C1N=C(c2ccc(Br)cc2)OC1=O]

$^1$H NMR (400 MHz, DMSO-$d_6$) δ 9.31 (s, 1H), 7.96 (d, 2H, J=8.4 Hz), 7.83 (d, 2H, J=8.4 Hz), 7.63 (s, 1H), 2.62 (s, 3H).

ESI (m/z) 350 (MH$^+$).

Example 1.23: 2-Cyclohexyl-4-(thiophen-2-ylmethylene)oxazol-5 (4H)-one (F23)

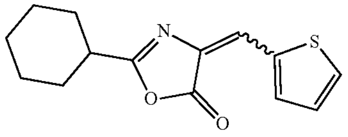 [SMILES: O=C1OC(C2CCCCC2)=NC1=Cc1cccs1]

$^1$H NMR (400 MHz, DMSO-$d_6$) δ 7.96 (d, 1H, J=5.2 Hz), 7.74 (d, 1H, J=3.6 Hz), 7.57 (s, 1H), 7.18 (t, 1H, J=4.2 Hz), 2.71-2.66 (m, 1H), 1.96-1.93 (m, 2H), 1.74-1.71 (m, 2H), 1.61-1.58 (m, 1H), 1.53-1.44 (m, 2H), 1.38-1.18 (m, 3H).

ESI (m/z) 262 (MH$^+$).

Example 1.24: 2-([1,1'-biphenyl]-4-yl)-4-((4-methylthiazol-5-yl)methylene)oxazol-5 (4H)-one (F24)

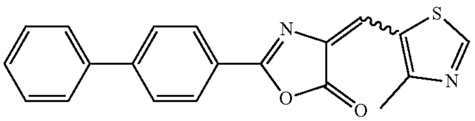 [SMILES: Cc1ncsc1C=C1N=C(c2ccc(-c3ccccc3)cc2)OC1=O]

$^1$H NMR (400 MHz, DMSO-$d_6$) δ 9.31 (s, 1H), 8.12 (d, 2H, J=8.4 Hz), 7.93 (d, 2H, J=8.0 Hz), 7.77 (d, 2H, J=7.6 Hz), 7.61 (s, 1H), 7.50 (t, 2H, J=7.4 Hz), 7.43 (t, 1H, J=7.4 Hz), 2.63 (s, 3H).

Example 1.25: 4-((1H-pyrrol-2-yl)methylene)-2-([1, 1'-biphenyl]-4-ylmethyl)oxazol-5(4H)-one (F25)

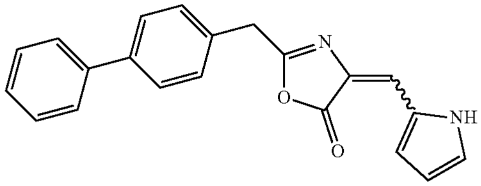 [SMILES: O=C1OC(Cc2ccc(-c3ccccc3)cc2)=NC1=Cc1ccc[nH]1]

$^1$H NMR (400 MHz, DMSO-$d_6$) δ 11.44 (s, 1H), 7.63 (d, 4H, J=8.0 Hz), 7.44-7.41 (m, 4H), 7.34-7.31 (m, 1H), 7.25 (s, 1H), 7.13 (s, 1H), 7.02 (s, 1H), 6.30 (s, 1H), 4.05 (s, 2H).

ESI (m/z) 329 (MH$^+$), 327 (MH$^-$).

Example 1.26: 4-((1H-pyrrol-2-yl)methylene)-2-(4-butylphenyl)oxazol-5(4H)-one (F26)

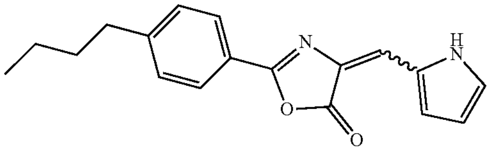 [SMILES: CCCCc1ccc(C2=NC(=Cc3ccc[nH]3)C(=O)O2)cc1]

$^1$H NMR (400 MHz, DMSO-$d_6$) δ 11.56 (s, 1H), 8.11 (d, 2H, J=7.9 Hz), 7.43 (d, 2H, J=8.0 Hz), 7.35 (s, 1H), 7.22 (s, 1H), 7.08 (s, 1H), 6.37 (s, 1H), 2.69 (t, 2H, J=7.6 Hz), 1.65-1.55 (m, 2H), 1.38-1.27 (m, 2H), 0.91 (t, 3H, J=7.3 Hz).

Example 1.27: 2-(4-(tert-butyl)phenyl)-4-((1-phenyl-1H-pyrrol-2-yl)methylene)oxazol-5 (4H)-one (F27)

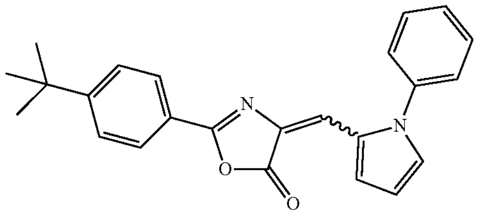 [SMILES: CC(C)(C)c1ccc(C2=NC(=Cc3cccn3-c3ccccc3)C(=O)O2)cc1]

$^1$H NMR (400 MHz, DMSO-$d_6$) δ 7.98 (d, 2H, J=8.4 Hz), 7.77 (d, 1H, J=3.9 Hz), 7.62-7.57 (m, 4H), 7.55-7.51 (m, 1H), 7.50-7.48 (m, 1H), 7.45 (d, 2H, J=7.5 Hz), 6.74 (s, 1H), 6.58 (t, 1H, J=3.4 Hz), 1.30 (s, 9H).

Example 1.28: 2-([1,1'-biphenyl]-4-ylmethyl)-4-(thiophen-2-ylmethylene)oxazol-5 (4H)-one (F28)

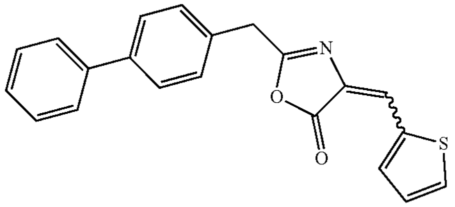 [SMILES: O=C1OC(Cc2ccc(-c3ccccc3)cc2)=NC1=Cc1cccs1]

$^1$H NMR (400 MHz, DMSO-$d_6$) δ 7.98 (d, 1H, J=4.8 Hz), 7.76 (d, 1H, J=3.6 Hz), 7.65 (s, 2H), 7.63 (s, 3H), 7.46-7.41 (m, 4H), 7.33 (t, 1H, J=7.2 Hz), 7.19 (t, 1H, J=4.4 Hz), 4.10 (s, 2H).

Example 1.29: 2-(2,3-dihydro-1H-indene-5-yl)-4-(thiophen-2-ylmethylene)oxazol-5 (4H)-one (F29)

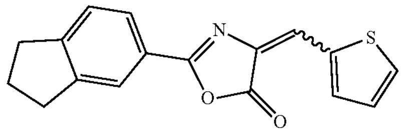 [SMILES: O=C1OC(c2ccc3c(c2)CCC3)=NC1=Cc1cccs1]

$^1$H NMR (400 MHz, DMSO-$d_6$) δ 8.01 (d, 1H, J=5.2 Hz), 7.89 (s, 1H), 7.83 (d, 1H, J=7.6 Hz), 7.80 (d, 1H, J=3.6 Hz), 7.65 (s, 1H), 7.43 (d, 1H, J=8.0 Hz), 7.23-7.21 (m, 1H), 2.93 (t, 4H, J=7.3 Hz), 2.08-2.00 (m, 2H).

ESI (m/z) 296 ($MH^+$).

Example 1.30: 4-((1H-pyrrol-2-yl)methylene)-2-(naphthalen-1-yl)oxazol-5(4H)-one (F30)

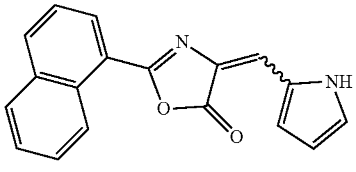 [SMILES: O=C1OC(c2cccc3ccccc23)=NC1=Cc1ccc[nH]1]

$^1$H NMR (400 MHz, DMSO-$d_6$) δ 11.62 (s, 1H), 9.31 (d, 1H, J=8.0 Hz), 8.29 (d, 1H, J=7.2 Hz), 8.20 (d, 1H, J=8.4 Hz), 8.06 (d, 1H, J=8.0 Hz), 7.76 (t, 1H, J=7.6 Hz), 7.65 (q, 2H, J=8.4 Hz), 7.36 (s, 1H), 7.28 (s, 2H), 6.43 (t, 1H, J=2.8 Hz).

ESI (m/z) 289 ($MH^+$).

Example 1.31: Methyl 4-(4-(furan-2-ylmethylene)-5-oxo-4,5-dihydrooxazol-2-yl)benzoate (F31)

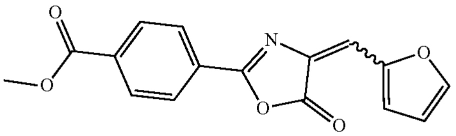 [SMILES: COC(=O)c1ccc(C2=NC(=Cc3ccco3)C(=O)O2)cc1]

$^1$H NMR (400 MHz, DMSO-$d_6$) δ 8.21 (s, 1H), 8.18 (s, 1H), 8.13 (s, 1H), 8.11-8.10 (m, 2H), 7.60 (d, 1H, J=3.2 Hz), 7.27 (s, 1H), 6.84-6.82 (m, 1H), 3.87 (s, 3H).

Example 1.32: Methyl 4-(5-oxo-4-(thiophen-3-ylmethylene)-4,5-dihydrooxazol-2-yl)benzoate (F32)

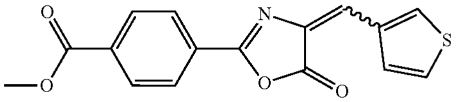 [SMILES: COC(=O)c1ccc(C2=NC(=Cc3ccsc3)C(=O)O2)cc1]

$^1$H NMR (400 MHz, DMSO-$d_6$) δ 8.47 (s, 1H), 8.16-8.00 (m, 5H), 7.70 (s, 1H), 7.44 (s, 1H), 3.85 (s, 3H).

Example 1.33: N-(4-(5-oxo-4-(thiophen-2-ylmethylene)-4,5-dihydrooxazol-2-yl)phenyl)acetamide (F33)

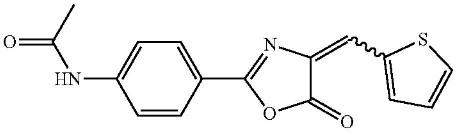 [SMILES: CC(=O)Nc1ccc(C2=NC(=Cc3cccs3)C(=O)O2)cc1]

Example 1.34: 2-(2-Methoxyphenyl)-4-(thiophen-2-ylmethylene)oxazol-5 (4H)-one (F34)

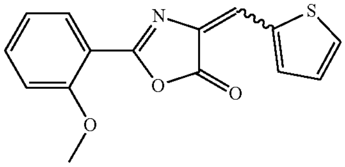 [SMILES: COc1ccccc1C1=NC(=Cc2cccs2)C(=O)O1]

Example 1.35: N-(tert-butyl)-4-(5-oxo-4-(thiophen-2-ylmethylene)-4,5-dihydrooxazol-2-yl)benzene sulfonamide (F35)

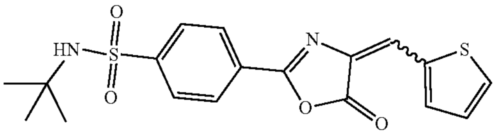 [SMILES: CC(C)(C)NS(=O)(=O)c1ccc(C2=NC(=Cc3cccs3)C(=O)O2)cc1]

Example 1.36: N-isopropyl-4-(5-oxo-4-(thiophen-2-ylmethylene)-4,5-dihydrooxazol-2-yl)benzene sulfonamide (F36)

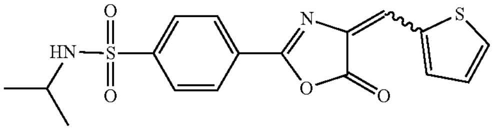 [SMILES: CC(C)NS(=O)(=O)c1ccc(C2=NC(=Cc3cccs3)C(=O)O2)cc1]

Example 1.37: 2-([1,1'-biphenyl]-4-yl)-4-(thiophen-2-ylmethylene)oxazol-5 (4H)-one (F37)

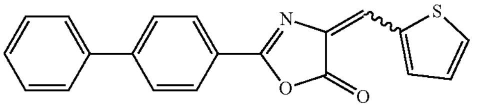 [SMILES: O=C1OC(c2ccc(-c3ccccc3)cc2)=NC1=Cc1cccs1]

$^1$H NMR (400 MHz, DMSO-$d_6$) δ 8.23 (d, 2H, J=8.3 Hz), 7.79-7.71 (m, 3H), 7.69-7.61 (m, 3H), 7.53-7.46 (m, 3H), 7.45-7.38 (m, 1H), 7.17 (t, 1H).

ESI (m/z) 332 ($MH^+$).

Example 1.38: 2-(4-(tert-butyl)phenyl)-4-(furan-2-ylmethylene)oxazol-5 (4H)-one (F38)

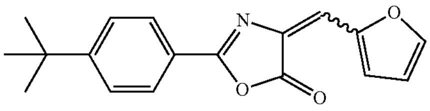 [SMILES: CC(C)(C)c1ccc(C2=NC(=Cc3ccco3)C(=O)O2)cc1]

$^1$H NMR (400 MHz, DMSO-$d_6$) δ 8.05 (s, 1H), 7.99 (d, 2H, J=8.4 Hz), 7.60 (d, 2H, J=8.4 Hz), 7.55 (d, 1H, J=3.2 Hz), 7.15 (s, 1H), 6.81 (br s, 1H), 1.29 (s, 9H).

ESI (m/z) 296 ($MH^+$).

Example 1.39: 2-(4-(tert-butyl)phenyl)-4-((1-methyl-1H-pyrazol-4-yl)methylene)oxazol-5(4H)-one (F39)

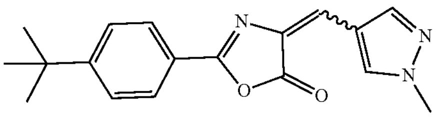 [SMILES: Cn1cc(C=C2N=C(c3ccc(C(C)(C)C)cc3)OC2=O)cn1]

$^1$H NMR (400 MHz, DMSO-$d_6$) δ 8.52 (s, 1H), 8.18 (s, 1H), 8.05 (d, 2H, J=8.5 Hz), 7.63 (d, 2H, J=8.5 Hz), 7.35 (s, 1H), 3.96 (s, 3H), 1.34 (s, 9H).

ESI (m/z) 310 ($MH^+$).

Example 1.40: 2-(4-(tert-butyl)phenyl)-4-(pyridin-3-ylmethylene)oxazol-5(4H)-one (F40)

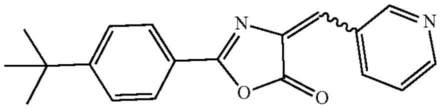 [SMILES: CC(C)(C)c1ccc(C2=NC(=Cc3cccnc3)C(=O)O2)cc1]

$^1$H NMR (400 MHz, DMSO-$d_6$) δ 9.28 (d, 1H, J=1.9 Hz), 8.78 (dt, 1H, J=8.1, 1.7 Hz), 8.65 (dd, 1H, J=4.8, 1.6 Hz), 8.09 (d, 2H), 7.68 (d, 2H, J=8.6 Hz), 7.61-7.56 (m, 1H), 7.40 (s, 1H), 1.34 (s, 9H).

ESI (m/z) 307 ($MH^+$).

Example 1.41: 2-(4-(tert-butyl)phenyl)-4-(pyridin-4-ylmethylene)oxazol-5(4H)-one (F41)

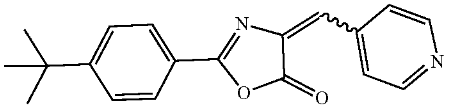 [SMILES: CC(C)(C)c1ccc(C2=NC(=Cc3ccncc3)C(=O)O2)cc1]

$^1$H NMR (400 MHz, DMSO-$d_6$) δ 8.71 (d, 2H, J=5.2 Hz), 8.13 (d, 2H, J=5.5 Hz), 8.07 (d, 2H), 7.66 (d, 2H, J=8.3 Hz), 7.27 (s, 1H), 1.31 (s, 9H).

ESI (m/z) 307 ($MH^+$).

Example 1.42: 2-([1,1'-biphenyl]-4-yl)-4-(pyridin-3-ylmethylene)oxazol-5(4H)-one (F42)

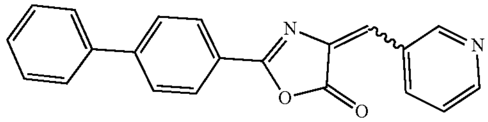 [SMILES: O=C1OC(c2ccc(-c3ccccc3)cc2)=NC1=Cc1cccnc1]

$^1$H NMR (400 MHz, DMSO-$d_6$) δ 9.25 (s, 1H), 8.78 (d, 1H, J=7.8 Hz), 8.63 (s, 1H), 8.19 (d, 2H, J=7.8 Hz), 7.92 (d, 2H, J=7.9 Hz), 7.77 (d, 2H, J=7.1 Hz), 7.61-7.54 (m, 1H), 7.50 (t, 2H, J=6.9 Hz), 7.47-7.36 (m, 2H).

ESI (m/z) 327 ($MH^+$).

Example 1.43: 2-(4-(tert-butyl)phenyl)-4-(4-(methylthio)benzylidene)oxazol-5 (4H)-one (F43)

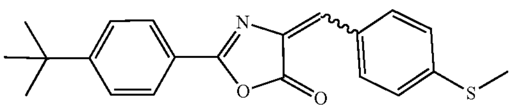 [SMILES: CSc1ccc(C=C2N=C(c3ccc(C(C)(C)C)cc3)OC2=O)cc1]

$^1$H NMR (400 MHz, DMSO-$d_6$) δ 8.20 (br s, 2H), 8.00 (br s, 2H), 7.63 (br s, 2H), 7.37 (s, 2H), 7.27 (s, 1H), 2.53 (s, 3H), 1.31 (s, 9H).

Example 1.44: 4-Benzylidene-2-(4-(tert-butyl)phenyl)oxazol-5 (4H)-one (F44)

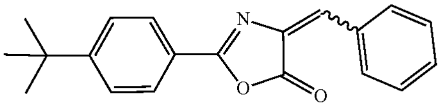 [SMILES: CC(C)(C)c1ccc(C2=NC(=Cc3ccccc3)C(=O)O2)cc1]

$^1$H NMR (400 MHz, DMSO-$d_6$) δ 8.26 (d, 2H, J=6.8 Hz), 8.00 (d, 2H, J=8.4 Hz), 7.61 (d, 2H, J=8.0 Hz), 7.52-7.45 (m, 3H), 7.28 (s, 1H), 1.29 (s, 9H).

ESI (m/z) 306 ($MH^+$).

Example 1.45: 2-(4-Bromophenyl)-4-(thiophen-2-ylmethylene)oxazol-5 (4H)-one (F45)

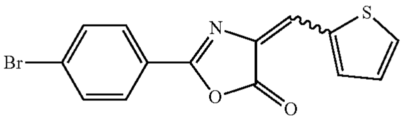 [SMILES: O=C1OC(c2ccc(Br)cc2)=NC1=Cc1cccs1]

$^1$H NMR (400 MHz, DMSO-$d_6$) δ 8.05 (s, 1H), 7.95 (d, 2H, J=7.6 Hz), 7.83 (s, 2H), 7.81 (s, 1H), 7.73 (s, 1H), 7.23 (s, 1H).

Example 1.46: 2-(4-Isopropylphenyl)-4-(thiophen-2-ylmethylene)oxazol-5(4H)-one (F46)

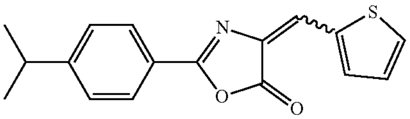 [SMILES: CC(C)c1ccc(C2=NC(=Cc3cccs3)C(=O)O2)cc1]

$^1$H NMR (400 MHz, DMSO-$d_6$) δ 8.02 (d, 1H, J=5.2 Hz), 7.97 (d, 2H, J=8.0 Hz), 7.81 (d, 1H, J=3.6 Hz), 7.67 (s, 1H), 7.48 (d, 2H, J=8.4 Hz), 7.22 (t, 1H, J=4.4 Hz), 3.02-2.92 (m, 1H), 1.21 (d, 6H, J=6.8 Hz).

ESI (m/z) 298 ($MH^+$).

Example 1.47: 2-(4-Isopropylphenyl)-4-(thiophen-3-ylmethylene)oxazol-5(4H)-one (F47)

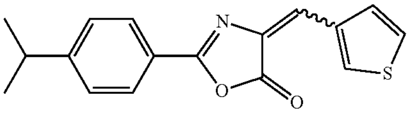 [SMILES: CC(C)c1ccc(C2=NC(=Cc3ccsc3)C(=O)O2)cc1]

$^1$H NMR (400 MHz, DMSO-$d_6$) δ 8.45 (d, 1H, J=2.8 Hz), 8.02-8.00 (m, 3H), 7.70 (q, 1H, J=2.8 Hz), 7.47 (d, 2H, J=7.2 Hz), 7.38 (s, 1H), 3.03-2.93 (m, 1H), 1.21 (d, 6H, J=6.8 Hz).

ESI (m/z) 298 ($MH^+$).

Example 1.48: 4-(Furan-2-ylmethylene)-2-(4-(trifluoromethyl)phenyl)oxazol-5(4H)-one (F48)

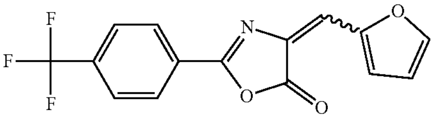 [SMILES: O=C1OC(c2ccc(C(F)(F)F)cc2)=NC1=Cc1ccco1]

$^1$H NMR (400 MHz, DMSO-$d_6$) δ 8.25 (d, 2H, J=8.2 Hz), 8.10 (s, 1H), 7.94 (d, 2H, J=8.3 Hz), 7.60 (d, 1H, J=3.5 Hz), 7.28 (s, 1H), 6.83-6.81 (m, 1H).

Example 1.49: 4-(Furan-2-ylmethylene)-2-(4-isopropylphenyl)oxazol-5 (4H)-one (F49)

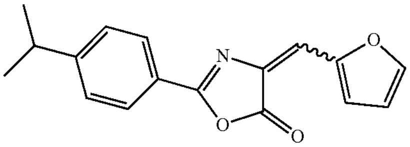 [SMILES: CC(C)c1ccc(C2=NC(=Cc3ccco3)C(=O)O2)cc1]

$^1$H NMR (400 MHz, DMSO-$d_6$) δ 8.04 (s, 1H), 7.97 (d, 2H, J=8.1 Hz), 7.54 (d, 1H, J=3.3 Hz), 7.44 (d, 2H, J=8.1 Hz), 7.13 (s, 1H), 6.83-6.76 (m, 1H), 3.01-2.88 (m, 1H), 1.19 (d, 6H, J=6.9 Hz).

Example 1.50: 2-(4-Bromophenyl)-4-(furan-2-ylmethylene)oxazol-5 (4H)-one)(F50)

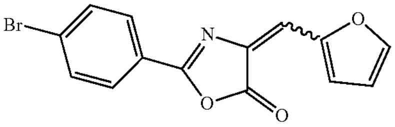 [SMILES: O=C1OC(c2ccc(Br)cc2)=NC1=Cc1ccco1]

$^1$H NMR (400 MHz, DMSO-$d_6$) δ 8.11 (s, 1H), 8.07-7.98 (m, 2H), 7.88-7.77 (m, 2H), 7.62 (s, 1H), 7.25 (s, 1H), 6.85 (s, 1H).

Example 1.51: 2-(4-Bromophenyl)-4-(thiophen-3-ylmethylene)oxazol-5(4H)-one (F51)

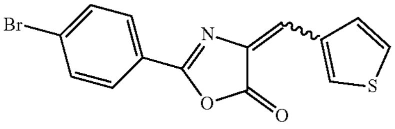 [SMILES: O=C1OC(c2ccc(Br)cc2)=NC1=Cc1ccsc1]

$^1$H NMR (400 MHz, DMSO-$d_6$) δ 8.47 (d, 1H, J=1.6 Hz), 8.01-7.99 (m, 3H), 7.80 (s, 1H), 7.78 (s, 1H), 7.70-7.68 (m, 1H), 7.43 (s, 1H).

Example 1.52: 2-(Naphthalen-2-yl)-4-(thiophen-2-ylmethylene)oxazol-5(4H)-one (F52)

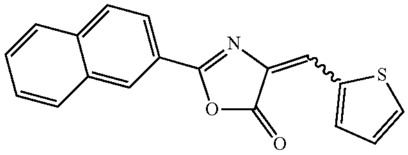 [SMILES: O=C1OC(c2ccc3ccccc3c2)=NC1=Cc1cccs1]

$^{1}H$ NMR (400 MHz, DMSO-$d_6$) δ 8.70 (s, 1H), 8.52 (d, 1H, J=2.4 Hz), 8.21-8.17 (m, 2H), 8.12 (s, 1H), 8.09 (t, 1H, J=4.8 Hz), 8.02 (d, 1H, J=8.0 Hz), 7.74-7.72 (m, 1H), 7.69-7.61 (m, 2H), 7.44 (s, 1H).

ESI (m/z) 306 ($MH^+$).

Example 1.53: 2-(4-Butylphenyl)-4-(thiophen-2-ylmethylene)oxazol-5(4H)-one (F53)

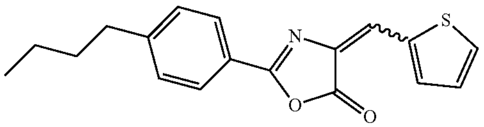 [SMILES: CCCCc1ccc(C2=NC(=Cc3cccs3)C(=O)O2)cc1]

$^{1}H$ NMR (400 MHz, DMSO-$d_6$) δ 8.02 (d, 1H, J=5.0 Hz), 7.96 (d, 2H, J=8.2 Hz), 7.81 (d, 1H, J=3.6 Hz), 7.67 (s, 1H), 7.42 (d, 2H, J=8.2 Hz), 7.25-7.20 (m, 1H), 2.66 (t, 2H, J=7.7 Hz), 1.61-1.51 (m, 2H), 1.37-1.22 (m, 2H), 0.87 (t, 3H, J=7.3 Hz).

Example 1.54: 2-(4-Butylphenyl)-4-(furan-2-ylmethylene)oxazol-5 (4H)-one (F54)

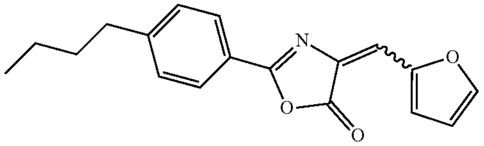 [SMILES: CCCCc1ccc(C2=NC(=Cc3ccco3)C(=O)O2)cc1]

$^{1}H$ NMR (400 MHz, DMSO-$d_6$) δ 8.09 (d, 1H, J=1.5 Hz), 8.02 (d, 2H, J=8.2 Hz), 7.60 (d, 1H, J=3.5 Hz), 7.45 (d, 2H, J=8.2 Hz), 7.19 (s, 1H), 6.86-6.83 (m, 1H), 2.69 (t, 2H, J=7.7 Hz), 1.66-1.54 (m, 2H), 1.39-1.27 (m, 2H), 0.91 (t, 3H, J=7.3 Hz).

Example 1.55: 2-(4-(difluoromethoxy)phenyl)-4-(thiophen-2-ylmethylene)oxazol-5(4H)-one (F55)

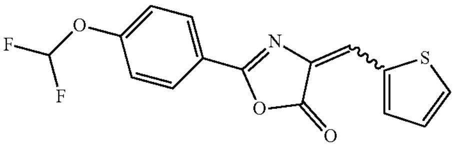 [SMILES: O=C1OC(c2ccc(OC(F)F)cc2)=NC1=Cc1cccs1]

$^{1}H$ NMR (400 MHz, DMSO-$d_6$) δ 8.10 (d, 2H, J=8.8 Hz), 8.03 (d, 1H, J=5.2 Hz), 7.82 (d, 1H, J=3.6 Hz), 7.69 (s, 1H), 7.41 (s, 1H), 7.38 (d, 2H, J=8.8 Hz), 7.24-7.22 (m, 1H).

Example 1.56: 2-(4-(tert-butyl)phenyl)-4-(thiophen-2-ylmethylene)oxazol-5 (4H)-one (F56)

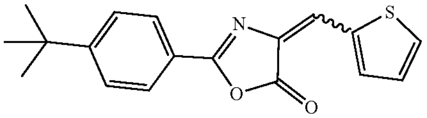 [SMILES: CC(C)(C)c1ccc(C2=NC(=Cc3cccs3)C(=O)O2)cc1]

$^{1}H$ NMR (400 MHz, DMSO-$d_6$) δ 8.02 (d, 1H, J=5.2 Hz), 7.96 (d, 2H, J=7.6 Hz), 7.80 (d, 1H, J=3.6 Hz), 7.66 (s, 1H), 7.61 (d, 2H, J=7.6 Hz), 7.22 (t, 1H, J=4.0 Hz), 1.30 (s, 9H). $^{13}C$ NMR (400 MHz, DMSO-$d_6$) δ 166.7, 162.1, 157.2, 137.6, 136.9, 136.6, 130.7, 129.6, 129.1, 129.1, 126.4, 126.4, 124.9, 122.8, 35.46, 31.2, 31.2, 31.2.

Example 1.57: 4-(2-Nitrobenzylidene)-2-phenyloxazol-5(4H)-one (F57)

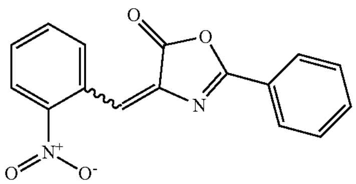 [SMILES: O=C1OC(c2ccccc2)=NC1=Cc1ccccc1[N+](=O)[O-]]

Example 1.58: 4-((2-(4-(tert-butyl)phenyl)-5-oxooxazol-4 (5H)-ylidene)methyl)phenylacetate (F58)

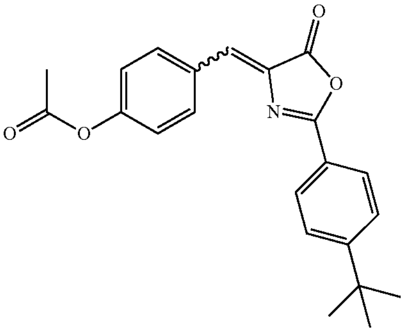 [SMILES: CC(=O)Oc1ccc(C=C2N=C(c3ccc(C(C)(C)C)cc3)OC2=O)cc1]

Example 1.59: 2-(3-Chlorobenzo[b]thiophen-2-yl)-4-(4-(dimethylamino)benzylidene)oxazol-5(4H)-one (F59)

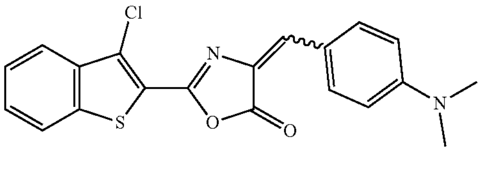 [SMILES: CN(C)c1ccc(C=C2N=C(c3sc4ccccc4c3Cl)OC2=O)cc1]

Example 1.60: 4-((2-(4-Methoxyphenyl)-5-oxooxazol-4(5H)-ylidene)methyl)benzoate (F60)

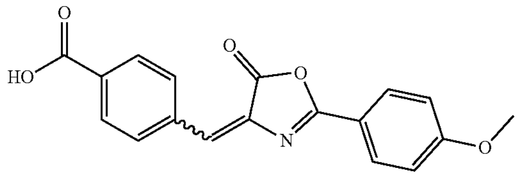 [SMILES: COc1ccc(C2=NC(=Cc3ccc(C(=O)O)cc3)C(=O)O2)cc1]

Example 1.61: 2-Phenyl-4-(thiophen-2-ylmethylene) oxazol-5(4H)-one (F61)

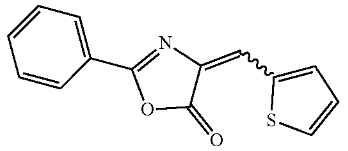 [SMILES: O=C1OC(c2ccccc2)=NC1=Cc1cccs1]

Example 1.62: 4-(4-Isopropylbenzylidene)-2-(naphthalen-1-yl)oxazol-5 (4H)-one (F62)

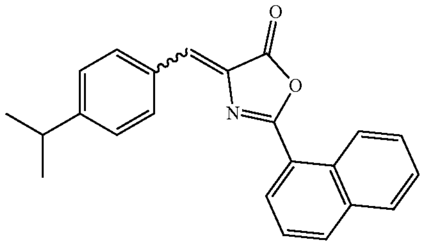 [SMILES: CC(C)c1ccc(C=C2N=C(c3cccc4ccccc34)OC2=O)cc1]

Example 1.63: 2-(3-Iodo-4-methylphenyl)-4-(thiophen-2-ylmethylene)oxazol-5(4H)-one (F63)

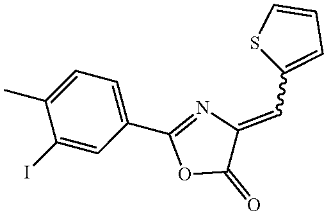 [SMILES: Cc1ccc(C2=NC(=Cc3cccs3)C(=O)O2)cc1I]

Example 1.64: 4-(4-(Benzyloxy)benzylidene)-2-(4-(tert-butyl)phenyl)oxazol-5 (4H)-one (F64)

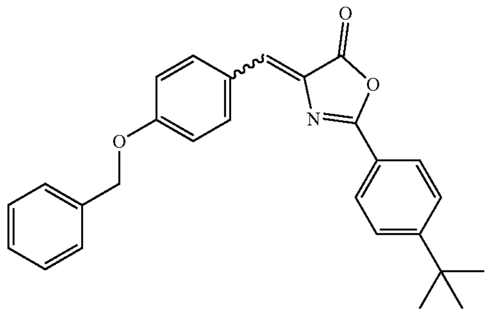 [SMILES: CC(C)(C)c1ccc(C2=NC(=Cc3ccc(OCc4ccccc4)cc3)C(=O)O2)cc1]

Example 1.65: 4-((1-(2-Chlorobenzyl)-1H-pyrrol-2-yl)methylene)-2-phenyloxazol-5(4H)-one (F65)

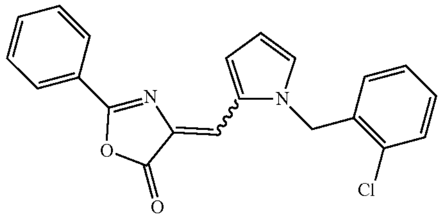 [SMILES: O=C1OC(c2ccccc2)=NC1=Cc1cccn1Cc1ccccc1Cl]

Example 1.66: N-(4-(4-(2-(Allyloxy)-4-(diethylamino)benzylidene)-5-oxo-4,5-dihydrooxazol-2-yl) phenyl)-5-bromonicotinamide (F66)

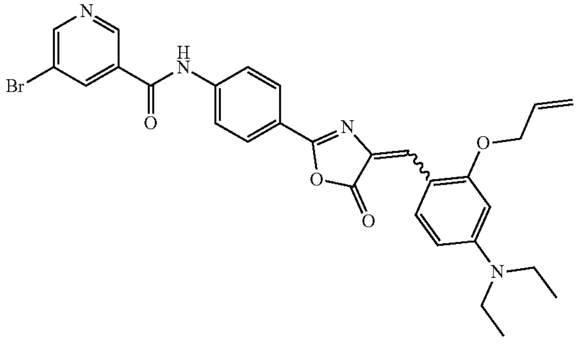 [SMILES: C=CCOc1cc(N(CC)CC)ccc1C=C1N=C(c2ccc(NC(=O)c3cncc(Br)c3)cc2)OC1=O]

Example 1.67: 4-((2-(2-Chlorophenyl)-5-oxooxazol-4(5H)-ylidene)methyl)phenyl4-(tert-butyl)benzoate (F67)

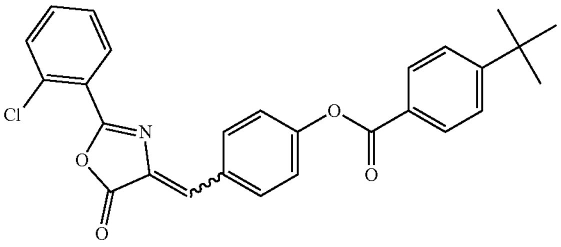 [SMILES: CC(C)(C)c1ccc(C(=O)Oc2ccc(C=C3N=C(c4ccccc4Cl)OC3=O)cc2)cc1]

Example 1.68: 4-((Z)-1-(3-ethyl-5-methoxybenzo[d]thiazol-2(3H)-ylidene)butan-2-ylidene)-2-phenyloxazol-5(4H)-one (F68)

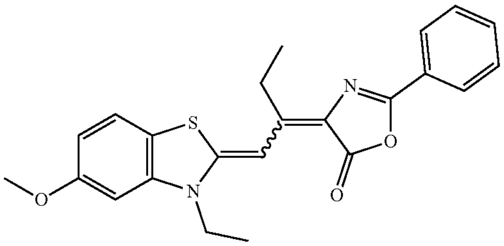 [SMILES: CCC(C=C1Sc2ccc(OC)cc2N1CC)=C1N=C(c2ccccc2)OC1=O]

Example 1.69: 4-((2-(4-Acetamidophenyl)-5-oxooxazol-4(5H)-ylidene)methyl)-2-ethoxyphenyl-thiophene-2-carboxylate (F69)

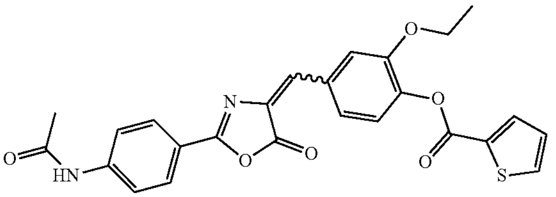 [SMILES: CCOc1cc(C=C2N=C(c3ccc(NC(C)=O)cc3)OC2=O)ccc1OC(=O)c1cccs1]

Example 1.70: 4-((6-Ethoxy-2-(phenylthio)quinolin-3-yl)methylene)-2-phenyloxazol-5(4H)-one (F70)

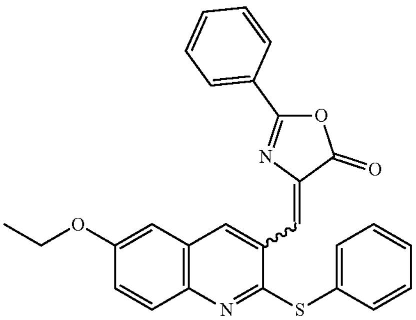 [SMILES: CCOc1ccc2nc(Sc3ccccc3)c(C=C3N=C(c4ccccc4)OC3=O)cc2c1]

Example 1.71: 2-(3-Bromophenyl)-4-((5-chloro-3-methyl-1-phenyl-1H-pyrazol-4-yl)methylene)oxazol-5(4H)-one (F71)

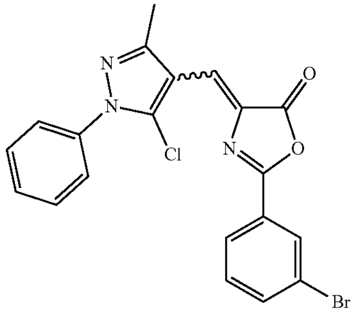 [SMILES: Cc1nn(-c2ccccc2)c(Cl)c1C=C1N=C(c2cccc(Br)c2)OC1=O]

Example 1.72: 4-((1-Acetyl-1H-indol-3-yl)methylene)-2-(4-bromophenyl)oxazol-5(4H)-one (F72)

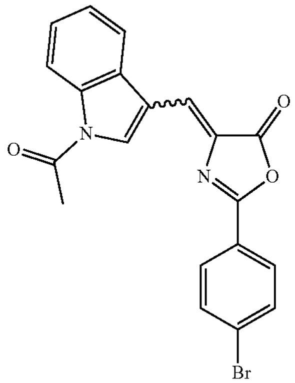 [SMILES: CC(=O)n1cc(C=C2N=C(c3ccc(Br)cc3)OC2=O)c2ccccc21]

Example 1.73: 2-(4-(tert-butyl)phenyl)-4-((5-(3-(trifluoromethyl)phenyl)furan-2-yl)methylene)oxazol-5(4H)-one (F73)

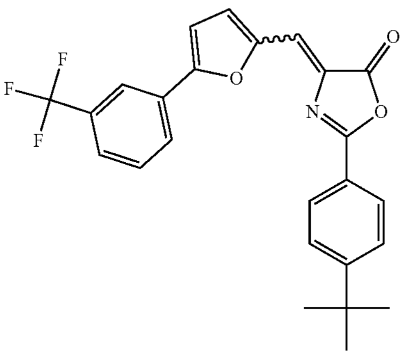 [SMILES: CC(C)(C)c1ccc(C2=NC(=Cc3ccc(-c4cccc(C(F)(F)F)c4)o3)C(=O)O2)cc1]

Example 1.74: 4-((7-Methoxy-2-oxo-1,2-dihydroquinolin-3-yl)methylene)-2-phenyloxazol-5(4H)-one (F74)

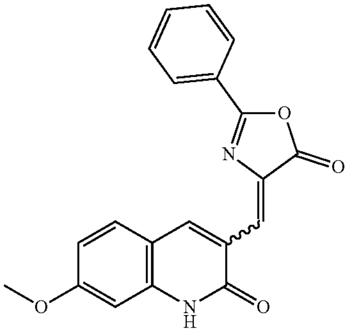 [SMILES: COc1ccc2cc(C=C3N=C(c4ccccc4)OC3=O)c(=O)[nH]c2c1]

Example 1.75: 2-(4-Methoxyphenyl)-4-(2-(thiophen-2-yl)-4H-chromen-4-ylidene)oxazol-5 (4H)-one (F75)

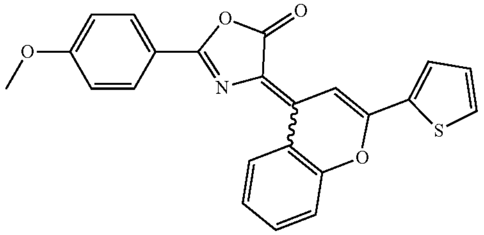 [SMILES: COc1ccc(C2=NC(=C3C=C(c4cccs4)Oc4ccccc43)C(=O)O2)cc1]

Example 1.76: N,N-Dimethyl-3-((5-oxo-2-(p-tolyl)oxazol-4(5H)-ylidene)methyl)-1H-indole-1-sulfonamide (F76)

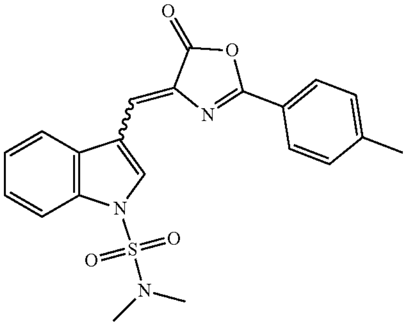 [SMILES: Cc1ccc(C2=NC(=Cc3cn(S(=O)(=O)N(C)C)c4ccccc34)C(=O)O2)cc1]

Example 1.77: 2-((2-(4-Chlorophenyl)-5-oxooxazol-4(5H)-ylidene)methyl)phenyl4-acetamido benzenesulfonate (F77)

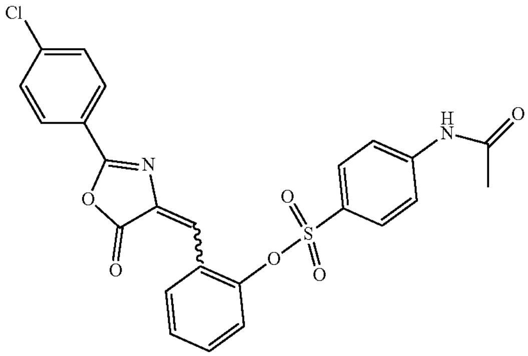 [SMILES: CC(=O)Nc1ccc(S(=O)(=O)Oc2ccccc2C=C2N=C(c3ccc(Cl)cc3)OC2=O)cc1]

Example 1.78: 4-((5-oxo-2-phenyloxazol-4(5H)-ylidene)methyl)phenylfuran-2-carboxylate (F78)

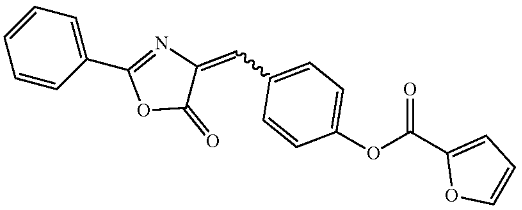 [SMILES: O=C1OC(c2ccccc2)=NC1=Cc1ccc(OC(=O)c2ccco2)cc1]

Example 1.79: 2,2'-(1,4-phenylene)bis(4-((5-methylfuran-2-yl)methylene)oxazol-5(4H)-one) (F79)

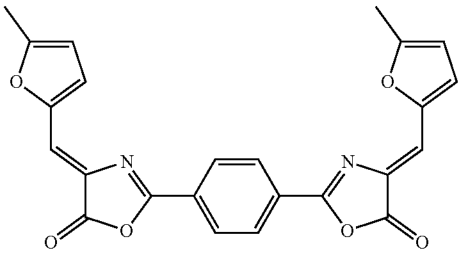 [SMILES: Cc1ccc(/C=C2\N=C(c3ccc(C4=N/C(=C\c5ccc(C)o5)C(=O)O4)cc3)OC2=O)o1]

Example 1.80: 2-((2-(4-(tert-butyl)phenyl)-5-oxooxazol-4(5H)-ylidene)methyl)phenylbenzne-sulfonate (F80)

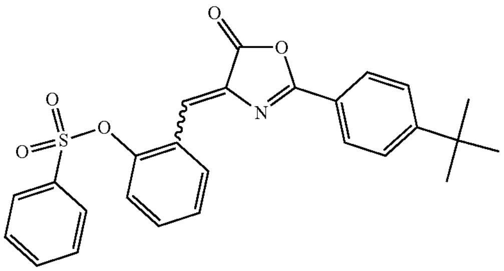 [SMILES: CC(C)(C)c1ccc(C2=NC(=Cc3ccccc3OS(=O)(=O)c3ccccc3)C(=O)O2)cc1]

Example 1.81: 4-((1-Acetyl-1H-indol-3-yl)methyl-ene)-2-(4-(tert-butyl)phenyl)oxazol-5 (4H)-one (F81)

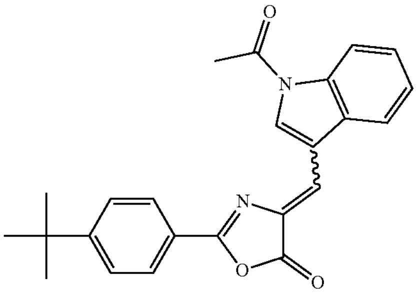 [SMILES: CC(=O)n1cc(C=C2N=C(c3ccc(C(C)(C)C)cc3)OC2=O)c2ccccc21]

Example 1.82: 4-((1-Acetyl-3-phenyl-1H-pyrazol-4-yl)methylene)-2-(4-(tert-butyl)phenyl)oxazol-5 (4H)-one (F82)

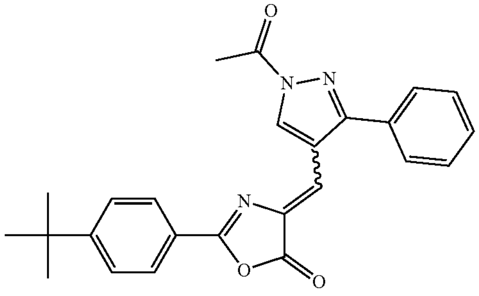 [SMILES: CC(=O)n1cc(C=C2N=C(c3ccc(C(C)(C)C)cc3)OC2=O)c(-c2ccccc2)n1]

Example 1.83: 4-((1,3-Diphenyl-1H-pyrazol-4-yl) methylene)-2-(p-tolyl)oxazol-5(4H)-one (F83)

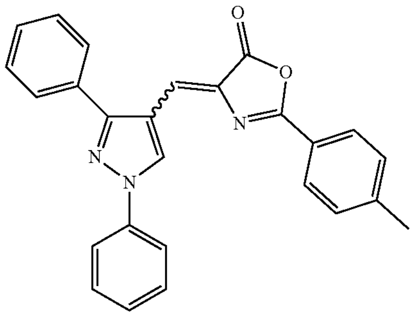 [SMILES: Cc1ccc(C2=NC(=Cc3cn(-c4ccccc4)nc3-c3ccccc3)C(=O)O2)cc1]

Example 1.84: 4-((6-Methoxy-2-oxo-1,2-dihydro-quinolin-3-yl)methylene)-2-phenyloxazol-5(4H)-one (F84)

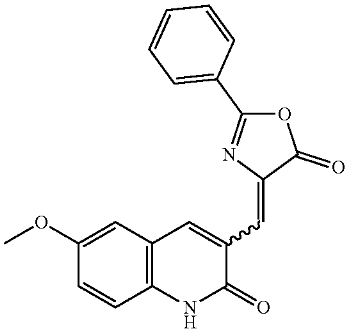 [SMILES: COc1ccc2[nH]c(=O)c(C=C3N=C(c4ccccc4)OC3=O)cc2c1]

Example 1.85: 4-(2,6-Diphenyl-4H-thiopyran-4-ylidene)-2-phenyloxazol-5(4H)-one (F85)

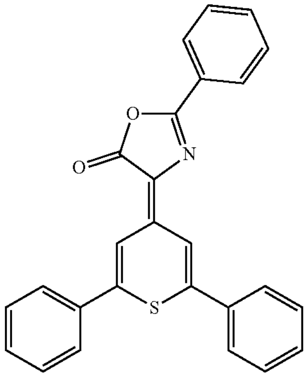 [SMILES: O=C1OC(c2ccccc2)=NC1=C1C=C(c2ccccc2)SC(c2ccccc2)=C1]

Example 1.86: N-(4-(4-(4-((2-chloroethyl)(methyl)amino)benzylidene)-5-oxo-4,5-dihydrooxazol-2-yl)phenyl)acetamide (F86)

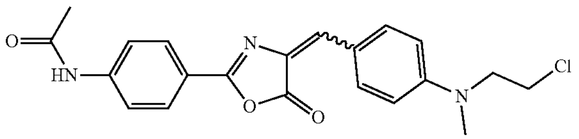 [SMILES: CC(=O)Nc1ccc(C2=NC(=Cc3ccc(N(C)CCCl)cc3)C(=O)O2)cc1]

Example 1.87: 2-(4-Methoxyphenyl)-4-(thiophen-2-ylmethylene)oxazol-5 (4H)-one (F87)

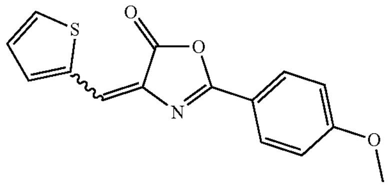 [SMILES: COc1ccc(C2=NC(=Cc3cccs3)C(=O)O2)cc1]

Example 1.88: 2-(4-Chlorophenyl)-4-(thiophen-2-ylmethylene)oxazol-5(4H)-one (F88)

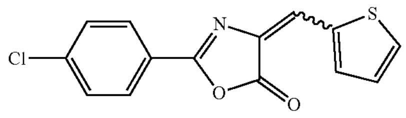 [SMILES: O=C1OC(c2ccc(Cl)cc2)=NC1=Cc1cccs1]

Example 1.89: 2-(Thiophen-2-yl)-4-(thiophen-2-ylmethylene)oxazol-5(4H)-one (F89)

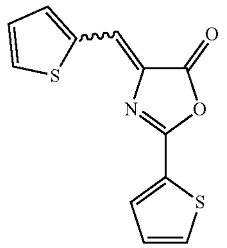 [SMILES: O=C1OC(c2cccs2)=NC1=Cc1cccs1]

Example 1.90: 4-(5-Oxo-4-(thiophen-2-ylmethylene)-4,5-dihydrooxazol-2-yl)phenylacetate (F90)

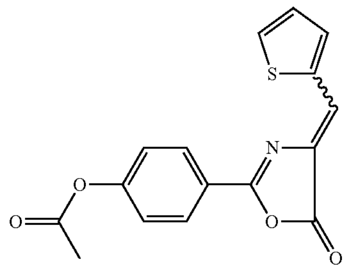 [SMILES: CC(=O)Oc1ccc(C2=NC(=Cc3cccs3)C(=O)O2)cc1]

Example 1.91: 2-(4-Chloro-3-nitrophenyl)-4-(thiophen-2-ylmethylene)oxazol-5(4H)-one (F91)

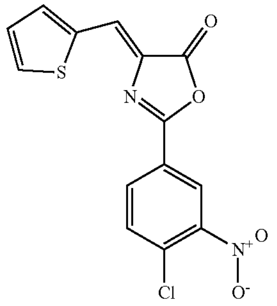

Example 1.92: 2-(2-Chlorophenyl)-4-(thiophen-2-ylmethylene)oxazol-5(4H)-one (F92)

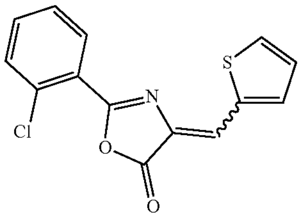 [SMILES: O=C1OC(c2ccccc2Cl)=NC1=Cc1cccs1]

Example 1.93: 2-(2-Chloro-4-nitrophenyl)-4-(thiophen-2-ylmethylene)oxazol-5(4H)-one (F93)

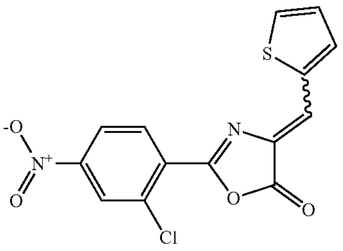

Example 1.94: 4-(Thiophen-2-ylmethylene)-2-(3,4,5-trimethoxyphenyl)oxazol-5(4H)-one (F94)

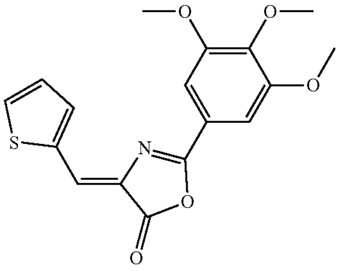 [SMILES: COc1cc(C2=N/C(=C\c3cccs3)C(=O)O2)cc(OC)c1OC]

Example 1.95: 2-(4-Phenoxyphenyl)-4-(thiophen-2-ylmethylene)oxazol-5(4H)-one (F95)

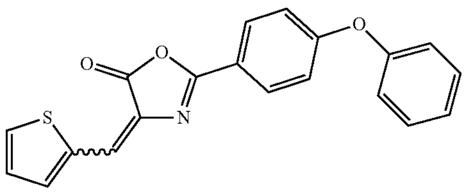 [SMILES: O=C1OC(c2ccc(Oc3ccccc3)cc2)=NC1=Cc1cccs1]

Example 1.96: 2-(4-(tert-butyl)phenyl)-4-((5-methylthiophen-2-yl)methylene)oxazol-5(4H)-one (F96)

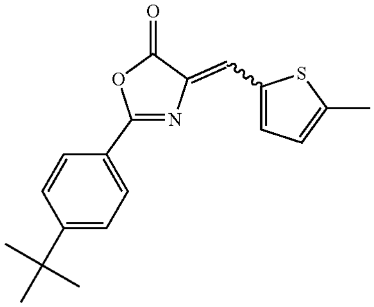 [SMILES: Cc1ccc(C=C2N=C(c3ccc(C(C)(C)C)cc3)OC2=O)s1]

Example 1.97: 2-(Benzo[d][1,3]dioxoyl-5-yl)-4-(thiophen-2-ylmethylene)oxazol-5(4H)-one (F97)

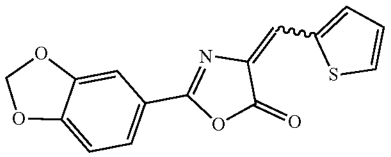 [SMILES: O=C1OC(c2ccc3c(c2)OCO3)=NC1=Cc1cccs1]

Example 1.98: 2-(4-(2-oxopyrrolidin-1-yl)phenyl)-4-(thiophen-2-ylmethylene)oxazol-5 (4H)-one (F98)

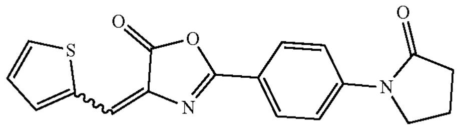 [SMILES: O=C1OC(c2ccc(N3CCCC3=O)cc2)=NC1=Cc1cccs1]

Example 1.99: 4-((5-Chlorothiophen-2-yl)methylene)-2-(4-methoxyphenyl)oxazol-5(4H)-one (F99)

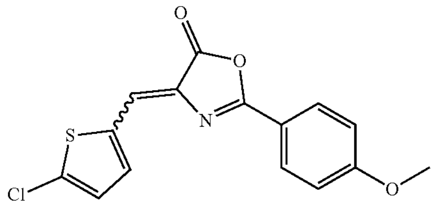 [SMILES: COc1ccc(C2=NC(=Cc3ccc(Cl)s3)C(=O)O2)cc1]

Example 1.100: 2-(Benzo[d][1,3]dioxoyl-5-yl)-4-((5-(piperidin-1-yl)thiophen-2-yl)methylene)oxazol-5(4H)-one (F100)

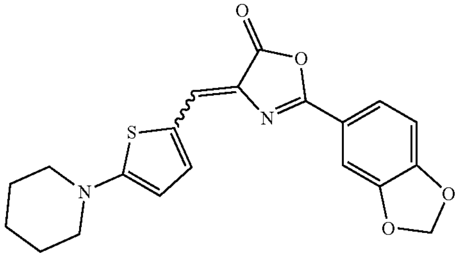 [SMILES: O=C1OC(c2ccc3c(c2)OCO3)=NC1=Cc1ccc(N2CCCCC2)s1]

Example 1.101: 2-(3,4-Diethoxyphenyl)-4-(thiophen-2-ylmethylene)oxazol-5(4H)-one (F101)

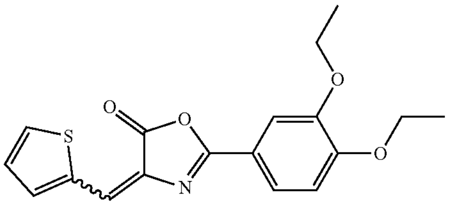 [SMILES: CCOc1ccc(C2=NC(=Cc3cccs3)C(=O)O2)cc1OCC]

Example 1.102: 2-(4-(Difluoromethoxy)-3-methoxyphenyl)-4-(thiophen-2-ylmethylene)oxazol-5 (4H)-one (F102)

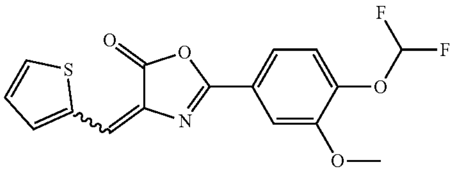 [SMILES: COc1cc(C2=NC(=Cc3cccs3)C(=O)O2)ccc1OC(F)F]

Example 1.103: 2-(5-Ethyl-4-methylthiophen-2-yl)-4-(thiophen-2-ylmethylene)oxazol-5(4H)-one (F103)

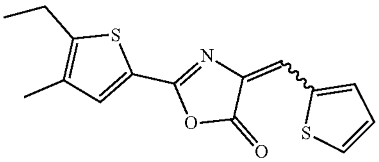 [SMILES: CCc1sc(C2=NC(=Cc3cccs3)C(=O)O2)cc1C]

Example 1.104: 2-(3-Methoxyphenyl)-4-(thiophen-2-ylmethylene)oxazol-5(4H)-one (F104)

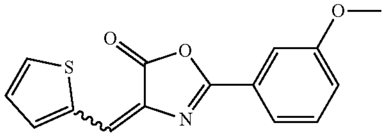 [SMILES: COc1cccc(C2=NC(=Cc3cccs3)C(=O)O2)c1]

Example 1.105: 4-((5-(Dimethylamino)thiophen-2-yl)methylene)-2-(naphthalen-2-yl)oxazol-5(4H)-one (F105)

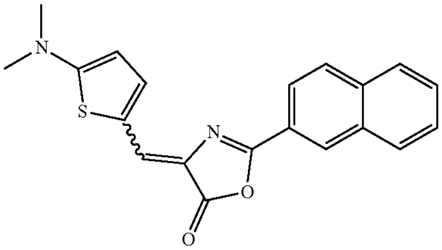 [SMILES: CN(C)c1ccc(C=C2N=C(c3ccc4ccccc4c3)OC2=O)s1]

Example 1.106: N-(4-(4-((4-bromothiophen-2-yl)methylene)-5-oxo-4,5-dihydrooxazol-2-yl)phenyl) acetamide (F106)

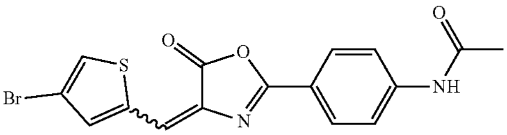 [SMILES: CC(=O)Nc1ccc(C2=NC(=Cc3cc(Br)cs3)C(=O)O2)cc1]

Example 1.107: N-(4-(4-((5-bromothiophen-2-yl)methylene)-5-oxo-4,5-dihydrooxazol-2-yl)phenyl) acetamide (F107)

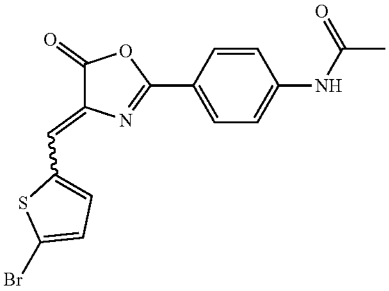 [SMILES: CC(=O)Nc1ccc(C2=NC(=Cc3ccc(Br)s3)C(=O)O2)cc1]

Example 1.108: N-(4-(4-((5-(dimethylamino)thiophen-2-yl)methylene)-5-oxo-4,5-dihydrooxazol-2-yl)phenyl) acetamide (F108)

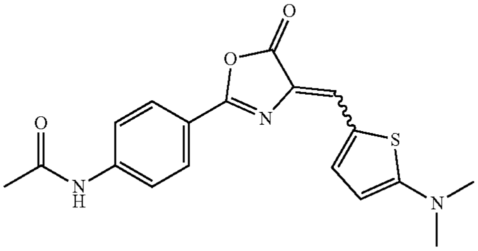 [SMILES: CC(=O)Nc1ccc(C2=NC(=Cc3ccc(N(C)C)s3)C(=O)O2)cc1]

Example 1.109: 2-(4-(Benzyloxy)phenyl)-4-(thiophen-2-ylmethylene)oxazol-5(4H)-one (F109)

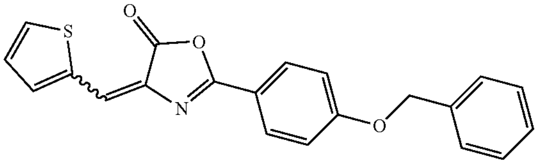 [SMILES: O=C1OC(c2ccc(OCc3ccccc3)cc2)=NC1=Cc1cccs1]

Example 1.110: 2-((E)-styryl)-4-(thiophen-2-ylmethylene)oxazol-5 (4H)-one (F110)

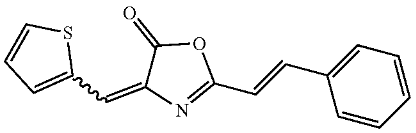 [SMILES: O=C1OC(/C=C/c2ccccc2)=NC1=Cc1cccs1]

Example 1.111: 2-(5-methylthiophen-2-yl)-4-(thiophen-2-ylmethylene)oxazol-5 (4H)-one (F111)

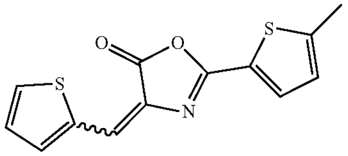 [SMILES: Cc1ccc(C2=NC(=Cc3cccs3)C(=O)O2)s1]

Example 1.112: N,N-diethyl-3-(5-oxo-4-(thiophen-2-ylmethylene)-4,5-dihydrooxazol-2-yl)benzene sulfonamide (F112)

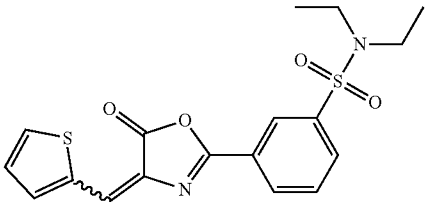 [SMILES: CCN(CC)S(=O)(=O)c1cccc(C2=NC(=Cc3cccs3)C(=O)O2)c1]

Example 1.113: 2-(2-Methoxyphenyl)-4-((2,4,5-trimethylthieno[2,3-d]pyrimidin-6-yl)methylene) oxazol-5(4H)-one (F113)

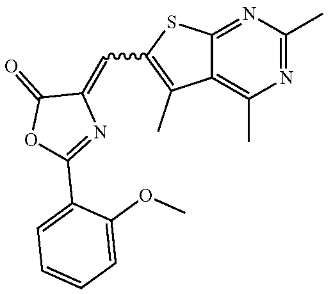 [SMILES: COc1ccccc1C1=NC(=Cc2sc3nc(C)nc(C)c3c2C)C(=O)O1]

Example 1.114: 4-((5-(Dimethylamino)thiophen-2-yl)methylene)-2-(2-methoxyphenyl)oxazol-5(4H)-one (F114)

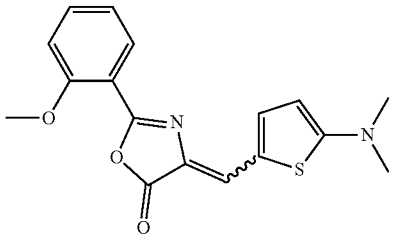

Example 1.115: 4-((5-Methylthiophen-2-yl)methylene)-2-(thiophen-2-yl)oxazol-5(4H)-one (F115)

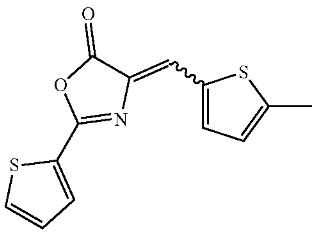 [SMILES: Cc1ccc(C=C2N=C(c3cccs3)OC2=O)s1]

Example 1.116: N,N-dimethyl-3-(5-oxo-4-(thiophen-2-ylmethylene)-4,5-dihydrooxazol-2-yl) benzenesulfonamide (F116)

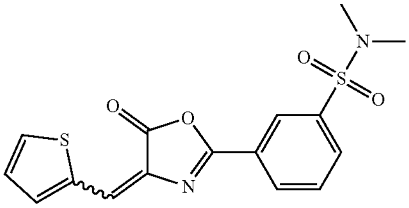 [SMILES: CN(C)S(=O)(=O)c1cccc(C2=NC(=Cc3cccs3)C(=O)O2)c1]

Example 1.117: 4-((5-Bromothiophen-2-yl)methylene)-2-(2-methoxyphenyl)oxazol-5(4H)-one (F117)

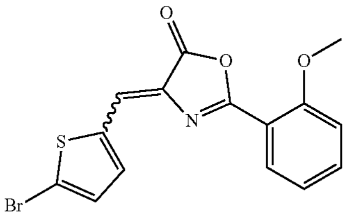 [SMILES: COc1ccccc1C1=NC(=Cc2ccc(Br)s2)C(=O)O1]

Example 1.118: 4-((5-Bromothiophen-2-yl)methylene)-2-(thiophen-2-yl)oxazol-5(4H)-one (F118)

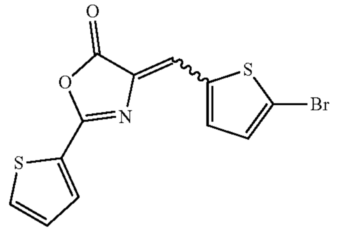 [SMILES: O=C1OC(c2cccs2)=NC1=Cc1ccc(Br)s1]

Example 1.119: 2-(5-methylthiophen-2-yl)-4-((5-methylthiophen-2-yl)methylene)oxazol-5 (4H)-one (F119)

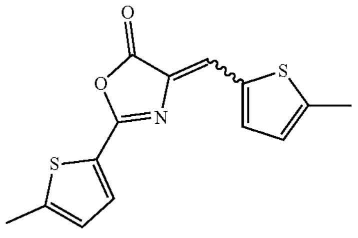

Example 1.120: 4-((5-(Piperidin-1-yl)thiophen-2-yl) methylene)-2-(thiophen-2-yl)oxazol-5 (4H)-one (F120)

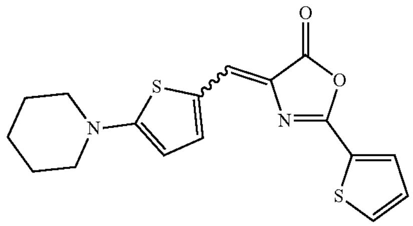 [SMILES: O=C1OC(c2cccs2)=NC1=Cc1ccc(N2CCCCC2)s1]

Example 1.121: 4-((5-Bromothiophen-2-yl)methylene)-2-(2-(difluoromethoxy)phenyl)oxazol-5(4H)-one (F121)

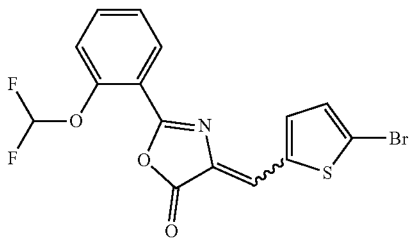 [SMILES: O=C1OC(c2ccccc2OC(F)F)=NC1=Cc1ccc(Br)s1]

Example 1.122: 2-(4-(tert-butyl)phenyl)-4-(2-(difluoromethoxy)benzylidene)oxazol-5(4H)-one (F122)

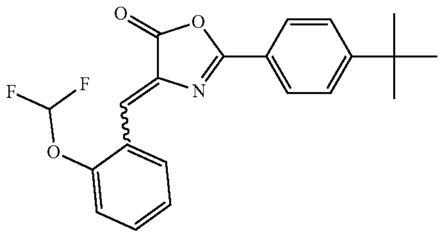 [SMILES: CC(C)(C)c1ccc(C2=NC(=Cc3ccccc3OC(F)F)C(=O)O2)cc1]

Example 1.123: 4-((1-(2-Chlorobenzyl)-1H-pyrazol-4-yl)methylene)-2-(naphthalen-2-yl)oxazol-5 (4H)-one (F123)

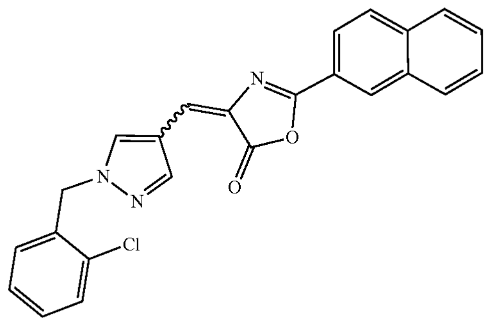 [SMILES: O=C1OC(c2ccc3ccccc3c2)=NC1=Cc1cnn(Cc2ccccc2Cl)c1]

Example 1.124: 2-(4-(tert-butyl)phenyl)-4-((1-phenyl-1H-pyrazol-4-yl)methylene)oxazol-5 (4H)-one (F124)

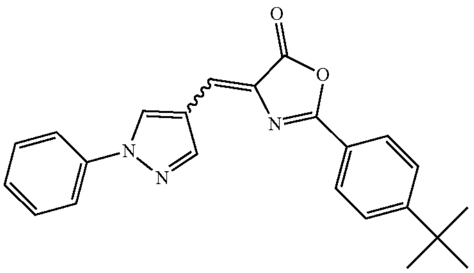 [SMILES: CC(C)(C)c1ccc(C2=NC(=Cc3cnn(-c4ccccc4)c3)C(=O)O2)cc1]

Example 1.125: 2-(2-methoxyphenyl)-4-((1-methyl-1H-pyrazol-4-yl)methylene)oxazol-5(4H)-one (F125)

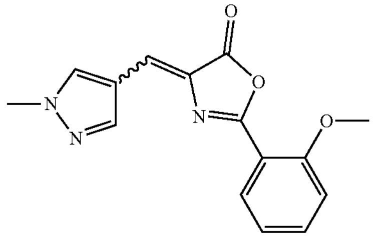

Example 1.126: N-(tert-butyl)-4-(4-((5-methylfuran-2-yl)methylene)-5-oxo-4,5-dihydrooxazol-2-yl) benzenesulfonamide (F126)

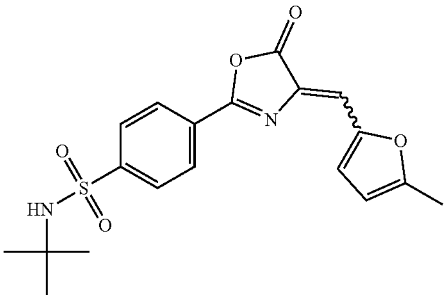 [SMILES: Cc1ccc(C=C2N=C(c3ccc(S(=O)(=O)NC(C)(C)C)cc3)OC2=O)o1]

Example 1.127: N,N-diethyl-4-(4-(1-methylpyridin-2(1H)-ylidene)-5-oxo-4,5-dihydrooxazol-2-yl)benzenesulfonamide (F127)

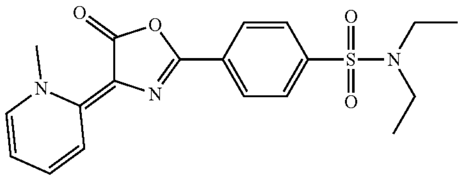 [SMILES: CCN(CC)S(=O)(=O)c1ccc(C2=N/C(=C3\C=CC=CN3C)C(=O)O2)cc1]

Example 1.128: 2-(4-((2-(2-methoxyphenyl)-5-oxooxazol-4(5H)-ylidene)methyl)phenoxy)acetamide (F128)

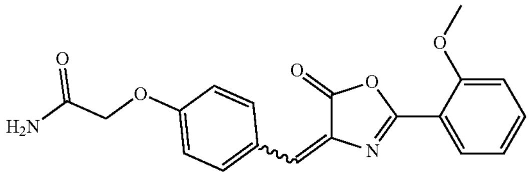 [SMILES: COc1ccccc1C1=NC(=Cc2ccc(OCC(N)=O)cc2)C(=O)O1]

Example 1.129: N-(4-((2-(4-isopropoxyphenyl)-5-oxooxazol-4(5H)-yl idene)methyl)phenyl)acetamide (F129)

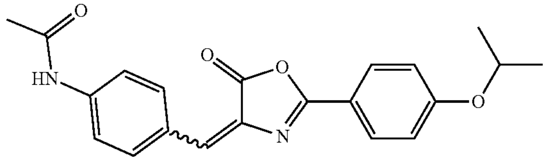 [SMILES: CC(=O)Nc1ccc(C=C2N=C(c3ccc(OC(C)C)cc3)OC2=O)cc1]

Example 1.130: 4-((1-Benzyl-1H-pyrazol-4-yl) methylene)-2-(4-isopropoxyphenyl)oxazol-5 (4H)-one (F130)

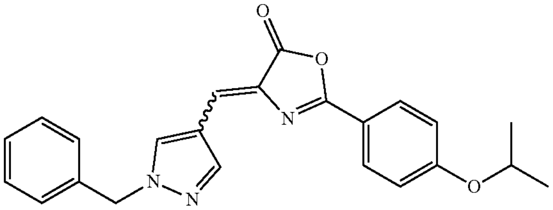 [SMILES: CC(C)Oc1ccc(C2=NC(=Cc3cnn(Cc4ccccc4)c3)C(=O)O2)cc1]

Example 1.131: N,N-diethyl-3-(4-((1-methyl-1H-pyrazol-4-yl)methylene)-5-oxo-4,5-dihydrooxazol-2-yl)benzenesulfonamide (F131)

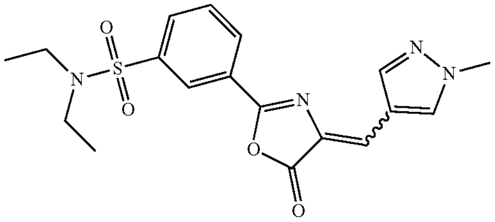 [SMILES: CCN(CC)S(=O)(=O)c1cccc(C2=NC(=Cc3cnn(C)c3)C(=O)O2)c1]

Example 1.132: 4-(4-(1H-1,2,4-thiazol-1-yl)benzylidene)-2-(2-iodophenyl)oxazol-5(4H)-one (F132)

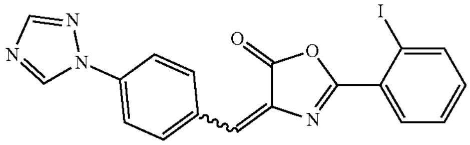 [SMILES: O=C1OC(c2ccccc2I)=NC1=Cc1ccc(-n2cncn2)cc1]

Example 1.133: 4-(4-((3,5-Dimethylisoxazol-4-yl) methoxy)-3-methoxybenzylidene)-2-(2-methoxyphenyl)oxazol-5 (4H)-one (F133)

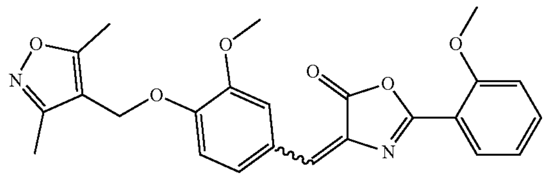 [SMILES: COc1cc(C=C2N=C(c3ccccc3OC)OC2=O)ccc1OCc1c(C)noc1C]

Example 1.134: N-(4-(4-(4-(1H-1,2,4-thiazol-1-yl) benzylidene)-5-oxo-4,5-dihydrooxazol-2-yl)phenyl) acetamide (F134)

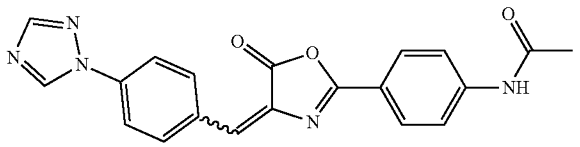 [SMILES: CC(=O)Nc1ccc(C2=NC(=Cc3ccc(-n4cncn4)cc3)C(=O)O2)cc1]

Example 1.135: 2-(2-(difluoromethoxy)phenyl)-4-((E)-3-(furan-2-yl)allylidene)oxazol-5 (4H)-one (F135)

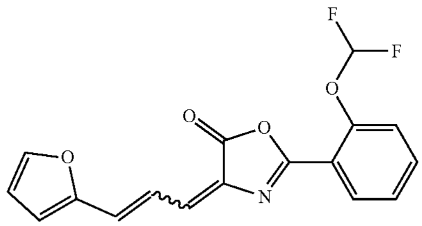 [SMILES: O=C1OC(c2ccccc2OC(F)F)=NC1=CC=Cc1ccco1]

Example 1.136: 4-((1-(tert-butyl)-1H-pyrazol-4-yl) methylene)-2-(2-methoxyphenyl)oxazol-5(4H)-one (F136)

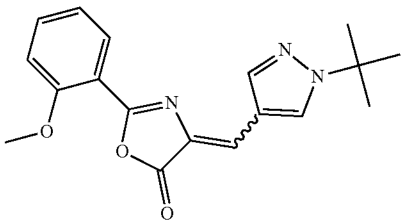 [SMILES: COc1ccccc1C1=NC(=Cc2cnn(C(C)(C)C)c2)C(=O)O1]

Example 1.137: 4-((4-Methylthiazol-5-yl)methylene)-2-(4-propylphenyl)oxazol-5(4H)-one (F137)

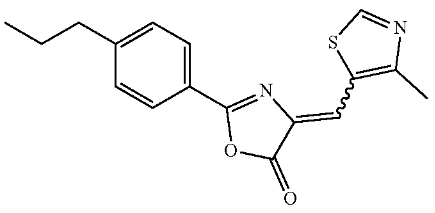 [SMILES: CCCc1ccc(C2=NC(=Cc3scnc3C)C(=O)O2)cc1]

$^1$H NMR (400 MHz, DMSO-$d_6$) δ 9.27 (s, 1H), 9.94 (d, 2H, J=8.0 Hz), 7.53 (s, 1H), 7.41 (d, 2H, J=8.0 Hz), 2.63 (t, 2H, J=7.6 Hz), 2.59 (s, 3H), 1.64-1.55 (m, 2H), 0.87 (t, 3H, J=7.2 Hz).

$^{13}$C NMR (400 MHz, DMSO-$d_6$) δ 166.1, 12.6, 160.62, 159.76, 149.2, 132.0, 129.9, 129.3, 126.5, 123.0, 121.3, 37.7, 24.1, 16.2, 14.0.

Example 1.138: 4-((1H-pyrrol-2-yl)methylene)-2-(4-butoxyphenyl)oxazol-5 (4H)-one (F138)

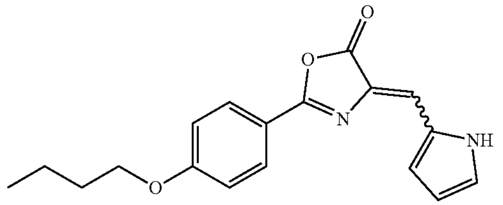 [SMILES: CCCCOc1ccc(C2=NC(=Cc3ccc[nH]3)C(=O)O2)cc1]

$^1$H NMR (400 MHz, DMSO-$d_6$) δ 11.50 (s, 1H), 8.08 (d, 2H, J=8.4 Hz), 7.29 (s, 1H), 7.13 (s, 1H), 7.07 (d, 2H, J=8.4 Hz), 7.00 (s, 1H), 6.31 (s, 1H), 4.03 (t, 2H, J=6.0 Hz), 1.70-1.67 (m, 2H), 1.45-1.36 (m, 2H), 0.91 (t, 3H, J=5.2 Hz).

Example 1.139: 2-(4-Hexylphenyl)-4-(thiophen-2-ylmethylene)oxazol-5 (4H)-one (F139)

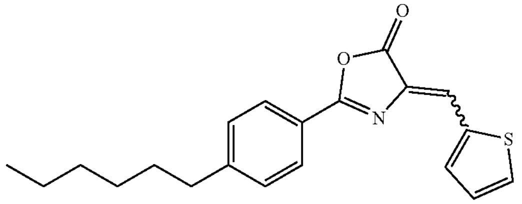 [SMILES: CCCCCCc1ccc(C2=NC(=Cc3cccs3)C(=O)O2)cc1]

$^1$H NMR (400 MHz, DMSO-$d_6$) δ 8.01 (d, 1H, J=3.6 Hz), 7.95 (d, 2H, J=8.0 Hz), 7.80 (br s, 1H), 7.66 (s, 1H), 7.41 (d, 2H, J=8.0 Hz), 7.22 (br s, 1H), 2.64 (t, 2H, J=7.2 Hz), 1.56 (br s 2H), 1.24 (s, 6H), 0.81 (br s, 3H).

$^{13}$C NMR (400 MHz, DMSO-$d_6$) δ 166.7, 162.2, 149.2, 137.6, 136.9, 136.6, 130.7, 129.7, 128.6, 128.2, 124.8, 123.0, 35.7, 31.5, 30.9, 28.7, 22.5, 14.4.

Example 1.140: 4-((1H-indol-2-yl)methylene)-2-(4-(tert-butyl)phenyl)oxazol-5(4H)-one (F140)

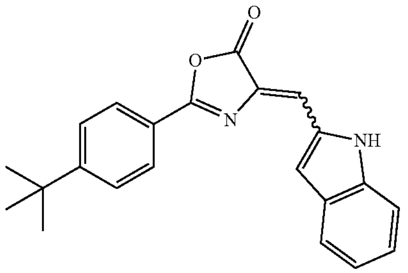 [SMILES: CC(C)(C)c1ccc(C2=NC(=Cc3cc4ccccc4[nH]3)C(=O)O2)cc1]

$^1$H NMR (400 MHz, DMSO-$d_6$) δ 11.27 (s, 1H), 8.18 (d, 2H, J=8.0 Hz), 7.63 (t, 4H, J=7.4 Hz), 7.35 (d, 2H, J=8.8 Hz), 7.25 (t, 1H, J=7.4 Hz), 7.05 (t, 1H, J=7.6 Hz), 1.30 (s, 9H).

$^{13}$C NMR (400 MHz, DMSO-$d_6$) δ 166.9, 161.9, 157.1, 139.7, 133.2, 130.8, 128.5, 128.2, 126.5, 125.6, 122.9, 122.1, 121.0, 120.8, 113.4, 113.0, 35.3, 31.2.

Example 1.141: 4-(Furan-2-ylmethylene)-2-(4-pentylphenyl)oxazol-5(4H)-one (F141)

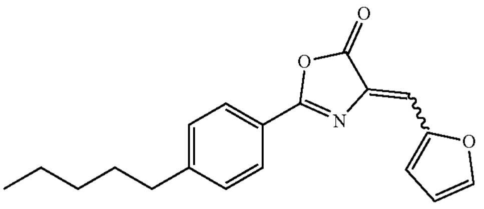 [SMILES: CCCCCc1ccc(C2=NC(=Cc3ccco3)C(=O)O2)cc1]

$^1$H NMR (400 MHz, DMSO-$d_6$) δ 8.05 (s, 1H), 7.97 (d, 2H, J=7.6 Hz), 7.56-7.55 (m, 1H), 7.40 (d, 2H, J=7.6 Hz), 7.15 (s, 1H), 6.80 (br s, $^1$H), 2.64 (t, 2H, J=7.4 Hz), 1.59-1.57 (m, 2H), 1.26 (br s, 4H), 0.82 (t, 3H, J=6.2 Hz).

$^{13}$C NMR (400 MHz, DMSO-$d_6$) δ 167.0, 162.8, 150.4, 149.3, 148.3, 130.5, 129.7, 128.4, 123.0, 120.8, 117.4, 114.6, 35.6, 31.3, 30.7, 22.3, 14.3.

Example 1.142: 2-(4-Butoxyphenyl)-4-(thiophen-2-ylmethylene)oxazol-5 (4H)-one (F142)

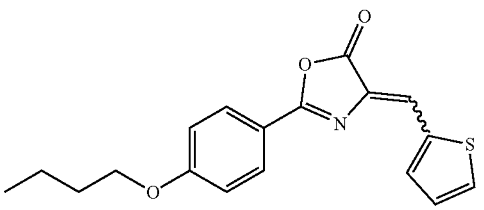 [SMILES: CCCCOc1ccc(C2=NC(=Cc3cccs3)C(=O)O2)cc1]

$^1$H NMR (400 MHz, DMSO-$d_6$) δ 7.98-7.96 (m, 3H), 7.78 (d, 1H, J=3.2 Hz), 7.60 (s, 1H), 7.21 (t, 1H, J=4.4 Hz), 7.12 (d, 2H, J=8.4 Hz), 4.05 (t, 2H, J=6.4 Hz), 1.73-1.66 (m, 2H), 1.46-1.37 (m, 2H), 0.91 (t, 3H, J=7.2 Hz).

$^{13}$C NMR (400 MHz, DMSO-$d_6$) δ 166.8, 163.4, 162.0, 137.7, 136.5, 136.1, 130.9, 130.3, 129.5, 123.8, 117.4, 115.8, 69.2, 31.0, 19.1, 14.1.

Example 1.143: 4-((1H-pyrrol-2-yl)methylene)-2-(4-propylphenyl)oxazol-5(4H)-one (F143)

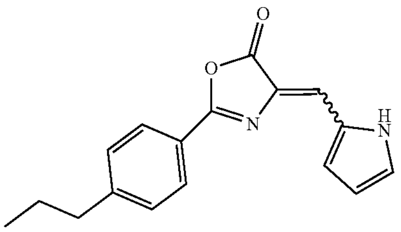

$^1$H NMR (400 MHz, DMSO-$d_6$) δ 11.52 (s, 1H), 8.07 (d, 2H, J=8.0 Hz), 7.39 (d, 2H, J=8.4 Hz), 7.31 (s, 1H), 7.19 (s, 1H), 7.04 (s, 1H), 6.34-6.32 (m, 1H), 2.63 (t, 2H, J=8.4 Hz), 1.65-1.56 (m, 2H), 0.88 (t, 3H, J=7.4 Hz).

ESI (m/z) 281 (MH+).

Example 1.144: 2-(4-Propylphenyl)-4-(thiophen-2-ylmethylene)oxazol-5(4H)-one (F144)

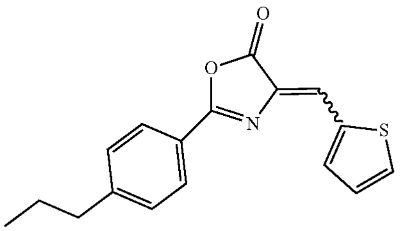

$^1$H NMR (400 MHz, DMSO-$d_6$) δ 8.02 (d, 1H, J=5.2 Hz), 7.96 (d, 2H, J=8.4 Hz), 7.81 (d, 1H, J=3.6 Hz), 7.67 (s, 1H), 7.42 (d, 2H, J=8.0 Hz), 7.23-7.21 (m, 1H), 2.64 (t, 2H, J=7.4 Hz), 1.65-1.56 (m, 2H), 0.88 (t, 3H, J=7.4 Hz).

ESI (m/z) 298 (MH+).

Example 1.145: 2-(4-Propylphenyl)-4-(thiophen-3-ylmethylene)oxazol-5 (4H)-one (F145)

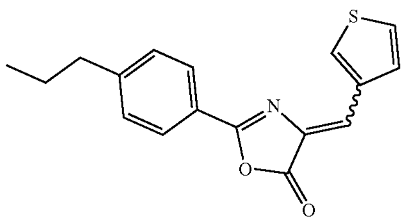 [SMILES: CCCc1ccc(C2=NC(=Cc3ccsc3)C(=O)O2)cc1]

$^1$H NMR (400 MHz, DMSO-$d_6$) δ 8.02 (d, 1H, J=5.2 Hz), 7.97 (d, 2H, J=4.4 Hz), 7.81 (d, 1H, J=3.6 Hz), 7.67 (s, 1H), 7.42 (d, 2H, J=8.4 Hz), 7.23-7.21 (m, 1H), 2.63 (t, 2H, J=8.4 Hz), 1.65-1.56 (m, 2H), 0.88 (t, 3H, J=7.2 Hz).

ESI (m/z) 298 (MH+).

Example 1.146: 4-(Furan-2-ylmethylene)-2-(4-propylphenyl)oxazol-5(4H)-one (F146)

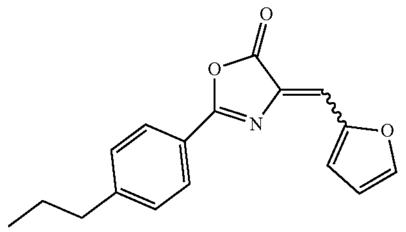 [SMILES: CCCc1ccc(C2=NC(=Cc3ccco3)C(=O)O2)cc1]

$^{1}$H NMR (400 MHz, DMSO-$d_6$) δ 8.05 (s, 1H), 7.98 (d, 2H, J=8.0 Hz), 7.56 (s, 1H), 7.41 (d, 2H, J=8.0 Hz), 7.15 (s, 1H), 6.80 (s, 1H), 2.63 (t, 2H, J=7.4 Hz), 1.63-1.57 (m, 2H), 0.87 (t, 3H, J=7.2 Hz).

$^{13}$C HMR (400 MHz, DMSO-$d_6$) δ 167.0, 162.8, 150.4, 149.0, 148.3, 130.5, 129.8 (2), 128.4 (2), 123.0, 120.8, 117.4, 114.6, 37.7, 24.1, 14.0.

ESI (m/z) 282 (MH+).

Example 1.147: 4-((1H-pyrrol-2-yl)methylene)-2-(4-hexylphenyl)oxazol-5(4H)-one (F147)

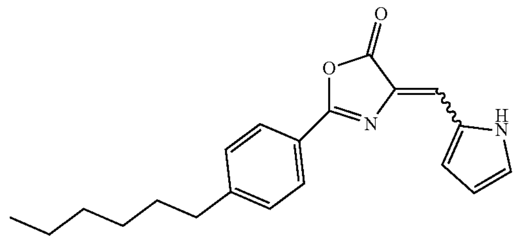 [SMILES: CCCCCCc1ccc(C2=NC(=Cc3ccc[nH]3)C(=O)O2)cc1]

ESI (m/z) 323 (MH+).

Example 1.148: 2-(4-(4-((1H-pyrrol-2-yl)methylene)-5-oxo-4,5-dihydrooxazol-2-yl)phenyl)-2-methylpropenenitrile (F148)

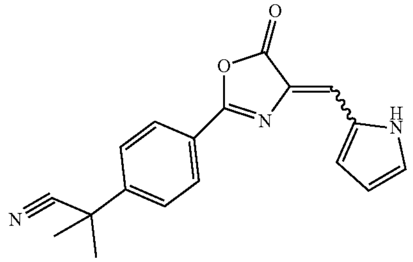 [SMILES: CC(C)(C#N)c1ccc(C2=NC(=Cc3ccc[nH]3)C(=O)O2)cc1]

ESI (m/z) 306 (MH+).

Example 1.149: 4-((1H-pyrrol-2-yl)methylene)-2-(3,5-dimethylphenyl)oxazol-5(4H)-one (F149)

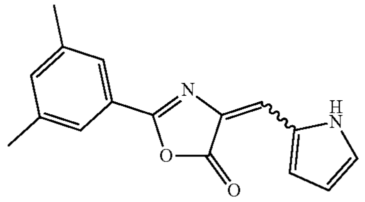 [SMILES: Cc1cc(C)cc(C2=NC(=Cc3ccc[nH]3)C(=O)O2)c1]

ESI (m/z) 267 (MH+).

Example 1.150: 2-(3,5-Dimethylphenyl)-4-(thiophen-2-ylmethylene)oxazol-5(4H)-one (F150)

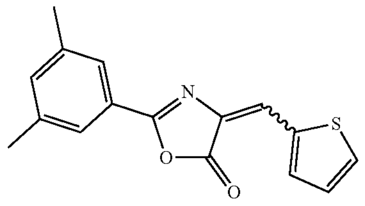 [SMILES: Cc1cc(C)cc(C2=NC(=Cc3cccs3)C(=O)O2)c1]

$^{1}$H NMR (400 MHz, DMSO-$d_6$) δ 8.01 (d, 1H, J=4.8 Hz), 7.79 (d, 1H, J=3.2 Hz), 7.65 (s, 1H), 7.63 (s, 1H), 7.28 (s, 1H), 7.21 (t, 1H, J=4.2 Hz), 2.33 (s, 6H)

ESI (m/z) 284 (MH+).

Example 2.1: Methyl 2-(4-(tert-butyl)benzamido)-3-(1H-pyrrol-2-yl)acrylate (G1)

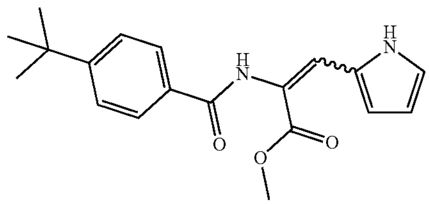 [SMILES: COC(=O)C(=Cc1ccc[nH]1)NC(=O)c1ccc(C(C)(C)C)cc1]

$^{1}$H NMR (400 MHz, DMSO-$d_6$) δ 11.56 (s, 1H), 9.73 (s, 1H), 7.94 (d, 2H, J=8.1 Hz), 7.50 (d, 2H, J=8.1 Hz), 7.45 (s, 1H), 6.97 (s, 1H), 6.54-6.47 (m, 1H), 6.12 (s, 1H), 3.64 (s, 3H), 1.29 (s, 9H).

Example 2.2: Methyl 2-(4-(tert-butyl)benzamido)-3-(thiophen-2-yl)acrylate (G2)

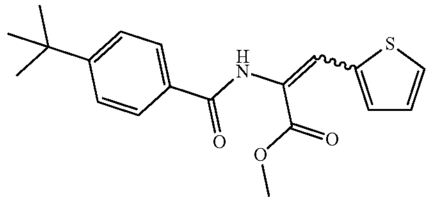 [SMILES: COC(=O)C(=Cc1cccs1)NC(=O)c1ccc(C(C)(C)C)cc1]

$^1$H NMR (400 MHz, DMSO-$d_6$) δ 9.77 (s, 1H), 7.95 (d, 2H, J=8.3 Hz), 7.88 (s, 1H), 7.70 (d, 1H, J=5.0 Hz), 7.57-7.50 (m, 3H), 7.12-7.09 (m, 1H), 3.69 (s, 3H), 1.29 (s, 9H).

Example 2.3: 2-(4-(tert-butyl)benzamido)-3-(thiophen-2-yl)acrylate (G3)

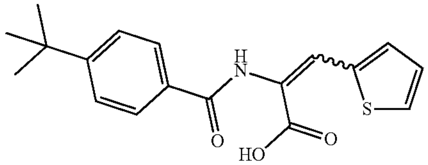 [SMILES: CC(C)(C)c1ccc(C(=O)NC(=Cc2cccs2)C(=O)O)cc1]

$^1$H NMR (400 MHz, DMSO-$d_6$) δ 12.62 (s, 1H), 9.64 (s, 1H), 7.93 (d, 2H, J=8.3 Hz), 7.83 (s, 1H), 7.66 (d, 1H, J=5.0 Hz), 7.54-7.49 (m, 3H), 7.09 (t, 1H, J=4.0 Hz), 1.29 (s, 9H).

ESI (m/z) 352 ($MNa^+$), 328 ($MH^-$).

Example 2.4: Methyl 2-(4-(tert-butyl)beznamido)-3-(furan-2-yl)acrylate (G4)

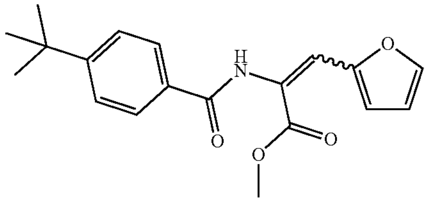 [SMILES: COC(=O)C(=Cc1ccco1)NC(=O)c1ccc(C(C)(C)C)cc1]

2-(4-(tert-butyl)phenyl)-4-(furan-2-ylmethylene)oxazol-5(4H)-one (F38) (300 mg, 1.02 mmol) was added to MeOH (10 ml) under stirring. When the suspension became a transparent solution, triethylamine (0.425 ml, 3.05 mmol) was added to the mixture, and it was stirred for 1 hour. After completing the reaction (TLC), the solvent was removed under decompression. It was passed through a filtration funnel and recrystallized with methanol to provide the resulting solid (2-(4-(tert-butyl) benzamido)-3-(furan-2-yl) acrylate (G4)

$^1$H NMR (400 MHz, DMSO-$d_6$) δ 9.87 (s, 1H), 7.92 (d, 2H, J=8.3 Hz), 7.81 (s, 1H), 7.51 (d, 2H, J=8.3 Hz), 7.24 (s, 1H), 6.84 (d, 1H, J=3.4 Hz), 6.60-6.57 (m, 1H), 3.68 (s, 3H), 1.29 (s, 9H).

ESI (m/z) 328 ($MH^+$), 350 ($MNa^+$), 326 ($MH^-$).

Example 2.5: 2-(4-(tert-butyl)benzamido)-3-(furan-2-yl)acrylate (G5)

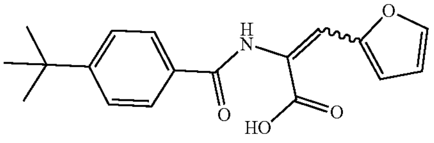 [SMILES: CC(C)(C)c1ccc(C(=O)NC(=Cc2ccco2)C(=O)O)cc1]

$^1$H NMR (400 MHz, DMSO-$d_6$) δ 12.67 (s, 1H), 9.72 (s, 1H), 7.90 (d, 2H, J=8.2 Hz), 7.78 (s, 1H), 7.50 (d, 2H, J=8.3 Hz), 7.23 (s, 1H), 6.78 (d, 1H, J=3.3 Hz), 6.58-6.55 (m, 1H), 1.28 (s, 9H).

ESI (m/z) 336 ($MNa^+$), 312 ($MH^-$).

Example 2.6: tert-butyl 2-(4-(tert-butyl)benzamido)-3-(1H-pyrrol-2-yl)acrylate (G6)

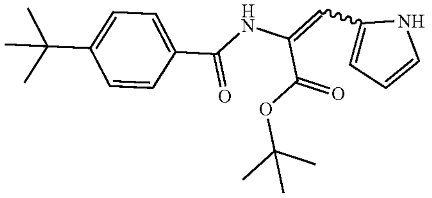 [SMILES: CC(C)(C)OC(=O)C(=Cc1ccc[nH]1)NC(=O)c1ccc(C(C)(C)C)cc1]

$^1$H NMR (400 MHz, DMSO-$d_6$) δ 11.24 (s, 1H), 9.49 (s, 1H), 7.90 (d, 2H, J=8.3 Hz), 7.50 (d, 2H, J=8.3 Hz), 7.33 (s, 1H), 6.94 (s, 1H), 6.48 (s, 1H), 6.10 (s, 1H), 1.39 (s, 9H), 1.29 (s, 9H).

Example 2.7: 2-(4-(tert-butyl)benzamido)-3-(1H-pyrrol-2-yl)acrylate (G7)

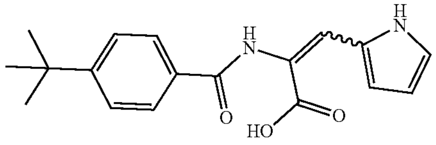 [SMILES: CC(C)(C)c1ccc(C(=O)NC(=Cc2ccc[nH]2)C(=O)O)cc1]

4-((1H-pyrrol-2-yl) methylene)-2-(4-(tert-butyl)phenyl) oxazol-5(4H)-one (F10) (1.02 mmol) was added to acetone (5 ml) under stirring. When the suspension became a transparent solution, 1% NaOH (3.05 mmol) was added to the mixture and it was stirred for 1 hours. After completing the reaction (TLS), it was acidified with 10% HCl and it was passed through a filtration funnel to provide a solid (2-(4-(tert-butyl)benzamido)-3-(1H-pyrrol-2-yl)acrylate (G7).

$^1$H NMR (400 MHz, DMSO-$d_6$) δ 12.23 (s, 1H), 11.24 (s, 1H), 9.48 (s, 1H), 7.92 (d, 2H, J=8.4 Hz), 7.50 (d, 2H, J=8.0 Hz), 7.43 (s, 1H), 6.95 (s, 1H), 6.47 (s, 1H), 6.11 (s, 1H), 1.29 (s, 9H).

Example 2.8: 2-(4-(tert-butyl)benzamido)-3-(thiophen-3-yl)acrylate (G8)

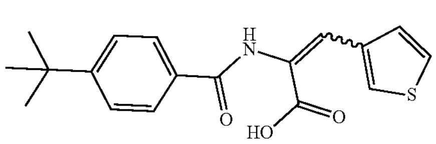 [SMILES: CC(C)(C)c1ccc(C(=O)NC(=Cc2ccsc2)C(=O)O)cc1]

$^1$H NMR (400 MHz, DMSO-$d_6$) δ 12.59 (S, 1H), 9.76 (s, 1H), 7.91 (d, 3H, J=9.6 Hz), 7.51 (d, 4H, J=7.2 Hz), 7.37 (d, 1H, J=4.8 Hz), 1.29 (s, 9H).

Example 2.9: 2-(4-(tert-butyl)benzamido)-3-(4-methylthiazol-5-yl)acrylate (G9)

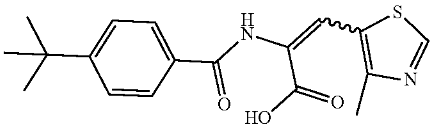 [SMILES: Cc1ncsc1C=C(NC(=O)c1ccc(C(C)(C)C)cc1)C(=O)O]

$^1$H NMR (400 MHz, DMSO-$d_6$) δ 12.83 (s, 1H), 9.73 (s, 1H), 9.00 (s, 1H), 7.92 (d, 2H, J=8.4 Hz), 7.74 (s, 1H), 7.53 (d, 2H, J=8.4 Hz), 2.47 (s, 3H), 1.29 (s, 9H).

Example 2.10: 2-(4-(tert-butyl)benzamido)-3-(1-methyl-1H-pyrazol-4-yl)acrylate (G10)

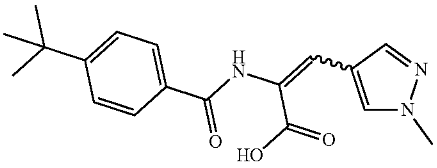 [SMILES: Cn1cc(C=C(NC(=O)c2ccc(C(C)(C)C)cc2)C(=O)O)cn1]

$^1$H NMR (400 MHz, DMSO-$d_6$) δ 12.39 (s, 1H), 9.57 (s, 1H), 7.95-7.88 (m, 3H), 7.61 (s, 1H), 7.51 (d, 2H, J=8.0 Hz), 7.39 (s, 1H), 3.79 (s, 3H), 1.29 (s, 9H).

ESI (m/z) 328 ($MH^+$), 350 ($MNa^+$), 327 ($MH^-$).

Example 2.11: Methyl 2-(4-butylbenzamido)-3-(1H-pyrrol-2-yl)acrylate (G11)

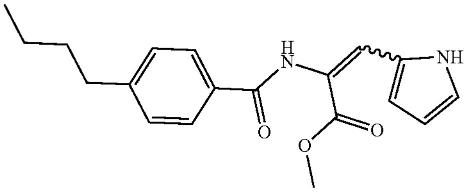 [SMILES: CCCCc1ccc(C(=O)NC(=Cc2ccc[nH]2)C(=O)OC)cc1]

$^1$H NMR (400 MHz, DMSO-$d_6$) δ 11.35 (s, 1H), 9.64 (s, 1H), 7.95 (d, 2H, J=6.7 Hz), 7.49 (s, 1H), 7.34 (d, 2H, J=6.8 Hz), 7.02 (s, 1H), 6.55 (s, 1H), 6.16 (s, 1H), 3.68 (s, 3H), 2.72-2.60 (m, 2H), 1.65-1.52 (m, 2H), 1.40-1.25 (m, 2H), 0.98-0.84 (m, 3H).

ESI (m/z) 327 ($MH^+$), 349 ($MNa^+$), 325 ($MH^-$).

Example 2.12: 2-(4-Butylbenzamido)-3-(thiophen-2-yl)acrylate (G12)

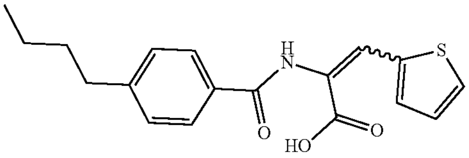 [SMILES: CCCCc1ccc(C(=O)NC(=Cc2cccs2)C(=O)O)cc1]

$^1$H NMR (400 MHz, DMSO-$d_6$) δ 12.67 (s, 1H), 9.67 (s, 1H), 7.95 (d, 2H, J=7.9 Hz), 7.87 (s, 1H), 7.70 (d, 1H, J=4.9 Hz), 7.59-7.49 (m, 1H), 7.36 (d, 2H, J=7.9 Hz), 7.13 (d, 1H, J=4.4 Hz), 2.67 (t, 2H, J=7.6 Hz), 1.66-1.55 (m, 2H), 1.40-1.26 (m, 2H), 0.91 (t, 3H, J=7.3 Hz).

ESI (m/z) 330 ($MH^+$), 328 ($MH^-$).

Example 2.13: 2-(4-(tert-butyl)benzamido)-3-(1-phenyl-1H-pyrrol-2-yl)acrylate (G13)

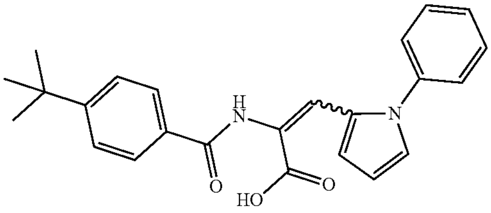 [SMILES: CC(C)(C)c1ccc(C(=O)NC(=Cc2cccn2-c2ccccc2)C(=O)O)cc1]

$^1$H NMR (400 MHz, DMSO-$d_6$) δ 12.39 (s, 1H), 9.70 (s, 1H), 7.98 (d, 2H, J=7.8 Hz), 7.65-7.49 (m, 5H), 7.38 (d, 2H, J=7.4 Hz), 7.23 (s, 1H), 7.16 (s, 1H), 6.78 (s, 1H), 6.34 (s, 1H), 1.33 (s, 9H).

ESI (m/z) 389 ($MH^+$), 387 ($MH^-$).

Example 2.14: Methyl 2-(4-(tert-butyl)benzamido)-3-(1-phenyl-1H-pyrrol-2-yl)acrylate (G14)

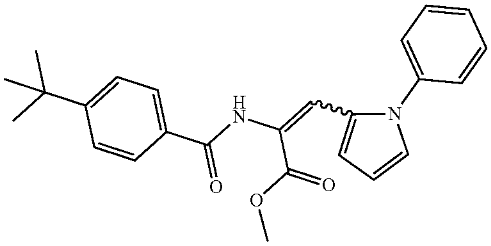 [SMILES: COC(=O)C(=Cc1cccn1-c1ccccc1)NC(=O)c1ccc(C(C)(C)C)cc1]

$^1$H NMR (400 MHz, DMSO-$d_6$) δ 9.81 (s, 1H), 7.96 (d, 2H, J=7.7 Hz), 7.62-7.45 (m, 5H), 7.35 (d, 2H, J=7.3 Hz), 7.22 (s, 1H), 7.11 (s, 1H), 6.78 (s, 1H), 6.33 (s, 1H), 3.58 (s, 3H), 1.30 (s, 9H).

ESI (m/z) 403 ($MH^+$), 425 ($MNa^+$), 401 ($MH^-$).

Example 2.15: Methyl 3-(1H-pyrrol-2-yl)-2-(4-(trifluoromethyl)benzamido)acrylate (G15)

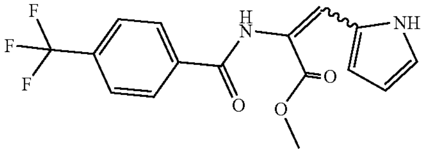 [SMILES: COC(=O)C(=Cc1ccc[nH]1)NC(=O)c1ccc(C(F)(F)F)cc1]

$^1$H NMR (400 MHz, DMSO-$d_6$) δ 11.37 (s, 1H), 9.98 (s, 1H), 8.22 (d, 2H, J=8.1 Hz), 7.93 (d, 2H, J=8.2 Hz), 7.53 (s, 1H), 7.04 (s, 1H), 6.56 (s, 1H), 6.18 (s, 1H), 3.70 (s, 3H).

ESI (m/z) 339 ($MH^+$), 361 ($MNa^+$), 337 ($MH^-$).

Example 2.16: 2-(4-Bromobenzamido)-3-(furan-2-yl)acrylate (G16)

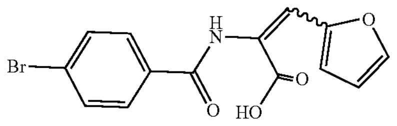 [SMILES: O=C(O)C(=Cc1ccco1)NC(=O)c1ccc(Br)cc1]

$^1$H NMR (400 MHz, DMSO-$d_6$) δ 12.78 (s, 1H), 9.93 (s, 1H), 7.94 (d, 2H, J=8.2 Hz), 7.82 (s, 1H), 7.75 (d, 2H, J=8.4 Hz), 7.30 (s, 1H), 6.84 (d, 1H, J=3.3 Hz), 6.64-6.58 (m, 1H).

ESI (m/z) 336 (MH$^+$), 338 (MH$^+$), 334 (MH$^-$), 335 (MH$^-$).

Example 2.17: Methyl 3-(furan-2-yl)-2-(4-(trifluoromethyl)benzamido)acrylate (G17)

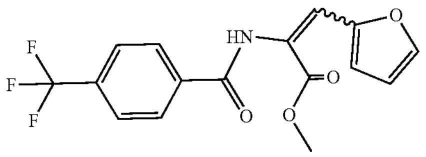 [SMILES: COC(=O)C(=Cc1ccco1)NC(=O)c1ccc(C(F)(F)F)cc1]

$^1$H NMR (400 MHz, DMSO-$d_6$) δ 10.23 (s, 1H), 8.19 (d, 2H, J=8.0 Hz), 7.93 (d, 2H, J=8.2 Hz), 7.88-7.86 (m, 1H), 7.35 (s, 1H), 6.93 (d, 1H, J=3.4 Hz), 6.66-6.62 (m, 1H), 3.73 (s, 3H).

ESI (m/z) 340 (MH$^+$), 362 (MNa$^+$), 338 (MH$^-$).

Example 2.18: 3-(Furan-2-yl)-2-(4-(trifluoromethyl)benzamido)acrylate (G18)

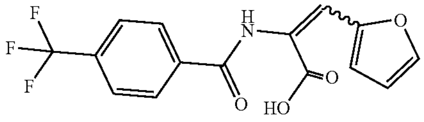 [SMILES: O=C(O)C(=Cc1ccco1)NC(=O)c1ccc(C(F)(F)F)cc1]

$^1$H NMR (400 MHz, DMSO-$d_6$) δ 12.83 (s, 1H), 10.10 (s, 1H), 8.19 (d, 2H, J=7.9 Hz), 7.93 (d, 2H, J=8.2 Hz), 7.83 (s, 1H), 7.34 (s, 1H), 6.87 (d, 1H, J=3.3 Hz), 6.63-6.59 (m, 1H).

ESI (m/z) 326 (MH$^+$), 324 (MH$^-$).

Example 2.19: 2-(4-Bromobenzamido)-3-(thiophen-2-yl)acrylate (G19)

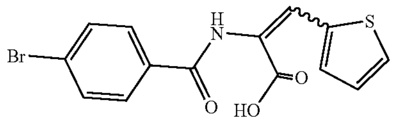 [SMILES: O=C(O)C(=Cc1cccs1)NC(=O)c1ccc(Br)cc1]

$^1$H NMR (400 MHz, DMSO-$d_6$) δ 12.74 (s, 1H), 9.87 (s, 1H), 7.98 (d, 2H, J=8.5 Hz), 7.90 (s, 1H), 7.78 (d, 2H, J=8.5 Hz), 7.72 (d, 1H, J=5.1 Hz), 7.56 (d, 1H, J=3.3 Hz), 7.16-7.12 (m, 1H).

ESI (m/z) 354 (MH$^+$), 352 (MH$^+$), 352 (MH$^-$), 350 (MH$^-$).

Example 2.20: Methyl 2-(4-bromobenzamido)-3-(furan-2-yl)acrylate (G20)

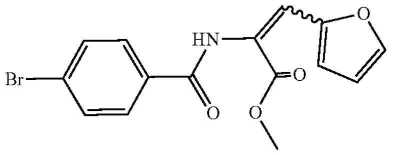 [SMILES: COC(=O)C(=Cc1ccco1)NC(=O)c1ccc(Br)cc1]

$^1$H NMR (400 MHz, DMSO-$d_6$) δ 10.03 (s, 1H), 7.91 (d, 2H, J=8.5 Hz), 7.82 (d, 1H, J=1.5 Hz), 7.72 (d, 2H, J=8.5 Hz), 7.27 (s, 1H), 6.86 (d, 1H, J=3.5 Hz), 6.61-6.58 (m, 1H), 3.69 (s, 3H).

ESI (m/z) 350 (MH$^+$), 352 (MH$^+$), 348 (MH$^-$), 350 (MH$^-$).

Example 2.21: 2-(4-Bromobenzamido)-3-(furan-2-yl)acrylate (G21)

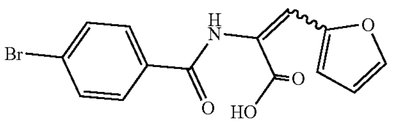 [SMILES: O=C(O)C(=Cc1ccco1)NC(=O)c1ccc(Br)cc1]

$^1$H NMR (400 MHz, DMSO-$d_6$) δ 12.78 (s, 1H), 9.93 (s, 1H), 7.94 (d, 2H, J=8.5 Hz), 7.82 (d, 1H, J=1.5 Hz), 7.75 (d, 2H, J=8.5 Hz), 7.31 (s, 1H), 6.84 (d, 1H, J=3.4 Hz), 6.63-6.59 (m, 1H).

ESI (m/z) 336 (MH$^+$), 338 (MH$^+$), 334 (MH$^-$), 336 (MH$^-$).

Example 2.22: 2-(4-Butylbenzamido)-3-(1H-pyrrol-2-yl)acrylate (G22)

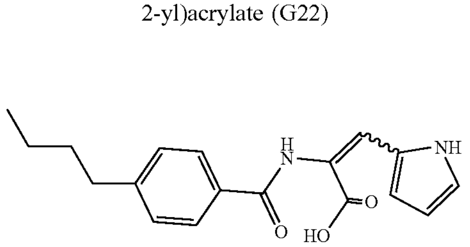

$^1$H NMR (400 MHz, DMSO-$d_6$) δ 12.28 (s, 1H), 11.28 (s, 1H), 9.51 (s, 1H), 7.94 (d, 2H, J=8.0 Hz), 7.47 (s, 1H), 7.33 (d, 2H, J=8.0 Hz), 6.99 (s, 1H), 6.51 (s, 1H), 6.14 (d, 1H, J=2.7 Hz), 2.66 (t, 2H, J=7.6 Hz), 1.64-1.54 (m, 2H), 1.38-1.27 (m, 2H), 0.91 (t, 3H, J=7.3 Hz).

Example 2.23: Methyl-2-(4-(tert-butyl)benzamido)-3-(1H-pyrrol-2-yl)acrylate (G23)

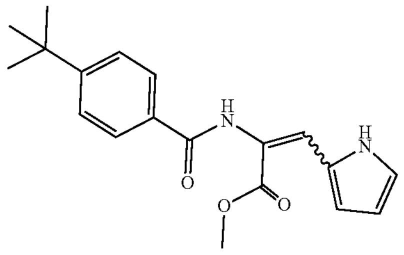 [SMILES: COC(=O)C(=Cc1ccc[nH]1)NC(=O)c1ccc(C(C)(C)C)cc1]

$^{1}H$ NMR (400 MHz, DMSO-$d_6$) δ 11.31 (s, 1H), 9.61 (s, 1H), 7.94 (d, 2H, J=8.0 Hz), 7.51 (d, 2H, J=8.0 Hz), 7.46 (s, 1H), 6.98 (s, 1H), 6.52 (s, $^{1}$H), 6.13 (s, 1H), 3.65 (s, 3H), 1.29 (s, 9H).

$^{13}C$ NMR (400 MHz, DMSO-$d_6$) δ 166.1, 165.9, 154.9, 131.4, 128.0, 126.6, 126.5, 125.6, 122.6, 119.7, 113.9, 111.0, 52.2, 35.1, 31.4.

Example 2.24: 2-(2-Naphthamido)-3-(thiophen-3-yl) acrylate (G24)

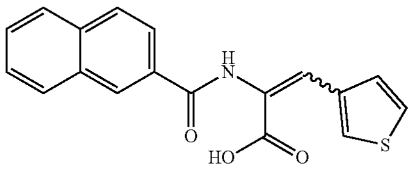 [SMILES: O=C(O)C(=Cc1ccsc1)NC(=O)c1ccc2ccccc2c1]

$^{1}H$ NMR (400 MHz, DMSO-$d_6$) δ 12.68 (s, 1H), 10.03 (s, 1H), 8.63 (s, 1H), 8.05-8.03 (m, 3H), 7.98 (d, 1H, J=7.6 Hz), 7.94 (br s, 1H), 7.64-7.59 (m, 2H), 7.56 (s, 1H), 7.53-7.52 (m, 1H), 7.41 (d, 1H, J=4.4 Hz).

$^{13}C$ NMR (400 MHz, DMSO-$d_6$) δ 166.9, 166.4, 135.8, 134.8, 132.6, 131.3, 130.3, 129.4, 128.7, 128.5, 128.3, 128.2, 128.1, 127.3, 127.2, 125.9, 124.7.

Example 2.25: 3-(Benzo[b]thiophen-3-yl)-2-(4-(tert-butyl)benzamido)acrylate (G25)

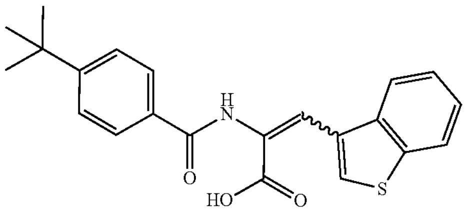 [SMILES: CC(C)(C)c1ccc(C(=O)NC(=Cc2csc3ccccc23)C(=O)O)cc1]

$^{1}H$ NMR (400 MHz, DMSO-$d_6$) δ 12.78 (s, 1H), 9.90 (s, 1H), 8.10 (s, 1H), 8.01 (d, 1H, J=7.6 Hz), 7.96 (d, 1H, J=7.6 Hz), 7.91 (d, 2H, J=8.0 Hz), 7.67 (s, 1H), 7.50 (d, 2H, J=8.0 Hz), 7.46-7.38 (m, 2H), 1.28 (s, 9H).

$^{13}C$ NMR (400 MHz, DMSO-$d_6$) δ 166.6, 166.3, 139.2, 138.5, 131.2, 129.5, 129.0, 128.9, 128.1, 125.6, 125.4, 125.2, 123.9, 123.4, 131.9, 35.1, 31.4.

Example 2.26: 2-(4-Isobutylbenzamido)-3-(1H-pyrrol-2-yl)acrylate (G26)

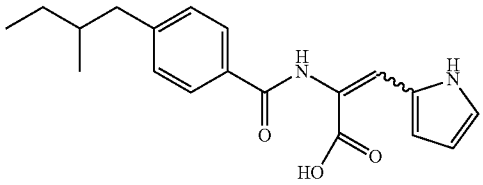 [SMILES: CCC(C)Cc1ccc(C(=O)NC(=Cc2ccc[nH]2)C(=O)O)cc1]

$^{1}H$ NMR (400 MHz, DMSO-$d_6$) δ 12.26 (2, 1H), 11.25 (s, 1H), 9.48 (s, 1H), 7.91 (d, 2H, J=7.2 Hz), 7.44 (s, 1H), 7.27 (d, 2H, J=7.6 Hz), 6.95 (s, 1H), 6.50 (s, 1H), 6.11 (s, 1H), 2.50 (d, 2H, J=2.8 Hz), 1.90-1.91 (m, 1H), 0.85 (d, 6H, J=6.8 Hz).

$^{13}C$ NMR (400 MHz, DMSO-$d_6$) δ 167.0, 165.9, 145.4, 132.0, 129.3, 129.0, 126.7, 126.1, 122.2, 120.7, 113.4, 110.8, 44.8, 30.0, 22.57.

Example 2.27: 2-(1-Naphthamido)-3-(4-methylthiazol-5-yl)acrylate (G27)

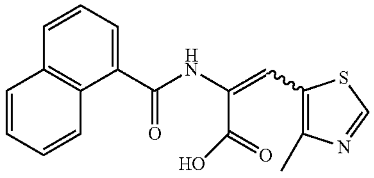 [SMILES: Cc1ncsc1C=C(NC(=O)c1cccc2ccccc12)C(=O)O]

$^{1}H$ NMR (400 MHz, DMSO-$d_6$) δ 12.98 (br s, 1H), 9.97 (s, 1H), 9.09 (s, 1H), 8.40-8.39 (m, 1H), 8.6 (d, 1H, J=8.0 Hz), 7.99-7.98 (m, 1H), 7.89 (d, 1H, J=7.2 Hz), 7.80 (s, 1H), 7.62 (t, 1H, J=7.6 Hz), 7.57-7.55 (m, 2H), 2.54 (s, 3H).

$^{13}C$ NMR (400 MHz, DMSO-$d_6$) δ 169.3, 166.1, 156.8, 156.6, 134.1, 133.6, 130.8, 130.3, 128.6, 127.3, 126.8, 126.2, 126.1, 126.0, 125.9, 125.4, 124.9, 16.1.

Example 2.28: 2-(4-Propylbenzamido)-3-(1H-pyrrol-2-yl)acrylate (G28)

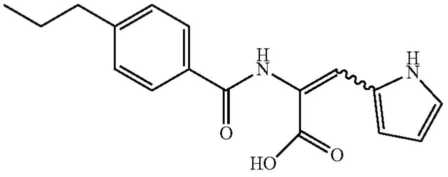 [SMILES: CCCc1ccc(C(=O)NC(=Cc2ccc[nH]2)C(=O)O)cc1]

$^{1}H$ NMR (400 MHz, DMSO-$d_6$) δ 12.30 (br s, 1H), 11.25 (s, 1H), 9.48 (s, 1H), 7.91 (d, 2H, J=7.6 Hz), 7.44 (s, 1H), 7.30 (d, 2H, J=4.0 Hz), 6.95 (s, 1H), 6.48 (s, 1H), 6.11 (s, 1H), 2.60 (t, 2H, J=7.2 Hz), 1.64-1.55 (m, 2H), 0.87 (t, 3H, J=7.0 Hz).

$^{13}C$ NMR (400 MHz, DMSO-$d_6$) δ 167.0, 165.9, 146.4, 131.9, 129.7, 128.1, 126.7, 126.1, 122.1, 120.7, 113.4, 110.8, 37.5, 24.3, 14.0.

Example 2.29: 2-(4-Butylbenzamido)-3-(thiophen-2-yl)acrylate (G29)

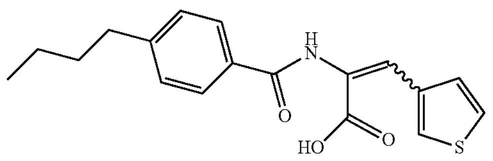 [SMILES: CCCCc1ccc(C(=O)NC(=Cc2ccsc2)C(=O)O)cc1]

$^{1}H$ NMR (400 MHz, DMSO-$d_6$) δ 12.61 (s, 1H), 9.76 (s, 1H), 7.89 (s, 3H), 7.54-7.52 (m, 1H), 7.51 (s, 1H), 7.37 (d, 1H, J=4.8 Hz), 7.31 (d, 2H, J=7.6 Hz), 2.62 (t, 2H, J=7.6 Hz), 1.59-1.51 (m, 2H), 1.33-1.24 (m, 2H), 0.87 (t, 3H, J=7.2 Hz).

ESI (m/z) 330 (MH+).

Example 2.30: 2-(4-Propylbenzamido)-3-(thiophen-2-yl)acrylate (G30)

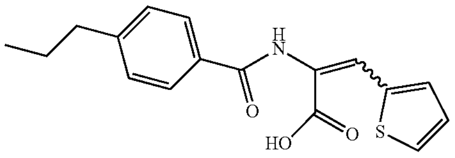 [SMILES: CCCc1ccc(C(=O)NC(=Cc2cccs2)C(=O)O)cc1]

$^{1}H$ NMR (400 MHz, DMSO-$d_6$) δ 12.64 (s, 1H), 9.65 (s, 1H), 7.93 (d, 2H, J=8.0 Hz), 7.85 (s, 1H), 7.66 (d, 1H, J=4.4 Hz), 7.51 (d, 1H, J=2.0 Hz), 7.32 (d, 2H, J=8.0 Hz), 7.10 (d, 1H, J=3.6 Hz), 2.60 (t, 2H, J=7.4 Hz), 1.63-1.56 (m, 2H), 0.88 (t, 3H, J=7.2 Hz).

$^{13}C$ HMR (400 MHz, DMSO-$d_6$) δ 166.5, 166.4, 146.7, 137.0, 133.8, 131.8, 131.7, 129.9, 128.8 (2), 128.2 (2), 127.5, 124.5, 37.5, 24.3, 14.1.

ESI (m/z) 316 (MH+).

Example 2.31: 2-(4-propylbenzamido)-3-(thiophen-2-yl)acrylate (G31)

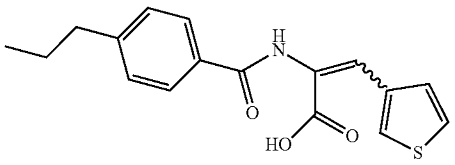 [SMILES: CCCc1ccc(C(=O)NC(=Cc2ccsc2)C(=O)O)cc1]

$^{1}H$ NMR (400 MHz, DMSO-$d_6$) δ 12.64 (s, 1H), 9.64 (s, 1H), 7.92 (d, 2H, J=7.6 Hz), 7.84 (s, 1H), 7.66 (d, 1H, J=4.4 Hz), 7.51 (s, 1H), 7.32 (d, 2H, J=7.6 Hz), 7.10-7.09 (m, 1H), 2.60 (t, 2H, J=7.4 Hz), 1.63-1.57 (m, 2H), 0.88 (t, 3H, J=7.6 Hz).

$^{13}C$ HMR (400 MHz, DMSO-$d_6$) δ 166.5, 166.4, 146.7, 136.9, 133.8, 131.8, 131.7, 129.8, 128.8 (2), 128.2 (2), 127.5, 124.5, 37.5, 24.4, 14.1.

ESI (m/z) 316 (MH+).

Example 2.32: 2-(4-(tert-butyl)benzamido)-3-(4-methylthiazol-5-yl)acrylate (G32)

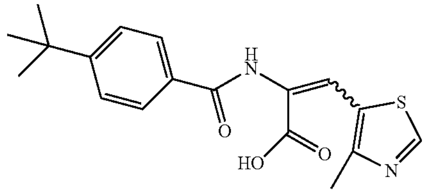 [SMILES: Cc1ncsc1C=C(NC(=O)c1ccc(C(C)(C)C)cc1)C(=O)O]

ESI (m/z) 345 (MH+).

Example 2.33: 2-(4-(tert-butyl)benzamido)-3-(1H-indol-2-yl)acrylate (G33)

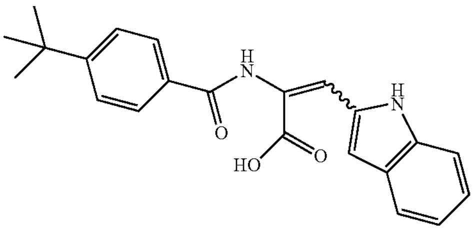 [SMILES: CC(C)(C)c1ccc(C(=O)NC(=Cc2cc3ccccc3[nH]2)C(=O)O)cc1]

ESI (m/z) 363 (MH+).

Example 2.34: 3-(Furan-2-yl)-2-(4-propylbenzamido)acrylate (G34)

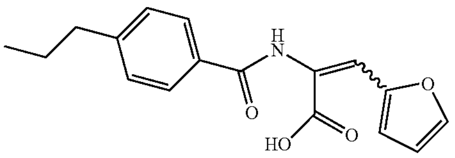 [SMILES: CCCc1ccc(C(=O)NC(=Cc2ccco2)C(=O)O)cc1]

$^{1}H$ NMR (400 MHz, DMSO-$d_6$) δ 12.69 (s, 1H), 9.72 (s, 1H), 7.89 (d, 2H, J=7.6 Hz), 7.78 (s, 1H), 7.30 (d, 2H, J=7.6 Hz), 7.24 (s, 1H), 6.78 (d, 1H, J=2.4 Hz), 6.57 (s, 1H), 2.60 (t, 2H, J=7.4 Hz), 1.64-1.55 (m, 2H), 0.87 (t, 3H, J=7.2 Hz).

$^{13}C$ HMR (400 MHz, DMSO-$d_6$) δ 166.4, 165.8, 149.8, 146.7, 145.6, 131.6, 128.8 (2), 128.2 (2), 124.9, 120.9, 115.7, 112.9, 37.5, 24.3, 14.0.

ESI (m/z) 300 (MH+).

Example 2.35: 3-(Furan-2-yl)-2-(4-pentylbenzamido)acrylate (G35)

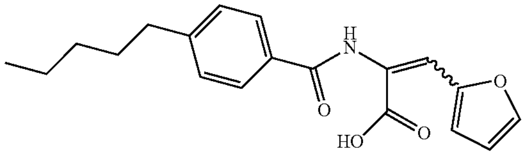 [SMILES: CCCCCc1ccc(C(=O)NC(=Cc2ccco2)C(=O)O)cc1]

$^{1}$H NMR (400 MHz, DMSO-$d_6$) δ 12.68 (s, 1H), 9.72 (s, 1H), 7.89 (d, 2H, J=7.6 Hz), 7.78 (s, 1H), 7.30 (d, 2H, J=7.2 Hz), 7.24 (s, 1H), 6.78 (d, 1H, J=3.2 Hz), 6.57 (t, 1H, J=1.4 Hz), 2.61 (t, 2H, J 7.4 Hz), 1.61-1.55 (m, 2H), 1.26 (s, 4H), 0.83 (t, 3H, J=6.8 Hz).

$^{13}$C HMR (400 MHz, DMSO-$d_6$) δ 166.4, 165.8, 149.8, 146.9, 145.6, 131.6, 128.7 (2), 128.2 (2), 124.9, 120.9, 115.7, 112.9, 35.4, 31.3, 30.8, 22.4, 14.3.

ESI (m/z) 328 (MH+).

Example 2.36: 2-(4-Butoxybenzamido)-3-(thiophen-2-yl)acrylate (G36)

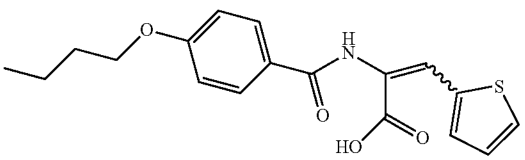 [SMILES: CCCCOc1ccc(C(=O)NC(=Cc2cccs2)C(=O)O)cc1]

$^{1}$H NMR (400 MHz, DMSO-$d_6$) δ 12.61 (s, 1H), 9.55 (s, 1H), 7.96 (d, 2H, J=8.4 Hz), 7.82 (s, 1H), 7.66 (d, 1H, J=4.8 Hz), 7.50 (d, 1H, J=2.4 Hz), 7.09 (t, 1H, J=4.2 Hz), 7.03 (d, 2H, J=8.4 Hz), 4.03 (t, 2H, J=6.4 Hz), 1.73-1.66 (m, 2H), 1.47-1.37 (m, 2H), 0.91 (t, 3H, J=7.4 Hz).

$^{13}$C HMR (400 MHz, DMSO-$d_6$) δ 166.5, 166.1, 161.9, 137.0, 133.7, 131.7, 130.1 (2), 129.7, 127.4, 126.3, 124.7, 114.5 (2), 67.9, 31.1, 19.1, 14.1.

ESI (m/z) 346 (MH+).

Example 2.37: 2-(4-Hexylbenzamido)-3-(thiophen-2-yl)acrylate (G37)

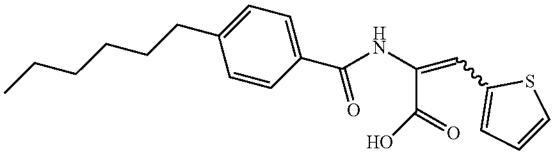 [SMILES: CCCCCCc1ccc(C(=O)NC(=Cc2cccs2)C(=O)O)cc1]

ESI (m/z) 358 (MH+).

Example 2.38: 2-(2,3-Dihydro-1H-indene-5-carboxamido)-3-(thiophen-2-yl)acrylate (G38)

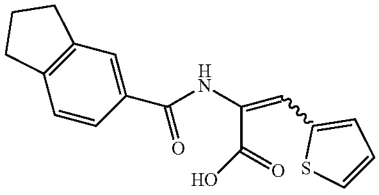 [SMILES: O=C(O)C(=Cc1cccs1)NC(=O)c1ccc2c(c1)CCC2]

$^{1}$H NMR (400 MHz, DMSO-$d_6$) δ 12.62 (s, 1H), 9.59 (s, 1H), 7.84 (d, 2H, J=7.4 Hz), 7.78 (d, 1H, J=7.6 Hz), 7.66 (d, 1H, J=4.0 Hz), 7.51 (br s, 1H), 7.33 (d, 1H, J=7.6 Hz), 7.10-7.09 (m, 1H), 2.90 (t, 4H, J=6.8 Hz), 2.05-2.01 (m, 2H)

ESI (m/z) 314 (MH+).

Example 2.39: 2-(4-(Difluoromethoxy)benzamido)-3-(thiophen-2-yl)acrylate (G39)

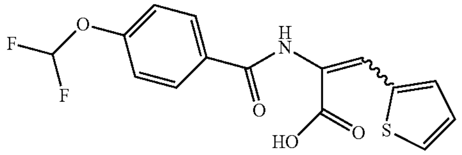 [SMILES: O=C(O)C(=Cc1cccs1)NC(=O)c1ccc(OC(F)F)cc1]

$^{1}$H NMR (400 MHz, DMSO-$d_6$) δ 12.69 (s, 1H), 9.77 (s, 1H), 8.07 (d, 2H, J=8.4 Hz), 7.86 (s, 1H), 7.68 (d, 1H, J=4.4 Hz), 7.55-7.53 (m, 1H), 7.36 (s, 1H), 7.31 (d, 2H, J=8.4 Hz), 7.10 (t, 1H, J=3.8 Hz).

ESI (m/z) 340 (MH+).

Example 2.40: 2-(4-Pentylbenzamido)-3-(thiophen-2-yl)acrylate (G40)

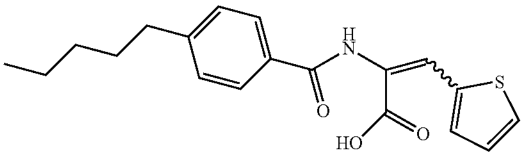 [SMILES: CCCCCc1ccc(C(=O)NC(=Cc2cccs2)C(=O)O)cc1]

$^{1}$H NMR (400 MHz, DMSO-$d_6$) δ 12.63 (s, 1H), 9.64 (s, 1H), 7.91 (d, 2H, J=8.4 Hz), 7.83 (s, 1H), 7.66 (d, 1H, J=4.8 Hz), 7.51 (d, 1H, J=2.8 Hz), 7.32 (d, 2H, J=8.0 Hz), 7.10-7.08 (m, 1H), 2.62 (t, 2H, J=8.0 Hz), 1.61-1.54 (m, 2H), 1.31-1.23 (m, 4H), 0.83 (t, 3H, J=8.0 Hz).

$^{13}$C HMR (400 MHz, DMSO-$d_6$) δ 166.5, 166.4, 146.9, 136.9, 133.8, 131.8, 131.7, 129.8, 128.7 (2), 128.2 (2), 127.5, 124.5, 35.4, 31.3, 30.8, 22.4, 14.3.

ESI (m/z) 344 (MH+).

Example 2.41: 2-(4-Butoxybenzamido)-3-(1H-pyrrol-2-yl)acrylate (G41)

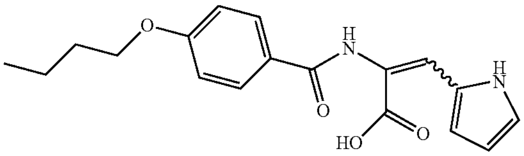 [SMILES: CCCCOc1ccc(C(=O)NC(=Cc2ccc[nH]2)C(=O)O)cc1]

$^{1}$H NMR (400 MHz, DMSO-$d_6$) δ 12.21 (s, 1H), 11.22 (s, 1H), 9.37 (s, 1H), 7.94 (d, 2H, J=8.4 Hz), 7.41 (s, 1H), 6.99 (d, 2H, J=8.4 Hz), 6.94 (s, 1H), 6.45 (s, 1H), 6.09 (s, 1H), 4.02 (t, 2H, J=8.3 Hz), 1.72-1.65 (m, 2H), 1.46-1.37 (m, 2H), 0.90 (t, 3H, J=7.4 Hz).

ESI (m/z) 329 (MH+).

Example 2.42: 2-(3,5-Dimethylbenzamido)-3-(thiophen-2-yl)acrylate (G42)

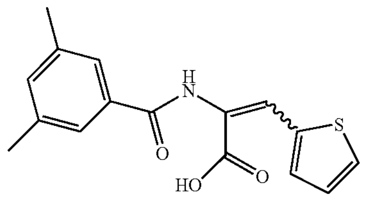 [SMILES: Cc1cc(C)cc(C(=O)NC(=Cc2cccs2)C(=O)O)c1]

$^1$H NMR (400 MHz, DMSO-$d_6$) δ 12.62 (s, 1H), 9.60 (s, 1H), 7.83 (s, 1H), 7.67 (d, 1H, J=4.8 Hz), 7.61 (s, 2H), 7.50 (d, 1H, J=2.0 Hz), 7.19 (s, 1H), 7.10-7.08 (m, 1H), 2.32 (s, 6H).

ESI (m/z) 302 (MH+).

Example 3: Function as Pendrin Inhibitor of Novel Compound

Example 3.1: Cell Culture

Chinese hamster ovary (CHO)-K1 cells were maintained in a DMEM medium containing 10% fetal bovine serum (FBS), 100 units/ml penicillin and 100 100 μg/ml streptomycin. CHO-K1 cells were stably transfected with pcDNA3.1 encoding halide sensor YFP-H148Q/I152L/F46L and human wild-type (WT)-pendrin. For distribution of primary culture of human nasal cavity epithelium (HNE) cells, passage-2 cells were seeded into transwell-transparent culture inserts with a pore size of 0.45 μm (Costar Co., Cambridge, MA) at a density of 2×10$^5$ cells/cm$^2$. The cells were maintained in a 1:1 mixture of Dulbecco's modified Eagle's medium (Lonza, Walkersville, MD) and bronchial epithelial growth medium (Lonza) supplemented with the following growth factors according to the manufacturer's instructions. After immersing the cells for the first 7 days, they were exposed to the apical air interface for the remainder of the culture period. After establishment of the air-liquid interface, the cells were used between 14 and 21 days. At all stages of culture, the cells were maintained at 37° C. under 5% $CO_2$ in an air incubator.

Example 3.2: Cell-Based High Throughput Screening

CHO-K1 cells expressing human WT pendrin and YFP-F46L/H148Q/I152L were plated on a 96-well microplate at a density of 2×10$^4$ cells per well and cultured for 48 hours. Each well of the cell cultured 96-well plate was washed with PBS of 200 μL twice and was filled with HEPES buffer solution of 50 μL, respectively. The test compound (1 μL) was added to the final concentration of 50 μM. After culturing at 37° C. for 10 minutes, the 96-well plate was positioned on FLUOstar Omega microplate reader (BMG Labtech, Ortenberg, Germany) for fluorescence analysis. By continuously (400 ms per point) recording fluorescence for 1 second (base line), each well was individually analyzed for pendrin-mediated $I^-$ inflow, and then at 1 second, 50 μL of NaI-substituted HEPES buffer solution (NaI replacing NaCl) was added using a liquid injector and the YFP fluorescence was recorded for 5 seconds. The initial iodide inflow rate was determined from the initial slope of fluorescence by nonlinear regression, after injection the iodide (See FIG. 1).

Example 3.3: Measurement of Short Circuit Current

Snapwell inserts containing the primary culture of ANO1- and CFTR-expressing FRT and human nasal cavity epithelium (HNE) cells were equipped on Ussing chamber (Physiologic Instruments, San Diego, CA, USA). To measure the short circuit current in HNE cells, the apical and basal baths were filled with a symmetric $HCO_3^-$ buffer solution. In case of ANO1- and CFTR-expression FRT, the apical bath was filled with a half-$Cl^-$ solution and the collateral bath was filled with a $HCO_3^-$ buffer solution. The basal membrane was penetrated with 250 μg/mL amphotericin B to measure the apical membrane current. The short circuit current and apical membrane current were measured with EVC4000 multi-channel V/I clamp (World Precision Instruments, Sarasota, FL, USA) and PowerLab 4/35 (AD Instruments, Castle Hill, Australia). Using Labchart Pro 7 (AD Instruments), data were recorded and analyzed. The sampling rate was 4 Hz.

Example 3.4: Cl—/I— Exchange Activity Measurement

For measurement of $Cl^-/I^-$ exchange activity, YFP fluorescence was measured in pendrin and halide sensor YFP expressing CHO-K1 cells. Each well of the cell cultured 96-well plate was washed with PBS of 200 μL twice, and was filled with HEPES buffer solution (140 mM NaCl, 5 mM KCl, 1 mM $MgCl_2$, 1 mM $CaCl_2$, 10 mM glucose and 10 mM HEPES (pH 7.4)), respectively. The test compound (1 μL) was added to the final concentration of 50 μM. After culturing at 37° C. for 10 minutes, the 96-well plate was positioned on FLUOstar Omega microplate reader (BMG Labtech, Ortenberg, Germany) for fluorescence analysis.

By continuously (400 ms per point) recording fluorescence for 1 second (base line), each well was individually analyzed for pendrin-mediated $I^-$ inflow, and then at 1 second, 50 μL of NaI-substituted HEPES buffer solution (140 mM NaI, 5 mM KCl, 1 mM $MgCl_2$, 1 mM $CaCl_2$, 10 mM glucose and 10 mM HEPES (pH 7.4)) was added using a liquid injector and the YFP fluorescence was recorded for 5 seconds. The initial iodide inflow rate was determined from the initial slope of fluorescence by nonlinear regression, after injection the iodide.

Example 3.5: Cl—/HCO3— Exchange Activity Measurement

For measurement of $Cl^-/HCO_3^-$ exchange activity, intracellular pH ($pH_i$) was measured in WT-pendrin expressing CHO-K1 and HNE cells using pH sensor SNARF5-AM (Molecular Probes). The cells were treated with 5 μM SNARF5-AM for 30 minutes, and then were equipped in a perfusion chamber on the stage of a reverse fluorescence microscope (Nikon, Tokyo, Japan) equipped with a cooled charge-coupled device camera (Zyla sCMOS), image acquisition and analysis software (Meta Imaging Series 7.7). The cells were perfused with a $HCO_3^-$ buffer solution containing 120 NaCl, 5 KCl, 1 $MgCl_2$, 1 $CaCl_2$, 10 D-glucose, 5 HEPES, and 25 $NaHCO_3$ (pH 7.4) (mM). To measure the $Cl^-/HCO_3^-$ exchange activity, the $HCO_3^-$ buffer solution was changed to $Cl^-$-free $HCO_3^-$ buffer solution. When external $Cl^-$-free $HCO_3^-$ buffer solution is applied, the outflow of $Cl^-$ and inflow of $HCO_3^-$ are increased by pendrin. To maintain the pH of the $HCO_3^-$ buffer solution, the solution was continuously gas treated with 95% $O_2$ and 5% $CO_2$. SNARF5 fluorescence was recorded at 515±10 nm of the excitation wavelength and 640±10 nm of the emission wavelength, and intracellular pH calibration was performed with a solution including 145 mM KCl, 10 mM HEPES and 5 mM nigericin having a calibrated pH to 6.2-7.6.

Example 3.6: Cl—/SCN— Exchange Activity Measurement

For measurement of $Cl^-/SCN^-$ exchange activity, YFP fluorescence was measured in pendrin and halide sensor YFP expressing CHO-K1 cells. To measure the $Cl^-/SCN^-$ exchange activity, HEPES buffer solution was changed to NaSCN-substituted HEPES buffer solution (140 mM NaSCN, 5 mM KCl, 1 mM $MgCl_2$, 1 mM $CaCl_2$, 10 mM glucose and 10 mM HEPES (pH 7.4)) for generation of an $SCN^-$ gradient driving $SCN^-$ inflow by pendrin. The YFP fluorescence change by $SCN^-$ inflow was monitored using FLUOstar Omega microplate reader (BMG Labtech) and MARS data analysis software (BMG Labtech).

Example 3.7: Cl—/OH— exchange activity measurement

For measurement of $Cl^-/OH^-$ exchange activity, intracellular pH ($pH_i$) was measured in WT-pendrin expressing CHO-K1 and HNE cells using pH sensor SNARF5-AM (Molecular Probes). The cells were treated with 5 μM SNARF5-AM for 30 minutes, and then were equipped in a perfusion chamber on the stage of a reverse fluorescence microscope (Nikon, Tokyo, Japan) equipped with a cooled charge-coupled device camera (Zyla sCMOS), image acquisition and analysis software (Meta Imaging Series 7.7). To measure the $Cl^-/OH^-$ exchange activity, HEPES buffer solution was changed to CV-free HEPES buffer solution for generation of an $Cl^-$ gradient driving $Cl^-$ outflow and $OH^-$ inflow of cytosol by pendrin.

Example 3.8: Protein Expression Measurement

CHO-K1 and HNE cells were lysed with a cytolytic buffer (50 mM Tris-HCl, pH 7.4, 1% Nonidet P-40, 0.25% sodium deoxycholate, 150 mM NaCl, 1 mM EDTA, 1 mM $Na_3VO_4$, and protease inhibiting mixture). The total cell lysates were under centrifugation at 15,000×g for 10 minutes at 4° C. to remove cellular debris and the same amount (50 μg protein or 5 μg protein/lane) of supernatant protein was isolated on 4-12% Tris-glycine precast gel (KOMA BIOTECH, Seoul, Korea) and transferred to PVDF membrane (Millipore, Billerica, MA, USA). The membrane was blocked with 5% fat-free skim milk in TBS containing 0.1% Tween 20 (TBST) or 5% bovine serum albumin in TBS at a room temperature for 1 hour. Then, the membrane was cultured at 4° C. overnight with a primary antibody against pendrin (sc-50346; Santa Cruz Biotechnology, Santa Cruz, CA, USA), NF-κB p65 (4764S; Cell Signaling Technology, Danvers, MA, USA), p-NF-κB p65 (3033S; Cell Signaling Technology), IkBα (9242S; Cell Signaling Technology), p-IkBα (9141S; Cell Signaling Technology), β-actin (sc-47778; Santa Cruz Biotechnology), or AN01 (ab64085; Abeam). After washing with 0.05% Tween 20 (TBST) in PBS, the blot was additionally cultured with a secondary antibody (Cell Signaling Technology, Danvers, MA) at a room temperature for 60 minutes. Then, the membrane was washed with TBST for 5 minutes three times, and then it was visualized using ECL Plus western blotting detection system ((GE Healthcare Amersham; Piscataway, NJ, USA).

Example 3.9: Real-Time RT-PCR Analysis

The total messenger RNA (mRNA) was extracted using TRIzol reagent (Invitrogen, Carlsbad, CA, USA), and was reverse-transcribed using a random hexamer primer, an oligo(dT) primer and SuperScript® III reverse transcriptase (Invitrogen). Quantitative real-time PCR was performed using StepOnePlus Real-Time PCR system (Applied Biosystems, Foster City, CA, USA) and Thunderbird SYBR qPCR mix (Tokyobo, Osaka, Japan). Thermal cycling conditions included the initial stage at 95° C. for 5 minutes, and subsequent 40 cycles at 95° C. for 10 seconds, at 55° C. for 20 seconds and at 72° C. for 10 minutes. The primer sequences were listed in Table 3 below.

TABLE 3

| mRNA | Primer seuquence | PCR product size |
|---|---|---|
| Pendrin | 5'-TTC CCA AAG TGC CAA TCC ATA G-3'<br>5'-CCG CAG TGA TCT CAC TCC AAC-3' | 83 bp |
| Ano1 | 5'-GGA GAA GCA GCA TCT ATT TG-3'<br>5'-GAT CTC ATA GAC AAT CGT GC-3' | 82 bp |
| CFTR | 5'-AGG AGG CAG TCT GTC CTG AA-3'<br>5'-CAC TGC TGG TAT GCT CTC CA-3' | 237 bp |
| ENaCα | 5'-CAG CCC ATA CCA GGT CTC AT-3'<br>5'-ATG GTG GTG TTG TTG CAG AA-3' | 221 bp |
| ENaCβ | 5'-TCC TAC CCT CGT CCC TAC CT-3'<br>5'-CCA GGA AGG AGA AAA CCA CA-3' | 151 bp |
| ENaCγ | 5'-ACC ACC AGC CAT GGT CTA AG-3'<br>5'-GTT CAG GTC CCG GGA TTT AT-3' | 211 bp |
| Duox1 | 5'-TTC ACG CAG CTC TGT GTC AA-3'<br>5'-AGG GAC AGA TCA TAT CCT GGC T-3' | 96 bp |
| Duox2 | 5'-ACG CAG CTC TGT GTC AAA GGT-3'<br>5'-TGA TGA ACG AGA CTC GAC AGC-3' | 90 bp |
| β-actin | 5'-GCA AAG ACC TGT ACG CCA ACA C-3'<br>5'-ATC TCC TTC TGC ATC CTG TC-3' | 82 bp |

As the result, the compounds showing the pendrin inhibitory activity at 30 μM were shown in Table 4 below, and $IC_{50}$ for the compounds showing the pendrin inhibitory activity of 50% or more at 30 μM was shown in Table 5 below.

TABLE 4

| Compound No. | Pendrin inhibitory activity at 30 μM (%) |
|---|---|
| F1 | 2.6 |
| F2 | 57.5 |
| F3 | 4.3 |
| F4 | 2.6 |
| FS | 3.5 |
| F6 | 3.7 |
| F7 | 2.8 |
| F8 | 72.5 |
| F9 | 52.5 |
| F10 | 100 |
| F11 | 3.6 |
| F12 | 100 |

TABLE 4-continued

| Compound No. | Pendrin inhibitory activity at 30 μM (%) |
|---|---|
| F13 | 3.8 |
| F14 | 33.1 |
| F15 | 3.8 |
| F16 | 3.1 |
| F17 | 6.9 |
| F18 | 3.4 |
| F19 | 54.8 |
| F20 | 82.9 |
| F21 | 2.9 |
| F22 | 2.4 |
| F23 | 2.1 |
| F24 | 3.6 |
| F25 | 3.8 |
| F26 | 69.9 |
| F27 | 2.8 |
| F28 | 2.2 |
| F29 | 3.3 |
| F30 | 3.9 |
| F31 | 4.2 |
| F32 | 3.7 |
| F33 | 88.7 |
| F34 | 82.8 |
| F35 | 87.2 |
| F36 | 89.6 |
| F37 | 3.5 |
| F38 | 92.6 |
| F39 | 58.8 |
| F40 | 92.3 |
| F41 | 27.5 |
| F42 | 4.2 |
| F43 | 5.4 |
| F44 | 3.5 |
| F45 | 4.6 |
| F46 | 53.8 |
| F47 | 33.2 |
| F48 | 2.4 |
| F49 | 89.1 |
| F50 | 3.7 |
| F51 | 2.7 |
| F52 | 4.1 |
| F53 | 3.1 |
| F54 | 2.6 |
| F55 | 3.8 |
| F56 | 84.7 |
| F57 | 16.1 |
| F58 | 2.5 |
| F59 | 1.8 |
| F60 | 3.1 |
| F61 | 2.2 |
| F62 | 2.4 |
| F63 | 1.6 |
| F64 | 2.8 |
| F65 | 1.7 |
| F66 | 2.3 |
| F67 | 3.2 |
| F68 | 4.3 |
| F69 | 3.8 |
| F70 | 3.1 |
| F71 | 4.4 |
| F72 | 2.8 |
| F73 | 2.9 |
| F74 | 2.4 |
| F75 | 2.3 |
| F76 | 1.9 |
| F77 | 2.6 |
| F78 | 1.7 |
| F79 | 3.2 |
| F80 | 1.9 |
| F81 | 3.4 |
| F82 | 2.7 |
| F83 | 2.4 |
| F84 | 3.4 |
| F85 | 2.9 |
| F86 | 3.3 |
| F87 | 3.6 |
| F88 | 2.4 |
| F89 | 2.8 |

TABLE 4-continued

| Compound No. | Pendrin inhibitory activity at 30 μM (%) |
|---|---|
| F90 | 3.3 |
| F91 | 3.9 |
| F92 | 2.2 |
| F93 | 2.5 |
| F94 | 1.9 |
| F95 | 3.8 |
| F96 | 3.4 |
| F97 | 2.9 |
| F98 | 3.3 |
| F99 | 2.4 |
| F100 | 2.5 |
| F101 | 1.8 |
| F102 | 2.7 |
| F103 | 3.7 |
| F104 | 3.5 |
| F105 | 3.1 |
| F106 | 3.3 |
| F107 | 2.9 |
| F108 | 2.3 |
| F109 | 2.4 |
| F110 | 2.9 |
| F111 | 30.8 |
| F112 | 3.1 |
| F113 | 3.5 |
| F114 | 3.9 |
| F115 | 2.8 |
| F116 | 2.6 |
| F117 | 2.3 |
| F118 | 2.1 |
| F119 | 1.7 |
| F120 | 1.9 |
| F121 | 3.4 |
| F122 | 3.8 |
| F123 | 2.4 |
| F124 | 2.0 |
| F125 | 1.0 |
| F126 | 2.5 |
| F127 | 3.6 |
| F128 | 1.9 |
| F129 | 2.3 |
| F130 | 2.7 |
| F131 | 2.1 |
| F132 | 3.9 |
| F133 | 4.1 |
| F134 | 3.4 |
| F135 | 2.8 |
| F136 | 2.4 |
| F137 | 3.1 |
| F138 | 2.7 |
| F139 | 2.5 |
| F140 | 3.3 |
| F141 | 1.9 |
| F142 | 2.4 |
| F143 | 87.4 |
| F144 | 21.3 |
| F145 | 20.8 |
| F146 | 26.1 |
| F147 | 3.4 |
| F148 | 100 |
| F149 | 4.8 |
| F150 | 6.9 |
| G1 | 2.9 |
| G2 | 3.8 |
| G3 | 55.6 |
| G4 | 4.4 |
| G5 | 60.9 |
| G6 | 4.7 |
| G7 | 82.1 |
| G8 | 68.8 |
| G9 | 3.9 |
| G10 | 4.3 |
| G11 | 3.5 |
| G12 | 48.1 |
| G13 | 22.4 |
| G14 | 2.5 |
| G15 | 3.4 |
| G16 | 1.8 |

TABLE 4-continued

| Compound No. | Pendrin inhibitory activity at 30 μM (%) |
|---|---|
| G17 | 1.1 |
| G18 | 2.7 |
| G19 | 3.9 |
| G20 | 3.4 |
| G21 | 4.1 |
| G22 | 89.2 |
| G23 | 2.7 |
| G24 | 1.9 |
| G25 | 42.1 |
| G26 | 85.6 |
| G27 | 2.2 |
| G28 | 53.5 |
| G29 | 81.7 |
| G30 | 29.7 |
| G31 | 3.9 |
| G32 | 2.1 |
| G33 | 5.4 |
| G34 | 38.2 |
| G35 | 94.0 |
| G36 | 4.8 |
| G37 | 97.9 |
| G38 | 2.5 |
| G39 | 3.2 |
| G40 | 88.6 |
| G41 | 25.1 |
| G42 | 2.7 |

TABLE 5

| Compound No. | $IC_{50}$ |
|---|---|
| F2 | 26.9 ± 2.95 μM |
| F8 | 20.5 ± 1.69 μM |
| F9 | 28.7 ± 2.25 μM |
| F10 | 0.08 ± 0.02 μM |
| F12 | 1.0 ± 0.15 μM |
| F19 | 20.1 ± 2.46 μM |
| F20 | 2.8 ± 0.26 μM |
| F26 | 12.8 ± 1.55 μM |
| F33 | 9.3 ± 0.68 μM |
| F34 | 8.6 ± 0.84 μM |
| F35 | 11.6 ± 1.25 μM |
| F36 | 14.8 ± 2.01 μM |
| F38 | 3.50 ± 0.27 μM |
| F39 | 25.8 ± 2.16 μM |
| F40 | 13.1 ± 1 36 μM |
| F46 | 22.7 ± 2.48 μM |
| F49 | 3.9 ± 0.36 μM |
| F56 | 3.3 ± 0.64 μM |
| F143 | 5.3 ± 0.69 μM |
| F148 | 0.2 ± 0.06 μM |
| G3 | 26.8 ± 2.54 μM |
| G5 | 22.6 ± 2.46 μM |
| G7 | 6.8 ± 0.66 μM |
| G8 | 20.2 ± 2.12 μM |
| G22 | 5.3 ± 0.58 μM |
| G26 | 10.2 ± 1.38 μM |
| G28 | 28.9 ± 2.18 μM |
| G29 | 16.7 ± 1.87 μM |
| G35 | 6.1 ± 0.88 μM |
| G37 | 8.2 ± 0.79 μM |
| G40 | 13.4 ± 1.69 μM |

In CHO-K1 cells overexpressing WT-pendrin and iodine sensitive YFP, the pendrin inhibitory effect of F56 was measured. This significantly inhibited the $Cl^-/I^-$ exchange activity of pendrin in a dose-dependent manner (FIG. 2).

The present inventors analyzed that F56 could also inhibit the $Cl^-/HCO_3^-$ exchange activity of pendrin. When the CHO-K1 cells overexpressing WT-pendrin and iodine sensitive YFP are treated with a high concentration $Cl^-$ solution, $Cl^-$ moves to the cells and $HCO_3^-$ moves outside of the cells, and this change induces acidification of intracellular pH with reduction of YFP fluorescence. Consequently, this significantly inhibited the $Cl^-/HCO_3^-$ exchange activity in a dose-dependent manner (FIG. 3).

Similar to the result of the $Cl^-/I^-$ exchange experiment, F56 inhibited the exchange activity strongly. F56 showed 50% inhibition of $Cl^-/I^-$ and $Cl^-/HCO_3^-$ exchange activity at ~3 μM and ~10 μM, respectively (FIG. 4(*a*) A).

On the other hand, F10 is confirmed to show the very higher activity than F56, and to strongly inhibit $Cl^-/I^-$, $Cl^-/SCN^-$, $Cl/HCO_3^-$, $Cl^-/OH^-$ anion exchange by pendrin (inhibitory effect of F10 on the Cl—/I— exchange activity: $IC_{50}$=~80 nM). Accordingly, it is confirmed that F10 is a very strong substance among pendrin inhibitors (FIG. 4(B)). In addition, G7 is a pharmaceutical metabolite of F10, which is a substance having lower efficacy than F10, but superior in acid stability.

Example 4: Airway Hypersensitiveness and Function to Reduce Mucin Expression in Asthma Mice of Novel Compound (F56)

Example 4.1: Thallium Flux Analysis

HEK-293T cells were stably transfected with hERG (human ether-a-go-go-related) gene, and seeded in a poly-L-lysine-coated 96 well plate at a density of $7\times10^4$ cells per well, and the cells were cultured for 48 hours. Four hours before analysis, for enhanced membrane expression of the hERG channel, the cells were converted from 37° C. to 28° C. In 4 hours, the medium was replaced with FluxOR (Invitrogen) loading buffer solution of 80 μL/well, and cultured in the dark place at 37° C. for 1 hour. The loading buffer solution was removed and the analysis buffer solution of 100 μL was added to each well. To measure the effect of F56 on the hERG channel, the cells were pretreated with F56 for 10 minutes. Four hours before adding a stimulus buffer containing thallium ion of 20 μL, FluxOR fluorescence (excitation/emission: 490/525 nm) was recorded and fluorescence was monitored for additional 56 seconds. FluxOR fluorescence was recorded and analyzed using FLUOstar Omega microplate reader (BMG Labtech, Ortenberg, Germany) and MARS data analysis software (BMG Labtech).

Example 4.2: Measurement of 5-HT2A Activity

FRT cells expressing human $5\text{-}HT_{2A}$, AN01 (abc) and YFP-F46L/H148Q/I152L were plated on a 96-well microplate at a density of $2\times10^4$ cells per well, and cultured for 48 hours. Each well of the 96-well plate was washed with 200 μL. PBS twice and was filled with 100 μL PBS. To measure the effect of F56 on the $5\text{-}HT_{2A}$ channel, the cells were pretreated with F56. After culturing at 37° C. for 10 minutes, the 96-well plate was placed on FLUOstar Omega microplate reader for YFP fluorescence measurement. By continuously (800 ms per point) recording YFP fluorescence for 2 seconds, each well was individually analyzed for $5\text{-}HT_{2A}$-mediated $I^-$ inflow (base line). Then, 140 mM $I^-$ solution containing 20 μM 5-HT (Sigma-Aldrich) of 100 μL was added at 2 seconds, and then YFP fluorescence was recorded for 10 seconds.

Example 4.3: ASL and Fluid Meniscus Volume Measurement

The total volume of ASL and fluid meniscus, which is fluid with the cell culture insert wall, was measured by fluid absorption through filter paper. Whatman filter paper (10 mm diameter circle; GE Healthcare) was placed on the apical size of a 12-well transwell insert (Costar Co.) for 10 seconds. The absorption of the ASL and fluid meniscus was measured from the weight change of the filter paper. The weight of the filter paper was measured using an analysis scale (Sartorius BP61S; Sartorius AG, Gottingen, Germany).

Example 4.4: Sensitization and Challenge with OVA

Experiments were performed using 8-week-old BALB/c mice. The experimental protocol was approved by the Animal Ethics Committee of Yonsei University. Mice were housed and maintained in an animal facility under standard laboratory conditions [12/12 hours light/dark cycle, controlled temperature (21±2° C.) and humidity (55±5%) and access to any food and water]. All the experiments were performed according to the guidelines of Yonsei University Animal Research Committee. Mice were divided to 3 groups, vehicle group (vehicle-treated PBS-sensitized and challenged mice), OVA group (vehicle-treated OVA-sensitized and challenged mice) and OVA+F56 group (F56-treated OVA-sensitized and challenged mice). Age and sex-matched 8-week-old mice were sensitized by i.p. injection of OVA (Sigma-Aldrich) on Days 0 and 14. The sensitization emulsion was composed of 50 μg OVA and 2 mg aluminum potassium sulfate in 200 μL saline solution. On Days 21, 22 and 23, sensitized mice were lightly anesthetized by isoflurane inhalation and challenged with 100 μg OVA in 30 μL saline solution administered intranasally. The control mice were treated in the same manner as PBS. F56 (10 mg/kg) was administered by i.p injection 12 hours before i.n. OVA challenge, respectively.

Example 4.5: Evaluation of Airway Responsiveness for Methacholine Challenge

The airway response for methacol (MCh) 24 hours after the last OVA exposure was measured using FlexiVent system (Scireq, Montreal, QC, Canada). Mice were anesthetized by intraperitoneal injection of the mixture of Zoletil (30 mg/kg; Virbac Laboratories, Carros, France) and Rompun (10 mg/kg; Bayer, Leverkusen, Germany), and then tracheostomy was performed to connect to FlexiVent. The base line airway resistance was measured after spraying saline solution for 10 seconds using Aeroneb ultrasonic nebulizer (SCIREQ). After measuring the base line, the mice were exposed to nebulized methacholine at an increased concentration (0, 1.56, 3.13, 6.25, 12.5 and 25 mg/mL). In addition, using whole body plethysmography (Buxco, Miami, FL, USA), the bronchial airway responsibility was measured. As a major index of the airway responsibility, enhanced pause (Penh) was used. Under the base line condition, Penh was measured for 2 minutes. Then, the mice were exposed to inhalation of PBS or MCh (25 mg/mL) for 2 minutes. The Penh result was expressed as an absolute value.

Example 4.6: Bronchoalveolar Lavage

After evaluation of the airway responsiveness, BAL was performed. The cells were pelleted by centrifugation and resuspended in PBS to obtain the number of cells. Cytospin was prepared with a cell centrifuge (Shandon Cytospin 4 cell centrifuge; Thermo Scientific, MA, USA, USA) and stained with Diff-Quik Stain Set (Dade Behring, USA, DE, USA) to evaluate inflammation.

Example 4.7: Histological Evaluation of Inflammation

For evaluation of airway inflammation, left lung was fixed in 4% paraformaldehyde overnight and embedded in paraffin. A histological slide was prepared from 5-μm section, and stained with hematoxylin and eosin (H&E). The inflammation score showing the severity of bronchial inflammation was evaluated by 3 blind observers using a method reported conventionally. To evaluate goblet cell hyperplasia, the section was stained with periodic acid-Schiff (PAS) using PAS staining kit (Sigma-Aldrich), according to the manufacturer's protocol. The nasal cavity mucous membrane and HNE cells collected on the transwell were softly washed with PBS and fixed with 4% paraformaldehyde. After deparaffinization and hydration, the slide was immersed in periodic acid solution at a room temperature for 5 minutes. After rinsing in distilled water, the slide was immersed in Schiff reagent at a room temperature for 15 minutes, and then washed in running tap water for 5 minutes.

Example 4.8: OVA-Specific IgE Measurement

According to the manufacturer's protocol, using Anti-Ovalbumin IgE (mouse) ELISA kit (Cayman Chemical, Ann Arbor, MI, USA), OVA-specific IgE in serum was measured. To measure the OVA-specific IgE level in serum, the diluted serum was added to an anti-IgG antibody-free coated 96-well plate, and then it was cultured with an OVA-biotin conjugate. The combined biotinylated OVA was detected with streptavidin-horseradish peroxidase (HRP) using 3, 3', 5, 5I-tetramethylbenzidine (TMB) as a substrate.

Example 4.9: Epithelial SCN— Transport

Nasal epithelial cells were plated on a transwell permeable supporter and cultured in ALI (air-liquid interface) for 14 days. After completely differentiated epithelial cells were cultured with IL-4 (Invitrogen, 10 ng/mL) for 48 hours, F56 (30 μM) or vehicle was added for 30 minutes. The transwell insert having cells was washed with PBS and the basal side was treated with 1 mL PBS containing 10 mM glucose and 5 μCi $S^{14}CN$ (total concentration $SCN^-$: 86 μM). The apical side of the transwell was filled with 0.5 mL PBS containing 5 μM amiloride to block epithelial sodium. Subsequently, the apical fluid was collected every 5 minutes and placed in scintillation vials for evaluation of radioactivity.

Example 4.10: Measurement of T3 and T4

The negative effect of F56 was examined by i.p administering of F56 10 mg/kg to female balb/c mice every 24 hours for 7 days. In 24 hours after the last administration, the hearing of mice was measured and serum was obtained. According to the manufacturer's protocol, the total serum level of triiodothyronine (T3) or thyroxine (T4) using a mouse ELISA kit (Calbiotech, T3043T-100 or T4044T-100).

Example 4.11: Auditory Brainstem Response (ABR)

The hearing level was measured in each mouse by measuring ABR threshold using an auditory-evoking potential workstation and BioSig software (Tucker-Davis Technologies, Alachua, FL, USA). The output from the speaker was calibrated using PCB 377C10 microphone (PCB Piezotronics, Inc. New York, NY, USA) and found to be within ±4 dB over the tested frequency range. After anesthetizing the mice, each ear was stimulated with an ear probe sealed inside the ear canal. The body temperature of the mice was maintained at 38° C. with an isothermal heating water-pad. The intensity of the click sound decreased from 70 dB SPL to 10 dB SPL with a 5-dB decrease. The mean value of ABR was calculated and the auditory threshold was defined as the lowest ABR response until wave I of ABR was no longer visually discernible.

Example 4.12: In Vitro Optical Imaging 8-week-old NF-β luciferase-dTomato reporter mice (Korea mouse phenotype center) were sensitized by i.p. injection of OVA (50 μg, Sigma-Aldrich) and 2 mg aluminum potassium sulfate on Days 0 and 14. On Days 21, 22 and 23, the sensitized mice were anesthetized by isoflurane inhalation and challenged with 150 μg OVA in 30 μL saline solution intranasally administered. The control mice were treated with the same method as PBS. F56 (10 mg/kg) was administered, respectively, before 12 hours, by i.p injection. NF-κ expression was compared in the lung of NF-kB reporter mice using IVIS system. The lung was separated from the mice and fluorescence imaging was performed using IVIS spectra (Ex 570, Em 620). The average fluorescence density of the images was analyzed using Living Image 4.3.1 software.

Example 4.13: Measurement of Tracheal Contraction

All experiments were performed using 4-week-old SD male rats. The experimental protocol was approved by the Animal Ethics Committee of Yonsei University. The rats were sacrificed and tracheal strips were separated. After the connective tissue was separated, the organ was cut into 3 mm long rings. The organ was mounted for tension recording under 1 g tension and equilibrated for 1 hour in an organ bath containing 25 mL of oxygenated physiological solution. The solution was gassed successively with 95% 02 and 5% $CO_2$ at 37° C. After 1 hours of stabilization, 0.3 μM carbachol (CCh) was used to induce a sustained contraction reaction in the organ bath. Once the sustained tension was established, F56 (30 μM) and forskolin (10 μM) and IBMX (100 μM) were applied to the bath. The organ contraction was measured using FORT 10G converter (World Precision Instruments, Sarasota, FL, USA) and PowerLab 4/35 (AD Instruments, Castle Hill, Australia). Data were recorded and analyzed using Labchart Pro 7 (AD Instruments).

Pendrin (SCL26A4), a transmembrane anion exchanger, exchanges $Cl^-$ with bases such as $HCO_3^-$, $I^-$, $OH^-$ and $SCN^-$, and is the most highly upregulated gene in bronchial biopsies from asthmatic patients. Interestingly, patients with a pendrin variant have a lower incidence of asthma and pendrin-null mice show reduced allergic airway inflammation. The present inventors have reported that a novel pendrin inhibitor, F56 (2-(4-(tert-butyl)phenyl)-4-(thiophen-2-ylmethylene)oxazol-5(4H)-one), which has a strong therapeutic effect on allergic inflammation in a mouse model of ovalbumin (OVA)-induced asthma, was isolated.

F56, 54,400 synthetic compounds were identified by cell-based high throughput screening (FIG. 5(*a*), A). F56 strongly inhibited the pendrin-mediated $Cl^-/SCN^-$, $Cl^-/I^-$, $Cl^-/HCO_3^-$ and $Cl^-/OH^-$ exchange activity in a dose-dependent manner (FIG. 5(*a*), B and C, and FIG. 6(*a*), A-c). F56 did not show cytotoxicity up to 30 μM in NIH3T3 and CHO-K1 cells, and inhibited the pendrin activity than the recently identified pendrin inhibitors, $PDS_{inh}$-A01 and $PDS_{inh}$-001 (FIG. 6(*a*), D-I). On the other hand, it was confirmed that F10 did not show any cytotoxicity up to 30 μM in NIH3T3 and CHO-K1 cells like F56 (FIG. 6(*b*)). F56 inhibited the human and mouse pendrin-mediated exchange with almost the same efficacy (FIG. 7(*a*), A and B). F56 weakly inhibited the $Cl^-/HCO_3^-$ exchange activity of SCL26A3 and SLC26A6 with $IC_{50}$>100 μM, and did not affect SCL26A7 and SLC26A9. The cystic fibrosis transmembrane conductance regulator (CFTR), anoctamin-1 (AN01), human ether-a-go-go-related gene (hERG) channel and 5-$HT_{2A}$ activity were not affected by F56 (FIG. 7(*a*), C-J). On the other hand, it was confirmed that F10 did not show any effect on the activity of CFTR, AN01 and hERG ion channels like F56 (FIG. 7(*b*)).

In primary culture of human nasal epithelial (HNE) and human bronchial epithelial (HBE) cells, IL-4 treatment strongly upregulated the pendrin expression and pendrin-mediated $Cl^-/HCO_3^-$ exchange activity, and F56 potentially inhibited the pendrin-mediated $Cl^-/HCO_3^-$ exchange activity (FIG. 5(*a*), D-F and FIG. 8(*a*), A-C). The present inventors observed the long-term treatment effect of F56 on the functional expression of pendrin and other ion channels involved in ASL regulation. Interestingly, the IL-4-induced upregulation of the $Cl^-/HCO_3^-$ exchange activity and pendrin protein expression level were strongly reduced by long-term treatment of F56 without changes of the mRNA expression level, but the IL-4-induced upregulation of AN01 was not affected (FIG. 5(*a*), G-I). On the other hand, it was confirmed that F10 did not show any effect on the mRNA expression of PDS like F56 (FIG. 5(*b*)). The mRNA expression level and ion channel activity of AN01, CFTR and ENaC did not change by the long-term treatment of F56 (FIG. 8(*a*), D-F). Meanwhile, it was confirmed that F10 did not show any effect on the mRNA expression of AN01, CFTR and ENaC like F56 (FIG. 8(*b*)).

The pretreatment with significantly weakened the OVA-induced airway sensitivity (FIG. 9(*a*), A), and reduced the number of eosinophils and neutrophils in BALF of OVA-sensitized mice. As the result of histological analysis, the increased number of goblet cells in the central airway with increased inflammation infiltration and increase epithelial thickness were weekended by treating with F56 in OVA-challenged mice. The average inflammation score of the OVA-challenged mice was significantly lower in the F56-treated group than the non-treated group, but the serum level of OVA-specific IgG was not changed by F56, and this shows that F56 does not act on the general allergic response mechanism (FIG. 10). On the other hand, it was confirmed that F10 reduced the airway resistance increased in the asthma mouse model induced by OVA like F56 (FIG. 9(*b*)).

According to the recent research, NF-kB activation by hypothiocyanite ($OSCN^-$) production increased through upregulation of pendrin, peroxidases and dual oxidase (Duox1/Duox2) in the airway epithelium was involved in the allergic airway inflammation. The $SCN^-$ concentration on the apical surface was significantly increased by IL-4 treatment and was inhibited by F56 (FIG. 9(*a*), B). Real-time PCR analysis showed that IL-4 treatment significantly increased the mRNA expression of Duox1, but did not affect Duox2, and F56 did not affect the mRNA expression of Duox1 or Duox2 (FIG. 9(*a*), c). The pretreatment of F56 significantly inhibited IL-4-induced activation of NF-kB in HNE cells (FIG. 9(*a*), D). In particular, the intranasal administration of NaSCN significantly blocked the inhibitory effect of F56 on the airway sensitivity, and removed the protective effect of F56 on the lung injury in OVA-challenged asthma mice (FIG. 9(*a*), E and F). In addition, F56 significantly blocked NF-kB activation in the lung of OVA-treated mice, and the treatment of $SCN^-$ inhibited the protective effect of F56 in transgenic NF-k B reporter mice (FIG. 10, G). When F56 was applied in the established model of allergic asthma, OVA-induced airway sensitivity and PAS positive cells were significantly reduced in the airway epithelium (FIG. 11). This result suggest that F56 may be useful for prevention and treatment of allergic asthma.

Pendrin is related to the airway inflammation-mediated upregulation of MUC5AC in the airway epithelium. In particular, according to the present invention, it was shown that the treatment with F56 significantly reduced the mRNA expression of IL-4-induced MUC5AC (FIG. 12(*a*), A). In addition, the pretreatment with F56 significantly reduced the IL-4 and IL-13-induced goblet cell hyperplasia in HNE cells (FIG. 12(*a*), B). The ASL thickness in the IL-13-treated primary culture of the airway epithelial cells was significantly higher in pendrin-mull mice and hearing-impaired patients having mutant SLC26A4 gene, compared to the control group. In HNE cells expressing wild-type pendrin, IL-4 and IL-13 treatment strongly increased the pendrin protein expression, and reduced the total volume of ASL and fluid meniscus, compared to the control group, and F56 treatment hardly reduced the total volume of ASL and fluid meniscus. However, the total volume was not changed by IL-4 and F56 in HNE cells expressing a mutant pendrin (F. 12(a), C-F). This result corresponds to the conventional research result which discovered that $PDS_{inh}$-A01 significantly increased the ASL depth in IL-13-treated HBE cells. The MUC5AC inhibition and increase in the ASL thickness by F56 may further provide a beneficial effect on airway inflammation disease such as COPD, cystic fibrosis and asthma. On the other hand, it was confirmed that F10 reduced the mRNA expression of MUC5AC in a concentration-dependent manner like F56 (FIG. 12(*b*)).

Since patients with an SLC26A4 gene mutation are associated with prelingual deafness and goiter, the alteration in a hearing or thyroid hormone level may be induced by pendrin inhibition. However, after treatment of F56 (10 mg/kg/day) for 1 week, the hearing threshold of T3 and T4 and plasma level were not changed (FIG. 13, A-C). In addition, F56 did not affect the tracheal smooth muscle (FIG. 13, D).

In summary, F56 reduced the airway sensitivity and airway inflammation by inhibition of the $SCN^-$/NF-kB route. In addition, F56 showed the protective effect on IL-4 and IL-3-induced goblet cell hyperplasia and ASL deficiency (FIG. 14). This result shows that the pendrin inhibitor is a promising candidate for treatment of allergic asthma.

Example 5: Reduction Function of Lipopolysaccharide-Induced Acute Lung Injury in Mice of Novel Compound (F56)

Example 5.1: Experimental Animal

From Orient Bio (Sungnam, Republic of Korea), 8-10-week-old wild-type male C57BL/6J mice having a body weight of 20-24 g were purchased. Food and water were provided to all the animals, and the similar optical cycle of day and night was applied. Transfected NF-κ reporter/SPC-Cre-ERT2 mice were used for IVIS in the present invention. Briefly, NF-κ reporter mice contain ROSA26 lox-STOP-lox-cassette inserted between a promoter and NF-κ gene. In general, a stop gene is positioned between loxP and loxP, and NF-κ is not expressed. NF-κ reporter/SPC-Cre-ERT2 mice were obtained by raising ROSA26R mice to surfactant protein C(SPC)-Cre-ERT2 mice. The Cre-ERT2 recombinase activity in these transfected mice was induced by tamoxifen. These NF-κ reporter/SPC-Cre-ERT2 mice express NF-κ activity in the alveolar epithelium by one of dTomato fluorescence or luciferase in presence of tamoxifen. Tamoxifen (Sigma, USA) was dissolved in a 10:1 sunflower seed oil/ethanol mixture (10 mg/mL). To each 4-week-old mouse, 100 mL tamoxifen/day was intraperitoneally injected for continuous 5 days. In 1 week after the last injection, mice were used for IVIS or in vivo imaging. From Yonsei University, transfected NF-κ reporter and SPC-Cre-ERT2 mice were provided.

Example 5.2: LPS-Induced ALI in Mouse Model

Mice were slightly anesthetized by isoflurane inhalation (Abbott Laboratory), and were maintained in a supine position with the head raised. LPS (*Escherichia coli,* 0111: B4, Sigma) (10 mg/kg) in 50 μL PBS was administered by intranasal (i.n.) inhalation. As the control group, 50 μL sterile PBS was intranasally provided. With the aid of a microsyringe from Hamilton, the administration solution was gradually released into the nostrils. In case of the pretreatment model, F56 (10 mg/kg) in 50 μL DMSO was intraperitoneally (i.p) administered before 1 hour of LPS inhalation. In case of the post-treatment model, two doses of F56 were administered at 6 hours and 12 hours after LPS inhalation. The mice of the pretreatment group were euthanized and in 48 hours after LPS inhalation, the lung was harvested. In the post-treatment model, euthanasia and sample collection occurred 24 hours after LPS administration. For $SCN^-$ experiment, after F56 treatment, 50

NaOH, $NaHCO_3$, or NaSCN (100 mM) was intranasally administered. For the control group, PBS was administered in the same manner.

Example 5.3: Separation of Bronchoalveolar Lavage

All mice were euthanized with fetal excessive amount of ketamine and xylazine. BALF was obtained by tracheal cannula using 1 mL sterile saline solution. BALF was centrifuged (4° C., 3000 rpm, 10 minutes) and the supernatant was stored at −80° C. for an additional analysis. The cell pellet was recomposed in 100 μL PBS, and used for the number of cells and cytospin sample. The total number of cells of each sample was determined using a hemocytometer (Marienfield), according to the manufacturer's protocol. Each sample in a 90 μL split amount was transferred to a slide chamber, and then the slide was inserted into the cytospin with outward facing. The slide was centrifuged at 800 rpm for 5 minutes, and then removed from the cell centrifuge, and dried before staining. The cytospin was prepared with a cell centrifuge (Shandon Cytospin 4 cytocentrifuge, Thermo Scientific, Waltham, MA, USA) and stained with Diff-Quik Stain Set (Dade Behring, Newark, DE, USA) to evaluate inflammation. The protein concentration of BAL supernatant was measured using BCA analysis (Thermo Fischer Scientific). 2 microliters of each sample and 198 μL of a working reagent were pipetted in a microplate well and completely mixed in a plate shaker for 30 minutes. After culturing at 37° C. for 30 minutes, the plate was cooled and the absorbance was read at 562 nm in a spectrophotometer.

Example 5.4: Lung Tissue Harvest and Histological Examination

The right lung was isolated and the pulmonary vasculature structure was flushed with saline solution under low pressure and stored at −80° C. before protein extraction. The left lung was inflated via tracheostomy with low-meting agarose (4%) in PBS at 25 cm $H_2O$ pressure until the pleural margin was sharpened. Then, the lung was excised and fixed overnight in 10% formaldehyde in PBS and embedded in paraffin for 5 μm sections. The left lung section was stained with H&E and subjectively evaluated with an optical microscope. Histopathology was reviewed in a blind method by two qualified researchers. Five easily identifiable pathological processes were scored using the weighted scale presented in the official ATS workshop report. Lung sections were processed using anti-rabbit SLC26A4 (ab98091, abcam) antibody for immunohistochemistry.

Example 5.5: Cl—/SCN— Exchange Measurement

Human pendrin (PDS) and YFP-F46L/H148Q/I152L temporarily transfected with human alveolar epithelial cells (hAEC) were plated on a 96-well plate at a density of $2\times10^4$ cells pe well and cultured for 48 hours. Each well of the 96-well plate was washed with 200 μL PBS twice and filled with 100 μL PBS. To measure the effect of F56 on the hPDS-mediated $Cl^-/SCN^-$ exchange activity, the cells were pretreated by F56. After culturing at 37° C. for 10 minutes, the 96-well plate was put on the stage of a reverse fluorescence microscope (Nikon, Tokyo, Japan) equipped with a cooled charge-coupled device camera (Zyla sCMOS), image acquisition and analysis software (Meta Imaging Series 7.7). By continuously (2 seconds per point) recording YFP fluorescence for 4 seconds, each well was individually analyzed for hPDS-mediated $SCN^-$ inflow. Then, 140 mM $SCN^-$ solution of 100 μL was added at 4 seconds and then the YFP fluorescence was recorded for 14 seconds.

Example 5.6: Real-Time RT-PCR Analysis

The total messenger RNA (mRNA) was extracted using TRIzol reagent (Invitrogen, Carlsbad, CA, USA), and was reverse-transcribed using a random hexamer primer, an oligo(dT) primer and SuperScript® III reverse transcriptase (Invitrogen). Quantitative real-time PCR was performed using StepOnePlus Real-Time PCR system (Applied Biosystems, Foster City, CA, USA) and Thunderbird SYBR qPCR mix (Tokyobo, Osaka, Japan). Thermal cycling conditions included the initial stage at 95° C. for 5 minutes, and subsequent 40 cycles at 95° C. for 10 seconds, at 55° C. for 20 seconds and at 72° C. for 10 minutes. The primer sequences were listed in Table 3 above.

Example 5.7: ELISA

In the lung lysates, the level of macrophage inflammatory protein (MIP-2), interleukin-1β (IL-1β 6 and tumor necrosis factor α (TNF-α) was measured using an ELISA kit (Millipore), according to the manufacturer's instructions.

Example 5.8: Protein Expression Measurement

The lung tissue was harvested and dissolved in a homogenization buffer (PRO-PREP™ extraction solution, iNtRON Biotechnology). The sample was centrifuged at 4° C. for 30 minutes at 13000 g. The supernatant protein concentration was determined by BCA analysis (Thermo Fisher Scientific). The same amount of protein was separated by SDS/PAGE and transferred to a nitrocellulose membrane. The membrane was blocked with 5% skim milk in TBS-T (TBS (170-6435, Bio-Rad Laboratories) and 1% Tween-20 (170-6531, Bio-Rad Laboratories) for 1 hours. Then, the membrane was cultured overnight with the primary antibody diluted with 5% skim milk in TBS-T at 4° C. After washing with TBS-T, the blot was cultured with horseradish peroxidase-combined secondary antibody and 5% skim milk in TBS-T at a room temperature for 1 hour, and then developed using Super-Signal West Pico chemiluminescence detection kit. The antibody used in the present invention includes rabbit SLC26A4 (ab98091, abcam), mouse phospho-Iκ (9246, Cell Signaling Technology), mouse Iκ (4814, Cell Signaling Technology), and rabbit α-tubulin (PA5-16891, Cell Signaling Technology). Western blot quantization was performed using ImageJ (Image Processing and Analysis in Java; NIH, USA) software.

Example 5.9: IVIS

Imaging of living animals and organs was performed using IVIS exercise imaging system Caliper Life Sciences, Preston Brook Runcorn, UK). IVIS system was composed with a cooled charge coupled device camera equipped in a light sample chamber. Fluorescence excite light was provided by a halogen lamp combined with an appropriate excite filter. Depending on the emission spectrum of irradiated FP, an emission filter was placed in front of the camera aperture to record light of a specific wavelength. The fluorescence imaging was obtained with an excitation wavelength of 554 nm and an emission wavelength of 581 nm (dTomato). Mice were divided into 3 groups for IVIS imaging (DMSO+PBS, DMSO+LPS and F56 (10 mg/kg, i.p)+LPS), and the lung was aseptically removed in 6 hours after LPS treatment. When the organs were imaged, in order to allow complete and consistent light penetration to minimize potential changes in the measurement due to the difference of the tissue thickness, they were placed evenly as possible. In Living Image software (version 3.2, Caliper Life Sciences), using an area of interest tool, fluorescence was quantified.

Example 5.10: Collection of Human Bronchoalveolar Lavage

41 ARDS patients due to pneumonia suffering from bronchoalveolar lavage were classified to ARDS group. 25 patients hospitalized for SPN evaluation without an evidence of lung inflammation were classified to the control group in Severance hospital from May, 2013 to September, 2015. Before the bronchial endoscopy, the subjects received local anesthesia (lidocaine) with a nebulizer and then sedated with midazolam and fentanyl. A bronchoscope was inserted and wedged into the mouth for BAL. According to a standardized protocol (pneumonia group: bronchi of lung lesion, control group: contralateral bronchi from lung mass), BAL was performed, and using about 30 mL 0.9% sterile saline solution, 10 cc BALF was obtained from each patient. BAL was centrifuged (10 minutes; 1500 g), and the supernatant was cryopreserved at −80° C. until use. Demographic and clinical data including age, gender, body mass index (BMI), comorbidities, BASL analysis, cause of pneumonia and final diagnosis were obtained from each participant as well as medical records. The supernatant pendrin level was measured using human SLC26A4 ELISA kit (MBS764789, Mybiosource), according to the manufacturer's instructions.

Example 5.11: Research Approval

All animal protocols were approved by Institutional Animal Protection Committee of Yonsei University College of Medicine (2016-0322). All animal experiments were performed in accordance with the recommendations of Guide for the Care and Use of Laboratory Animals of National Institute of Health. The human research protocol was reviewed and approved by Institute Review Committee of Yonsei University Health Department, Severance Hospital, Seoul, Korea (ARDS group IRB No. 4-2013-0585, control group IRB No. 4-2014-1014). Prior written consent was obtained from the patients or protectors regarding the use of the BALF sample.

As expected, LPS injection into the organ induced ALI in WT mice. The total cell number and protein concentration in bronchoalveolar lavage (BALF) was significantly increased after LPS treatment (FIG. 15A). In addition, lung histology showed leukocyte infiltration and lung injury in WT mice (FIG. 15B). On the contrary, LPS did not increase the cell number or protein concentration in pendrin-null mice (FIG. 15C). Furthermore, lung histology showed deficiency of leukocyte infiltration and lung injury in pendrin-null mice after LPS treatment (FIG. 15*d*). The average body weight change after LPS injection of 48 hours was more remarkable in WT mice than pendrin-null mice (−3.38 g vs. −1.75 g, $p<0.01$, FIG. 1E). This result suggests that pendrin plays an essential role in development of LPS-induced ALI.

As described above, a novel pendrin inhibitor, F56 was identified through high throughput screening of 54,400 synthetic compounds. F56 strongly inhibited the $Cl^-/I^-$, $Cl^-/SCN^-$, $Cl^-/HCO_3^-$ and $Cl^-/OH^-$ exchange activity in a dose-dependent manner, and strongly reduced the protein expression level of pendrin in nasal cavity bronchial epithelium, but did not reduce the mRNA expression level of pendrin.

The present inventors investigated the effect of LPS and F56 on the mRNA and protein levels of pendrin in human alveolar epithelial cells (hAEC). LPS treatment significantly increased the mRNA expression level and protein expression level of pendrin, F56 reduced the protein expression level of pendrin, but did not change the mRNA expression level of pendrin in hAEC (FIGS. 16B and 16C). In addition, F56 intensively inhibited the $Cl^-/SCN^-$ exchange activity ($IC_{50}$=4.7±0.82 mM) of pendrin in hAEC transfected with wild-type human pendrin (FIG. 16D). As described above, it was shown that upregulation of pendrin could activate NF-β by increasing hypothiocyanite ($OSCN^-$) production through upregulation of double oxidase (Duox1/Duox2) in the airway epithelium of allergic inflammation. Real-time PCR analysis showed that LPS treatment significantly increased the mRNA expression level of Duox2, and F56 did not change the mRNA expression level of Duox2 (FIG. 16E).

To investigate the protective function of F56 in the LPS-induced ALI mouse model, mice were treated with F56 1 hours before intranasal injection of LPS, and euthanized in 48 hours after LPS treatment (FIG. 17A). It was shown that F56 (10 mg/kg)-pretreated mice had the reduced BASL total cell number and protein concentration level, compared to vehicle-treated mice (FIGS. 17B and 17C). In addition, F56 pretreatment significantly reduced the lung injury score, compared vehicle-treated mice, in which leukocyte infiltration occurred after LPS exposure was inhibited (FIGS. 17D and 17E). To determine whether F56 treatment after LPS injury was effective, mice were treated with F56 in 6 hours and 12 hours after LPS intranasal injection, and then euthanized in 24 hours after LPS administration (FIG. 17F). F56 treatment after LPS injection corresponded to the result of F56 pretreatment experiment, and considerably reduced the BALF total cell number and protein concentration as well as lung injury score (FIG. 17G-17I).

To confirm the fundamental therapeutic effect mechanism of F56 in LPS-induced ALI, the present inventors provided anions ($OH^-$, $HCO_3^-$, and $SCN^-$) secreted by pendrin. Intranasal application of NaSCN (50 μL of 100 μM) blocked the protective effect of F56 in LPS-induced ALI; and the BAPS total cell number and lung injury score were increased, compared with the group treated with LPS alone. However, administration of NaOH and $NaHCO_3$ did not change the effect of F56 in LPS-induced ALI mice (FIGS. 18A and 18B). In addition, histological analysis discovered that the protective effect of F56 on the inflammatory cell infiltration and lung injury after LPS administration was abolished by NaSCN administration (FIG. 18C). More interestingly, while the simultaneous application of LPS and NaSCN induced strong lung injury in pendrin-null mice, administration of LPS alone did not induce ALI (FIG. 18D). These data strongly show that the treatment effect of F56 was caused by $SCN^-$ transport function inhibition of pendrin.

The present inventors further dissected the signaling pathway by behavior of F56 in the LPS-induced ALI model using NF-κ reporter/SPC-Cre-$ER^{T2}$ mice. Quantification fluorescence was measured using an in vivo optical imaging (IVIS) image of mouse lung aseptically removed right before imaging. The fluorescence of the excised lung increased after LPS treatment, and this was inhibited by F56 (FIGS. 19A and 19B). This result suggests that NF-κ activation was inhibited by F56 in LPS-injected mice. Immunoblot analysis showed that the NF-κ pathway was related to F56 action. Phospho-Iκ protein expression, showing NF-κ activation increased after LPS administration, and F56 treatment before LPS significantly reduced Phospho-Iκ expression (FIGS. 19C and 19D).

The level of cytokine including IL-1B tumor necrosis factor-α and macrophage inflammatory protein (MIP)-2 was significantly increased after LPS administration, compared to PBS (FIG. 19E-19H). The difference was not statistically significant, but IL-6 had a tendency to increase, compared to PBS. In contrast, the level of pro-inflammatory cytokine was reduced in F56 pretreated mice compared to that receiving vehicle (DMSO) treatment after LPS administration (FIG. 19E-19H).

To translate in vitro and in vivo opinions to human disease, the present inventors measured patients due to pneumonia (ARDS group, n=41) and patients having solitary pulmonary nodule (SPN) without inflammation (control group, n=25). The clinical characteristics of patients were shown in Table 6 below.

TABLE 6

| | Control group (n = 25) | ARDSB (n = 41) | P |
|---|---|---|---|
| Age, year, mean ± SD | 63.8 ± 9.7 | 65.9 ± 13.6 | 0.517 |
| Gender, male, N (%) | 20 (80.0) | 32 (78.0) | 0.851 |
| BMI ($kg/m^2$), mean ± SD | 24.5 ± 4.3 | 22.6 ± 3.0 | 0.040 |
| ICU Presence, N (%) | 0 | 41 (100) | — |
| Intubation/ARDS, N (%) | 0 | 41 (100) | — |

TABLE 6-continued

| | Control group (n = 25) | ARDSB (n = 41) | P |
|---|---|---|---|
| P/F ratio, mean ± SD | — | 157.3 ± 052.8 | — |
| Bacteremia, N (%) | 0 | 9 (22.0) | — |
| Retention time, d, Median value (IQR) | 2 (1-2) | 36 (26-57) | — |
| Day 28 mortality | 0 | 10 (24.4) | — |
| In-hospital mortality | 0 | 28 (68.3) | — |
| Pendrin value, ng/mL, mean ± SD | 6.83 ± 6.91 | 24.86 ± 9.28 | <0.001 |

[A]Values are expressed as mean ± SD, median values (interquartile range, IQR), or number (%).
[B]ARDS due to pneumonia
[C]BMI, body mass index; ICU, intensive care unit; ARDS, acute respiratory distress syndrome; P/F, $PaO_2/FIO_2$ The average age was not significantly different between the control group and ARDS group (63.8 vs. 65.9, p=0.517), and males were predominant in both groups (80% vs. 78%, p=0.851). Among ARDS patients, the mean hospital stay was 36 days and the Day 28 mortality was 24.4% (Table 1). The pendrin level was significantly elevated in BALF of ARDS patients (n=41) compared to the control group (n=25) (mean, 24.86 vs. 6.83 ng/mL, p<0.001) (FIG. 20).

In conclusion, new evidence strongly suggests that pendrin is a key protein in pathogenesis of airway inflammatory disease, including asthma, chronic obstructive pulmonary disease and rhinitis. The present inventors demonstrated that the pendrin expression level was increased in the LPS-treated mouse airway. In addition, the present inventors did not develop in LPS-induced ALI pendrin null mice, and this strongly indicated an important role of pendrin in ALI pathogenesis. This is consistent with a recent report that pendrin expression was enhanced in LPS-induced ALI, and non-specific pendrin inhibitors attenuated ALI in mice. This evidence encouraged the present inventors to develop a pendrin inhibitor as a new drug for treatment of ALI. The present inventors screened 54,400 synthetic compounds and found a specific pendrin inhibitor (F56) that did not affect the transport of other ions such as cystic fibrosis transmembrane conductance regulator (CFTR) and calcium activated chloride channel (CaCC). Pendrin expression was upregulated by LPS treatment in human alveolar epithelium, which was effectively inhibited with F56. Surprisingly, F56 almost completely blocked the development of LPS-induced ALI in mice. Furthermore, F56 administration of after LPS treatment attenuated lung injury in mice, and this indicated that the clinical treatment period of the pendrin inhibitor was wide enough to include the period after ALI. The present inventors found that the pendrin expression was increased in BALF and LPS-treated mouse airway from pneumonia patients, and this strongly suggested a high potential for clinical application of pendrin inhibitors in inflammatory airway disease.

The role of pendrin in the ALI model and basic mechanism of the therapeutic effect of F56 is unclear. The present inventors focused on the $Cl^-/SCN^-$ exchange activity of pendrin and hypothiocyanite ($OSCN^-$), and this is synthesized from $SCN^-$ transported through various anion transporters (including pendrin) by lactoperoxidase in the airway epithelium. $OSCN^-$ is known to be part of an important innate defense system against microorganisms in the airway and induces airway inflammation in the airway epithelium. According to the recent research, IL-4 upregulates the $Cl^-/SCN^-$ exchange activity of pendrin and increases $OSCN^-$ production, and this induces NF-κ activation and causes airway inflammation in a murine allergic asthma model. The present inventors showed that when NaSCN was added to the airway of mice, the therapeutic effect of F56 on the lung injury disappeared. In addition, NaSCN application induced lung injury also in pendrin null mice, but did not result in LPS-induced ALI. These data indicate that the airway surface $SCN^-$ transported by pendrin is an essential component of LPS-induced airway inflammation.

NF-κ is an important determinant of the inflammatory response in the airway, and its inhibition attenuates in vivo ALI. In addition, the present inventors observed that F56 inhibited LPS-induced NF-κ activation and subsequent cytokine production in the murine ALI model and alveolar epithelium. Collectively, the data according to the present invention showed that the pendrin inhibitor action method resulted from F56 blocking the intraepithelial transport of $SCN^-$ followed by inhibition of $OSCN^-$ production and NF-κ activation. This inhibited the pro-inflammatory cytokine production (FIG. 21). This is a very similar action mode to that found in an asthma mouse model which attenuates the OVA-induced allergic airway inflammation by that a pendrin inhibitor inhibited pendrin/OSCN—/NF-κ cascade (18). However, considering previous reports showing that LPS may activate NF-κ through a TLR4/MyD88 pathway (28, 28), it is unknown why YS-01 almost completely inhibits LPS-induced ALI. Nevertheless, the deficiency of the ALI phenotype caused by NaSCN in pendrin null mice strongly shows that pendrin-mediated OSCN dominantly activates NF-κ cascade in the LPS-induced ALI model. This is a very similar action mode to that in the asthma mouse model according to the present invention, in which the pendrin inhibitor inhibits pendrin/$OSCN^-$/NF-κ cascade to attenuate OVA-induced allergic airway inflammation. However, considering previous reports showing that LPS may activate NF-κ through a TLR4/MyD88 pathway, it is unknown why F56 almost completely inhibits LPS-induced ALI. Nevertheless, the deficiency of the ALI phenotype caused by NaSCN in pendrin null mice strongly shows that pendrin-mediated $OSCN^-$ dominantly activates NF-κ cascade in the LPS-induced ALI model.

Although important treatment for ALI patients has improved, ALI/ARDS mortality remains high and medical treatment options for ALI/ARDS are limited. Since F56 has shown potent therapeutic effects in the ALI murine model, pendrin may become a new target for the treatment of ALI/ARDS. It is promising that pendrin expression is upregulated in BALF of pneumonia patients, thereby increasing the potential clinical therapeutic benefit of pendrin inhibitors for ALI/ARDS. In addition, F56 has low cytotoxicity and is chemically stable and operates at the nanomolar level; and it is an excellent compound for further development of final candidates for clinical trials.

In other words, the present inventors demonstrated that pendrin is essential for LPS-induced ALI and the compound (F56) inhibiting pendrin strongly inhibited LPS-induced ALI. According to the present invention, the pendrin inhibitor is a promising new drug class for ALI treatment.

The invention claimed is:

1. A compound selected from the group consisting of the following compounds listed in Table 1, an E- or Z-isomer thereof, an optical isomer thereof, a mixture of two isomers selected from the E-isomer, Z-isomer and optical isomer thereof, a pharmaceutically acceptable salt thereof, or a solvate thereof:

TABLE 1
| Compound No. | Structural Formula |
|---|---|
| F2 | 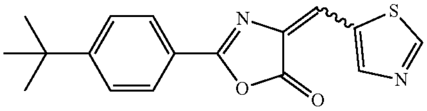 [SMILES: CC(C)(C)c1ccc(C2=NC(=Cc3cncs3)C(=O)O2)cc1] |
| F8 | 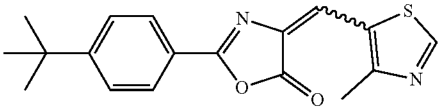 [SMILES: Cc1ncsc1C=C1N=C(c2ccc(C(C)(C)C)cc2)OC1=O] |
| F10 | 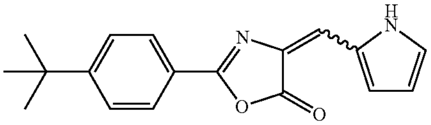 [SMILES: CC(C)(C)c1ccc(C2=NC(=Cc3ccc[nH]3)C(=O)O2)cc1] |
| F12 | 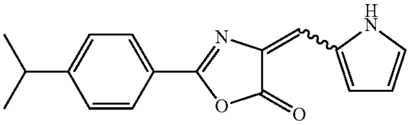 [SMILES: CC(C)c1ccc(C2=NC(=Cc3ccc[nH]3)C(=O)O2)cc1] |
| F19 | 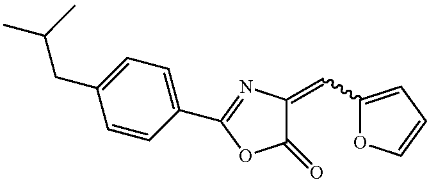 [SMILES: CC(C)Cc1ccc(C2=NC(=Cc3ccco3)C(=O)O2)cc1] |
| F20 | 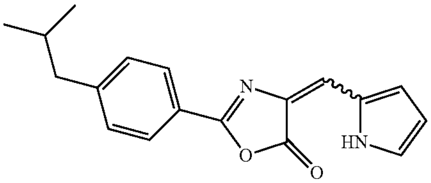 [SMILES: CC(C)Cc1ccc(C2=NC(=Cc3ccc[nH]3)C(=O)O2)cc1] |
| F26 | 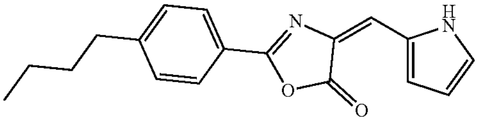 [SMILES: CCCCc1ccc(C2=N/C(=C/c3ccc[nH]3)C(=O)O2)cc1] |
| F143 | 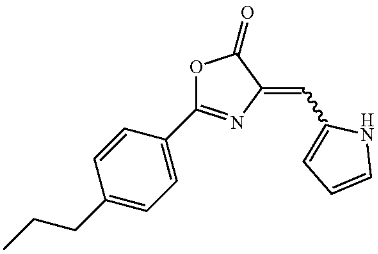 [SMILES: CCCc1ccc(C2=NC(=Cc3ccc[nH]3)C(=O)O2)cc1] |
| F148 | 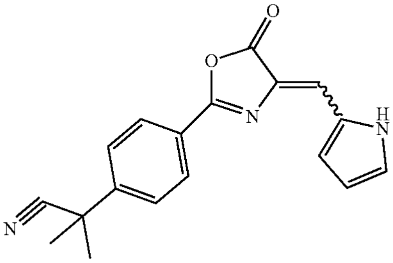 [SMILES: CC(C)(C#N)c1ccc(C2=NC(=Cc3ccc[nH]3)C(=O)O2)cc1] |

TABLE 1-continued
| Compound No. | Structural Formula |
|---|---|
| G3 | 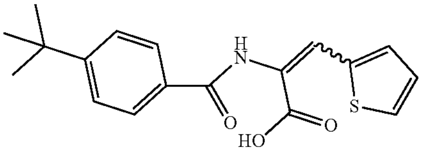 [SMILES: CC(C)(C)c1ccc(C(=O)NC(=Cc2cccs2)C(=O)O)cc1] |
| G7 | 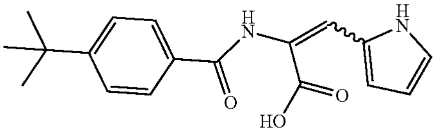 [SMILES: CC(C)(C)c1ccc(C(=O)NC(=Cc2ccc[nH]2)C(=O)O)cc1] |
| G8 | 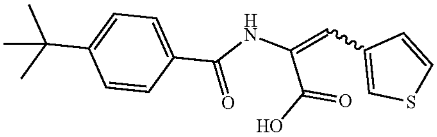 [SMILES: CC(C)(C)c1ccc(C(=O)NC(=Cc2ccsc2)C(=O)O)cc1] |
| G22 | 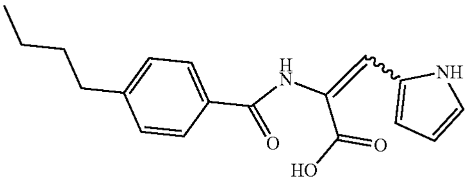 [SMILES: CCCCc1ccc(C(=O)NC(=Cc2ccc[nH]2)C(=O)O)cc1] |
| G26 | 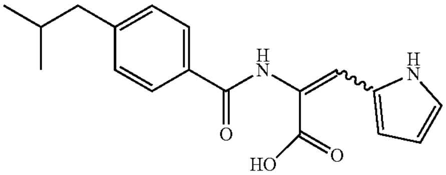 [SMILES: CC(C)Cc1ccc(C(=O)NC(=Cc2ccc[nH]2)C(=O)O)cc1] |
| G28 | 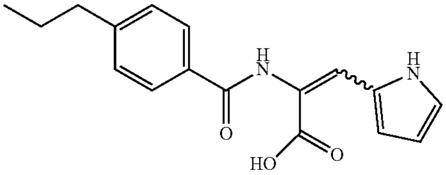 [SMILES: CCCc1ccc(C(=O)NC(=Cc2ccc[nH]2)C(=O)O)cc1] |
| G29 | 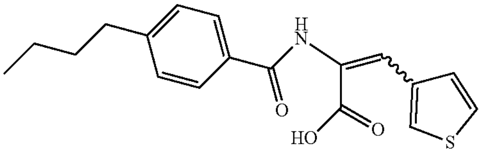 [SMILES: CCCCc1ccc(C(=O)NC(=Cc2ccsc2)C(=O)O)cc1] |
| G35 | 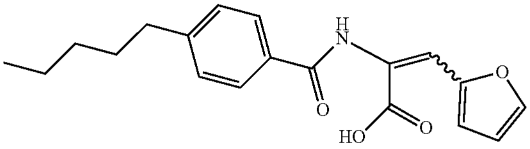 [SMILES: CCCCCc1ccc(C(=O)NC(=Cc2ccco2)C(=O)O)cc1] |
| G37 | 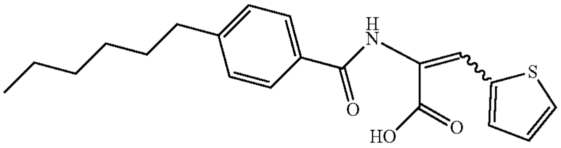 [SMILES: CCCCCCc1ccc(C(=O)NC(=Cc2cccs2)C(=O)O)cc1] |

TABLE 1-continued

| Compound No. | Structural Formula |
| --- | --- |
| G40 | 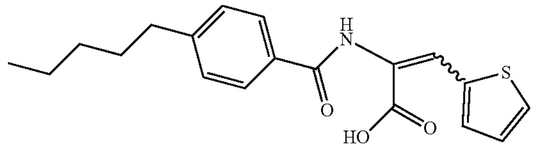 [SMILES: CCCCCc1ccc(C(=O)NC(=Cc2cccs2)C(=O)O)cc1] |

2. A composition comprising the compound, E- or Z-isomer thereof, optical isomer thereof, a mixture of two isomers selected from the E-isomer, Z-isomer, and optical isomer thereof, pharmaceutically acceptable salt thereof or solvate thereof according to claim 1 as an active ingredient.

3. The composition according to claim 2, further comprising a pharmaceutically acceptable carrier.

4. The composition according to claim 2, further comprising another pharmaceutical ingredient.

* * * * *